United States Patent [19]

Nagahara et al.

[11] Patent Number: 5,620,991
[45] Date of Patent: Apr. 15, 1997

[54] AROMATIC AMIDINE DERIVATIVES AND SALTS THEREOF

[75] Inventors: Takayasu Nagahara; Naoaki Kanaya; Kazue Inamura; Yukio Yokoyama, all of Tokyo, Japan

[73] Assignee: Daiichi Pharmaceutical Co., Ltd., Tokyo, Japan

[21] Appl. No.: 471,173

[22] Filed: Jun. 6, 1995

Related U.S. Application Data

[63] Continuation of Ser. No. 282,571, Jul. 29, 1994, abandoned, which is a continuation of Ser. No. 969,396, Oct. 30, 1992, abandoned.

[30] Foreign Application Priority Data

Oct. 31, 1991 [JP] Japan ................. 3-286088

[51] Int. Cl.[6] .................. A61K 31/445; C07D 211/06
[52] U.S. Cl. .................. 514/319; 514/320; 514/321; 514/322; 514/323; 514/324; 546/196; 546/198; 546/199; 546/201; 546/202; 546/205
[58] Field of Search .................. 546/196, 198, 546/199, 201, 202, 205; 514/319, 320, 321, 322, 323, 324

[56] References Cited

U.S. PATENT DOCUMENTS

| | | | |
|---|---|---|---|
| 4,634,783 | 1/1987 | Fuji | 549/475 |
| 4,952,562 | 8/1990 | Klein | 514/18 |
| 5,256,812 | 10/1993 | Alig | 560/35 |
| 5,258,398 | 11/1993 | Klein | 514/399 |

OTHER PUBLICATIONS

*Thrombosis Research*, vol. 19, pp. 339–349, 1980, "Strategies for Anticoagulation With Synthetic Protease Inhibitors –Xa Inhibitors Versus Thrombin Inhibitors", R.R. Tidwell et al.

*Primary Examiner*—Ceila Chang
*Attorney, Agent, or Firm*—Sughrue, Mion, Zinn, Macpeak & Seas

[57] ABSTRACT

An anticoagulant agent which comprises, as an active ingredient, an aromatic amidine derivative represented by the following general formula (1) or a salt thereof:

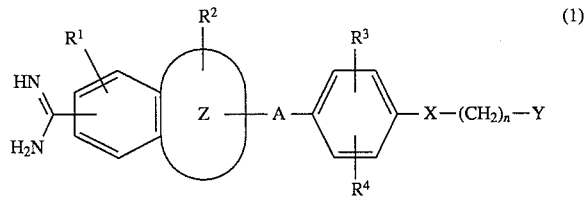

wherein the group represented by

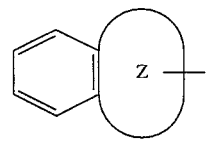

is a group selected from indolyl, benzofuranyl, benzothienyl, benzimidazolyl, benzoxazolyl, benzothiazolyl, naphthyl, tetrahydronaphthyl and indanyl; X is a single bond, an oxygen atom, a sulfur atom or a carbonyl group; and Y is a saturated or unsaturated 5- or 6-membered heterocyclic moiety or cyclic hydrocarbon moiety optionally having a substituent group, an amino group optionally having a substituent group or an aminoalkyl group optionally having a substituent group.

The inventive compound has a high anticoagulant capacity based on its excellent FXa inhibition activity.

7 Claims, No Drawings

AROMATIC AMIDINE DERIVATIVES AND SALTS THEREOF

This is a continuation of parent application Ser. No. 08/282,571, filed Jul. 29, 1994; now abandoned which is a continuation of application Ser. No. 07/969,396, filed Oct. 30, 1992, now abandoned.

FIELD OF THE INVENTION

This invention relates to aromatic amidine derivatives and salts thereof, which are capable of showing a strong anticoagulant effect through reversible inhibition of activated blood coagulation factor X (hereinafter, referred to as "FXa") and can be administered orally. The invention also relates to an anticoagulant, or a thrombosis- or embolism-preventing or treating agent that contains the aromatic amidine derivative or a salt thereof as an active ingredient.

BACKGROUND OF THE INVENTION

Attempts have been made in the prior art to develop an antithrombin agent as an antithrombotic agent. However, it has been known that such an antithrombin agent is apt to cause bleeding tendency and difficulty to manage haemostasis because it inhibits blood coagulation and also thrombin induced platelet aggregation. With the aim of overcoming such problems, the development of anticoagulant agents has been attempted based on a inhibitory mechanism other than the thrombin inhibition. As a result of such efforts, 1,2-bis(5-amidino-2-benzofuranyl)ethane (hereinafter, referred to as "DABE") represented by the following formula (2) has been found as an anticoagulant agent based on FXa inhibition (*Thrombosis Research*, vol.19, pp. 339–349, 1980):

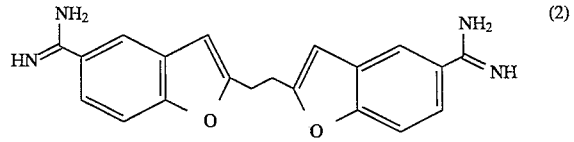

However, DABE has the disadvantages that it has both FXa and thrombin inhibitory activities which cannot be separated sufficiently from each other, it has a very low water solubility, and it does not show its anticoagulant effect when administered orally. Consequently, great attention has been directed, from a clinical point of view, toward the development of a drug which is highly specific and potent inhibitor for FXa, has a high water solubility, and is effective in oral administration.

SUMMARY OF THE INVENTION

In view of the above, the present inventors have conducted intensive studies on the synthesis of various types of aromatic amidine derivatives and evaluated their pharmacological properties. As a result of such efforts, they have found that an aromatic amidine derivative represented by the following general formula (1) or a salt thereof possesses excellent water solubility, shows a strong anticoaguiant effect through its highly specific and reversible FXa-inhibiting activity even in the case of oral administration, and is useful as a drug for the prevention and treatment of various thrombosis- and embolism-based diseases. The present invention has been accomplished on the basis of these findings.

That is, according to the present invention, there is provided an aromatic amidine derivative represented by the following general formula (1) or a pharmaceutically acceptable salt thereof:

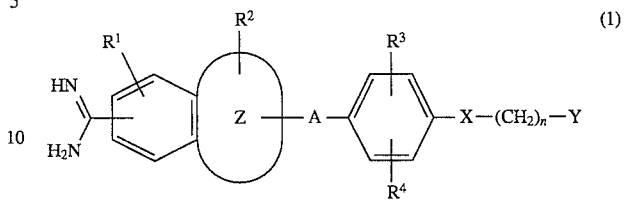

wherein $R^1$ is a hydrogen atom or a lower alkoxy group; $R^2$ is a hydrogen atom, a lower alky group, a lower alkoxy group, a carboxyl group, an alkoxycarbonyl group, a carboxyalkyl group or an alkoxycarbonylalkyl group; $R^3$ is a hydrogen atom, a carboxyl group, an alkoxycarbonyl group, a carboxyalkyl group, an alkoxycarbonylalkyl group, a carboxyalkoxy group or an alkoxycarbonylalkoxy group; $R^4$ is a hydrogen atom, a hydroxyl group, a lower alkyl group or a lower alkoxy group; n is an integer of 0 to 4; A is an alkylene group having a carbon number of 1 to 4, which may have 1 or 2 substituents selected from the group consisting of hydroxyalkyl, carboxyl, alkoxycarbonyl, carboxyalkyl and alkoxycarbonylalkyl; X is a single bond, an oxygen atom, a sulfur atom or a carbonyl group; Y is a saturated or unsaturated 5- or 6-membered heterocyclic moiety or cyclic hydrocarbon moiety optionally having a substituent, an amino group optionally having a substituent, or an aminoalkyl group optionally having a substituent; and the group represented by

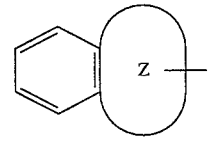

is a member selected from the group consisting of indolyl, benzofuranyl, benzothienyl, benzimidazolyl, benzoxazolyl, benzothiazolyl, naphthyl, tetrahydronaphthyl and indanyl, preferably an indolyl, benzofuranyl, benzothienyl, benzimidazolyl, benzothiazolyl, naphthyl or tetrahydronaphthyl group, more preferably an indolyl, benzothienyl or naphthyl group.

The present invention also provides an anti-coagulation agent, or a thrombosis- or embolism-preventing or treating agent which contains a compound of general formula (1) or a salt thereof as an active ingredient.

DETAILED DESCRIPTION OF THE INVENTION

In the compound of the present invention represented by general formula (1), any straight chain, branched chain or cyclic alkyl group having 1 to 6 carbon atoms may be used as the lower alkyl group. Illustrative examples include methyl, ethyl, propyl, isopropyl, butyl, sec- or tert-butyl, pentyl, hexyl, cyclopropyl, cyclobutyl, cyclopentyl, cyclohexyl and the like. The lower alkoxy group may have 1 to 6 carbon atoms. Illustrative examples include methoxy, ethoxy, propoxy, isopropoxy, butoxy, sec- or tert-butoxy and the like. The alkoxycarbonyl, carboxyalkyl, alkoxycarbonylalkyl, carboxyalkoxy, alkoxycarbonylalkoxy and hydroxyalkyl groups preferably have 1 to 6 carbon atoms, more preferably 1 to 4 carbon atoms, respectively. Illustrative examples of the alkoxycarbonyl group include methoxycarbonyl, ethoxycarbonyl, propoxycarbonyl, butoxycarbonyl and the like. Illustrative examples of the carboxyalkyl group include carboxymethyl, carboxyethyl, carboxypropyl and the like. Illustrative examples of the alkoxycarbonylalkyl group include methoxycarbonylmethyl, ethoxycarbonylmethyl, propoxycarbonylmethyl, methoxycarbonylethyl, ethoxycarbonylethyl, methoxycarbonylpropyl, ethoxycarbonylpropyl and the like. Illustrative examples of the carboxyalkoxy group include carboxymethoxy, carboxyethoxy, carboxypropoxy and the like. Illustrative examples of the alkoxycarbonylalkoxy group include methoxycarbonylmethoxy, ethoxycarbonylmethoxy, propoxycarbonylmethoxy, methoxycarbonylethoxy, ethoxycarbonylethoxy and the like. Illustrative examples of the hydroxyalkyl group include hydroxymethyl, hydroxyethyl, hydroxypropyl, hydroxybutyl and the like. Illustrative examples of the alkylene group having 1 to 4 carbon atoms and represented by A include methylene, ethylene, trimethylene, tetramethylene and the like.

The saturated or unsaturated 5- or 6-membered heterocyclic moiety may contain preferably one or two heteroatom(s) selected from nitrogen and oxygen atoms. Illustrative examples of such a preferred type of heterocyclic rings include pyrrolidine, piperidine, imidazoline, piperazine, tetrahydrofuran, hexahydropyrimidine, pyrrole, imidazole, pyrazine, pyrrolidinone, piperidinone, morpholine and the like. More preferable are pyrrolidine and piperidine which contain one nitrogen atom as the hetero-atom. Illustrative examples of the saturated or unsaturated cyclic hydrocarbon moiety include cyclopentyl, cyclohexyl and the like. Illustrative examples of the aminoalkyl group include aminomethyl, aminoethyl, aminopropyl and the like. Illustrative examples of the substituents applicable to these heterocyclic moieties and cyclic hydrocarbon moieties include preferably lower alkyl, lower alkanoyl, carbamoyl, mono- or dialkylcarbamoyl, formimidoyl, alkanoimidoyl, benzimidoyl, carboxyl, alkoxycarbonyl, carboxyalkyl, alkylcarbonylalkyl, aminoalkyl, alkanoylamino, alkanoylaminoalkyl, imino, alkoxycarbonylimino and the like, more preferably formimidoyl and alkanoimidoyl groups. Illustrative examples of the substituents applicable to these amino groups and amino moieties of aminoalkyl groups include preferably lower alkyl, pyradinyl, pyrrolidinyl, carbamoyl, mono- or dialkylcarbamoyl, lower alkanoyl, formimidoyl, alkanoimidoyl, benzimidoyl, alkoxycarbonyl and the like, more preferably pyrazinyl, pyrrolidinyl, formimidoyl, alkanoimidoyl groups. In this instance, each of the alkyl, alkoxy, alkanoyl and the like listed above may preferably have a carbon number of from 1 to 6.

The compound of formula (1) of the present invention may have an optical isomerism or a stereoisomerism due to the presence of an asymmetric carbon atom. An optical isomer, a stereoisomer and a mixture thereof are included in the scope of the present invention.

Salts of the compound of formula (1) of the present invention are not particularly limited, provided that they are pharmaceutically acceptable. Illustrative examples of such salts include: inorganic acid salts such as hydrochloride, hydrobromide, hydroiodide, phosphate, nitrate, sulfate and the like; organic sulfonic acid salts such as methane sulfonate, 2-hydroxyethane sulfonate, p-toluene sulfonate and the like; and organic carboxylic acid salts such as acetate, propanoate, oxalate, malonate, succinate, glutarate, adipate, tartarate, maleate, malate, mandelate and the like.

Most preferred examples of the compound of formula (1) of the present invention are as follows:

2-[4-[((3S)-1-acetimidoyl-3-pyrrolidinyl)oxy]phenyl]-3-(7-amidino-2-naphthyl)propionic acid;

(+)-2-[4-[((3S)-1-acetimidoyl-3-pyrrolidinyl)oxy]phenyl]-3-(7-amidino-2-naphthyl)propionic acid;

(2S)-2-[4-[((3S)-1-acetimidoyl-3-pyrrolidinyl)oxy]phenyl]-3-(7-amidino-2-naphthyl)propionic acid;

(2R)-2-[4-[((3R)-1-acetimidoyl-3-pyrrolidinyl)oxy]phenyl]-3-(7-amidino-2-naphthyl)propionic acid;

2-[4-[(1-acetimidoyl-4-piperidinyl)oxy]phenyl]-3-(7-amidino-2-naphthyl)propionic acid;

(+)-2-[4-[(1-acetimidoyl-4-piperidinyl)oxy]phenyl]-3-(7-amidino-2-naphthyl)propionic acid;

2-[4-[(1-acetimidoyl-4-piperidinyl)oxy]phenyl]-3-(5-amidinobenzo[b]thien-2-yl)propionic acid;

2-[4-[((2S)-1-acetimidoyl-2-pyrrolidinyl)methoxy]phenyl]-3-(5-amidinobenzo[b]thien-2-yl)propionic acid;

(+)-2-[4-[((2S)-1-acetimidoyl-2-pyrrolidinyl)methoxy]phenyl]-3-(5-amidinobenzo[b]thien-2-yl)propionic acid;

3-[4-[((3S)-1-acetimidoyl-3-pyrrolidinyl)oxy]phenyl]-4-(5-amidinobenzo[b]thien-2-yl)butyric acid;

2-[4-[((3S)-1-acetimidoyl-3-pyrrolidinyl)oxy]phenyl]-3-(6-amidino-1-ethyl-2-indolyl)propionic acid;

2-[4-[((3R)-1-acetimidoyl-3-pyrrolidinyl)oxy]phenyl]-3-(6-amidino-1-ethyl-2-indolyl)propionic acid; and 2-[4-[(1-acetimidoyl-4-piperidinyl)oxy]phenyl]-3-(6-amidino-1-ethyl-2-indolyl)propionic acid.

Basically, the compound of formula (1) of the present invention can be produced for example in accordance with the following reaction formulae. Namely, the nitrile form of the formula (3) is reacted with an alcohol ($R^5OH$) in the presence of a hydrogen halide. The resulting imidate form (4) is reacted with ammonia to obtain an aromatic amidine derivative (1a).

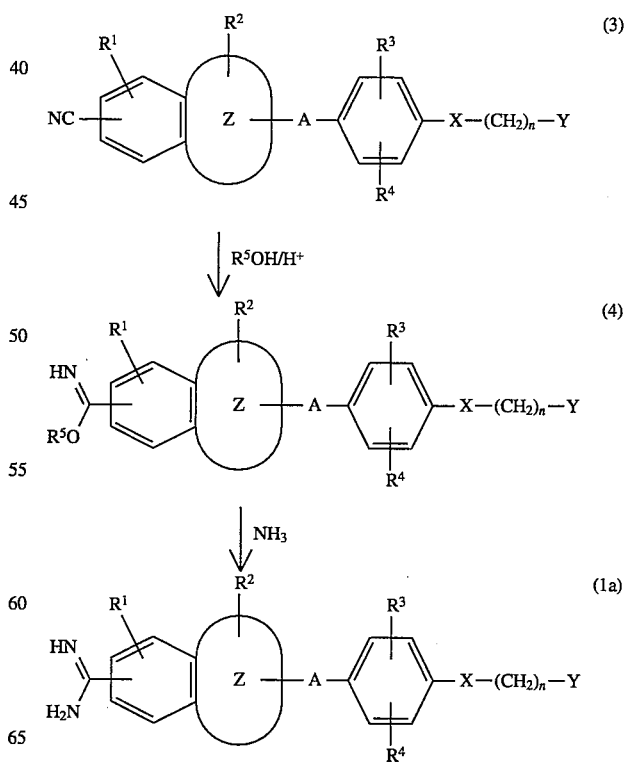

In the above formulae, $R^1$, $R^2$, $R^3$, $R^4$, n, A, X, Y and

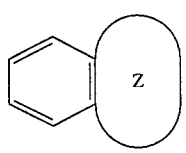

are the same as described above, and $R^5$ is a lower alkyl group.

The above reaction sequence is described in detail. Reaction of the nitrile form (3) with an alcohol ($R^5$OH) may be effected for example by allowing the nitrile form (3) to react with the equimolar or an excess amount of an alcohol ($R^5$OH) having 1 to 6 carbon atoms, such as methanol, ethanol, propanol or the like, in the presence of a hydrogen halide such as hydrogen chloride, hydrogen bromide or the like. If necessary, a solvent may be used which is selected for example from aliphatic ethers such as diethyl ether and the like, halogenated hydrocarbons such as chloroform, dichloromethane and the like, aprotic solvents such as benzene and the like, and mixtures thereof. In general, the reaction is carried at a temperature of from $-20°$ C. to $60°$ C. for a period of 3 to 220 hours. Preferably, the reaction may be carried out at a temperature of from $-8°$ C. to $30°$ C. for a period of 10 to 96 hours in the presence of an excess amount of methanol or ethanol using a halogenated hydrocarbon solvent such as chloroform or dichloromethane.

Reaction of the thus obtained imidate form (4) with ammonia may be effected by allowing the imidate form (4) to react with ammonia in a solvent or a mixed solvent system which is selected for example from alcohols having 1 to 4 carbon atoms, such as ethanol, propanol and the like, aliphatic ethers such as diethyl ether and the like, halogenated hydrocarbons such as chloroform and the like, aprotic solvents such as benzene and the like, and N,N'-dimethylformamide and dimethylsulfoxide. The reaction may be carried out at a temperature of from $-10°$ C. to $140°$ C. for a period of 0.5 to 200 hours, preferably at a temperature of from $-8°$ C. to $30°$ C. for a period of 10 to 96 hours in ethanol.

When the nitrile form (3) to be used as a starting material has a carboxyl group or an alkoxycarbonyl group, the carboxyl or alkoxycarbonyl group is esterified by a formation reaction of an imidate or exposed to ester interchange with the alcohol ($R^5$OH) to be used. As a consequence, since a carboxyl group in a compound (1a) obtained by this reaction is esterified, it is necessary to subject the compound (1a) to hydrolysis when an aromatic amidine derivative having a free carboxyl group is produced.

The hydrolysis reaction may be effected by treating the compound (1a) in an aqueous solution of an inorganic acid Such as hydrochloric acid, sulfuric acid or the like or an organic acid such as tosyl acid or the like, at a temperature of from $-10°$ C. to a reflux temperature, preferably from $-5°$ C. to a reflux temperature, for a period of from 0.5 to 550 hours, preferably from 0.5 to 350 hours.

When the compound (1a) contains a group which is susceptible to hydrolysis by a strong acid, it is preferable to protect the amidino group with a protective group such as tert-butoxycarbonyl or the like prior to the hydrolysis reaction, thereafter carrying out ester hydrolysis under basic conditions and subsequent deprotection. Protection of the amidino group may be effected by allowing the compound (1a) to react with 2-(tert-butoxycarbonyloxyimino)-2-phenylacetonitrile in water, methanol, ethanol, tetrahydrofuran, dioxane, acetone or a mixture thereof, in the presence of a base such as 1,8-diazabicyclo[5.4.0]-7-undecene or the like. The reaction may be carried out at a temperature of from $0°$ to $50°$ C., preferably from $5°$ to $30°$ C., for a period of from 0.5 to 48 hours, preferably from 1 to 24 hours.

Ester hydrolysis of the thus protected compound and subsequent deprotection may be effected by treatment of the protected compound with an aqueous solution of sodium hydroxide or potassium hydroxide and then with hydrochloric acid, in water or a water-containing solvent such as of ethanol, methanol, tetrahydrofuran, dioxane or the like. The ester hydrolysis reaction may be carried out at a temperature of from $0°$ to $50°$ C., preferably from $5°$ to $30°$ C., for a period of from 0.5 to 48 hours, preferably from 1 to 24 hours. The deprotection reaction may be carried out at a temperature of from $0°$ to $60°$ C., preferably at $25°$ C., for a period of from 0.5 to 24 hours, preferably from 1 to 6 hours.

When two alkoxycarbonyl groups are linked to one carbon atom in group A of the compound (1a), hydrolysis and decarboxylation may be carried out at the same time in accordance with the following reaction sequence:

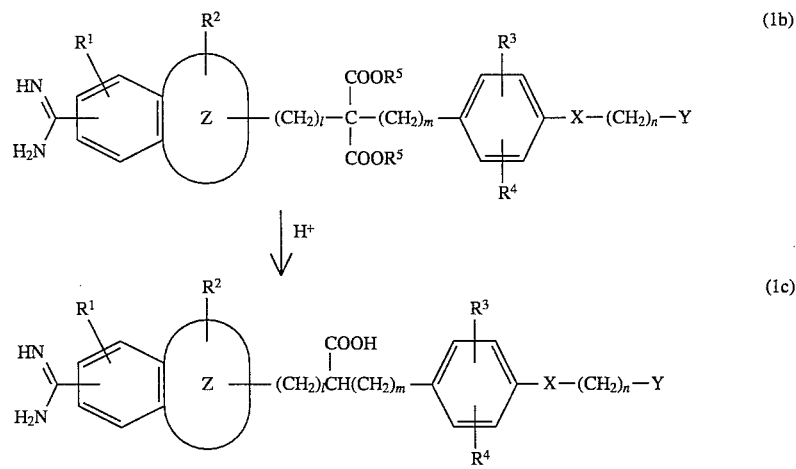

In the above formulae, each of 1 and m is 0 or 1, while $R^1$, $R^2$, $R^3$, $R^4$, $R^5$, n, X, Y and

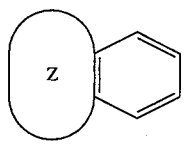

are the same as described above.

This reaction may be carried out in an aqueous solution of an inorganic acid such as hydrochloric acid, sulfuric acid or the like or an organic acid such as tosyl acid or the like, at a temperature of from −20° C. to a reflux temperature, preferably from −5° C. to a reflux temperature, for a period of from 0.5 to 550 hours, preferably from 0.5 to 350 hours.

When a compound (1e) having an imidoyl group in its group Y is produced as a compound of formula (1) of the present invention, it may be obtained by allowing a compound (1d) having a primary or secondary amino group in its group Y to react with an imidate compound (5) in accordance with the following reaction sequence:

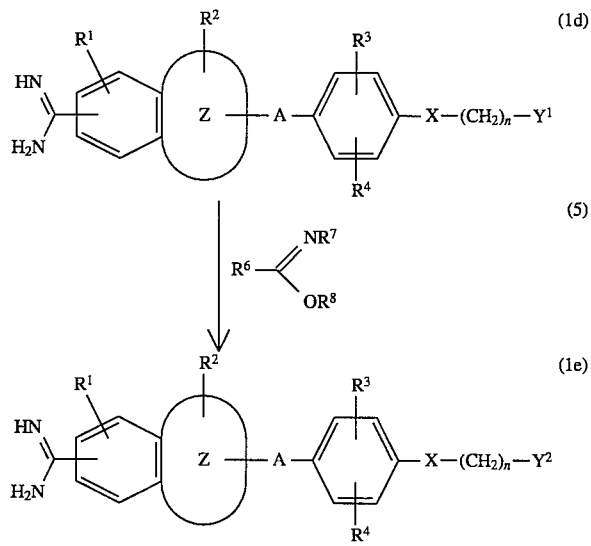

In the above formulae, $Y^1$ is a variety of the aforementioned Y groups having a primary or secondary amino group as a substituent, $Y^2$ is another variety of the aforementioned Y groups having an imidyl group as a substituent, each of $R^6$ and $R^7$ is a hydrogen atom, a lower alkyl group or a phenyl group and $R^8$ is a lower alkyl group or a benzyl group, while $R^1$, $R^2$, $R^3$, $R^4$, n, A, X and

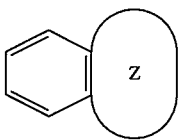

are the same as described above.

This reaction may be effected for example by allowing compound (1d) to react with the equimolar or an excess amount of imidate compound (5) in the presence of a base such as triethylamine, sodium hydroxide, potassium hydroxide or the like, in water or a solvent or a mixed solvent system which is selected for example from alcohols having 1 to 4 carbon atoms such as ethanol, propanol and the like, aliphatic ethers such as diethyl ether and the like, halogenated hydrocarbons such as chloroform and the like, and N,N'-dimethylformamide and dimethylsulfoxide. The reaction may be carried out at a temperature of from −20° C. to 70° C. for a period of from 1 minute to 168 hours, preferably at a temperature of from −10° C. to 40° C. for a period of from 1 minute to 72 hours.

When the imidoyl form (1e) has a alkoxycarbonyl group, the alkoxycarbonyl group may be hydrolyzed to a carboxylic group.

The hydrolysis reaction may be effected by treating the compound (1e) in an aqueous solution of an inorganic acid such as hydrochloric acid, sulfuric acid or the like or an organic acid such as tosyl acid or the like, at a temperature of from −10° C. to a reflux temperature, preferably from −5° C. to a reflux temperature, for a period of from 0.5 to 550 hours, preferably from 0.5 to 350 hours.

According to the present invention, when a material compound has a substituent such as a carboxyl group, an amino group or the like, it is preferable to protect such a functional group prior to necessary reactions, and thereafter detaching the protective group. On the other hand, the formation reaction of an amidine, the formation reaction of an imidate and the like may be carried without protecting such a functional group. In this instance, protection of the primary or secondary amino group may be effected by use of a protective group such as tert-butoxycarbonyl, benzyloxycarbonyl, p-nitrobenzyloxycarbonyl, triphenylmethyl or the like.

In addition, an alkoxycarbonyl-substituted compound may be obtained for example in accordance with the following reaction sequence, by carrying out ester hydrolysis after the formation reaction of an amidine or an imidate, followed, if necessary, by re-esterification:

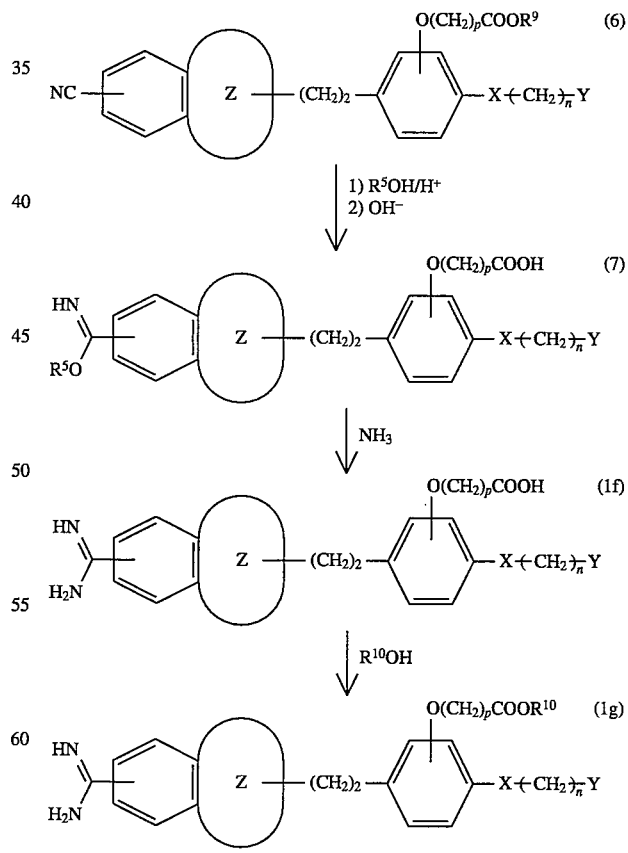

In the above formulae, $R^9$ is a hydrogen atom or a lower alkyl group, $R^{10}$ is a lower alkyl group and p is an integer of 1 or 2, while $R^5$, n, X, Y and

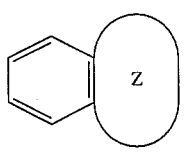

are the same as described above.

That is, a nitrile compound represented by formula (6) is allowed to react with an alcohol ($R^5OH$) in the presence of a hydrogen halide, and the resulting imidate.ester compound is hydrolyzed by a base treatment to obtain an imidate-carboxylic acid derivative (7) which is subsequently reacted with ammonia to obtain an amidino group-substituted aromatic compound (1f). By subjecting compound (1f) to esterification, a compound (1g) is produced.

Reaction of the nitrile compound (6) with an alcohol ($R^5OH$) may be effected for example by allowing the nitrile compound (6) to react with the equimolar or an excess amount of an alcohol ($R^5OH$) having 1 to 6 carbon atoms, such as methanol, ethanol, propanol or the like, in the presence of a hydrogen halide such as hydrogen chloride, hydrogen bromide or the like. If necessary, a solvent or a solvent mixture may be used which is selected, for example, from aliphatic ethers such as diethyl ether and the like, halogenated hydrocarbons such as chloroform, dichloromethane and the like and aprotic solvents such as benzene. The reaction may be carried out at a temperature of from −10° C. to 60° C. for a period of from 3 to 120 hours. Preferably, it may be effected at a temperature of from −8° C. to 30° C. for a period of from 10 to 96 hours in a halogenated hydrocarbon solvent such as chloroform or dichloromethane in the presence of an excess amount of methanol or ethanol. After concentrating and drying the resulting reaction mixture, the remaining solid material is treated with a strong alkali solution to effect neutralization and ester hydrolysis, thereby obtaining the imidate.carboxylic acid derivative represented by formula (7). The reaction may be carried out generally at a temperature of from −10° C. to 60° C. for a period of from 0.2 to 5 hours, preferably at a temperature of from 0° to 25° C. for a period of from 0.5 to 2 hours, in an aqueous solution of sodium hydroxide or potassium hydroxide.

Reaction of the thus obtained imidate-carboxylic acid derivative (7) with ammonia may be effected for example by allowing the derivative (7) to react with ammonium chloride, ammonia or a mixture thereof, in a solvent or a mixed solvent system which is selected for example from alcohols having 1 to 4 carbon atoms such as ethanol, propanol and the like, aliphatic ethers such as diethyl ether and the like, halogenated hydrocarbons such as chloroform and the like, aprotic solvents such as benzene and the like and N,N-dimethylformamide and dimethylsulfoxide. The reaction may be carried out generally at a temperature of from −10° C. to 140° C. for a period of from 0.5 to 200 hours, preferably at a temperature of from −8° C. to 30° C. for a period of from 10 to 96 hours, in ethanol.

Esterification of the amidino compound represented by formula (1f) may be effected, for example, by allowing compound (1f) to react with a thionyl halide such as thionyl chloride, thionyl bromide or the like in an alcohol having 1 to 4 carbon atoms such as ethanol, propanol or the like. The reaction may be carried out generally at a temperature of from 0° C. to a reflux temperature for a period of from 10 minutes to 36 hours, preferably at a temperature of from 10° to 60° C. for a period of from 10 minutes to 24 hours.

Crystallization of a compound of formula (1) of the present invention may be effected for example by treating the reaction-completed solution with a strongly basic (OH) type ion exchange resin, or with sodium hydroxide, potassium hydroxide or the like, to adjust the number of added salts, preferably to 1. The resulting solution is treated at a temperature of from −10° C. to 30° C., preferably from 0° to 25° C., in water or a solvent such as methanol, ethanol, isopropanol, acetone or the like or a mixture thereof, preferably in a water/ethanol mixture system.

The thus obtained aromatic amidine derivative of formula (1) or a salt thereof has a specific and excellent capacity to inhibit FXa and is useful as an anticoagulant agent, as well as a preventive agent and a therapeutic agent for thrombosis and embolism. Since a compound of formula (1) can exhibit its effect even when administered orally, it can be applied to both oral and parenteral administrations. The compound of the present invention may be administered by optionally changing its dose depending on symptoms, age, weight and the like of each patient. In the case of oral administration, the compound may be administered generally in a dose of from 5 to 1,000 mg/day/adult, preferably from 10 to 500 mg/day/adult. Examples of dosage forms include tablets, capsules, powders, granules and the like which can be prepared in the usual way using generally used additives such as fillers, lubricants, binders and the like. In the case of parenteral administration, the compound may be administered by subcutaneous injection, intravenous injection or intravenous drip infusion in a dose of from 0.1 to 100 mg/day/adult, preferably from 0.5 to 30 mg/day/adult.

Since the compound of the present invention shows a high anticoagulant function based on its excellent FXa inhibition activity, it does not react with platelets and can be applied to various diseases caused by thrombosis and embolism, such as cerebral infarction, cerebral thrombosis, cerebral embolism, transient cerebral ischemic attack (TIA), myocardial infarction, unstable angina, pulmonary infarction, pulmonary embolism, Berger disease, deep venous thrombosis, disseminated intravascular coagulation syndrome, thrombus formation after artificial blood vessel operation, artificial valve replacement, percutaneous transluminal colonary angioplasty (PTCA), or percutaneous transluminal coronary recanalization (PTCR), obstruction after recirculation of blood, thrombus formation during extracorporeal circulation and the like.

The following reference, inventive and test examples are provided to illustrate further the present invention. It is to be understood, however, that the examples are for the purpose of illustration only and are not intended as a definition of the limits of the invention.

REFERENCE EXAMPLE 1

Preparation of (5-cyano-3-methyl-2-benzofuranyl) methyltriphenylphosphonium chloride a) 13.31 g of 2-acetyl-4-bromophenol, 11.0 g of ethyl bromoacetate and 9.7 g of anhydrous potassium carbonate were refluxed under heating in 70 ml of acetone for 2 hours. Insoluble materials were removed by filtration, and the resulting filtrate was concentrated and dried. The residue thus obtained was dissolved in chloroform, washed with water, and then dried to remove the solvent. The thus treated residue was washed with a mixed solvent system of ethanol and n-hexane to isolate insoluble crystals by filtration. In this way, 16.82 g of ethyl (2-acetyl-4-bromophenyl)oxyacetate was obtained in the form of colorless plate crystals. mp: 66°–68° C.

b) 16.8 g of ethyl (2-acetyl-4-bromophenyl)oxyacetate obtained in the above step a) was dissolved in 100 ml of anhydrous ethanol to which 1.2 g of metallic sodium has been dissolved in advance, and the resulting solution was stirred at room temperature for 1.5 hours. The reaction solution was poured into water and extracted with ethyl acetate, and the resulting organic layer was washed with water, and then dried. After distilling off the solvent, precipitated crystals were collected by filtration and washed with ethanol to obtain 5.3 g of ethyl 5-bromo-3-methyl-2-benzofurancarboxylate in the form of colorless fine needle crystals.

mp: 96°–97° C.

$^1$H-NMR (CDCl$_3$) δ:1.44 (3H, t, J=8Hz), 2.54 (3H, s), 4.45 (2H, q, J=8Hz), 7.43 (2H), 7.73 (1H, s)

c) In a stream of nitrogen, 4.9 g of ethyl 5-bromo-3-methyl-2-benzofurancarboxylate obtained in the above step b), 2.0 g of cuprous cyanide and a catalytically effective amount of copper sulfate were stirred in 40 ml of N-methyl-2-pyrrolidone for 6 hours at 200° C. After cooling, the reaction solution was poured into water to remove insoluble materials by filtration. The resulting filtrate was extracted with ethyl acetate, and the organic layer was washed with water, and then concentrated and dried to collect precipitated crystals. In this way, 3.16 g of ethyl 5-cyano-3-methyl-2-benzofurancarboxylate in the form of light brown crystals.

mp: 156°–158° C.

$^1$H-NMR (CDCl$_3$) δ:1.45 (3H, t, J=8Hz), 2.60 (3H, s), 4.45 (2H, q, J=8Hz), 7.67 (2H), 7.99 (1H, s)

d) 3.1 g of ethyl 5-cyano-3-methyl-2-benzofurancarboxylate obtained in the above step c) was dissolved in 60 ml of tetrahydrofuran. To this were added, with ice cooling, 2.1 g of calcium iodide (4H$_2$O), 0.63 g of sodium borohydride and a catalytically effective amount of sodium bicarbonate. The resulting mixture was stirred at room temperature for 18 hours, followed by further addition of 2.1 g of calcium iodide (4H$_2$O) and 0.63 g of sodium borohydride and by additional stirring at room temperature for 18 hours.

The resulting reaction solution was diluted with ethyl acetate, washed with water and then dried to remove the solvent. The residue thus obtained was subjected to silica gel column chromatography using chloroform as an eluant. In this way, 1.96 g of purified 2-hydroxymethyl-3-methyl-5-benzofurancarbonitrile was obtained.

$^1$H-NMR (CDCl$_3$) δ:1.8 (1H, br), 2.28 (3H, s), 4.78 (2H, s), 7.52 (2H), 7.82 (1H, s)

e) 1.92 g of 2-hydroxymethyl-3-methyl-5-benzofurancarbonitrile obtained in the above step d) was added to 50 ml of diethyl ether, followed by the addition of 3 drops of pyridine and 1.65 ml of thionyl chloride during ice cooling, and the resulting mixture was stirred at room temperature for 4.5 hours. The reaction solution was poured into ice water and extracted with chloroform, and the resulting organic layer was washed with water, saturated sodium bicarbonate aqueous solution and water in that order, followed by concentration and drying. In this way, 1.68 g of 2-chloromethyl-3-methyl-5-benzofurancarbonitrile was obtained.

f) 1.68 g of 2-chloromethyl-3-methyl-5-benzofurancarbonitrile obtained in the above step e) and 3 g of triphenylphosphine were refluxed under heating in xylene for 5 hours. After cooling, precipitated crystals were collected by filtration to obtain 3.63 g of the title compound.

mp: >270° C.

$^1$H-NMR (CDCl$_3$) δ: 2.0 (1.5H, s), 2.04 (1.5H, s), 6.09 (2H, d, J=16Hz), 7.7 (18H, m)

REFERENCE EXAMPLE 2

Preparation of (5-cyano-3-benzofuranyl)methyltriphenylphosphonium bromide a) 12.15 g of ethyl 5-cyano-3-methyl-2-benzofurancarboxylate obtained in the step c) of Reference Example 1 was dissolved in 60 ml of ethanol, followed by the addition of 5 g of sodium hydroxide and 100 ml of water, and the resulting mixture was stirred at 30° to 40° C. for 2 hours. After ice cooling, the resulting reaction solution was adjusted to pH 2 with dilute HCl solution, and crystals thus precipitated were collected by filtration and dried. In this way, 10.6 g of 5-cyano-3-methyl-2-benzofurancarboxylic acid was obtained in the form of colorless prism crystals.

mp: (sublimation at 275°–285° C.)

$^1$H-NMR (CDCl$_3$) δ:2.54 (3H, s), 7.88 (2H), 8.44 (1H)

b) 10.64 g of 5-cyano-3-methyl-2-benzofurancarboxylic acid obtained in the above step a) and 2.5 g of copper powder were added to 65 ml of quinoline, and the mixture was stirred at 210° C. for 30 minutes. After adding lice water and adjusting to pH 1 with HCl, the reaction mixture thus treated was extracted with chloroform, and the resulting organic layer was dried under a reduced pressure. The residue thus obtained was subjected to silica gel column chromatography using toluene as an eluant. In this way, 6.89 g of purified colorless 3-methyl-5-benzofurancarbonitrile was obtained.

mp: 73° C.

$^1$H-NMR (CDCl$_3$) δ: 2.26 (3H, d, J=1.5Hz), 7.53 (3H), 7.85 (1H, s)

c) 7.28 g of 3-methyl-5-benzofurancarbonitrile obtained in the above step b) was dissolved in 50 ml of carbon tetrachloride and subjected to reflux under light irradiation condition. To the resulting reaction solution was gradually added a mixture consisting of 8.25 g of N-bromosuccinimide and 160 mg of 2,2-azobis-iso-butylonitrile. After refluxing under heating for 3 hours, precipitated materials were removed by filtration, and the resulting filtrate was dried. The thus dried residue was subjected to purification by silica gel column chromatography using toluene as an eluant, thereby obtaining 8.65 g of a mixture (2:5) of the starting material 3-methyl-5benzofurancarbonitrile and 3-bromomethyl-5-benzofurancarbonitrile. 8.65 g of the thus obtained crude bromomethyl compound was dissolved in xylene, 10 g of triphenylphosphine was added to the resulting solution, and the thus prepared mixture was heated for 20 minutes. After cooling, the precipitate thus formed was collected by filtration to obtain 14.73 g of the title compound in the form of colorless crystals.

mp: >290° C.

$^1$H-NMR (CDCl$_3$) δ:5.88 (2H, d, J=16Hz), 7.0–8.0 (19H, m)

REFERENCE EXAMPLE 3

Preparation of (5-cyano-7-methoxy-2-benzofuranyl)methyltriphenylphosphonium chloride a) 10.0 g of 5-bromo-2-hydroxy-3-methoxybenzaldehyde was dissolved in 39 ml of N,N-dimethylformamide, and the resulting solution was mixed with 11.9 g of anhydrous potassium carbonate and stirred at room temperature. 5.0 g of chloroacetone was added dropwise to the above reaction solution at the same temperature, followed by additional 1 hour of stirring at an elevated temperature of 80° C. The resulting reaction solution was diluted with ethyl acetate and adjusted to pH 2 with concentrated hydrochloric acid, and the resulting organic layer was collected. The organic layer was dried to distill off the solvent, and the resulting residue was purified by silica gel column chromatography, thereby obtaining 4.0 g of 2-acetyl-5-bromo-7-methoxybenzofuran.
mp: 107°–109° C.
$^1$H-NMR (CDCl$_3$) δ:2.62 (3H, s), 3.83 (3H, s), 7.02 (1H), 7.39 (2H)

b) To 107.6 ml of 5N sodium hydroxide aqueous solution was added dropwise 26.8 g of bromine at a temperature of −5° C. or below. To this was further added dropwise and slowly a 100 ml dioxane solution containing 15.0 g of 2-acetyl-5-bromo-7-methoxybenzofuran obtained in the above step a). After completion of the dropwise addition, the temperature of the resulting reaction solution was increased gradually to 60° C. and then stirred for 30 minutes. After cooling, the resulting reaction solution was adjusted to pH 2 with concentrated hydrochloric acid and then extracted with ethyl acetate. The resulting organic layer was concentrated to dryness, and crystals thus precipitated were collected by filtration to obtain 5-bromo-7-methoxy-2-benzofurancarboxylic acid. The thus obtained crystals were suspended in 200 ml of ethanol, and 10 ml of thionyl chloride was added dropwise to the suspension with stirring at room temperature. The resulting reaction solution was refluxed under heating for 2 hours. After cooling, the thus treated reaction solution was neutralized with saturated sodium bicarbonate aqueous solution, and then mixed with water to collect precipitated crystals by filtration. The crystals thus collected were purified by silica gel column chromatography using chloroform as an eluant to obtain 11.33 g of ethyl 5-bromo-7-methoxy-2-benzofurancarboxylate.
$^1$H-NMR (CDCl$_3$) δ:1.41 (3H, t, J=7.0Hz), 4.00 (3H, s), 4.43 (2H, q, J=7Hz), 7.02 (1H, d), 7.39 (1H, d), 7.42 (1H, s)

c) a mixture consisting of 2.0 g of ethyl 5-bromo-7-methoxy-2-benzofurancarboxylate obtained in the above step b), 1.26 g of cuprous cyanide, 100 ml of N-methyl-2-pyrrolidone and a catalytically effective amount of copper sulfate was stirred at 180° to 190° C. for 2 hours in a stream of argon. After cooling, a toluene/ethyl acetate mixture (1:1) and water were added to the reaction solution to remove insoluble materials, and the resulting organic layer was washed with water, and then dried. After distilling off the solvent, precipitated crystals were collected by filtration and washed with ethanol to obtain 1.2 g of ethyl 5-cyano-7-methoxy-2-benzofurancarboxylate.
$^1$H-NMR (CDCl$_3$) δ:1.43 (3H, t, J=7.0Hz), 4.06 (3H, s), 4.46 (2H, t, J=7.0Hz), 7.10 (1H, d, J=1.0Hz), 7.53 (1H, s), 7.64 (1H, d)

d) 8.55 g of ethyl 5-cyano-7-methoxy-2-benzofurancarboxylate obtained in the above step c) was dissolved in 250 ml of tetrahydrofuran. During cooling on an ice bath, the resulting solution was mixed with 13.74 g of calcium iodide (4H$_2$O), 2.12 g of sodium borohydride and a catalytically effective amount of sodium bicarbonate, and the resulting mixture was stirred at room temperature for 1.5 hours, followed by further addition of 13.74 g of calcium iodide (4H$_2$O) and 2.12 g of sodium borohydride and additional stirring at room temperature for 1 hour. During cooling on an ice bath, the resulting reaction solution was adjusted to pH 2 with concentrated hydrochloric acid, and the solvent was removed by distillation. The resulting residue was extracted with chloroform, washed with water and then dried to distill off the solvent. The thus treated residue was purified by silica gel column chromatography using a mixture of chloroform and ethanol as an eluant, thereby obtaining 1.96 g of 2-hydroxymethyl-7-methoxy-5-benzofurancarbonitrile.
mp: 149°–150° C.
$^1$H-NMR (CDCl$_3$) δ: 2.17 (1H, t, J=6.1Hz), 4.02 (3H, s), 4.80 (2H, d, J=6.1Hz), 6.71 (1H, s), 6.99 (1H, d, J=1.3Hz), 7.50 (1H, d, J=1.3Hz)

e) 5.0 g of 2-hydroxymethyl-7-methoxy-5-benzofurancarbonitrile obtained in the above step d) was dissolved in 100 ml of diethyl ether, followed by the addition of a few drops of pyridine. With cooling on an ice bath and with stirring, 5.86 g of thionyl chloride was added dropwise to the above solution. After completion of the dropwise addition, temperature of the resulting solution was increased gradually to room temperature, and the stirring was continued for additional 1 hour at the room temperature. During cooling on an ice bath, water was added to the resulting reaction solution, and the thus formed organic layer was collected, washed with water and then dried to remove the solvent, thereby obtaining 2-chloromethyl-7-methoxy-5-benzofurancarbonitrile. The chloromethyl compound thus obtained and 9.67 g of triphenylphosphine were refluxed under heating for 18 hours in 50 ml of xylene. After cooling, crystals thus precipitated were collected by filtration to obtain 10.54 g of the title compound.
$^1$H-NMR (DMSO-d$_6$) δ:3.89 (3H, s), 5.6–6.0 (2H, br)

REFERENCE EXAMPLE 4

Preparation of (5-cyanobenzo[b]thien-2-yl)methyltriphenylphosphonium chloride a) 8.13 g of 5-bromosalicylaldehyde was dissolved in 100 ml of acetone, followed by the addition of 6.7 g of anhydrous potassium carbonate. With stirring at room temperature, 5.0 g of N,N-dimethylthiocarbamoyl chloride was added to the above solution, and the stirring was continued for two hours. The resulting reaction solution was poured into ice water, and crystals thus precipitated were collected by filtration, and dried to obtain 9.2 g of 5-bromo-2-[(N,N-dimethylthiocarbamoyl)oxy]benzaldehyde.
mp: 141°–143° C.
IR (KBr): 1690, 1596, 1546, 1470, 1396 cm$^{-1}$
$^1$H-NMR (CDCl$_3$) δ: 3.42 (3H, s), 3.47 (3H, s), 7.03 (1H, d, J=8.3Hz), 7.72 (1H, dd, J=8.3 and 2.2Hz), 8.01 (1H, d, J=2.2Hz)

b) 9.0 g of 5-bromo-2-[(N,N-dimethylthiocarbamoyl)oxy]benzaldehyde obtained in the above step a) was melted by heating it for 10 minutes on an oil bath of 210° to 220° C. The resulting product was dissolved in a 1 ml of toluene, followed by the addition of 6 ml of methanol. Crystals thus precipitated were collected by filtration to obtain 4.0 g of crude 5-bromo-2-[(N,N-dimethylcarbamoyl)thio]benzaldehyde.
mp: 118°–120° C.
IR (KBr): 1677, 1365, 1185 cm$^{-1}$
$^1$H-NMR (CDCl$_3$) δ:3.09 (6H, s), 7.31 (1H, d, J=9.6Hz), 7.70 (1H, dd, J=9.6 and 1.8Hz), 8.14 (1H, d, J=1.8Hz), 10.25 (1H, s)

c) 21.0 g of 5-bromo-2-[(N,N-dimethylcarbamoyl)thio] benzaldehyde was dissolved in 50 ml of methyl orthoformate. The resulting solution was mixed with 1.0 g of p-toluenesulfonate, and refluxed under heating for 50 minutes. After cooling, the resulting reaction solution was poured into saturated sodium bicarbonate solution and extracted with benzene. The resulting organic layer was dried to remove the solvent. The residue thus obtained was dissolved in 100 ml of methanol, followed by adding 37 ml of 2N sodium hydroxide and by refluxing under heating for 1 hour in a stream of nitrogen. After cooling, the resulting reaction solution was adjusted to pH 1 with concentrated hydrochloric acid, extracted with benzene, and then dried to remove the solvent. The residue thus obtained was dissolved in 20 ml of acetone and added dropwise, at room temperature, to a stirred mixture consisting of 6.74 g of chloroacetone, 22.1 g of anhydrous potassium carbonate and 150 ml of acetone. After 30 minutes of stirring, the resulting reaction mixture was refluxed under heating for 30 minutes. After cooling, insoluble materials were removed by filtration, and the resulting filtrate was concentrated to dryness. The thus obtained residue was purified by silica gel column chromatography using toluene as an elution solvent and the resulting product was recrystallized from ethanol to obtain 7.5 g of 2-acetyl-5-bromobenzo[b]thiophene.
mp: 120°–121° C.
IR (KBr): 1668, 1512, 1326, 1266 cm$^{-1}$
$^1$H-NMR (CDCl$_3$) δ:2.67 (3H, s), 7.54 (1H, dd, J=8.8 and 1.8Hz), 7.75 (1H, d, J=8.8Hz), 7.85 (1H, s), 8.03 (1H, d, J=1.8Hz)

d) With stirring, 5.4 ml of bromine was added dropwise to 5N sodium hydroxide aqueous solution which has been cooled to −5° C. to 0° C. To this was added dropwise, at a temperature of −5° C. or below, a 50 ml dioxane solution of 2-acetyl-5-bromobenzo[b]thiophene obtained in the above step c). The resulting mixture was stirred for 30 minutes at room temperature and then for 30 minutes at 50° C. With ice cooling, the resulting reaction solution was adjusted to pH 2 with concentrated hydrochloric acid, and crystals thus precipitated were collected by filtration and washed with water. The crystals thus obtained were dissolved in ethyl acetate, and the solution was dried and concentrated. Crystals thus precipitated were collected by filtration and washed with toluene to obtain 6.6 g of 5-bromobenzo[b]-thiophene-2-carboxylic acid.
mp: 238°–241° C.
IR (KBr): 1671, 1554, 1518, 1443 cm$^{-1}$
$^1$H-NMR (CDCl$_3$) δ:7.57 (1H, dd, J=8.6 and 1.8Hz), 7.82 (1H, d, J=8.6Hz), 8.00 (1H, s), 8.07 (1H, d, J=1.8Hz)

e) 6.4 g of 5-bromobenzo[b]thiophene-2-carboxylic acid obtained in the above step d) was suspended in 250 ml of ethanol. With cooling on an ice bath and with stirring, 4.45 g of thionyl chloride was added dropwise to the suspension prepared above, followed by refluxing under heating for 1 hour. With ice cooling, 8.15 g of thionyl chloride was further added dropwise to the resulting mixture, followed by refluxing under heating 2 hours. The resulting reaction solution was concentrated and adjusted to pH 9 with saturated sodium bicarbonate aqueous solution. Crystals thus precipitated were collected by filtration and dried to obtain 7.0 g of ethyl 5-bromobenzo[b]thiophene-2-carboxylate. A portion of thee thus obtained compound was recrystallized from methanol to obtain needle crystals.
mp: 94°–95° C.
$^1$H-NMR (CDCl$_3$) δ:1.42 (3H, t, J=7.0Hz), 4.41 (2H, q, J=7.0Hz), 7.54 (1H, dd, J=8.8 and 1.8Hz), 7.73 (1H, d, J=8.8Hz), 7.96 (1H, s), 8.01 (1H, d)

f) 7.0 g of ethyl 5-bromobenzo[b]thiophene-2-carboxylate obtained in the above step e) and 5.4 g of cuprous cyanide were suspended in 70 ml of N-methyl-2-pyrrolidone, and the suspension was stirred for 2 hours with heating at a temperature of 200° C. in a stream of nitrogen. After cooling, the reaction mixture was diluted with ethyl acetate, insoluble materials were removed by filtration, and the resulting filtrate was washed with water and dried. After distilling off the solvent, the crystals precipitated were collected by filtration and washed with ethanol to obtain 5.02 g of ethyl 5-cyanobenzo[b]thiophene-2-carboxylate as crystals.
mp: 138°–139° C.
IR (KBr): 2232, 1728, 1262 cm$^{-1}$
$^1$H-NMR (CDCl$_3$) δ:1.43 (3H, t, J=7.0Hz), 4.45 (2H, q, J=7.0Hz), 7.70 (1H, dd, J=9.0 and 1.8Hz), 8.04 (1H, d, J=9.0Hz), 8.08 (1H), 8.20 (1H)

g) To 150 ml of tetrahydrofuran were added 4.92 g of ethyl 5-cyanobenzo[b]thiophene-2-carboxylate obtained in the above step f) and then 3.33 g of calcium iodide (4H$_2$O). With ice cooling and stirring, 1.0 g of sodium borohydride and a catalytically effective amount of sodium bicarbonate were added to the above mixture, and the resulting mixture was stirred at room temperature for 1 hour. After further addition of 3.33 g of calcium iodide (4H$_2$O), 1.0 g of sodium borohydride was added to the mixture which was cooled on an ice bath with stirring, and the resulting mixture was stirred at room temperature. After stirring for 1 hour, 3.33 g of calcium iodide (4H$_2$O) was again added to the stirred mixture, followed by further addition of 1.0 g of sodium borohydride to the resulting mixture which was cooled on an ice bath with stirring and by subsequent stirring at room temperature for 1 hour. The thus obtained reaction solution was diluted with water, extracted with ethyl acetate, and then dried to remove the solvent. Thereafter, the crystals thus precipitated were collected by filtration and washed with a mixture of benzene and n-hexane to obtain 4.0 g of 2-hydroxymethylbenzo[b]thiophene-5-carbonitrile.
mp: 78°–79° C.
IR (KBr): 3496, 2236, 1026 cm$^{-1}$
$^1$H-NMR (CDCl$_3$) δ: 4.97 (2H, s) 7.26 (1H), 7.51 (1H, dd, J =8.3 and 1.8Hz), 7.90 (1H, d, J=8.3Hz), 8.03 (1H)

h) 4.0 g of 2-hydroxymethylbenzo[b]thiophene-5-carbonitrile obtained in the above step g) was dissolved in 100 ml of diethyl ether, followed by the addition of 0.1 ml of pyridine. A 5 ml diethyl ether solution of 5.5 g of thionyl chloride was added to the above solution under ice cooling and stirring, and the resulting mixture was stirred at room temperature for 2 hours. The resulting reaction solution was poured into ice water and extracted with benzene. The resulting organic layer was washed with saturated sodium bicarbonate aqueous solution and concentrated to dryness. The residue thus obtained was dissolved in 100 ml of xylene, and the solution was mixed with 7.2 g of triphenylphosphine, and refluxed under heating for 10 hours. Thereafter, the thus precipitated crystals were collected by filtration to obtain 6.3 g of the title compound.
mp: 271°–274° C. (decomposition)
$^1$H-NMR (CDCl$_3$) δ:6.70 (2H, d, J=15.1Hz), 7.30–8.10 (19H, m)

REFERENCE EXAMPLE 5

Preparation of (7-cyano-2-naphthyl)methyltriphenylphosphonium bromide a) 11.0 g of 7-methyl-2-naphthalenecarboxylic acid obtained in accordance with the procedure disclosed in *Australian Journal of Chemistry* (vol.18, pp. 1351–1364, 1965) was mixed with 70 ml of thionyl chloride and refluxed under heating for 4 hours. The resulting reaction solution was concentrated to dryness. To the residue thus obtained was added 300 ml of concentrated aqueous ammonia under cooling. The mixture was stirred at room temperature for 3 hours, and then extracted with ethyl acetate. The resulting organic layer was washed with water and then with saturated sodium chloride aqueous solution, followed by drying and removing the solvent. In this way, 8.5 g of 7-methyl-2-naphthalenecarboxamide was obtained in the form of colorless needle crystals.
mp: 210° to 212° C.
$^1$H-NMR (DMSO-d$_6$) δ: 2.50 (3H, s), 7.4–8.5 (6H, m)

b) 8.0 g of 7-methyl-2-naphthalenecarboxamide obtained in the above step a) was suspended in 100 ml of tetrahydrofuran, to which was further added, at room temperature, a 100 ml carbon tetrachloride solution containing 22.66 g of triphenylphosphine. The resulting mixture was stirred at room temperature for 30 minutes and then at 60° C. for 40 hours. After cooling to room temperature, insoluble materials were removed by filtration, and the resulting filtrate was concentrated under a reduced pressure. 28.35 g of the resulting residue was applied to silica gel column chromatography, and eluted with a mixed solvent system of n-hexane and ethyl acetate, thereby obtaining 5.73 g of 7-methyl-2-naphthalenecarbonitrile in the form of colorless crystals. mp: 134°–136° C.

$^1$H-NMR (CDCl$_3$) δ:2.54 (3H, s)i, 7.4–8.2 (6H, m)

c) 5.7 g of 7-methyl-2-naphthalenecarbonitrile obtained in the above step b) was suspended in 100 ml of carbon tetrachloride. To this were added 6.37 g of N-bromosuccinimide and 30 mg of 2,2-azobis-iso-butylonitrile. After refluxing under heating for 2 hours, the resulting reaction solution was diluted with dichloromethane, washed with water and then with saturated sodium chloride aqueous solution, followed by drying. By distilling off the solvent, 8.34 g of 7-bromomethyl-2-naphthalenecarbonitrile was obtained in the form of light yellow needle crystals. mp: 110°–116° C.

$^1$H-NMR (CDCl$_3$) δ:4.65 (2H, s), 7.55–8.28 (6H, m)

d) 8.34 g of 7-bromomethyl-2-naphthalenecarbonitrile obtained in the above step c) was dissolved in 200 ml of xylene, the solution was mixed with 11.6 g of triphenylphosphine and the mixture was refluxed under heating for 16 hours. Diethyl ether was added to the resulting reaction solution, and crystals thus precipitated were collected by filtration and dried, thereby obtaining 12.10 g of the title compound.

$^1$H-NMR (CDCl$_3$) δ:5.96 (2H, d, J=15.3Hz), 7.1–8.0 (21H, m)

REFERENCE EXAMPLE 6

Preparation of (6-cyano-1-methyl-2-indolyl)methyltriphenylphosphonium bromide a) 1.5 g of methyl 6-cyano-2-indolecarboxylate obtained in accordance with the procedure disclosed in *Liebigs Annalen der Chemie* (1986, pp. 438–455) was dissolved in 20 ml of N,N-dimethylformamide. 320 mg of 60% sodium hydride was added to the above solution under ice cooling and stirring, and the resulting mixture was stirred at room temperature for 10 minutes. To this was further added 0.47 ml of methyl iodide, followed by stirring at room temperature for 2 hours. Saturated ammonium chloride aqueous solution was added to the resulting reaction solution, and crystals thus precipitated were collected by filtration, and washed with methanol. The thus washed crystals were recrystallized from a mixture of dichloromethane and methanol to obtain 1.4 g of methyl 6-cyano-1-methyl-2-indolecarboxylate.

$^1$H-NMR (DMSO-d$_6$) δ:3.92 (3H, s), 4.10 (3H, s), 7.42 (1H, s), 7.52 (1H, dd), 7.98 (1H, d), 8.38 (1H, br)

b) 5.7 g of methyl 6-cyano-1-methyl-2-indolecarboxylate obtained in the above step a) was dissolved in 120 ml of tetrahydrofuran. With cooling on an ice bath and with stirring, a catalytically effective amount of sodium bicarbonate, 5.6 g of calcium iodide and 1.8 g of sodium borohydride were added to the above solution, and the mixture was stirred for 5 hours. The resulting reaction solution was mixed with ice water and acetic acid, tetrahydrofuran was distilled off from the mixture, and the thus treated reaction solution was extracted with ethyl acetate, followed by drying. After distilling off the solvent, the residue thus obtained was dissolved in 50 ml of dichloromethane. 10 ml dichloromethane solution containing 1 ml of phosphorus tribromide was added dropwise to the above reaction solution under ice cooling and stirring, and the resulting mixture was stirred at the same temperature for 2 hours and then at room temperature for 2 hours. The thus treated reaction solution was mixed with ice water, washed with sodium carbonate aqueous solution, and then dried. The resulting organic layer was concentrated by a factor of about 2 under a reduced pressure, mixed with 15 g of triphenylphosphine, and then refluxed under heating for 12 hours. Thereafter, the precipitate thus formed was collected by filtration to obtain 10.5 g of the title compound.

$^1$H-NMR (DMSO-d$_6$) δ:3.33 (3H, s), 5.55 (2H, d), 6.26 (1H, s), 7.20–8.10 (18H, m)

The following compounds of Reference Examples 7 and 8 were prepared in a manner similar to the procedure of Reference Example 6.

REFERENCE EXAMPLE 7

(6-cyano-1-ethyl-2-indolyl)methyltriphenylphosphonium bromide $^1$H-NMR (DMSO-d$_6$) δ: 1.01 (3H, t), 3.83 (2H), 5.57 (2H, d), 6.26 (1H, s), 7.39 (1H, d), 7.59 (1H, d), 7.70–8.00 (16H, m)

REFERENCE EXAMPLE 8

[1-(2-chloroethyl)-6-cyano-2-indolyl]methyltriphenylphosphonium bromide $^1$H-NMR (DMSO-d$_6$) δ:3.40–3.80 (2H), 4.30–4.60 (2H), 5.60 (2H, d), 6.25 (1H, s), 7.10–8.00 (18H, m)

REFERENCE EXAMPLE 9

Preparation of 2-bromomethyl-5-benzothiazolecarbonitrile a) 28.0 g of 5-bromo-2-methylbenzothiazole was dissolved in 200 ml of N-methyl-2-pyrrolidone, the solution thus prepared was mixed with 13.8 g of cuprous cyanide and a catalytically effective amount of copper sulfate, and the mixture was stirred for 4 hours with heating at a temperature of 180° to 190° C. in a stream of nitrogen. The resulting reaction solution was poured into water, and insoluble materials thus formed were collected by filtration. The thus collected insoluble materials were mixed with a mixture consisting of 22 ml of methylenediamine and 50 ml of water, and the resulting mixture was stirred thoroughly. After extraction with benzene, the resulting organic layer was washed with water, and dried to distill of benzene. Thereafter, the residue thus formed was washed with ethanol to obtain 10.22 g of 2-methyl-5-benzothiazolecarbonitrile in the form of light brown crystals. mp: 158°–160° C.

$^1$H-NMR (CDCl$_3$) δ:2.90 (3H, s), 7.60 (1H, dd), 7.95 (1H, d), 8.25 (1H, d)

b) 7.46 g of 2-methyl-5-benzothiazolecarbonitrile obtained in the above step a) was dissolved in 250 ml of carbon tetrachloride, and the solution was subjected to reflux under a light irradiation condition. To the resulting reaction solution was gradually added a mixture consisting of 7.62 g of N-bromosuccinimide and 150 mg of 2,2-azobis-iso-butylonitrile, followed by refluxing under heating for 20 hours. After cooling, insoluble materials were removed by filtration, and the solvent was distilled off. Thereafter, the residue thus formed was purified by silica gel column chromatography using toluene as an elution solvent, thereby obtaining 2.18 g of the title compound in the form of light yellow prism crystals.

mp: 185°–186° C.

$^1$H-NMR (CDCl$_3$) δ:4.83 (2H, s), 7.67 (1H, dd), 8.02 (1H, d), 8.34 (1H, d)

REFERENCE EXAMPLE 10

Preparation of (6-cyano-1,2,3,4-tetrahydro-2-naphthyl)-methyltriphenylphosphonium p-toluene sulfonate a) 10.0 g of methyl 6-hydroxymethyl-5,6,7,8-tetrahydro-2-naphthalenecarboxylate was added to 3.82 g of 2,3-dihydropyrane. After further adding 5 drops of concentrated sulfuric acid, the resulting mixture was stirred for 1 hour. To this were further added 1.00 g of 2,3-dihydropyrane and 3 drops of concentrated sulfuric acid, followed by stirring for 5 hours. The resulting reaction mixture was mixed with 100 ml of diethyl ether, and the mixture was washed with saturated sodium bicarbonate aqueous solution, water and saturated sodium chloride aqueous solution in that order, followed by drying. By distilling off the solvent, 13.72 g of methyl 6-[(2-tetrahydropyranyl)oxymethyl]-5,6,7,8-tetrahydro-2-naphthalenecarboxylate was obtained in the form of yellow oil.

$^1$H-NMR (CDCl$_3$) δ: 1.50–3.00 (13H, m), 3.30–4.10 (4H, m), 3.86 (3H, s), 4.60 (1H, br), 7.10 (1H, d), 7.80–7.90 (2H, m)

b) 13.72 g of methyl 6-[(2-tetrahydropyranyl)oxymethyl]-5,6,7,8-tetrahydro-2-naphthalenecarboxylate obtained in the above step a) was dissolved in 180 ml of methanol. After further adding a solution containing 2.96 g of sodium hydroxide in 60 ml of water, the resulting mixture was refluxed under heating for 3 hours. After cooling, the resulting reaction solution was concentrated under reduced pressure, mixed with chloroform and water, and then neutralized with acetic acid. The resulting organic layer was washed with water and then with saturated sodium chloride aqueous solution, followed by drying. After distilling off the solvent, the resulting residue was crystallized in isopropyl ether to obtain 10.51 g of 6-[(2-tetrahydropyranyl)oxymethyl]-5,6,7,8-tetrahydro-2-naphthalenecarboxylic acid.

$^1$H-NMR (CDCl$_3$) δ:1.50–3.00 (13H, m), 3.30–4.00 (4H, m), 4.60 (1H, br), 7.16 (1H, d), 7.80–7.90 (2H, m)

c) 12.0 g of 6-[(2-tetrahydropyranyl)oxymethyl]-5,6,7,8-tetrahydro-2-naphthalenecarboxylic acid obtained in the above step b) and 4.1 g of triethylamine were dissolved in 100 ml of tetrahydrofuran, and the resulting solution was cooled down to −15° C. To this was added, with stirring, 5.64 g of chloroformic isobutyl ester. The resulting reaction solution was stirred for 20 minutes at the same temperature and then poured in 200 ml of ice-cold ethanol containing 14% (w/v) of ammonia. After removing insoluble materials by filtration, the resulting filtrate was dried under a reduced pressure. The residue thus obtained was purified by silica gel column chromatography using a mixed solvent system consisting of n-hexane and ethyl acetate as an elution solvent, and the purified product was crystallized in isopropyl ether to obtain 7.20 g of 6-[(2-tetrahydropyranyl)oxymethyl]-5,6,7,8-tetrahydro-2-naphthalenecarboxamide.

$^1$H-NMR (CDCl$_3$) δ:1.40–3.00 (13H, m), 3.30–4.00 (4H, m), 4.60 (1H, br), 6.10 (2H, br), 7.20 (1H, d), 7.50–7.70 (2H, m)

d) 15 0 g of 6-[(2-tetrahydropyranyl)oxymethyl]-5,6,7,8-tetrahydro-2-naphthalenecarboxamide obtained in the above step c) was suspended in 60 ml of dioxane. After adding 8.35 ml of pyridine, the resulting suspension was cooled down to −8° C. to 0° C.

Then, 7.89 ml of anhydrous trifluoroacetate was added dropwise thereto under stirring. The resulting reaction solution was stirred at −5° C. for 30 minutes and then at room temperature for 2 hours. The thus treated reaction solution was diluted with chloroform, and then washed with water and saturated sodium chloride aqueous solution in that order. Thereafter, the resulting organic layer was dried and the solvent was distilled off to obtain 9.78 g of 6-[(2-tetrahydropyranyl)oxymethyl]-5,6,7,8-tetrahydro-2-naphthalenecarbonitrile in the form of oil.

$^1$H-NMR (CDCl$_3$) δ:1.50–3.00 (13H, m), 3.30–4.00 (4H, m), 4.61 (1H, br), 7.05–7.50 (3H, m)

e) 9.78 g of 6-[(2-tetrahydropyranyl)oxymethyl]-5,6,7,8-tetrahydro-2-naphthalenecarbonitrile was dissolved in 100 ml of ethanol. After adding 100 mg of p-toluenesulfonic acid, the resulting mixture was stirred at room temperature for 15 hours. The resulting reaction solution was neutralized with saturated sodium bicarbonate aqueous solution, followed by the removal of the solvent by distillation. The residue thus obtained was dissolved in chloroform, and the solution was washed with water and then with saturated sodium chloride aqueous solution. The resulting organic layer was dried and the solvent was distilled off. Thereafter, 5.26 g of 6-hydroxymethyl-5,6,7,8-tetrahydro-2-naphthalenecarbonitrile was crystallized from isopropanol in the form of colorless crystals.

mp: 83°–85° C.

$^1$H-NMR (CDCl$_3$) δ:1.30–3.00 (7H, m), 3.64 (2H, d, J=6.0Hz), 7.05–7.50 (3H, m)

f) 15.0 g of 6-hydroxymethyl-5,6,7,8-tetrahydro-2-naphthalenecarbonitrile obtained in the above step e) and 30.5 g of p-toluenesulfonyl chloride were dissolved in 150 ml of pyridine, and the solution was stirred at room temperature for 15 hours. The resulting reaction solution was poured into ice water, and the thus precipitated crystals were collected by filtration, washed with water and isopropanol in that order, and then dried. In this way, 24.72 g of colorless 5,6,7,8-tetrahydro-6-[(p-toluenesulfonyl)oxymethyl]-2-naphthalenecarbonitrile was obtained.

mp: 100°–102° C.

$^1$H-NMR (CDCl$_3$) δ:1.20–3.80 (7H, m), 2.47 (3H, s), 4.00 (2H, d, J=6.0Hz), 7.10 (1H, d, J=9.0Hz), 7.30–7.50 (4H, m), 7.80 (2H, d)

g) 24.00 g of 5,6,7,8-tetrahydro-6-[(p-toluenesulfonyl)oxymethyl]-2-naphthalenecarbonitrile and 18.38 g of triphenylphosphine were mixed, and then heated at a temperature of 130° to 140° C. for 15 hours in a sealed container. The resulting reaction product was crystallized from an acetone/n-hexane mixture to obtain 23.3 g of the title compound in the form of light yellow powder.

$^1$H-NMR (CDCl$_3$) δ:1.40–2.90 (7H, m), 2.27 (3H, s), 3.60–3.90 (2H, m), 6.80–7.30 (5H, m), 7.40–8.00 (17H, m)

REFERENCE EXAMPLE 11

Preparation of (6-cyano-2-naphthyl)methyltriphenylphosphonium bromide a) 6.11 g of 6-methyl-2-naphthalenecarbonitrile was dissolved in 100 ml of carbon tetrachloride, and the solution was mixed with 6.63 g of N-bromosuccinimide and 30 mg of 2,2-azobis-iso-butylonitrile. After refluxing under heating for 4 hours, the resulting reaction solution was mixed with chloroform, washed with water, and then dried. By distilling off the solvent, 7.07 g of colorless 6-bromomethyl-2-naphthalenecarbonitrile was obtained.
mp: 134°–137° C.
$^1$H-NMR (CDCl$_3$) δ: 4.65 (2H, s), 7.60–7.80 (2H, m), 7.80–8.00 (3H, m), 8.22 (1H, s)

b) 2.0 g of 6-bromomethyl-2-naphthalenecarbonitrile obtained in the above step a) and 2.77 g of triphenylphosphine were dissolved in 50 ml of xylene. After refluxing under heating for 18 hours, precipitated crystals were collected by filtration to obtain 3.31 g of the title compound.
mp: >270° C.
$^1$H-NMR (CDCl$_3$) δ: 5.93 (2H, d, J=15.2Hz), 7.40–8.00 (21H, m)

REFERENCE EXAMPLE 12

Preparation of (S)-(+)-3-hydroxytetrahydrofuran 0.23 g of p-toluenesulfonic acid was added to 25 g of (S)-(–)-1,2,4-butanetriol, and the mixture was stirred at 100° C. for 5 minutes and then at 180° to 200° C. for 10 minutes. The resulting reaction mixture was subjected to distillation to collect a fraction of 95°–100° C./30 mmHg, thereby obtaining 16.2 g of the title compound as an oily material.
$^1$H-NMR (CDCl$_3$) δ:1.80–2.20 (2H, m), 3.76 (2H, d), 3.70–4.10 (2H, m), 4.40–4.60 (1H, m)

REFERENCE EXAMPLE 13

Preparation of ethyl 2-[4-[[((3S)-1-tert-butoxycarbonyl-3-pyrrolidinyl)oxy]phenyl]-2-oxoacetate To 40 ml of tetrahydrofuran were dissolved 1.8 g of ethyl 2-(4-hydroxyphenyl)-2-oxoacetate, 1.74 g of (3R)-1-tert-butoxycarbonyl-3-hydroxypyrrolidine and 2.92 g of triphenylphosphine. At room temperature, 1.94 g of diethyl azodicarboxylate was added to the above solution, and the resulting mixture was stirred for 18 hours. After distilling off the solvent, the residue thus obtained was dissolved in ethyl acetate, and the solution was washed with water, and then dried. Thereafter, the solvent was distilled-off, and the resulting residue was purified by silica gel column chromatography using a toluene/chloroform mixture as an eluant, thereby obtaining 2.53 g of the title compound as a viscous yellow oil.
$^1$H-NMR (CDCl$_3$) δ:1.41 (3H, t, J=7.0Hz), 1.46 (9H, s), 2.00–2.40 (2H, m), 3.00–3.75 (4H, m), 4.43 (2H, q, J=7.0Hz), 5.00 (1H, br), 6.93 (2H, d, J=9.0Hz), 8.00 (2H, d, J=9.0Hz)

The following compounds of Reference Examples 14 to 25 were prepared in the same manner as described in Reference Example 13.

REFERENCE EXAMPLE 14 methyl 2-4-[((3S)-1-tert-butoxycarbonyl-3-pyrrolidinyl)oxy]phenyl]-2-oxoacetate
viscous yellow oil

REFERENCE EXAMPLE 15 ethyl 2-[4-[((3R)-1-tert-butoxycarbonyl-3-pyrrolidinyl)oxy]phenyl]-2-oxoacetate
viscous yellow oil
$^1$H-NMR (CDCl$_3$) δ: 1.40 (3H, t, J=7.0Hz), 1.46 (9H, s), 2.00–2.35 (2H, m), 3.45–3.75 (4H, m), 4.40 (2H, q, J=7.0Hz), 4.9–5.1 (1H, br), 6.95 (2H, d, J=9.0Hz), 8.00 (2H, d, J=9.0Hz)

REFERENCE EXAMPLE 16 ethyl 2-[4-[((2S)-1-tert-butoxycarbonyl-2-pyrrolidinyl)methoxy]phenyl]-2-oxoacetate
viscous yellow oil
$^1$H-NMR (CDCl$_3$) δ:1.41 (3H, t), 1.47 (9H, s), 2.0 (4H, br), 3.37 (2H, br), 4.20 (3H, br), 4.43 (2H, q), 7.0 (2H, d), 7.95 (2H, d)

REFERENCE EXAMPLE 17 ethyl 2-[4-[((2S,4S)-1-tert-butoxycarbonyl-2-carbamoyl-4-pyrrolidinyl)oxy]phenyl]-2-oxoacetate
viscous yellow oil
$^1$H-NMR (CDCl$_3$) δ:1.42 (3H, t, J=7.0Hz), 1.48 (9H, s), 2.20–2.90 (2H, br), 3.64–3.90 (2H, br), 4.30–4.60 (1H, br), 4.42 (2H, q, J=7.0Hz), 5.06 (1H, br), 6.97 (2H, d, J=9.0Hz), 8.07 (2H, d, J=9.0Hz)

REFERENCE EXAMPLE 18 ethyl 2-[4-[((2S, 4S)-1-tert-butoxycarbonyl-2-dimethyl-carbamoyl-4-pyrrolidinyl)oxy]phenyl]-2-oxoacetate
viscous yellow oil
$^1$H-NMR (CDCl$_3$) δ: 1.37–1.50 (12H, m), 1.96–2.30 (1H, m), 2.50–2.82 (1H, m), 2.90–3.15 (6H, br), 3.70 (1H, dd, J=10.8 and 5.1Hz), 3.90–4.16 (1H, m), 4.46 (2H, q, J=7.0Hz), 4.60–5.14 (2H, m), 7.00 (2H, d, J=9.4Hz), 8.08 (2H, d, J=9.4Hz)

REFERENCE EXAMPLE 19 ethyl 2-[4-[2-(tert-butoxycarbonylamino)-1-(tert-butoxycarbonylaminomethyl)ethoxy]phenyl]-2-oxoacetate
viscous yellow oil
$^1$H-NMR (CDCl$_3$) δ: 1.00–1.70 (21H, br), 2.80–3.80 (4H, m), 4.20–4.60 (3H, m), 7.10 (2H, d, J=8.3Hz), 7.98 (2H, d, J =8.3Hz)

REFERENCE EXAMPLE 20 ethyl 2-[4-[(1-tert-butoxycarbonyl-4-piperidinyl)oxy]phenyl]-2-oxoacetate
viscous yellow oil
$^1$H-NMR (CDCl$_3$) δ: 1.35 (3H, t, J=6Hz), 1.49 (9H, s), 1.8–2.0 (4H, m), 3.2–4.0 (4H, m), 4.46 (2H, q, J=6Hz), 4.6–4.8 (1H, m), 7.01 (2H, d, J=9Hz), 8.04 (2H, d, J=9Hz)

REFERENCE EXAMPLE 21 ethyl 2-[4-(2-tert-butoxycarbonylaminoethoxy)phenyl]-2-oxoacetate
viscous yellow oil
$^1$H-NMR (CDCl$_3$) δ:1.42 (3H, t, J=7.0Hz), 1.46 (9H, s), 3.56 (2H, q, J=5.4Hz), 4.12 (2H, quintet, J=5.4Hz), 4.44 (2H, q, J=7.0Hz), 5.04 (1H, br), 6.98 (2H, d, J=9.0Hz), 8.00 (2H, d, J=9.0Hz)

REFERENCE EXAMPLE 22 ethyl 2-[4-[(1-tert-butoxycarbonyl-4-piperidinyl)methoxy]phenyl]-2-oxoacetate viscous yellow oil $^1$H-NMR (CDCl$_3$) δ: 1.2–1.3 (2H, m), 1.42 (3H, t, J=7.1Hz), 1.47 (9H, s), 1.65–1.80 (2H, m), 3.89 (2H, d), 4.10–4.25 (2H, m), 4.43 (2H, q, J=7.1Hz), 6.95 (2H, d, J=8.8Hz), 7.99 (2H, d, J=8.8Hz)

REFERENCE EXAMPLE 23 ethyl 2-[4-[((2S)-1-tert-butoxycarbonyl-5-oxo-2-pyrrolidinyl)methoxy]phenyl]-2-oxoacetate viscous yellow oil $^1$H-NMR (CDCl$_3$) δ: 1.35 (3H, t), 1.41 (9H), 1.80–2.20 (2H, m), 2.47 (2H, t), 4.05 (2H, br), 4.41 (2H, q), 4.70–5.00 (1H, m), 6.98 (2H, d), 8.00 (2H, d)

REFERENCE EXAMPLE 24 ethyl 2-[4-[((2R,4S)-1-tert-butoxycarbonyl-2-methyl-4-pyrrolidinyl)oxy]phenyl]-2-oxoacetate viscous yellow oil $^1$H-NMR (CDCl$_3$) δ:1.20–1.42 (6H, m), 1.47 (9H, s), 2.20–2.60 (1H, m), 3.50–3.80 (2H, m), 3.90–4.22 (1H, m), 4.42 (2H, q), 4.90–5.10 (1H, m), 6.95 (2H, d), 8.00 (2H, d)

REFERENCE EXAMPLE 25 methyl 2-oxo-2-[4-[((3)-tetrahydro-3-furanyl)oxy]phenyl]acetate

Viscous yellow oil

REFERENCE EXAMPLE 26 ethyl 2-[4-[((3S)-1-tert-butoxycarbonyl-3-pyrrolidinyl)oxy]phenyl]-2-ethoxycarbonylacetate a) 27.7 g of ethyl 4-methoxyphenylacetate and 34 ml of diethyl carbonate were dissolved in 150 ml of N,N-dimethylformamide, and the solution was subjected to reflux under heating, while gradually adding 6.5 g of sodium hydride for 1 hour. After further refluxing under heating for 2 hours, the resulting reaction solution was poured into a mixture of ice water and hydrochloric acid, followed by extraction with ethyl acetate. The resulting organic layer was washed with water, and then dried to distill off the solvent. The residue thus obtained was purified by silica gel column chromatography using toluene as an eluant, thereby obtaining 26.7 g of ethyl 2-ethoxycarbonyl-2-(4-methoxyphenyl)acetate in the form of light yellow oil.

$^1$H-NMR (CDCl$_3$) δ: 1.25 (6H, t, J=7.0Hz), 3.79 (3H, s), 4.20 (4H, q, J=7.0Hz), 4.55 (1H, s), 6.88 (2H, d, J=8.0Hz), 7.32 (2H, d, J=8.0Hz)

b) 5.8 g of ethyl 2-ethoxycarbonyl-2-(4-methoxyphenyl)acetate obtained in the above step a) was dissolved in 70 ml of dichloromethane, and the solution was cooled down to −40° C. With stirring, to this was added dropwise 6.2 ml of boron tribromide dissolved in 5 ml of dichloromethane. After completion of the dropwise addition, the solution was warmed up to room temperature, and stirred for 30 minutes. The resulting reaction solution was poured into a mixture of ice water and hydrochloric acid, followed by extraction with chloroform. The resulting organic layer was dried to distill off the solvent, and the residue thus obtained was purified by silica gel column chromatography using chloroform as an eluant, thereby obtaining 4.7 g of ethyl 2-ethoxycarbonyl-2-(4-hydroxyphenyl)acetate in the form of colorless oil.

$^1$H-NMR (CDCl$_3$) δ:1.27 (6H, t, J=7.0Hz), 4.22 (4H, q, J=7.0Hz), 4.55 (1H, s), 5.66 (1H, br), 6.76 (2H, d, J=8.0Hz), 7.25 (2H, d, J=8.0Hz)

c) In 150 ml of tetrahydrofuran were dissolved 4.7 g of ethyl 2-ethoxycarbonyl-2-(4-hydroxyphenyl)acetate obtained in the above step b), 6.58 g of triphenylphosphine and 4.7 g of (3R)-1-tert-butoxycarbonyl-3-hydroxypyrrolidine. With stirring, 4.37 g of diethyl azodicarboxylate was added to the thus prepared solution, and the stirring was continued for 18 hours. After distilling-off the solvent, the resulting residue was purified by silica gel column chromatography using a toluene/ethyl acetate mixture as an eluant, thereby obtaining 4.0 g of the title compound in the form of colorless oil.

$^1$H-NMR (CDCl$_3$) δ:1.25 (6H, t, J=7.0Hz), 1.46 (9H, s), 2.1 (2H, br), 3.55 (4H, br), 4.20 (4H, q, J=7.0Hz), 4.52 (1H, s), 4.82 (1H, br), 6.82 (2H, d, J=8.0Hz), 7.28 (2H, d, J =8.0Hz)

REFERENCE EXAMPLE 27 ethyl 2-[4-[((2R)-1-tert-butoxycarbonyl-2-pyrrolidinyl)methoxy]phenyl]-2-ethoxycarbonylacetate This compound was prepared in accordance with the procedure described in Reference Example 26.

viscous oil $^1$H-NMR (CDCl$_3$) δ:1.25 (6H, t, J=7.0Hz), 1.47 (9H, s), 2.0 (4H, br), 3.40 (2H, br), 3.9 (1H), 4.20 (6H), 4.54 (1H, s), 6.82 (2H, d, J=8.0Hz), 7.28 (2H, d, J=8.0Hz)

REFERENCE EXAMPLE 28 ethyl 2-ethoxycarbonyl-2-[4-[(2-imidazolin-2-yl)methoxy]phenyl]acetate a) To 150 ml of acetone were added 14.58 g of ethyl 2-ethoxycarbonyl-2-(4-hydroxyphenyl)acetate, 8.8 g of bromoacetonitrile and 9.6 g of anhydrous potassium carbonate. After refluxing under heating for 5 hours, insoluble materials were removed by filtration, and the resulting filtrate was concentrated to dryness. The residue thus obtained was purified by silica gel column chromatography using toluene as an elution solvent, thereby obtaining 14.2 g of ethyl 2-[4-(cyanomethoxy)phenyl]-2-ethoxycarbonylacetate in the form of colorless oil.

$^1$H-NMR (CDCl$_3$) δ:1.26 (6H, t, J=8.0Hz), 4.22 (4H, q, J=8.0Hz), 4.58 (1H, s), 4.75 (2H, s), 7.02 (2H, d, J=9.0Hz), 7.36 (2H, d, J=9.0Hz)

b) 14.2 g of ethyl 2-[4-(cyanomethoxy)phenyl]-2-ethoxycarbonylacetate obtained in the above step a) was dissolved in a mixture consisting of 20 ml of ethanol and 150 ml of diethyl ether. The resulting solution was stirred at room temperature for 18 hours with ice cooling in a blowing stream of hydrogen chloride. By distilling-off the solvent, 16.9 g of ethyl 2-ethoxycarbonyl-2-[4-(2-ethoxy-2-iminoethoxy)phenyl]acetate hydrochloride in a solid form.

c) With ice cooling and stirring, 40 ml of ethanol solution containing 3.6 g of ethyl 2-ethoxycarbonyl-2-[4-(2-ethoxy-2-iminoethoxy]phenyl]acetate obtained in the above step b) was added dropwise to a 10 ml ethanol solution containing 0.6 g of ethylenediamine, and the resulting mixture was stirred at room temperature for 1.5 hours, followed by refluxing under heating for 0.5 hours. After cooling, the resulting reaction solution was adjusted to an acidic pH with ethanol containing 13% (w/v) of hydrochloric acid, and then concentrated to dryness. The residue thus obtained was dissolved in water and washed with diethyl ether. Thereafter, the resulting water layer was adjusted to pH 9–10 with dilute sodium hydroxide aqueous solution, and crystals thus precipitated were collected by filtration. In this way, 1.83 g of the title compound was obtained in the form of colorless crystals.

mp: 72–110° C. (gradual wetting)
FAB MS (m/z): 335 (M$^+$+1)
$^1$H-NMR (CDCl$_3$) δ: 1.23 (6H, t, J=8.0Hz), 3.62 (4H, s), 4.10 (4H, q, J=8.0Hz), 4.52 (1H, s), 4.68 (2H, s), 6.94 (2H, d, J=10.0Hz), 7.26 (2H, d, J=10.0Hz)

REFERENCE EXAMPLE 29

Preparation of ethyl 2-[4-[((3S)-1-tert-butoxycarbonyl-3-pyrrolidinyl)oxy]phenyl]-3-(5-cyano-2-benzofuranyl)propionate a) 3.12 g of ethyl 2-[4-[((3S)-1-tert-butoxycarbonyl-3-pyrrolidinyl)oxy]phenyl]-2-oxoacetate was dissolved in 100 ml of tetrahydrofuran, followed by the addition of 4.65 g of (5-cyano-2-benzofuranyl)methyltriphenylphosphonium chloride. To the thus prepared solution was added 400 mg of 60% sodium hydride. With stirring, to the resulting mixture was added dropwise 3 ml of ethanol, followed by stirring at room temperature for 1 hour. The resulting reaction solution was neutralized with 10% citric acid solution, extracted with ethyl acetate, and then dried to distill off the solvent. Thereafter, the residue thus obtained was subjected to silica gel column chromatography using a toluene/ethyl acetate mixture as an elution solvent, thereby obtaining 3.1 g of ethyl 2-[4-[((3S)-1-tert-butoxycarbonyl-3-pyrrolidinyl)oxy] phenyl]-3-(5-cyano-2-benzofuranyl)acrylate in the form of viscous oil as a mixture of E and Z forms. A portion of the thus obtained compound was separated into E and Z forms.

E form (less polar):
$^1$H-NMR (CDCl$_3$) δ: 1.32 (3H, t, J=7.6Hz), 1.49 (9H, s), 1.70–2.40 (2H, m), 3.30–3.80 (4H, m), 4.30 (2H, q, J=7.6Hz), 4.92 (1H, br), 6.62 (1H, s), 6.94 (2H, d, J=9.0Hz), 7.24 (2H, d, J=9.0Hz), 7.38 (1H, d, J=8.6Hz), 7.56 (1H, d, J=8.6Hz), 7.74 (1H, s), 7.77 (1H, s)

Z form:
$^1$H-NMR (CDCl$_3$) δ: 1.10–1.60 (12H, m), 2.00–2.30 (2H, m), 3.30–3.80 (4H, m), 4.50 (2H, q, J=7.2Hz), 4.92 (1H, br), 6.76 (1H, s), 6.81 (1H, s), 6.88 (2H, d, J=8.75Hz), 7.88 (2H, d, J=8.75Hz), 7.31–7.60 (2H), 7.85 (1H, s)

b) 3.1 g of ethyl 2-[4-[((3S)-1-tert-butoxy-carbonyl-3-pyrrolidinyl)oxy]phenyl]-3-(5-cyano-2-benzofuranyl)acrylate obtained in the above step a) was dissolved in a mixed solvent system of 100 ml of tetrahydrofuran and 100 ml of ethanol. To this was added 700 mg of palladium oxide.1H$_2$O.barium sulfate which had been prepared in accordance with the procedure disclosed in *Angewandte Chemie,* vol.67, p.785, 1955. After catalytic hydrogenation under normal pressure for 6 hours, the catalyst was removed by filtration, and the resulting filtrate was concentrated. Thereafter, the thus obtained residue was subjected to silica gel column chromatography using a toluene/ethyl acetate mixture as an elution solvent, thereby obtaining 1.9 g of the title compound as a viscous oil.

$^1$-NMR (CDCl$_3$) δ: 1.00–1.40 (3H, m), 1.46 (9H, s), 2.00–2.30 (2H, m), 3.16 (1H, dd, J=14.4 and 7.2Hz), 3.40–3.80 (5H, m), 3.90–4.30 (3H, m), 4.94 (1H, br), 6.40 (1H, s), 6.80 (2H, d, J=8.7Hz), 7.25 (2H, d, J=8.7Hz), 7.46 (2H, s), 7.76 (1H, s)

REFERENCE EXAMPLE 30

Preparation of ethyl 2-[4-[((3S)-1-tert-butoxycarbonyl-3-pyrrolidinyl)oxy]phenyl]-3-(7-cyano-2-naphthyl)propionate a) 8.40 g of (7-cyano-2-naphthyl)methyltriphenylphosphoniumbromide and 5.0 g of ethyl 2-[4-[((3S)-1-tert-butoxycarbonyl-3-pyrrolidinyl)oxy]phenyl]-2-oxoacetate were suspended in a mixture of 100 ml of tetrahydrofuran and 100 ml of ethanol. With stirring, to the resulting suspension was added 2.51 g of 1,8-diazabicyclo[5.4.0]-7-undecene, followed by stirring for 3 hours at room temperature. After distilling off the solvent, the residue thus obtained was subjected to silica gel column chromatography using a n-hexane/ethyl acetate mixture as an elution solvent, thereby obtaining 6.06 g of ethyl 2-[4-[((3S)-1-tert-butoxycarbonyl-3-pyrrolidinyl)oxy]phenyl]-3-(7-cyano-2-naphthyl)acrylate as a mixture of E and Z forms. A portion of the thus obtained compound was separated into E and Z forms.

E form:
mp: 104°–106° C. (crystallization in ethanol)
$^1$H-NMR (CDCl$_3$) δ: 1.35 (3H, t, J=7.3Hz), 1.48 (9H, s), 2.05–2.30 (2H, m), 3.45–3.70 (4H, m), 4.31 (2H, q, J=7.3Hz), 4.92 (1H, br), 6.86 (2H, d, J=8.8 Hz), 7.16 (2H, d, J=8.8Hz), 7.20 (1H, dd, J=8.8 and 1.5 Hz), 7.56 (1H, dd, J=8.3 and 1.5Hz), 7.62 (1H, d, J=8.8 Hz), 7.73 (1H, s), 7.80 (1H, d, J=8.3Hz), 7.93 (1H, s), 8.07 (1H, s)

Z form:
$^1$H-NMR (CDCl$_3$) δ:1.19 (3H, t, J=7.3Hz), 1.48 (9H, s), 2.05–2.30 (2H, m), 3.45–3.70 (4H, m), 4.29 (2H, q, J=7.3Hz), 4.93 (1H, br), 6.90 (2H, d, J=8.8Hz), 7.09 (1H, s), 7.44 (2H, d), 7.60 (1H, dd, J=8.3 and 1.5Hz), 7.63 (1H, dd, J=8.8 and 1.5Hz), 7.85 (1H, d, J=8.8Hz), 7.88 (1H, s), 7.90 (1H, d, J=8.3Hz), 8.18 (1H, s)

b) 6.06 g of ethyl 2-[4-[((3S)-1-tert-butoxy-carbonyl-3-pyrrolidinyl)oxy]phenyl]-3-(7-cyano-2-naphthyl)acrylate obtained as a mixture of E and Z forms in the above step a) was dissolved in a mixed solvent system of 80 ml of tetrahydrofuran and 80 ml of ethanol. To this was added 2.0 g of palladium oxide.1H$_2$O.barium sulfate. After catalytic hydrogenation under normal pressure for 3.5 hours, the catalyst was removed by filtration, and the solvent was distilled off. Thereafter, the thus obtained residue was subjected to silica gel column chromatography using a n-hexane/ethyl acetate mixture as an elution solvent, thereby obtaining 6.24 g of the title compound in a partially solidified form.

$^1$H-NMR (CDCl$_3$) δ:1.11 (3H, t, J=7.3Hz), 1.47 (9H, s), 2.00–2.33 (2H, m), 3.18 (1H, dd, J=14.2 and 6.8Hz), 3.40–3.65 (5H, m), 3.88 (1H, t, J=7.5Hz), 4.06 (2H, q, J=7.3Hz), 4.85 (1H, br), 6.80 12H, d, J=8.8Hz), 7.24 (2H, d), 7.42 (1H, dd, J=8.8 and 1.5Hz), 7.54 (1H, dd, J=8.3 and 1.5Hz), 7.62 (1H, s), 7.77 (1H, d, J=8.8Hz), 7.85 (1H, d, J=8.3Hz), 8.13 (1H, s)

The following compounds of Reference Examples 31 to 39 were prepared in accordance with the procedure described in Reference Example 30.

REFERENCE EXAMPLE 31 ethyl 2-[4-[((3R)-1-tert-butoxycarbonyl-3-pyrrolidinyl)oxy]phenyl]-3-(7-cyano-2-naphthyl)propionate $^1$H-NMR (CDCl$_3$) δ:1.11 (3H, t, J=7.3Hz), 1.47 (9H, s), 2.00–2.35 (2H, m), 3.18 (1H, dd, J=14.2 and 6.8Hz), 3.40–3.70 (5H, m), 3.88 (1H, br), 4.06 (2H, q, J=7.3Hz), 4.85 (1H, br), 6.80 (2H, d, J=8.8Hz), 7.24 (2H), 7.42 (1H, dd, J=8.8 and 1.5Hz), 7.54 (1H, dd, J=8.3 and 1.5Hz), 7.62 (1H, s), 7.77 (1H, d, J=8.8Hz), 7.84 (1H, d, J=8.3Hz), 8.11 (1H, s)

REFERENCE EXAMPLE 32 ethyl 2-[4-[(1-tert-butoxycarbonyl-4-piperidinyl)oxy]phenyl]3-(7-cyano-2-naphthyl)propionate
$^1$H-NMR (CDCl$_3$) δ:1.11 (3H, t), 1.49 (9H, s), 1.70–2.00 (4H, m), 3.00–4.10 (9H, m), 4.45 (1H, br), 6.80–8.10 (10H, m)
FAB MS (m/z): 418 (M$^+$+1)

REFERENCE EXAMPLE 33 ethyl 2-[4[((2S,4S)-1-tert-butoxycarbonyl-2-carbamoyl-4-pyrrolidinyl)oxy]phenyl]-3-(5-cyano-2-benzofuranyl)propionate
viscous oil
$^1$H-NMR (CDCl$_3$) δ: 1.16 (3H, t, J=7.0Hz), 1.47 (9H, s), 2.10–2.80 (2H, br), 3.16 (1H, dd, J=14.4 and 7.2Hz), 3.40–4.50 (6H, m), 5.08 (1H, br), 5.80 (1H, br), 6.39 (1H, s), 6.76 (2H, d, J=8.35Hz), 7.26 (2H, d, J=8.35Hz), 7.50 (2H, s), 7.80 (1H)

REFERENCE EXAMPLE 34 ethyl 2-[4-[((2S,4S)-1-tert-butoxycarbonyl-2-dimethylcarbamoyl-4-pyrrolidinyl)oxy]phenyl]-3-(5-cyano-2-benzofuranyl)propionate
viscous oil
$^1$H-NMR (CDCl$_3$) δ:1.23 (3H, t), 1.44 (9H, s), 1.90–2.30 (1H, br), 2.40–2.80 (1H, br), 2.98 (1H, s), 3.10–4.23 (7H, m), 4.40–5.00 (2H, br), 6.38 (1H, s), 6.90 (2H, d, J=8.3Hz), 7.20 (2H, d, J=8.35Hz), 7.45 (2H, s), 7.76 (1H, s)

REFERENCE EXAMPLE 35 ethyl 2-[4-[((3S)-1-tert-butoxycarbonyl-3-pyrrolidinyl)oxy]phenyl]3-(5-cyano-3-methyl-2-benzofuranyl)propionate
viscous oil
$^1$H-NMR (CDCl$_3$) δ: 1.16 (3H, t), 1.47 (9H, s), 2.02 (3H, s), 2.1 (2H, br), 3.1 (1H, br), 3.6 (5H, br), 4.1 (3H, m), 4.85 (1H, br), 6.83 (2H, d), 7.15 (2H, d), 7.46 (2H), 7.7 (1H, s)

REFERENCE EXAMPLE 36 ethyl 2-[4-[((3S)-1-tert-butoxycarbonyl-3-pyrrolidinyl)oxy]phenyl]-3-(5-cyano-7-methoxy-2-benzofuranyl)propionate
viscous yellow oil
$^1$H-NMR (CDCl$_3$) δ:1.17 (3H, t, J=7Hz), 1.46 (9H, s), 2.00–2.30 (2H, m), 3.16 (1H, dd, J=14.5 and 7.4Hz), 3.40–3.76 (5H, m), 3.80–4.30 (3H, m), 4.02 (3H, s), 4.70–5.00 (1H, br), 6.37 (1H, s), 6.80 (2H, d, J=8.75Hz), 6.95 (1H, d, J=1.3Hz), 7.23 (2H, d, J=8.75Hz), 7.41 (1H, d, J=1.3Hz)

REFERENCE EXAMPLE 37 ethyl 2-[4-[((3S)-1-tert-butoxycarbonyl-3-pyrrolidinyl)oxy]phenyl]-3-(5-cyano-3-benzofuranyl)propionate
viscous oil
$^1$H-NMR (CDCl$_3$) δ:1.14 (3H, t), 1.45 (9H, s), 2.12 (2H, br), 2.90–4.00 (7H, m), 4.08 (2H, q), 4.84 (1H, br), 6.85 (2H, d), 7.2 (2H, d), 7.41 (1H, s), 7.50 (2H), 7.72 (1H)

REFERENCE EXAMPLE 38 ethyl 2-[4-[((3S)-1-tert-butoxycarbonyl-3-pyrrolidinyl)oxy]phenyl]-3-(6-cyano-2-naphthyl)propionate
$^1$H-NMR (CDCl$_3$) δ: 1.25 (3H, t, J=7.0Hz), 1.46 (9H, s), 2.00–2.20 (2H, m), 3.00–4.00 (7H, m), 4.08 (2H, q), 4.85 (1H, br), 6.80–8.20 (10H, m)

REFERENCE EXAMPLE 39 ethyl 2-[4-[(1-tert-butoxycarbonyl-4-piperidinyl)methoxy]phenyl]-3-(7-cyano-2-naphthyl)propionate
$^1$H-NMR (DMSO-d$_6$) δ:1.01 (3H, t, J=7.1Hz), 1.1–1.2 (2H, m), 1.39 (9H, s), 1.68–1.76 (2H, m), 2.65–2.75 (2H, m), 3.78 (2H, d), 3.9–4.1 (5H, m), 4.55–4.65 (1H, m), 6.85 (2H, d, J=8.3Hz), 7.25 (2H, d, J=8.3Hz), 7.55–7.65 (1H, m), 7.68–7.73 (1H, m), 7.82 (1H, s), 7.90–7.95 (1H, m), 8.03 (1H, d, J=8.8Hz), 8.44 (1H, s)

REFERENCE EXAMPLE 40

Preparation of ethyl (+)-2-[4-[((3S)-1-tert-butoxycarbonyl-3-pyrrolidinyl)oxy]phenyl]-3-(7-cyano-2-naphthyl)propionate and ethyl (−)-2-[4-[((3S)-1-tert-butoxycarbonyl-3-pyrrolidinyl)oxy]phenyl]-3-(7-cyano-2-naphthyl)propionate 2.0 g of ethyl 2-[4-[((3S)-1-tert-butoxycarbonyl-3-pyrrolidinyl)oxy]phenyl]-3-(7-cyano-2-naphthyl)propionate was dissolved in 10 ml of ethanol under warming. After cooling to room temperature, crystals thus precipitated were collected by filtration, and then recrystallized from ethanol twice to obtain 640 mg of ethyl (+)-2-[4-[((3S)-1-tert-butoxycarbonyl-3-pyrrolidinyl)oxy]phenyl]-3-(7-cyano-2-naphthyl)propionate.
mp: 132°–133.5° C.
$[α]_D^{24}$ =+117.4° (c=1.008, CHCl$_3$)
$^1$H-NMR (CDCl$_3$) δ:1.11 (3H, t, J=7.3Hz), 1.47 (9H, s), 2.00–2.30 (2H, m), 3.18 (1H, dd, J=14.2 and 6.8Hz), 3.40–3.70 (5H, m), 3.87 (1H, t, J=7.6Hz), 4.00–4.10 (2H, m), 4.85 (1H, br), 6.80 (2H, d, J=8.8Hz), 7.20–7.30 (2H, m), 7.42 (1H, d, J=8.3Hz), 7.55 (1H, .d, J=8.3Hz), 7.63 (1H, s), 7.77 (1H, d, J=8.3Hz), 7.85 (1H, d, J=8.3Hz), 8.12 (1H, s)
HPLC: Column; an amylose-based column for use in the separation of optical isomers (CHIRALPAK AD, 4.66 φ×250 mm, Daicel Chemical Industries, Ltd.)
Solvent; iso-propanol:n-hexane=15:85 (v/v)
Flow rate; 1 ml/min
Column temperature; 25° C.
Retention time; 31.37 minutes
The filtrate was concentrated to dryness and crystallized from a n-hexane/ethanol mixture. The crystals thus collected were recrystallized from the same mixed solvent system to obtain 80 mg of ethyl (−)-2-[4-[((3S)-1-tert-butoxycarbonyl-3-pyrrolidinyl)oxy]phenyl]-3-(7-cyano-2-naphthyl)propionate.
mp 82.5°–85.0° C.
$[α]_D^{24}$+−85.0° (c =0.53, CHCl$_3$)
$^1$H-NMR (CDCl$_3$) δ:1.11 (3H, t, J=7.3Hz), 1.47 (9H, s), 2.00–2.30 (2H, m), 3.18 (1H, dd, J=14.2 and 6.8Hz), 3.40–3.66 (5H, m), 3.87 (1H, t, J=7.6Hz), 4.00–4.10 (2H, m), 4.85 (1H, br), 6.80 (2H, d, J=8.8Hz), 7.20–7.30 (2H, m), 7.42 (1H, d, J=8.3Hz), 7.56 (1H, d, J=8.3Hz), 7.62 (1H, s), 7.77 (1H, d, J=8.3Hz), 7.85 (1H, d, J=8.3Hz), 8.12 (1H, s)

HPLC: Column; an amylose-based column for use in the separation of optical isomers (CHIRALPAK AD, 4.6φ× 250 mm, Daicel Chemical Industries, Ltd.)
Solvent; iso-propanol:n-hexane=15:85 (v/v)
Flow rate; 1 ml/min
Column temperature; 25° C.
Retention time; 23.22 minutes

REFERENCE EXAMPLE 41

Preparation of ethyl 3-(5-cyano-2-benzofuranyl)-2-[4-[(3S)-1-methyl-3-pyrrolidinyl)oxy]phenyl]propionate 1.8 g of ethyl 2-[4-[((3S)-1-tert-butoxycarbonyl-3-pyrrolidinyl)oxy]phenyl]-3-(5-cyano-2-benzofuranyl)propionate was dissolved in 28 ml of formic acid, and the solution was stirred at 70° C. for 1 hour. The resulting reaction solution was concentrated to dryness, and the residue thus obtained was dissolved in 8 ml of formic acid. 0.29 ml of 37% formaldehyde was added thereto, and then refluxed under heating for 4 hours. After cooling, the reaction solution was mixed with chloroform, and then adjusted to pH 10–11 with aqueous ammonia, and the resulting organic layer was collected and dried. Thereafter, the solvent was distilled off, and the resulting residue was purified by silica gel column chromatography using a chloroform/methanol mixture as an eluant. In this way, 1.07 g of the title compound was obtained in an oily form.
$^1$H-NMR (CDCl$_3$) δ:1.16 (3H, t, J=7.2Hz), 1.60–2.30 (2H, m), 2.38 (3H, s), 2.00–4.00 (7H, m), 4.11 (2H, q, J=7.2Hz), 4.60–4.90 (1H, br), 6.39 (1H, s), 6.78 (2H, d, J=8.8Hz), 7.21 (2H, d, J=8.8 Hz), 7.47 (2H, s), 7.77 (1H, s)

REFERENCE EXAMPLE 42

Preparation of ethyl 2-[4-[((3S)-1-acetyl-3-pyrrolidinyl)oxy]phenyl]-3-(5-cyano-2-benzofuranyl)propionate 2.3 g of ethyl 2-[4-[((3S)-1-tert-butoxycarbonyl-3-pyrrolidinyl)oxy]phenyl]-3-(5-cyano-2-benzofuranyl)propionate was dissolved in 3 ml of anisole, 25 ml of trifluoroacetic acid was added to the above solution with ice cooling, and the resulting mixture was stirred at room temperature for 1 hour. After distilling off trifluoroacetic acid under reduced pressure, the residue thus obtained was adjusted to pH 10–11 with saturated sodium bicarbonate aqueous solution, extracted with chloroform, and then dried. At room temperature, the resulting organic layer was mixed with 2 ml of triethylamine and then with 555 mg of acetyl chloride, followed by stirring at the same temperature for 0.5 hours. After distilling off the solvent, the resulting residue was subjected to silica gel column chromatography using a chloroform/ethanol mixture as an eluant to obtain 1.8 g of the title compound.
$^1$H-NMR (CDCl$_3$) δ:1.17 (3H, t, J=7.0Hz), 2.04 (1.5H) 2.08 (1.5H), 3.14 (1H, dd, J=15.1 and 3.6Hz), 3.40–4.30 (8H, m), 4.70–5.04 (1H, br), 6.40 (1H, s), 6.60–6.92 (2H, m), 7.10 (2H, m), 7.47 (2H, s), 7.77 (1H, s)

REFERENCE EXAMPLE 43

Preparation of ethyl 3-(5-cyano-2-benzofuranyl)-2-[4-[((3S)-1-dimethylcarbamoyl-3-pyrrolidinyl)oxy]phenyl]propionate 2.3 g of ethyl 2-[4-[((3S)-1-tert-butoxycarbonyl-3-pyrrolidinyl)oxy]phenyl]-3-(5-cyano-2-benzofuranyl)propionate was dissolved in 3 ml of anisole. 25 ml of trifluoroacetic acid was added to the above solution with ice cooling, and the resulting mixture was stirred at room temperature for 1 hour. After distilling off trifluoroacetic acid under reduced pressure, the residue thus obtained was adjusted to pH 10–11 with saturated sodium bicarbonate aqueous solution, extracted with chloroform, and then dried. At room temperature, the resulting organic layer was mixed with 2 ml of triethylamine and then with 760 mg of N,N-dimethylcarbamoyl chloride, followed by stirring at the same temperature for 1 hour. After distilling off the solvent, the resulting residue was subjected to silica gel column chromatography using a chloroform/ethanol mixture as an eluant to obtain 1.7 g of the title compound.
$^1$H-NMR (CDCl$_3$) δ: 1.17 (3H, t, J=7.0Hz), 1.9–2.20 (2H, m) 2.86 (6H, s), 3.14 (1H, dd, J=16.0 and 7.2Hz), 3.30–4.50 (8H, m), 4.72–4.96 (1H, br),6.41(1H, s), 6.83 (2H, d, J =8.7Hz), 7.25 (2H, d, J=8.7Hz), 7.49 (2H, s), 7.78 (1H, s)

REFERENCE EXAMPLE 44

Preparation of ethyl 2-(4-acetoxyphenyl)-2-oxoacetate 7.25 g of ethyl 2-(4-hydroxyphenyl)-2-oxoacetate was dissolved in 15 ml of pyridine, followed by adding 4 ml of acetic anhydride and then stirring at room temperature for 1 hour. The resulting reaction solution was poured into water, and extracted with diethyl ether. The resulting organic layer was washed with water, and then concentrated to dryness. Thereafter, the residue was dissolved in benzene, and then concentrated to obtain 8.3 g of the title compound in an oily form.
$^1$H-NMR (CDCl$_3$) δ: 1.41 (3H, t), 2.32 (3H, s), 4.43 (2H, q), 7.29 (2H, d), 8.01 (2H, d)

REFERENCE EXAMPLE 45

Preparation of ethyl 3-(5-cyano-2-benzofuranyl)-2-(4-hyroxyphenyl)propionate a) 15.93 g of (5-cyano-2-benzofuranyl)methyltriphenylphosphonium chloride and 8.29 g of ethyl 2-(4-acetoxyphenyl)-2-oxoacetate were dissolved in a mixture solution of 80 ml of tetrahydrofuran and 80 ml of ethanol. At room temperature, 5.34 g of 1,8-diazabicyclo[5.4.0]-7-undecene was added to the above solution, and the mixture was stirred for 18 hours at the same temperature. The resulting reaction solution was concentrated to dryness, and the residue was purified by silica gel column chromatography using a toluene/ethyl acetate mixture as an eluant to obtain 11.28 g of ethyl 2-(4-acetoxyphenyl)-3-(5-cyano-2-benzofuranyl)acrylate in the form of light yellow crystals as a mixture of E and Z forms.
$^1$H-NMR (CDCl$_3$) δ: 1.32 (3H, t), 2.36 (3H, s), 4.30 (2H, q), 6.30 (1H, s), 7.2–7.8 (8H, m)

b) 3.8 g of ethyl 2-(4-acetoxyphenyl)-3-(5-cyano-2-benzofuranyl)acrylate obtained in the above step a) was dissolved in an ethanol/tetrahydrofuran mixture solvent. The resulting solution was mixed with 750 mg of palladium oxide.1H$_2$O.barium sulfate and subjected to catalytic hydrogenation under normal pressure. After removing the catalyst by filtration, the resulting filtrate was concentrated to dryness to obtain 3.8 g of ethyl 2-(4-acetoxyphenyl)-3-(5-cyano-2-benzofuranyl)propionate.

¹H-NMR (CDCl₃) δ:1.16 (3H, t, J=7.2Hz), 2.25 (3H, s), 3.20 (1H, dd, J=16.2 and 7.0Hz), 3.40–4.30 (4H, m), 6.50 (1H, s), 7.10 (2H, d, J=8.3Hz), 7.40 (2H, d, J=8.3Hz), 7.56 (2H, s), 7.86 (1H, s)

c) 8.1 g of ethyl 2-(4-acetoxyphenyl)-3-(5-cyano-2-benzofuranyl)propionate obtained in the above step b) was dissolved in 100 ml of ethanol solution containing 15% of ammonia, and the resulting solution was allowed to stand still for 18 hours at room temperature. Thereafter, the resulting reaction solution was concentrated to dryness, and the residue was purified by silica gel column chromatography using chloroform as an eluant. In this way, 5.62 g of the title compound was obtained in the form of colorless crystals.

mp: 140°–142° C.
¹H-NMR (CDCl₃) δ:1.15 (3H, t), 3.0–4.0 (3H, m), 4.1 (2H, q), 4.98 (1H, s), 6.39 (1H, s), 6.76 (2H, d), 7.15 (2H, d), 7.45 (2H), 7.75 (1H)

REFERENCE EXAMPLE 46

Preparation of ethyl 3-(5-cyano-2-benzofuranyl)-3-(4-hydroxyphenyl)propionate a) To 150 ml of acetone were suspended 20 g of 5-bromosalicylaldehyde, 22.9 g of 2-bromo-4-methoxyacetophenone and 27.6 g of anhydrous potassium carbonate. After stirring at room temperature for 4 hours, the resulting reaction solution was concentrated to dryness, and then mixed with water to collect precipitated crystals by filtration. After washing with water and subsequent recrystallization from ethanol, 14.02 g of 5-bromo-2-(4-methoxybenzoyl)benzofuran was obtained in the form of colorless prism crystals.

mp: 143°–146° C.
IR (KBr): 1644, 1605, 1257 cm⁻¹
¹H-NMR (DMSO-d₆) δ:3.35 (3H, s), 7.15 (2H, d, J=9Hz), 7.72 (3H, m), 8.0–8.2 (3H)

b) 15.0 g of 5-bromo-2-(4-methoxybenzoyl)benzofuran obtained in the above step a) and 6.09 g of cuprous cyanide were suspended in 75 ml of N-methyl-2-pyrrolidone, and the suspension was stirred at 200° to 220° C. for 5 hours in a stream of nitrogen. After cooling, the reaction solution was diluted with chloroform to remove insoluble materials by filtration, and the resulting filtrate was washed with dilute hydrochloric acid. After drying the organic layer and subsequent concentration under a reduced pressure, 6.60 g of 2-(4-methoxybenzoyl)-5-benzofurancarbonitrile was obtained as a brown powder.

IR (KBr): 2224, 1644 cm⁻¹
¹H-NMR (DMSO-d₆) δ:3.30 (3H, s), 7.15 (2H, d, J=9Hz), 7.83 (1H, s), 8.00 (2H, d), 8.07 (2H, d, J=9Hz), 8.42 (1H, s)

c) 1.85 g of ethyl diethylphosphonoacetate was dissolved in 20 ml of tetrahydrofuran. With stirring at room temperature, 320 mg of 60% sodium hydride was added to the above solution, and the stirring was continued until the reaction solution became clear. After 10 minutes, 1.75 g of 2-(4-methoxybenzoyl)-5-benzofurancarbonitrile obtained in the above step b) was added to the above reaction solution, and the mixture was refluxed under heating for 30 minutes. After cooling, the resulting reaction mixture was concentrated to dryness. The residue thus obtained was mixed with dilute hydrochloric acid, extracted with dichloromethane, washed with saturated sodium chloride aqueous solution, and then concentrated to dryness. The resulting residue was purified by silica gel column chromatography using a n-hexane/dichloromethane mixture as an eluant, thereby obtaining 1.78 g of ethyl 3-(5-cyano-2-benzofuranyl)-3-(4-methoxyphenyl)acrylate as a mixture of E and Z forms.

¹H-NMR (CDCl₃) δ:1.20 (3H, t, J=7Hz), 3.84 (3H, s), 4.18 (2H, q, J=7Hz), 6.32 (1H, s), 6.8–7.4 (5H, m), 7.56 (2H, s), 7.93 (1H, br)

d) 1.78 g of the E/Z mixture of ethyl 3-(5-cyano-2-benzofuranyl)-3-(4-methoxyphenyl)acrylate obtained in the above step c) was dissolved in a solvent mixture of 6 ml of tetrahydrofuran and 20 ml of ethanol. 200 mg of 5% palladium carbon catalyst was added to the above solution, and the mixture was subjected to catalytic hydrogenation under normal pressure for 1.5 hours. After removing the catalyst by filtration, the resulting filtrate was concentrated to dryness to obtain 1.79 g of ethyl 3-(5-cyano-2-benzofuranyl)-3-(4-methoxyphenyl)propionate.

¹H-NMR (CDCl₃) δ:1.29 (3H, t, J=7Hz), 2.9–3.1 (2H, m), 3.78 (3H, s), 4.09 (2H, q, J=7Hz), 4.5–4.7 (1H, m), 6.47 (1H, s), 6.88 (2H, d, J=9Hz), 7.24 (2H, d, J=9Hz), 7.47 (2H, s), 7.80 (1H, s)

e) 1.79 g of ethyl 3-(5-cyano-2-benzofuranyl)-3-(4-methoxyphenyl)propionate obtained in the above step d) was dissolved in 20 ml of anhydrous dichloromethane, and the solution was cooled down to −50° C. To this solution was added dropwise a 10 ml dichloromethane solution containing 1.36 ml boron tribromide. The resulting mixture was gradually warmed up, and stirred at room temperature for 3 hours. Thereafter, the reaction solution was diluted with dichloromethane, and the resulting organic layer was washed with dilute hydrochloric acid and then with saturated sodium chloride aqueous solution, followed by concentration to dryness. In this way, 1.34 g of the title compound was obtained in an oily form.

¹H-NMR (CDCl₃) δ:1.15 (3H, t, J=7Hz), 2.9–3.3 (2H, m), 4.09 (2H, q, J=7Hz), 4.5–4.7 (1H, m), 6.15 (1H, br), 6.46 (1H, s), 6.80 (2H, d, J=9Hz), 7.15 (2H, d, J=9Hz), 7.42 (2H, s), 7.76 (1H, s)

REFERENCE EXAMPLE 47

Preparation of ethyl 2-(2-(5-cyano-2-benzofuranyl)ethyl)-5-hydroxybenzoate a) 4.87 g of 2-formyl-5-methoxybenzoic acid was dissolved in 30 ml of chloroform. With stirring at room temperature, a benzene/n-hexane (1:1) mixture solution of diphenyldiazomethane prepared in accordance with the procedure disclosed in *Journal of the Chemical Society* (Parkin I, pp. 2030–2033, 1975) was added to the above solution until the reaction solution showed a purplish red color. The resulting reaction solution was subjected to purification by silica gel column chromatography using a toluene/ethyl acetate mixture as an eluant to obtain 8.2 g of diphenylmethyl 2-formyl-5-methoxybenzoate as a viscous oil.

¹H-NMR (CDCl₃) δ:3.87 (3H, s), 7.13 (1H, dd, J=11.5 and 2.9Hz), 7.20 (1H, s), 7.24 (11H, m), 7.97 (1H, d, J=11.5Hz), 10.45 (1H, s)

b) 6.0 g of diphenylethyl 2-formyl-5-methoxybenzoate obtained in the above step a) and 8.1 g of (5-cyano-2-benzofuranyl)methyltriphenylphosphonium chloride were dissolved in a mixture solvent of 70 ml of tetrahydrofuran and 70 ml of methanol. With stirring at room temperature, 2.91 g of 1,8-diazabicyclo[5.4.0]-7-undecene was added to the above solution, and the mixture was stirred for 2 hours at thee same temperature. After distilling off the solvent, the resulting residue was subjected to purification by silica gel column chromatography using a toluene/chloroform mixture as an eluant to obtain 8.2 g of diphenylmethyl 2-[2-(5-cyano-2-benzofuranyl)vinyl]-5-methoxybenzoate as a mixture of E and Z forms.

¹H-NMR (CDCl₃) δ:3.84 (1H, s), 3.88 (3H, s), 6.20–8.28 (19H, m)

c) 8.2 g of the E/Z mixture of diphenylmethyl 2-[2-(5-cyano-2-benzofuranyl)vinyl]-5-methoxybenzoate obtained in the above step b) was dissolved in a solvent mixture of 60 ml of tetrahydrofuran and 60 ml of ethanol. 2.0 g of palladium oxide.1H₂O.barium sulfate was added to the above solution, and the mixture was subjected to catalytic hydrogenation under normal pressure. After removing the catalyst by filtration, the resulting filtrate was concentrated to collect precipitated crystals by filtration, thereby obtaining 4.45 g of 2-[2-(5-cyano-2-benzofuranyl)ethyl]-5-methoxybenzoic acid.

mp: 179°–182° C.

¹H-NMR (CDCl₃) δ:2.90–3.42 (4H, m), 3.75 (3H, s), 6.67 (1H, s), 7.01 (1H, dd, J=8.7 and 2.2Hz), 7.24 (1H, d, J=8.7Hz), 7.34 (1H, d, J=2.2Hz), 7.69 (2H, s), 8.06 (1H, s), 12.98 (1H, br)

FD MS (m/z): 321 (M⁺), 311, 283 d) 4.45 g of 2-[2-(5-cyano-2-benzofuranyl)ethyl]-5-methoxybenzoic acid obtained in the above step c) was dissolved in 200 ml of ethanol, and the solution was mixed with 4 ml of concentrated sulfuric acid, and refluxed under heating for 16 hours. After cooling, the resulting reaction solution was neutralized with saturated sodium bicarbonate aqueous solution, and ethanol was removed by distillation. The residue thus obtained was extracted with ethyl acetate, and dried to distill off the solvent. The resulting residue was purified by silica gel column chromatography, and then recrystallized from n-hexane to obtain 4.11 g of ethyl 2-[2-(5-cyano-2-benzofuranyl)ethyl]-5-methoxybenzoate in the form of colorless needle crystals.

mp: 92°–93° C.

¹H-NMR (CDCl₃) δ: 1.38 (3H, t, J=7.0Hz), 2.90–3.48 (4H, m), 3.82 (3H, s), 4.34 (2H, q, J=7.0Hz), 6.41 (1H, s), 6.96 (1H, dd, J=8.7 and 2.6Hz), 7.10 (1H, d, J=8.7Hz), 7.46 (1H, d, J=2.6Hz), 7.48 (2H, s), 7.79 (1H, s)

e) 4.11 g of ethyl 2-[2-(5-cyano-2-benzofuranyl)ethyl]-5-methoxybenzoate obtained in the above step d) was dissolved in 40 ml of dichloromethane, and the solution was cooled down to −78° C. 8.85 g of boron tribromide was added dropwise to the above solution at the same temperature, and the mixture was gradually warmed up to −5° C. to 0° C., and stirred for 1 hour. The resulting reaction solution was poured into ice water, and extracted with ethyl acetate. The resulting organic layer was washed with 4N hydrochloric acid and then with water, followed by drying and removal of the solvent. Thereafter, the resulting residue was purified by silica gel column chromatography to obtain 2.80 g of the title compound in the form of prism crystals.

mp: 133°–135° C.

¹H-NMR (CDCl₃) δ:1.40 (3H, t, J=7.0Hz), 2.96–3.50 (4H, m), 4.36 (2H, q, J=7.0Hz), 6.45 (1H, s), 6.93 (1H, dd, J=8.7 and 2.9Hz), 7.13 (1H, d, J=8.7Hz), 7.50 (1H, d, J=2.9Hz), 7.56 (2H, s), 7.84 (1H, s)

REFERENCE EXAMPLE 48

Preparation of ethyl 2-[2-[2-(5-cyano-2-benzofuranyl)ethyl]-5-hydroxyphenyl]acetate a) 2.0 g of 2-[2-(5-cyano-2-benzofuranyl)ethyl]-5-methoxybenzoic acid was suspended in 10 ml of benzene, and the suspension was mixed with 1 ml of thionyl chloride. By refluxing under heating the resulting mixture for 1 hour and subsequently concentrating to dryness, crude acid chloride was obtained.

A mixture solution consisting of 10 ml of n-hexane solution containing 10% (w/v) trimethylsilyldiazomethane, 1.3 ml of triethylamine, 10 ml of acetonitrile and 10 ml of tetrahydrofuran was cooled to −5° C. With stirring, to this was added dropwise a 5 ml acetonitrile solution of the crude acid chloride prepared above. The resulting reaction solution was stirred at 0° C. for 48 hours, and the solvent was subsequently distilled off under a reduced pressure at a low temperature. The residue thus obtained was dissolved in a mixture solvent of 4 ml of collidine and 4 ml of benzyl alcohol, and the resulting solution was stirred at 180° C. for 7 minutes in a stream of nitrogen. The resulting reaction solution was dissolved in benzene, washed with 10% citric acid, and then dried. After distilling off the solvent, the resulting residue was subjected to silica gel column chromatography using a toluene/ethyl acetate mixture as an eluant to obtain 830 mg of benzyl 2-[2-[2-(5-cyano-2-benzofuranyl)ethyl]-5-methoxyphenyl]acetate.

mp: 127°–128° C.

¹H-NMR (CDCl₃) δ:3.00 (4H), 3.68 (2H, s), 3.76 (3H, s), 5.13 (2H, s), 6.32 (1H, s), 6.76 (1H, dd, J=7.9 and 1.3Hz), 6.80 (1H, s), 7.08 (1H, d, J=7.9Hz), 7.30 (5H, s), 7.48 (1H, d, J=1.3Hz), 7.77 (1H, s)

b) 855 mg of benzyl 2-[2-[2-(5-cyano-2-benzofuranyl)ethyl]-5-methoxyphenyl]acetate obtained in the above step a) was dissolved in 20 ml of dichloromethane, and the solution was cooled down to −50° C. To this solution was added dropwise a 5 ml dichloromethane solution containing 1.75 g of boron tribromide, followed by gradually increasing temperature to 15° C. and stirring at the increased temperature for 20 minutes. The resulting reaction solution was extracted with ethyl acetate, washed with dilute hydrochloric acid, and then dried. After concentration to dryness, the resulting residue was dissolved in 30 ml of ethanol, mixed with 2 ml of thionyl chloride, and then refluxed under heating for 1 hour. After cooling, the reaction solution was diluted with ethyl acetate, and the resulting organic layer was washed with water, and dried to distill of the solvent. The thus obtained residue was purified by subjecting it to silica gel column chromatography using chloroform as an eluant. In this way, 680 mg of the title compound was obtained in the form of powder.

mp: 84°–86° C.

¹H-NMR (CDCl₃) δ:1.25 (3H, t, J=7.0Hz), 3.02 (4H), 3.59 (2H, s), 4.57 (2H, q, J=7.0Hz), 6.19 (1H, s), 6.41 (1H, s), 6.55–6.84 (2H, m), 6.99 (1H, d, J=7.9Hz), 7.48 (2H, s), 7.77 (1H, s)

REFERENCE EXAMPLE 49

Preparation of ethyl 5-cyano-2-[2-(4-hydroxyphenyl)ethyl]-3-benzofurancarboxylate a) 91.5 g of (5-bromo-2-benzofuranyl)methyltriphenylphosphonium chloride and 25 g of p-anisaldehyde were dissolved in a mixture solvent of 180 ml of tetrahydrofuran and 180 ml of ethanol. With stirring at room temperature, 27.58 g of 1,8-diazabicyclo[5.4.0]-7-undecene was added to the above solution, and the mixture was stirred for 18 hours. Thereafter, the reaction solution was concentrated to collect precipitated crystals by filtration, thereby obtaining 32.8 g of 5-bromo-2-[2-(4-methoxyphenyl)vinyl]benzofuran as one of the stereoisomers.

mp: 190°–194° C.

¹H-NMR (CDCl₃) δ:3.83 (3H, s), 6.54 (1H, s), 6.9 (3H), 7.25 (1H, d, J=17Hz), 7.31 (2H), 7.45 (2H, d), 7.62 (1H)

The filtrate obtained above was concentrated to dryness, and the resulting residue was purified by subjecting it to silica gel column chromatography using toluene as an eluant, thereby obtaining 22 g of 5-bromo-2-[2-(4-methoxyphenyl)vinyl]benzofuran as the other stereoisomer.

¹H-NMR (CDCl₃) δ:3.84 (3H, s), 6.35 (1H, d, J=14Hz), 6.53 (1H, s), 6.62 (1H, d, J=14Hz), 6.9 (2H, d), 7.24 (2H), 7.3 (2H, d), 7.38 (1H)

b) 84 g of a mixture of the two stereoisomers of 5-bromo-2-[2-(4-methoxyphenyl)vinyl]benzofuran obtained in the above step a) was dissolved in 600 ml of dichloromethane. With ice cooling and stirring, 18.5 ml of acetyl chloride was added to the above solution, followed by dropwise addition of 28.9 ml of titanium tetrachloride. The resulting reaction solution was poured into ice water, and extracted with chloroform, and the resulting organic layer was washed with dilute hydrochloric acid and then with water, followed by drying to distill off the solvent. Thereafter, the resulting residue was suspended in ether to collect insoluble crystals by filtration, thereby obtaining 76 g of 3-acetyl-5-bromo-2-[2-(4-methoxyphenyl)vinyl]benzofuran in the form of yellow fine needle crystals (the same isomer is formed from both of the E and Z forms).
mp: 163°–165° C.

¹H-NMR (CDCl₃) δ:2.69 (3H, s), 3.85 (3H, s), 6.95 (2H, d, J=10Hz), 7.4 (2H, m), 7.6 (2H, d, J=10Hz), 7.65 (2H, s), 8.08 (1H)

c) A mixture of 20.7 g of 3-acetyl-5-bromo-2-[2-(4-methoxyphenyl)vinyl]benzofuran obtained in the above step b), 6 g of cuprous cyanide and 800 ml of N-methyl-2-pyrrolidone was stirred at 210° to 220° C. for 8.5 hours in a stream of nitrogen. The resulting reaction solution was poured into ice water to remove precipitated materials by filtration, and the resulting filtrate was extracted with ethyl acetate. After removing insoluble materials by filtration, the resulting organic layer was washed with water and dried to distill off the solvent. The residue thus obtained was subjected to silica gel column chromatography using toluene as an eluant, and the resulting product was washed with methanol. In this way, 7.82 g of 3-acetyl-2-[2-(4-methoxyphenyl)vinyl]-5-benzofurancarbonitrile was obtained in the form of yellow fine crystals.
mp: 190°–191° C.

¹H-NMR (CDCl₃) δ:2.69 (3H, s), 3.85 (3H, s), 6.98 (2H, d, J=10Hz), 7.50–7.80 (6H, m), 8.36 (1H)

d) 7.8 g of 3-acetyl-2-[2-(4-methoxyphenyl)vinyl]-5-benzofurancarbonitrile obtained in the above step c) was dissolved in a solvent mixture of 600 ml of tetrahydrofuran and 500 ml of ethanol. 900 mg of palladium oxide.1H₂O.barium sulfate was added to the above solution, and the mixture was subjected to catalytic hydrogenation under normal pressure for 3.5 hours. After removing the catalyst by filtration, the resulting filtrate was concentrated to dryness. The residue thus obtained was extracted with ethyl acetate, and the resulting organic layer was washed with water, and dried to distill off the solvent. Thereafter, the residue thus obtained was washed with methanol to collect precipitated crystals by filtration, thereby obtaining 5.47 g of 3-acetyl-2-[2-(4-methoxyphenyl)ethyl]-5-benzofurancarbonitrile in the form of colorless prism crystals.
mp: 130°–131° C.

¹H-NMR (CDCl₃) δ: 2.54 (3H, s), 3.04 (2H, m), 3.4 (2H, m), 3.77 (3H, s), 6.85 (2H, d, J=10Hz), 7.05 (2H, d), 7.57 (2H, s), 8.33 (1H)

e) 5.2 g of sodiumhydroxide was dissolved in 30 ml of water, and the solution was cooled to a temperature of 0° C. or below. With stirring, to this were added dropwise 2.7 ml of bromine and then 40 ml of a dioxane solution containing 4.14 g of 3-acetyl-2-[2-(4-methoxyphenyl)ethyl]-5-benzofurancarbonitrile obtained in the above step d). The resulting mixture was stirred at 0° C. for 45 minutes with ice cooling for 1 hour. The resulting reaction solution was mixed with water, adjusted to pH 2 with concentrated hydrochloric acid, and then extracted with chloroform. The resulting organic layer was washed with water and dried to distill off the solvent. Thereafter, the resulting residue was purified by subjecting it to silica gel column chromatography using chloroform as an eluant, thereby obtaining 1.44 g of 5-cyano-2-[2-(4-methoxyphenyl)ethyl]-3-benzofurancarboxylic acid.
mp: 205°–208° C. (recrystallization from methanol, fine prism crystals)

¹H-NMR (CDCl₃) δ:3.13 (2H, m), 3.5 (2H, m), 3.78 (3H, s), 6.83 (2H, d), 7.07 (2H, d), 7.56 (2H, s), 8.34 (1H)

f) 1.81 g of 5-cyano-2-[2-(4-methoxyphenyl)ethyl]-3-benzofurancarboxyliic acid obtained in the above step e) was added to 5 ml of thionyl chloride, and the mixture was refluxed under heated for 1 hour. The resulting reaction solution was concentrated to dryness, and the residue was mixed with ethanol and stirred at 50° C. for 30 minutes. Crystals thus precipitated were collected by filtration to obtain 1.82 g of ethyl 5-cyano-2-(2-(4-methoxyphenyl)ethyl)-3-benzofurancarboxylate.
mp: 135°–139° C. (fine prism crystals)
IR (KBr): 2224, 1695, 1614, 1587, 1515 cm⁻¹ g) 1.78 g of ethyl 5-cyano-2-[2-(4-methoxyphenyl)ethyl]-3-benzofurancarboxylate obtained in the above step f) was treated in the same manner as described in step e) of Reference Example 46 to obtain 2.27 g of the title compound in the form of fine needle crystals.
mp: 182°–183° C.

¹H-NMR (CDCl₃) δ:1.45 (3H, t, J=8.0Hz), 3.0 (2H, m), 3.4 (2H, m), 4.4 (2H, q, J=8.0Hz), 6.7 (2H, d), 7.1 (2H, d), 7.55 (2H), 8.29 (1H)

REFERENCE EXAMPLE 50

Preparation of ethyl [5-cyano-2-(2-(4-hydroxyphenyl)ethyl]-3-benzofuranyl)acetate a) 128 g of 5-bromo-2-[2-(4-methoxyphenyl)vinyl]benzofuran as a mixture of two stereoisomers was dissolved in a solvent mixture of 1.3 l of tetrahydrofuran and 0.7 l of ethanol. The resulting solution was mixed with 3.0 g of platinum dioxide and subjected to 4 hours of catalytic hydrogenation undernormal pressure. Thereafter, the catalyst was removed by filtration, the resulting filtrate was concentrated, and crystals thus precipitated were collected by filtration and washed with ethanol. In this way, 97.08 g of 5-bromo-2-[2-(4-methoxyphenyl)ethyl]benzofuran was obtained.
mp: 109°–111° C.

¹H-NMR (CDCl₃) δ: 3.00 (4H, s), 3.77 (3H, s), 6.28 (1H, s), 6.88 (2H, d, J=9.0Hz), 7.08 (2H, d, J=9.0Hz), 7.32 (2H), 7.60 (1H)

b) 97 g of 5-bromo-2-[2-(4-methoxyphenyl)ethyl]benzofuran obtained in the above step a) was treated in the same manner as described in step b) of Reference Example 49 to obtain 79.9 g of 3-acetyl-5-bromo-2-[2-(4-methoxyphenyl)ethyl]benzofuran.
mp: 100°–101° C.

¹H-NMR (CDCl₃) δ:2.52 (3H, s), 3.05 (2H, m), 3.35 (2H, m), 3.76 (3H, s), 6.80 (2H, d, J=9.0Hz), 7.10 (2H, d, J=9.0Hz), 7.35 (2H, m), 8.05 (1H)

c) 79.9 g of 3-acetyl-5-bromo-2-[2-(4-methoxyphenyl)ethyl]benzofuran obtained in the above step b) was treated in the same manner as described in step e) of Reference Example 49 to obtain 64.2 g of 5-bromo-2-[2-(4-methoxyphenyl)ethyl]-3-benzofurancarboxylic acid.

¹H-NMR (DMSO-d₆) δ:3.00 (2H, m), 3.35 (2H, m), 3.69 (3H, s), 6.80 (2H, d, J=8.0Hz), 7.07 (2H, d,-J=8.0Hz), 7.50 (1H, dd), 7.55 (1H, d), 8.00 (1H, d)

d) 64.2 g of 5-bromo-2-[2-(4-methoxyphenyl)ethyl]-3-benzofurancarboxylic acid obtained in the above step c) was suspended in 900 ml of ethanol. 30 ml of thionyl chloride was added dropwise to the above suspension with ice cooling. After refluxing under heating for 5 hours, 50 ml of thionyl chloride was further added dropwise to the resulting reaction mixture, followed by additional refluxing under heating for 3 hours. The reaction solution thus obtained was concentrated to dryness, and the resulting residue was mixed with water to collect insoluble materials by filtration. The thus collected insoluble materials were dissolved in ethyl acetate and washed with a saturated sodium bicarbonate aqueous solution, water, a saturated sodium chloride aqueous solution in that order, followed by drying to distill off the solvent. Thereafter, the resulting residue was suspended in ethanol and then collected by filtration to obtain 59.23 g of ethyl 5-bromo-2-[2-(4-methoxyphenyl)ethyl]-3-benzofurancarboxylate.
mp: 73°–75° C.

¹H-NMR (CDCl₃) δ:1.43 (3H, t, J=8.9Hz), 3.10 (2H, m), 3.40 (2H, m), 3.77 (3H, s), 4.40 (2H, q, J=8.9Hz), 6.80 (2H, d), 7.2 (2H, d), 7.33 (2H, m), 8.10 (1H)

e) 35.5 g of ethyl 5-bromo-2-[2-(4-methoxyphenyl)ethyl]-3-benzofurancarboxylate obtained in the above step d) was dissolved in 400 ml of tetrahydrofuran, followed by the gradual addition of 3.5 g of lithium-aluminum hydride and, subsequently, 1 hour of stirring at room temperature. The resulting reaction solution was poured into water, adjusted to pH 2 with hydrochloric acid and then extracted with benzene. Thereafter, the resulting organic layer was washed with water, and then concentrated to dryness to obtain 30 g of 5-bromo-3-hydroxymethyl-2-[2-(4-methoxyphenyl)ethyl]benzofuran in the form of crystals.
mp: 65°–75° C.

¹H-NMR (CDCl₃) δ:2.95 (4H, s), 3.69 (3H, s), 4.33 (2H, s), 6.77 (2H, d), 6.90 (2H, d), 7.26 (2H, m), 7.65 (1H)

f) 30 g of 5-bromo-3-hydroxymethyl-2-[2-(4-methoxyphenyl)ethyl]benzofuran obtained in the above step e) was suspended in 150 ml of diethyl ether. To this was added 12 drops of pyridine. With ice cooling, 12 ml of thionyl chloride was further added dropwise. The reaction mixture thus prepared was stirred for 1 hour at room temperature. The resulting reaction solution was poured into ice water, and extracted with diethyl ether. Thereafter, the resulting organic layer was washed with water and then With saturated sodium bicarbonate aqueous solution, followed by concentration to dryness, thereby obtaining 28.3 g of 5-bromo-3-chloromethyl-2-[2-(4-methoxyphenyl)ethyl]benzofuran.
mp: 70°–75° C.

¹H-NMR (CDCl₃) δ: 3.00 (4H, s), 3.76 (3H, s), 4.38 (2H, s), 6.82 (2H, d), 6.97 (2H, d), 7.31 (2H), 7.68 (1H)

g) To 75 ml of acetonitrile were added 10.82 g of 5-bromo-3-chloromethyl-2-[2-(4-methoxyphenyl)ethyl]benzofuran obtained in the above step f), 3.7 g of potassium cyanide and 0.6 g of 18-crown-6-ether. The thus prepared mixture was refluxed under heating for 2.5 hours. The reaction solution thus obtained was mixed with water, and extracted with benzene, and the resulting organic layer was washed with water, and dried to distill off the solvent. Thereafter, the resulting residue was purified by subjecting it to silica gel column chromatography using a toluene/n-hexane mixture as an eluant, thereby obtaining 9.17 g of 5-bromo-3-cyanomethyl-2-[2-(4-methoxyphenyl)ethyl]benzofuran.

¹H-NMR (CDCl₃) δ:2.95 (4H, s), 3.20 (2H, s), 3.73 (3H, s), 6.80 (2H, d), 6.90 (2H, d), 7.33 (2H), 7.61 (1H)

h) 9.17 g of 5-bromo-3-cyanomethyl-2-[2-(4-methoxyphenyl)ethyl]benzofuran obtained in the above step g) was added to a mixture solution of 100 ml of ethanol and 5 ml of concentrated sulfuric acid, and the resulting mixture was refluxed under heating for 18 hours. The resulting reaction solution was poured into water and extracted with ethyl acetate, Thereafter, the resulting organic layer was washed with water, a saturated sodium bicarbonate aqueous solution and water in that order, followed by drying to distill off the solvent. In this way, 8.96 g of ethyl [5-bromo-2-[2-(4-methoxyphenyl)ethyl]-3-benzofuranyl]acetate was obtained.

¹H-NMR (CDCl₃) δ:1.21 (3H, t, J=7.0Hz), 2.96 (4H, s), 3.34 (2H, s), 3.74 (3H, s), 4.10 (2H, q, J=7.0Hz), 6.80 (2H, d, J=9Hz), 7.00 (2H, d, J=7.0Hz), 7.28 (2H), 7.59 (1H)

i) 8.2 g of ethyl [5-bromo-2-[2-(4-methoxyphenyl)ethyl] 3-benzofuranyl]acetate obtained in the above step h) was treated in the same manner as described in step c) of Reference Example 49 to obtain 4.5 g of ethyl [5-cyano-2-[2-(4-methoxyphenyl)ethyl]-3-benzofuranyl]acetate in the form of colorless needle crystals.
mp: 85°–86° C.

¹H-NMR (CDCl₃) δ:1.23 (3H, t, J=7.0Hz), 3.01 (4H, s), 3.40 (2H, s), 3.75 (3H, s), 4.11 (2H, q, J=7.0Hz), 6.80 (2H, d, J=9Hz), 7.00 (2H, d, J=7.0Hz), 7.47 (2H), 7.81 (1H)

j) 4.45 g of ethyl [5-cyano-2-[2-(4-methoxyphenyl)ethyl]-3-benzofuranyl]acetate obtained in the above step i) was treated in the same manner as described in step e) of Reference Example 46 to obtain 2.98 g of the title compound in the form of colorless crystals.
mp: 134°–136° C.

¹-NMR (CDCl₃) δ:1.22 (3H, t, J=7.0Hz), 2.98 (4H, s), 3.39 (2H, s), 4.12 (2H, q, J=7.0Hz), 6.74 (2H, q, J=9.0Hz), 6.91 (2H, d, J=7.0Hz), 7.48 (2H), 7.80 (1H)

REFERENCE EXAMPLE 51

Preparation of ethyl 3-[2-[2-(5-cyanobenzo[b]thien-2-yl)ethyl]-4-ethoxy-5-hydroxyphenyl]propionate a) 20.0 g of Ferulic acid was dissolved in 250 ml of methanol and subjected to catalytic reduction under normal pressure for 3 hours in the presence of 10% palladium carbon catalyst (50% wet type). After removing the catalyst by filtration, the resulting filtrate was concentrated to collect precipitated crystals by filtration, thereby obtaining 19.3 g of 3-(4-hydroxy-3-methoxyphenyl)propionic acid.
mp: 87°–89° C.

¹H-NMR (CDCl₃) δ:2.5–3.0 (4H, m), 3.85 (3H, s), 6.5–6.9 (3H, m)

b) 19.3 g of 3-(4-hydroxy-3-methoxyphenyl)propionic acid obtained in the above step a) was dissolved in 300 ml of ethanol. After adding 2.0 ml of concentrated sulfuric acid, the resulting mixture was refluxed under heating for 2 hours. The resulting reaction solution was concentrated under a reduced pressure, extracted with chloroform, washed with water, and then dried. By distilling off the solvent, 23.0 of ethyl 3-(4-hydroxy-3-methoxyphenyl)propionate was obtained in an oily form.

$^1$H-NMR (CDCl$_3$) δ:1.23 (3H, t, J=7.2Hz), 2.4–3.0 (4H, m), 3.85 (3H, s), 4.12 (2H, q, J=7.12Hz), 6.6–6.9 (3H, m)

c) 10.0 g of ethyl 3-(4-hydroxy-3-methoxyphenyl)propionate obtained in the above step b) was dissolved in 300 ml of tetrahydrofuran. 1.96 g of 60% sodium hydride was subsequently added. The thus prepared mixture was stirred at 50° C. for 30 minutes. To this was added dropwise 7.17 g of ethyl bromide. After refluxing under heating for 6 hours, the resulting reaction solution was poured into water, extracted with chloroform, washed with water, and then concentrated under a reduced pressure. Thereafter, the resulting residue was subjected to silica gel column chromatography using chloroform as an eluant, thereby obtaining 5.6 g of oily ethyl 3-(4-ethoxy-3-methoxyphenyl)propionate.

$^1$H-NMR (CDCl$_3$) δ:1.23 (3H, t, J=7.2Hz), 1.43 (3H, t, J=7.1Hz), 2.4–3.0 (4H, m), 3.85 (3H, s), 4.06 (2H, q, J=7.1Hz), 4.11 (2H, q, J=7.12Hz), 6.7–6.9 (3H, m)

d) 9.3 g of ethyl 3-(4-ethoxy-3-methoxyphenyl)propionate obtained in the above step c) was dissolved in 10 ml of acetic acid, followed by adding 7.4 g of chloromethyl methyl ether and subsequently stirring at room temperature for 22 hours. The resulting reaction solution was poured into ice water, extracted with ethyl acetate, washed with water and then dried to distill off the solvent. The residue thus obtained was dissolved in 10 ml of xylene, and the solution was mixed with 8.54 g of triphenylphosphine. The resulting mixture was stirred at room temperature for 18 hours and then at 70° to 80° C. for 5 hours. After cooling, xylene was removed by decantation, and the remaining portion was solidified by adding n-hexane to obtain 6.0 g of crude [5-ethoxy-2-(2-ethoxycarbonylethyl)-4-methoxyphenyl] methyltriphenylphosphonium chloride.

e) To a mixture solution of 50 ml of tetrahydrofuran and 50 ml of ethanol were dissolved 1.5 g of 5-cyanobenzo[b]thiophene-2-carbaldehyde and 6.34 g of crude [5-ethoxy-2-(2-ethoxycarbonylethyl)-4-methoxyphenyl]methyltriphenylphosphonium chloride obtained in the above step d). 1.83 g of 1,8-diazabicyclo[5.4.0]-7-undecene was added thereto, followed by stirring at room temperature for 18 hours. The resulting reaction solution was concentrated under a reduced pressure, and the residue was dissolved in a mixture solution of 20 ml of tetrahydrofuran and 20 ml of ethanol. The thus prepared solution was mixed with 1.70 g of 10% palladium carbon catalyst (50% wet type) and subjected to catalytic hydrogenation under normal pressure until hydrogen absorption was completed. After removing the catalyst by filtration, the solvent was distilled off. By subjecting the resulting residue to silica gel column chromatography, 1.2 g of oily ethyl 3-[2-[2-(5-cyanobenzo[b]thien-2-yl)ethyl]-4-ethoxy-5-methoxyphenyl]propionate was obtained.

$^1$H-NMR (CDCl$_3$) δ:1.24 (3H, t, J=7.1Hz), 1.36 (3H, t, J=7.0Hz), 2.4–3.3 (8H, m), 3.84 (3H, s), 3.98 (2H, q, J=7.0Hz), 4.13 (2H, q, J=7.1Hz), 6.64 (1H, s), 6.70(1H, s), 7.04 (1H, s), 7.46 (1H, dd, J=8.4 and 1.5Hz), 7.83(1H, d, J=8.4Hz), 7.96 (1H, s)

f) 2.1 g of ethyl 3-[2-[2-(5-cyanobenzo[b]thien-2-yl)ethyl]-4-ethoxy-5-methoxyphenyl]propionate obtained in the above step e) was dissolved in 20 ml of γ-collidine, followed by adding 7.94 g of lithium iodide and subsequently refluxing under heating for 18 hours. The resulting reaction solution was poured into water, extracted with chloroform, washed with water, and then dried. After distilling off the solvent, the residue thus obtained was dissolved in 100 ml of ethanol, mixed with 0.3 ml of concentrated sulfuric acid, and then refluxed under heating for 1 hour. After distilling off the solvent under a reduced pressure, the resulting reaction solution was diluted with chloroform, washed with water, and then dried to distill off the solvent. Thereafter, the resulting residue was subjected to purification by subjecting it to silica gel column chromatography using chloroform as an eluant. In this way, 2.0 g of the title compound was obtained in an oily form.

$^1$H-NMR (CDCl$_3$) δ:1.24 (3H, t, J=7.1Hz), 1.35 (3H, t, J=7.0Hz), 2.4–3.3 (8H, m), 3.98 (2H, q, J=7.0Hz), 4.13 (2H, q, J=7.1Hz), 6.60(1H, s), 6.75 (1H, s), 7.44 (1H, dd, J =8.4 and 1.5Hz), 7.82 (1H, d, J=8.4Hz), 7.96 (1H, s), 7.94 (1H, s)

REFERENCE EXAMPLE 52

Preparation of ethyl-3-[3-[2-(5-cyanobenzo[b]thien-2-yl)ethyl]-5-hydroxyphenyl]propionate a) 33.5 g of 6-methoxy-2-tetralone was dissolved in 27.6 ml of ethanol, followed by subsequently adding 37.8 ml of ethyl orthoformate and one drop of concentrated sulfuric acid. The mixture2thus prepared was stirred at 100° C. for 4 hours. After distilling off the solvent under a reduced pressure, the resulting residue was subjected to silica gel column chromatography using chloroform as an eluant. Fractions of interest were pooled and concentrated to collect precipitated crystals, thereby obtaining 5.82 g of 3,4-dihydro-2-ethoxy-6-methoxynaphthalene.

$^1$H-NMR (CDCl$_3$) δ:1.37 (3H, t, J=7.0Hz), 2.20–3.00 (4H, m), 3.79 (3H, s), 3.84 (2H, q, J=7.0Hz), 5.48 (1H, s), 6.60–7.00 (3H, m)

b) 5.8 g of 3,4-dihydro-2-ethoxy-6-methoxy-naphthalene obtained in the above step a) was dissolved in a mixture solution of 90 ml of ethanol and 10 ml of dichloromethane. With stirring at a cooled temperature of −20° C., ozone was bubbled into the solution prepared above to effect oxidation. 10 ml of dimethylsulfide was added dropwise and gradually to the resulting reaction solution at the same temperature, followed by stirring at room temperature for 30 minutes. After distilling off the solvent under a reduced pressure, the resulting residue was dissolved in 100 ml of a tetrahydrofuran/ethanol mixture (1:1). To this were added 12.5 g of (5-cyanobenzo[b]thien-2-yl)methyltriphenylphosphonium chloride and 4.46 ml of 1,8-diazabicyclo[5.4.0]-7-undecene in that order, followed by 5 hours of stirring. The resulting reaction solution was concentrated under a reduced pressure, and the residue thus obtained was purified by subjecting it to silica gel column chromatography using chloroform as an eluant. The thus purified product was dissolved in 60 ml of ethanol/tetrahydrofuran mixture (1:1), and the resulting solution was mixed with 3.9 g of 10% palladium carbon catalyst (50% wet type). By subjecting the thus prepared mixture to catalytic hydrogenation under normal pressure for 3 hours, 2.75 g of ethyl 3-[2-[2-(5-cyanobenzo[b]thien-2-yl)ethyl]-5-methoxyphenyl]propionate was obtained.

$^1$H-NMR (CDCl$_3$) δ:1.22 (3H, t, J=7.2Hz), 2.2–3.4 (8H, m), 3.76 (3H, s), 4.16 (2H, q, J=7.2Hz), 6.60–7.30 (4H, m), 7.48 (1H, d, J=8.2Hz), 7.85 (1H, d, J=8.2Hz), 7.99 (1H, s)

c) 2.75 g of ethyl 3-[2-[2-(5-cyanobenzo[b]-thien-2-yl)ethyl]-5-methoxyphenyl)propionate obtained in the above step b) was treated in the same manner as described in step e) of Reference Example 46 to obtain 2.3 g of the title compound in an oily form.

$^1$H-NMR (CDCl$_3$) δ:1.23 (3H, t, J=7.1Hz), 2.4–3.34 (8H, m), 4.13 (2H, q, J=7.2Hz), 5.60 (1H, s), 6.50–7.20 (3H, m), 7.25 (1H, s), 7.44 (1H, d, J=8.3Hz), 7.82 (1H, d, J=8.3Hz), 7.92 (1H, s)

REFERENCE EXAMPLE 53

Preparation of ethyl 2-(5-cyanobenzo[b]thien-2-yl)-3-(4-hydroxyphenyl]propionate a) 0.5 g of 5-bromo-2-hydroxymethylbenzo[b]thiophene was dissolved in 20 ml of dichloromethane, followed by the addition of 230 mg of phosphorus tribromide. After 1 hour of stirring at room temperature, the resulting reaction solution was mixed with water, washed with a saturated sodium bicarbonate aqueous solution, and then dried to distill off the solvent. The resulting residue was dissolved in a mixture solvent of 10 ml of acetonitrile and 3 ml of dimethylsulfoxide, followed by the addition of 300 mg of cuprous cyanide and subsequently refluxing under heating for 2 hours. After cooling, toluene was added to the reaction solution to remove insoluble materials by filtration, and the resulting filtrate was washed with water, dried, and concentrated. By collecting precipitated crystals by filtration, 200 mg of 5-bromo-2-cyanomethylbenzo[b]thiophene was obtained.
mp: 94°–96° C.
$^1$H-NMR (CDCl$_3$) δ:3.98 (2H, s), 7.25 (1H, s), 7.42 (1H, dd, J=8.5 and 1.8Hz), 7.65 (1H, d, J=8.5Hz), 7.90 (1H, d, J=1.8Hz)

b) 12.0 g of 5-bromo-2-cyanomethylbenzo[b]thiophene obtained in the above step a) was dissolved in 80 ml of ethanol, followed by the addition of 1.0 ml of water and 7 ml of concentrated sulfuric acid. After refluxing under heating for 7 hours, the resulting reaction solution was mixed with 40 ml of ethanol, 15 ml of concentrated sulfuric acid and 0.5 ml of water, and the mixture was refluxed under heating for 2 hours. After cooling, the resulting reaction solution was mixed with water, and extracted with an equal volume mixture of toluene and ethyl acetate. The resulting organic layer was washed with water and saturated sodium bicarbonate aqueous solution in that order, and then dried to distill off the solvent. Thereafter, the resulting residue was subjected to silica gel column chromatography to obtain 8.0 g of ethyl 2-(5-bromobenzo[b]thien-2-yl)acetate.
mp: 56°–57° C.
$^1$H-NMR (CDCl$_3$) δ:1.28 (3H, t, J=7.0Hz), 3.88 (2H, s), 4.23 (2H, q, J=7.0Hz), 7.11 (1H, s), 7.38 (1H, dd, J=8.3 and 1.8Hz), 7.68 (1H, d, J=8.3Hz), 7.82 (1H, d, J=1.8Hz)

c) 800 mg of ethyl 2-(5-bromobenzo[b]thien-2-yl)acetate obtained in the above step b) and 965 mg of diethyl carbonate were dissolved in 4 ml of N,N-dimethylformamide. With heating in an oil bath of 120° to 130° C., 162 mg of sodium hydride (60%) was added to the above solution. After 10 minutes of stirring at the same temperature, 30 mg of sodium hydride (60%) was added to the reaction solution, and the stirring was continued for another 10 minutes. The resulting reaction solution was diluted with an equal volume mixture of toluene and ethyl acetate, washed with dilute hydrochloric acid and water in that order, and then dried. After distilling off the solvent, the resulting residue was purified by subjecting it to silica gel column chromatography using a toluene/ethyl acetate mixture as an eluant. In this way, 600 mg of ethyl 2-(5-bromobenzo[b]thien-2-yl)-2-ethoxycarbonylacetate.
$^1$H-NMR (CDCl$_3$) δ:1.28 (6H, t, J=7.0Hz), 4.25 (4H, q, J=7.0Hz), 4.95 (1H, s), 7.17 (1H, s), 7.35 (1H, dd, J=8.3 and 2.1Hz), 7.62 (1H, d, J=8.3Hz), 7.83 (1H, d, J=2.1Hz)

d) 6.2 g of ethyl 2-(5-bromobenzo[b]thien-2-yl)-2-ethoxycarbonylacetate obtained in the above step c) and 5.2 g of 4-methoxybenzyl chloride were dissolved in 30 ml of N,N-dimethylformamide. At room temperature, 1.34 g of sodium hydride (60%) was added to the above solution, and the mixture was stirred for 3 hours. With ice cooling, the resulting reaction solution was mixed with 10% citric acid aqueous solution, extracted with toluene, washed with water, and then dried. After distilling off the solvent, the resulting residue was subjected to silica gel column chromatography using toluene as an elution solvent to obtain 8.2 g of ethyl 2-(5-bromobenzo[b]thien-2-yl)-2-ethoxycarbonyl-3-(4-methoxyphenyl)propionate.
mp: 58°–60° C.
$^1$H-NMR (CDCl$_3$) δ:1.22 (6H, t, J=7.0Hz), 3.65 (5H, s), 4.30 (4H, q, J=7.0Hz), 6.60 (2H, d, J=8.5Hz), 6.79 (2H, d, J=8.5Hz), 7.31 (1H, s), 7.35 (1H, dd, J=8.8 and 1.8Hz), 7.60 (1H, d, J=8.8Hz), 7.82 (1H, d, J=1.8Hz)

e) 3.0 g of ethyl 2-(5-bromobenzo[b]thien-2-yl)-2-ethoxycarbonyl-3-(4-methoxyphenyl)propionate obtained in the above step d) was dissolved in 25 ml of ethanol. 0.91 g of potassium hydroxide dissolved in 2.5 ml of water was added to the above solution, and the mixture was stirred at room temperature for 4 days. With ice cooling, the thus obtained reaction solution was mixed with dilute hydrochloric acid and extracted with ethyl acetate, and the resulting organic layer was washed with water, and dried to distill off the solvent. The resulting residue was dissolved in 60 ml of ethanol, mixed with 4 ml of concentrated sulfuric acid, and then refluxed under heating for 1 hour. After ice cooling, the resulting reaction solution was washed with saturated sodium bicarbonate aqueous solution, and then with water, followed by drying to distill off the solvent. Thereafter, the resulting residue was purified by subjecting it to silica gel column chromatography to obtain 1.6 g of ethyl 2-(5-bromobenzo[b]thien-2-yl)-3-(4-methoxyphenyl)propionate.
mp: 62°–65° C.
$^1$H-NMR (CDCl$_3$) δ: 1.15 (3H, t, J=7.0Hz), 3.08 (1H, dd, J=13.5 and 7.3Hz), 3.37 (1H, dd, J=13.5 and 7.3Hz), 3.71 (3H, s), 4.10 (2H, q, J=7.0Hz), 4.14 (1H, t, J=7.3Hz), 6.75 (2H, d, J=8.7Hz), 6.83 (1H, s), 7.05 (2H, d, J=8.7Hz), 7.30 (1H, dd, J=8.8 and 2.3Hz), 7.57 (1H, d, J=8.8Hz), 7.74 (1H, d, J=2.3Hz)

f) 1.6 g of ethyl 2-(5-bromobenzo[b]thien-2-yl)-3-(4-methoxyphenyl)propionate obtained in the above step e) was treated in the same manner as described in step c) of Reference Example 49 to obtain 1.0 g of ethyl 2-(5-cyanobenzo[b]thien-2-yl)-3-(4-methoxyphenyl)propionate.
mp: 93°–96° C.
$^1$H-NMR (CDCl$_3$) δ:1.17 (3H, t, J=7.0Hz), 3.09 (1H, dd, J=14.0 and 8.0Hz), 3.39 (1H, dd, J=14.0 and 8.0Hz), 3.73 (3H, s), 4.12 (2H, q, J=7.0Hz), 4.16 (1H, t), 6.75 (2H, d, J=8.8Hz), 7.05 (2H, d, J=8.8Hz), 7.13 (1H, s), 7.43 (1H, dd, J=8.3 and 1.3Hz), 7.81 (1H, d, J=8.3Hz), 7.92 (1H, br)

g) 3.3 g of ethyl 2-(5-cyanobenzo[b]thien-2-yl)-3-(4-methoxyphenyl)propionate obtained in the above step f) was treated in the same manner as described in step e) of Reference Example 46 to obtain 2.8 g of the title compound.
mp: 146°–147° C.
$^1$H-NMR (CDCl$_3$) δ:1.19 (3H, t, J=7.0Hz), 3.09 (1H, dd, J=13.5 and 7.5Hz), 3.38 (1H, dd, J=13.5 and 7.5Hz), 4.13 (2H, q, J=7.0Hz), 4.18 (1H, t), 6.70 (2H, d, J=8.5Hz), 7.00 (2H, d, J=8.5Hz), 7.15 (1H, s), 7.47 (1H, dd, J=8.3 and 1.3Hz), 7.85 (1H, d, J=8.3Hz), 7.95 (1H, br)

REFERENCE EXAMPLE 54

Preparation of ethyl 2-[4-[((2S)-1-tert-butoxycarbonyl-2-pyrrolidinyl)methoxy]phenyl]-3-(5-cyano-2-benzofuranyl)propionate 1.04 g of diethyl azodicarboxylate was added to 300 ml of a tetrahydrofuran solution containing 1 g of ethyl 3-(5-cyano-2-benzofuranyl )-2-(4-hydroxyphenyl)propionate, 1.2 g of (2S)-1-tert-butoxycarbonyl-2-pyrrolidinemethanol and 1.56 g of triphenylphosphine, and the thus prepared mixture was stirred at room temperature for 18 hours. To the resulting reaction solution were added 0.6 g of (2S)-1-tert-butoxycarbonyl-2-pyrrolidinemethanol, 0.78 g of triphenylphosphine and 0.52 g of diethyl azodicarboxylate, followed by additional stirring at room temperature for 18 hours. Thereafter, the reaction solution thus obtained was concentrated to dryness, and the resulting residue was purified by subjecting it to silica gel column chromatography using a toluene/ethyl acetate mixture as an eluant. In this way, 790 mg of the title compound was obtained in the form of colorless oil.

$^1$H-NMR (CDCl$_3$) δ:1.15 (3H, t), 1.46 (9H, s), 1.98 (4H, br), 3.0–4.2 (8H, m), 4.1 (2H), 6.37 (1H, s), 6.9 (2H, d), 7.2 (2H, d), 7.45 (2H), 7.76 (1H, s)

The following compounds of Reference Examples 55 to 61 were prepared in accordance with the procedure of Reference Example 54.

REFERENCE EXAMPLE 55 ethyl 3-[4-[((3S)-1-tert-butoxycarbonyl-3-pyrrolidinyl)oxy]phenyl]-3-(5-cyano-2-benzofuranyl)propionate $^1$H-NMR (CDCl$_3$) δ:1.16 (3H, t, J=7Hz), 1.46 (9H, s), 2.0–2.2 (2H, m), 2.8–3.2 (2H, m), 3.5–3.7 (4H, m), 4.10 (2H, q, J=7Hz), 4.5–4.7 (1H, m), 4.9 (1H, m), 6.49 (1H, s), 6.82 (2H, d, J=9Hz), 7.23 (2H, d, J=9Hz), 7.47 (2H, s), 7.80 (1H, s)

REFERENCE EXAMPLE 56 ethyl 5-[((3S)-1-tert-butoxycarbonyl-3-pyrrolidinyl)oxy]-2-[-2-(5-cyano-2-benzofuranyl)ethyl]benzoate $^1$H-NMR (CDCl$_3$) δ:1.38 (3H, t, J=7.0Hz), 1.48 (9H, s), 2.00–2.30 (2H, m), 2.96–3.76 (8H, m), 4.36 (2H, q), 4.90 (1H, br), 6.44 (1H, s), 6.93 (1H, dd, J=8.8 and 2.7Hz), 7.15 (1H, d, J=8.8Hz), 7.48 (1H, d, J=2.7Hz), 7.52 (2H, s), 7.80 (1H, s)

REFERENCE EXAMPLE 57 ethyl 2-[5-[((3S)-1-tert-butoxycarbonyl-3-pyrrolidinyl)oxy]-2-[2-(5-cyano-2-benzofuranyl)ethyl]phenyl]acetate $^1$H-NMR (CDCl$_3$) δ:1.25 (3H, t, J=7.0Hz), 1.47 (9H, s), 1.90–2.30 (2H, m), 3.04 (4H, s), 3.36–3.70 (6H, m), 4.16 (2H, q, J=7.0Hz), 4.90–5.12 (1H, br), 6.42 (1H, s), 6.60–6.80 (2H, m), 7.08 (1H, d, J=7.6Hz), 7.48 (2H, s), 7.77 (1H, d, J=0.87Hz)

REFERENCE EXAMPLE 58 ethyl 2-[2-[4-[((3S)-1-tert-butoxycarbonyl-3-pyrrolidinyl)oxy]phenyl]ethyl]-5-cyano-3-benzofurancarboxylate $^1$H-NMR (CDCl$_3$) δ:1.46 (12H, m), 2.05 (2H, m), 2.95 (2H, m), 3.5 (6H, m), 4.4(2H, q), 4.80 (1H, br), 6.82 (2H, d), 7.08 (2H, d), 7.55 (2H), 8.30 (1H)

REFERENCE EXAMPLE 59 ethyl 3-[5-[((3S)-1-tert-butoxycarbonyl-3-pyrrolidinyl)oxy]2-[2-(5-cyanobenzo[b]thien-2-yl)ethyl]-4-ethoxyphenyl]propionate $^1$H-NMR (CDCl$_3$) δ:1.23 (3H, t, J=7.2Hz), 1.33 (3H, t, J=7.0Hz), 1,47 (9H, s), 2.00–3.30 (10H, m), 3.4–3.7 (4H, m), 3.94 (2H, q, J=7.0Hz), 4.12 (2H, q, J=7.2Hz), 4.70–5.00 (1H, br), 6.67 (1H, s), 6.72 (1H, s), 7.05 (1H, s), 7.46 (1H, dd, J=8.4 and 1.6Hz), 7.84 (1H, d, J=8.4Hz), 7.95 (1H, d, J=1.6Hz)

REFERENCE EXAMPLE 60 ethyl 3-[5-[((3S)-1-tert-butoxycarbonyl-3-pyrrolidinyl)oxy]-2-[2-(5-cyanobenzo[b]thien-2-yl)ethyl]phenyl]propionate mp: 117°–119° C.
$^1$H-NMR (CDCl$_3$) δ:1.24 (3H, t, J=7.1Hz), 1.47 (9H, s), 1.6–3.6 (14H, m), 4.13 (2H, q, J=7.1Hz), 4.6–4.9 (1H, m), 6.50–7.20 (4H, m), 7.45 (1H, d, J=8.5Hz), 7.83 (1H, d, J =8.5Hz), 7.95 (1H, s)

REFERENCE EXAMPLE 61 ethyl 3-[4-[((3S)-1-tert-butoxycarbonyl-3-pyrrolidinyl)oxy]phenyl]-2-(5-cyanobenzo[b]thien-2-yl)propionate $^1$H-NMR (CDCl$_1$) δ:1.16 (3H, t, J=7.0Hz), 1.45 (9H, s), 3.08 (1H, dd, J=13.7 and 7.4Hz), 3.30–3.70 (5H, m), 4.11 (2H, q, J=7.0Hz), 4.00–4.30 (1H), 6.72 (2H, d, J=8.3Hz), 7.07 (2H, d, J=8.3Hz), 7.10 (1H, s), 7.40 (1H, dd, J=8.3 and 1.3Hz), 7.77 (1H, d, J=8.3Hz), 7.89 (1H, br)

REFERENCE EXAMPLE 62

Preparation of methyl 3-[5-cyano-2-benzofuranyl]-2-[4-[(tetrahydro-3-furanyl)oxy]phenyl]propionate In 30 ml of tetrahydrofuran were dissolved 3 g of 3-hydroxytetrahydrofuran, 6.5 g of methyl 2-(4-hydroxyphenyl)-2-oxoacetate and 9 g of triphenylphosphine. The thus prepared solution was mixed with 6.5 g of diethyl azodicarboxylate, and the mixture was stirred for 2 hours. After distilling off the solvent, the resulting residue was purified by subjecting it to silica gel column chromatography using dichloromethane as an eluant, thereby obtaining 7.5 g of methyl 2-4-[(tetrahydro-3-furanyl)oxy]phenyl]-2-oxoacetate in an oily form.

In a mixture solvent of 30 ml of tetrahydrofuran and 50 ml of methanol were dissolved 2.2 g of methyl 2-[4-[(tetrahydro-3-furanyl)oxy]phenyl]-2-oxoacetate obtained above and 3.6 g of (5-cyano-2-benzofuranyl)methyltriphenylphosphonium chloride. With ice cooling, to the thus prepared solution was added 1.5 ml of 1,8-diazabicyclo [5.4.0]-7-undecene. After 18 hours of stirring at room temperature, the reaction solution was concentrated to dryness, and the resulting residue was purified by subjecting it to silica gel column chromatography using a chloroform/acetone mixture as an eluant, thereby obtaining methyl 3-(5-cyano-2-benzofuranyl)-2-[4-[(tetrahydro-3-furanyl)oxy]phenyl]acrylate as a mixture of E and Z forms. The acrylic acid derivative thus obtained was dissolved in 80 ml of methanol, mixed with 4 g of palladium oxide.1H$_2$O.barium sulfate and then subjected to catalytic hydrogenation under normal pressure. Thereafter, the catalyst was removed by filtration, the resulting filtrate was concentrated to dryness, and the thus obtained residue was purified by subjecting it to silica gel column chromatography using a chloroform/acetone mixture as an eluant. In this way, 2.5 g of the title compound was obtained.

$^1$H-NMR (CDCl$_3$) δ:2.0–2.3 (2H, m), 3.2 (1H, dd), 3.6 (1H, dd), 3.65 (3H, s), 3.97 (2H, d), 3.8–4.2 (1H, m), 4.8–5.0 (1H, m), 6.40 (1H, s), 6.8 (2H, d), 7.25 (2H, d), 7.5 (2H, s), 7.79 (1H, s)

REFERENCE EXAMPLE 63

Preparation of methyl 3-(5-cyano-2-indolyl)-2-[4-[((3R)-tetrahydro-3-furanyl)oxy]phenyl]propionate In 30 ml of tetrahydrofuran were dissolved 3.0 g of (S)-(+)-3-hydroxytetrahydrofuran, 6.6 g of methyl 2-(4-hydroxyphenyl)-2-oxoacetate and 8.90 g of triphenylphosphine. The thus prepared solution was mixed with 6.0 g of diethyl azodicarboxylate, and the mixture was stirred for 2 hours. After distilling off the solvent, the resulting residue was purified by subjecting it to silica gel column chromatography using chloroform as an eluant, thereby obtaining 4.60 g of methyl 2-[4-[((3R)-tetrahydro-3-furanyl)oxy]phenyl]-2-oxoacetate in an oily form.

In a mixture solvent of 30 ml of tetrahydrofuran and 30 ml of methanol were dissolved 1.70 g of methyl 2-[4-[((3R)-tetrahydro-3-furanyl)oxy]phenyl]-2-oxoacetate obtained above and 3.0 g of (5-cyano-2-indolyl)methyltriphenylphosphonium bromide. To the thus prepared solution was added 2.1 ml of 1,8-diazabicyclo[5.4.0]-7-undecene during stirring under ice cooling, followed by stirring at room temperature for 2 hours. After distilling off the solvent, the resulting residue was purified by subjecting it to silica gel column chromatography using a chloroform/acetone mixture as an elution solvent, thereby obtaining methyl 3-(5-cyano-2-indolyl)-2-[4-[((3R)-tetrahydro-3-furanyl)oxy]phenyl]acrylate as a mixture of E and Z forms. The E/Z mixture thus obtained was dissolved in 50 ml of methanol, mixed with 4.0 g of palladium oxide.1H$_2$O.barium sulfate and then subjected to catalytic hydrogenation under normal pressure for 3 hours. Thereafter, the catalyst was removed by filtration, solvent in the resulting filtrate was distilled off, and the thus obtained residue was purified by subjecting it to silica gel column chromatography using a chloroform/acetone mixture as an elution solvent. In this way, 1.50 g of the title compound was obtained as a viscous oily material.

$^1$H-NMR (CDCl$_3$) δ:3.10 (1H, dd), 3.60 (3H, s), 3.78–4.10 (5H, m), 4.75–5.00 (1H, m), 6.25 (1H, br), 6.80 (2H, d), 7.20 (2H, d), 7.30–7.90 (3H, m), 10.00 (1H, s)

REFERENCE EXAMPLE 64

Preparation of methyl 3-(5-cyano-2-indolyl)-2-[4-[((3S)-tetrahydro-3-furanyl)oxy]phenyl]propionate a) In 80 ml of tetrahydrofuran were dissolved 5.0 g of (S)-(+)-3-hydroxytetrahydrofuran, 3.3 g of formic acid and 17.0 g of triphenylphosphine. With ice cooling and with stirring, 12.0 g of diethyl azodicarboxylate was added dropwise to the above solution. After stirring at room temperature for 2 hours, the solvent was distilled off, and the resulting residue was purified by subjecting it to silica gel column chromatography using chloroform as an elution solvent, thereby obtaining (S)-(+)-tetrahydro-3-furanyl formate which was subsequently dissolved in 50 ml of ethanol. With stirring, 5.0 g of sodium hydroxide dissolved in 5 ml of water was added to the above ester solution, followed by stirring for 3 hours. After distilling off the solvent, the resulting residue was dissolved in diethyl ether, and insoluble materials were removed by filtration. By distilling off the solvent, 4.50 g of crude (R)-(−)-3-hydroxytetrahydrofuran was obtained.

b) The crude (R)-(−)-3-hydroxytetrahydrofuran obtained in the above step a) was treated in the same manner as described in Reference Example 63 to obtain 1.50 g of the title compound as a viscous oily material.

$^1$H-NMR (CDCl$_3$) δ:3.15 (1H, dd), 3.65 (3H, s), 3.80–4.20 (5H, m), 4.80–5.05 (1H, m), 6.30 (1H, br), 6.82 (2H, d), 7.22 (2H, d), 7.30–7.90 (3H, m), 9.30 (1H, br)

REFERENCE EXAMPLE 65

Preparation of methyl 3-[4-[((3S)-1-tert-butoxycarbonyl-3-pyrrolidinyl)oxy]phenyl]-2-(5-cyano-2-benzofuranyl)propionate a) 21.0 g of 2-acetyl-5-benzofurancarbonitrile was dissolved in 300 ml of dichloromethane. With stirring at a temperature of −10° C., 30 ml of dichloromethane solution containing 18.2 g of bromine was added dropwise to the above solution. After gradually warming up to ice-cold temperature, the resulting reaction solution was mixed with chloroform and washed with 10% sodium thiosulfate aqueous solution. After drying the organic layer and subsequent concentration to dryness, the resulting residue was recrystallized from a benzene/n-hexane mixture to obtain 21.0 g of 2-(2-bromo-1-oxoethyl)-5-benzofurancarbonitrile in the form of colorless crystals.

mp: 156°–158° C.

IR (KBr): 2228, 1696, 1616, 1564, 1290, 1166, 1122 cm$^{-1}$ $^1$H-NMR (CDCl$_3$) δ: 4.44 (2H, s), 7.60–7.90 (3H, m), 8.11 (1H, s),

FD MS (m/z): 263 (M$^+$), 265 (M$^+$)

b) 444 mg of selenium dioxide was dissolved in 10 ml of dry methanol with heating, followed by the addition of 1.056 g of 2-(2-bromo-1-oxoethyl)-5-benzofurancarbonitrile obtained in the above step a). The thus prepared mixture was refluxed under heating for 12 hours. After cooling, insoluble materials were removed by filtration, and the resulting filtrate was concentrated to dryness. Thereafter, the resulting residue was purified by subjecting it to silica gel column chromatography using a toluene/ethyl acetate mixture as an eluant, thereby obtaining 129 mg of methyl 2-(5-cyano-2-benzofuranyl)-2-oxoacetate in the form of colorless needle crystals.

mp: 196°–199° C.

IR (KBr): 1740, 1674, 1614, 1552 cm$^{-1}$ $^1$H-NMR (CDCl$_3$) δ:4.03 (3H, s), 7.66–7.96 (2H, m), 8.17 (2H, s)

FD MS (m/z): 321 (M$^+$+92), 229 (M$^+$)

c) 3.1 g of methyl 2-(5-cyano-2-benzofuranyl)-2-oxoacetate obtained in the above step b) and 6.2 g of (4-methoxyphenyl)methyltriphenylphosphonium chloride were dissolved in a mixture solvent of 100 ml of tetrahydrofuran and 100 ml of methanol. With stirring at room temperature, 2.19 g of 1,8-diazabicyclo[5.4.0]-7-undecene was added to the above solution, and the stirring was continued for 1 hour. To this were further added 1.3 g of (4-methoxyphenyl)methyltriphenylphosphonium chloride and 0.65 g of 1,8-diazabicyclo[5.4.0]-7-undecene. After stirring for 1 hour and subsequently removing the solvent by distillation, the resulting residue was purified by subjecting it to silica gel column chromatography using chloroform as an eluant, thereby obtaining a viscous and oily olefinic compound as a mixture of E and Z forms.

$^1$H-NMR (CDCl$_3$) δ:3.78 (1.5H, s), 3.84 (3H, s), 3.87 (1.5H, s), 6.60 (9H, m)

The olefinic compound obtained above was dissolved in a solvent mixture of 100 ml of tetrahydrofuran and 100 ml of methanol, followed by the addition of 1.1 g of palladium.1H$_2$O.bariumsulfate and by subsequent catalytic hydrogenation under normal pressure for 3 hours. After removing the catalyst by filtration and distilling off the solvent, the resulting residue was purified by subjecting it to silica gel column chromatography to obtain 4.2 g of viscous and oily methyl 2-(5-cyano-2-benzofuranyl)-3-(4-methoxyphenyl)propionate.

$^1$H-NMR (CDCl$_3$) δ:3.20 (1H, dd, J=14.4 and 7.8Hz), 3.41 (1H, dd, J=14.4 and 7.4Hz), 3.69 (3H, s), 3.75 (3H, s), 4.10 (1H, dd, J=7.8 and 7.4Hz), 6.60 (1H, s), 6.76 (2H, d, J=8.8Hz), 7.05 (2H, d, J=8.8Hz), 7.53 (2H), 7.82 (1H, s)

d) 4.2 g of methyl 2-(5-cyano-2-benzofuranyl)-3-(4-methoxyphenyl)propionate obtained in the above step c) was dissolved in 150 ml of dichloromethane, and the solution was cooled down to −50° C. With stirring, to this was added dropwise 30 ml of a dichloromethane solution containing 9.97 g of boron tribromide. The temperature of the resulting reaction solution was gradually increased to 15° C. After 30 minutes of stirring at this temperature, the reaction solution was diluted with chloroform, washed with dilute hydrochloric acid, and then dried to distill off the solvent. The resulting residue was subjected to silica gel column chromatography using a chloroform/ethanol mixture as an eluant, and the solvent in pooled fractions of interest was concentrated to precipitate crystals. The crystals thus precipitated were washed with benzene, and collected by filtration, thereby obtaining 3.1 g of methyl 2-(5-cyano-2-benzofuranyl)-3-(4-hydroxyphenyl)propionate in the form of colorless crystals. mp: 110°–111° C.

IR (KBr): 2228, 1722, 1594, 1518, 1272 cm$^{-1}$ $^1$H-NMR (CDCl$_3$) δ: 3.18 (1H, dd, J=14.4 and 7.8Hz), 3.36 (1H, dd, J=14.4 and 7.4Hz), 3.69 (3H, s), 4.09 (1H, dd, J=7.8 and 7.4Hz), 6.60 (1H, s), 6.69 (2H, d, J=8.4Hz), 7.00 (2H, d, J=8.4Hz), 7.53 (2H, s), 7.83 (1H, s)

e) In 150 ml of dry tetrahydrofuran were dissolved 3.0 g of methyl 2-(5-cyano-2-benzofuranyl)-3-(4-hydroxyphenyl)propionate obtained in the above step d), 1.92 g of (3R)-1-tert-butoxycarbonyl-3-hydroxypyrrolidine and 2.69 g of triphenylphosphine. With stirring at room temperature, 1.79 g of diethyl azodicarboxylate was added to the thus prepared solution, and the stirring was continued for 1 hour. After distilling off the solvent, the resulting residue was subjected to silica gel column chromatography using a toluene/ethyl acetate mixture as an eluant, thereby obtaining a mixture consisting of the starting material methyl 2-(5-cyano-2-benzofuranyl)-3-(4-hydroxyphenyl)propionate and the title compound.

The mixture thus obtained was dissolved in 100 ml of tetrahydrofuran. To this were added 0.95 g of (3R)-1-tert-butoxycarbonyl-3-hydroxypyrrolidine, 1.35 g of triphenylphosphine and 0.85 g of diethyl azodicarboxylate in that order. The resulting mixture was stirred at room temperature for 16 hours. Thereafter, the resulting reaction solution was treated and purified in the same manner as described above to obtain 2.02 g of the title compound in a viscous and oily form.

$^1$H-NMR (CDCl$_3$) δ:1.46 (9H, s), 1.88–2.24 (2H, m), 3.10–3.60 (6H, m), 3.69 (3H, s), 4.10 (1H, t), 4.81 (1H, br), 6.61 (1H, s), 6.73 (2H, d, J=8.3Hz), 7.04 (2H, d, J=8.3Hz), 7.54 (2H, s), 7.83 (1H, s)

FD MS (m/z): 321 (M$^+$)

REFERENCE EXAMPLE 66

Preparation of ethyl 3-[4-[((3S)-1-tert-butoxycarbonyl-3-pyrrolidinyl)oxy]phenyl]-4-5-cyanobenzo[b]thien-2-yl)-butyrate a) 14.2 g of ethyl 2-ethoxycarbonyl-2-(4-methoxyphenyl)acetate was dissolved in 150 ml of tetrahydrofuran. 2.6 g of sodium hydride (oil type, 60%) was added to the above solution while stirring under ice cooling, and the stirring was continued for 20 minutes. To this was further added 17.2 g of 5-bromo-2-bromomethylbenzo[b]thiophene. After stirring at room temperature for 18 hours, the resulting reaction solution was mixed with ammonium chloride aqueous solution, and then extracted with ethyl acetate. After drying to distill off the solvent, the resulting residue was subjected to silica gel column chromatography using chloroform as an elution solvent, thereby obtaining 24.2 g of ethyl 3-(5-bromobenzo[b]thien-2-yl)-2-ethoxycarbonyl-2-(4-methoxyphenyl)propionate.

$^1$H-NMR (CDCl$_3$) δ:1.2 (6H, t), 3.78 (3H, s), 3.85 (2H, s), 6.75–7.0 (3H, m), 7.2–7.8 (5H, m)

b) A solution of 7.3 g of potassium hydroxide dissolved in 20 ml of water was added to 200 ml of an ethanol solution containing 24.2 g of 3-(5-bromobenzo[b]thien-2-yl)-2-ethoxycarbonyl-2-(4-methoxyphenyl)propionate obtained in the above step a), and the thus prepared mixture was stirred for 4 days. The resulting reaction solution was poured into cooled dilute hydrochloric acid to collect precipitated crystals by filtration. The thus collected crystals were dissolved in ethyl acetate, and then dried. After distilling off the solvent, the resulting residue was dissolved in 200 ml of ethanol, mixed with 3 ml of concentrated sulfuric acid, and then refluxed under heating for 2 hours. After cooling, the resulting reaction solution was concentrated, mixed with chloroform, washed with water, and then dried. After distilling off the solvent, the resulting residue was purified by subjecting it to silica gel column chromatography using chloroform as an eluant, thereby obtaining 20 g of ethyl 3-(5-bromobenzo[b]thien-2-yl)-2-(4-methoxyphenyl)propionate.

$^1$H-NMR (CDCl$_3$) δ: 1.17 (3H, t), 3.2 (1H, dd), 3.55 (1H, dd), 3.77 (3H, s), 3.81 (1H, dd), 4.10 (2H, q), 6.82 (2H, d), 7.2–7.8 (6H, m)

c) 20 g of ethyl 3-(5-bromobenzo[b]thien-2-yl)-2-(4-methoxyphenyl)propionate obtained in the above step b) was dissolved in 200 ml of tetrahydrofuran, followed by the addition of 12 g of sodium borohydride. To the mixture was added dropwise 80 ml of methanol under ice cooling. After stirring for 3 hours, the resulting reaction solution was adjusted to pH 6 with concentrated hydrochloric acid, and then extracted with ethyl acetate. The resulting organic layer was dried to distill off the solvent, and the thus obtained residue was subjected to silica gel column chromatography using a chloroform/methanol mixture as an elution solvent to obtain 16 g of 3-(5-bromobenzo[b]thien-2-yl)-2-(4-methoxyphenyl)-1-propanol.

$^1$H-NMR (CDCl$_3$) δ:2.9–3.4 (3H, m), 3.73 (3H, s), 3.62–3.90 (2H, br), 6.70–7.80 (8H, m)

d) 16 g of 3-(5-bromobenzo[b]thien-2-yl)-2-(4-methoxyphenyl)-1-propanol obtained in the above step c) was dissolved in 40 ml of dichloromethane. To the mixture were added 6.3 ml of triethylamine and 4 ml of methanesulfonyl chloride while stirring under ice cooling. After stirring at the same temperature for 2 hours, the resulting reaction solution was mixed with dichloromethane, washed with water and then dried. After distilling off the solvent, the resulting residue was purified by subjecting it to silica gel column chromatography using chloroform as an elution solvent, thereby obtaining 18.5 g of 3-(5-bromobenzo[b]-thien-2-yl)-2-(4-methoxyphenyl)propyl methanesulfonate.

$^1$H-NMR (CDCl$_3$) δ: 3.78 (3H, s), 3.9–4.5 (3H, m), 3.70 (3H, s), 4.3 (2H, m), 6.70–7.80 (8H, m)

e) 1.2 g of sodium cyanide was dissolved in 30 ml of dimethyl sulfoxide at a temperature of 90° C. To this was gradually added 18.5 g of 3-(5-bromobenzo[b]thien-2-yl)-2-(4-methoxyphenyl)propyl methanesulfonate, followed by stirring at 80° C. for 1 hour. The resulting reaction solution was mixed with an ethyl acetate/toluene mixture, washed with water, and then dried to distill off the solvent. Crystals thus precipitated were washed with ethanol and dried to obtain 5 g of 3-(5-bromobenzo[b]thien-2-yl)-2-(4-methoxyphenyl)butyronitrile. The same compound was also obtained with a yield of 2 g, by concentrating the ethanol solution resulting from the washing of crystals and subjecting the concentrate to silica gel column chromatography using chloroform as an elution solvent.

$^1$H-NMR (CDCl$_3$) δ:2.5–2.7 (2H, br), 3.2–3.4 (3H, br), 3.76 (3H, s), 6.70–7.80 (8H, m)

MS m/z: 386, 388 f) 7 g of 3-(5-bromobenzo[b]thien-2-yl)-2-(4-methoxyphenyl)butyronitrile obtained in the above step e) was suspended in 80 ml of ethanol, followed by the addition of 5 ml of concentrated sulfuric acid and a few drops of water. The thus prepared mixture was refluxed under heating for 7 days. After distilling off the solvent, the thus obtained reaction solution was mixed with chloroform and water, and the resulting organic layer was dried to distill off the solvent. Thereafter, the resulting residue was subjected to silica gel column chromatography using chloroform as an elution solvent to obtain 6.3g of ethyl 4-(5-bromobenzo[b]thien-2-yl)-3-(4-methoxyphenyl)butyrate.

$^1$H-NMR (CDCl$_3$) δ: 1.12 (3H, t), 2.65 (2H, dd), 3.10–3.80 (3H, m), 3.76 (3H, s), 4.01 (2H, q), 6.70–6.95 (3H, m), 7.10 (2H, d), 7.20–7.40 (1H), 7.55 (1H, d), 7.72 (1H, d)

FAB MS (m/z): 433, 435 g) 6.0 g of ethyl 4-(5-bromobenzo[b]thien-2-yl)-3-(4-methoxyphenyl)butyrate obtained in the above step f) was dissolved in 50 ml of N-methyl-2-pyrrolidone, followed by the addition of 1.6 g of cuprous cyanide and a catalytically effective amount of copper sulfate. The mixture thus prepared was stirred at a temperature of 190° to 200° C. in a stream of argon. After cooling, the resulting reaction solution was mixed with ethyl acetate and toluene and then washed with water, followed by drying to distill off the solvent. Thereafter, the resulting residue was purified by subjecting it to silica gel column chromatography using a chloroform/acetone mixture as an elution solvent, thereby obtaining 4.5 g of ethyl 4-(5-cyanobenzo[b]thien-2-yl)-3-(4-methoxyphenyl)butyrate.

$^1$H-NMR (CDCl$_3$) δ: 1.18 (3H, t), 2.70 (2H, dd), 3.16–3.70 (3H, m), 3.78 (3H, s), 4.02 (2H, q), 6.85 (2H, d), 6.98 (1H, s), 7.18 (2H, d), 7.5 (1H, dd), 7.8 (1H, d), 7.96 (1H, d)

h) 4.5 g of ethyl 4-(5-cyanobenzo[b]thien-2-yl)-3-(4-methoxyphenyl)butyrate obtained in the above step g) was dissolved in 20 ml of dichloromethane. 3.4 ml of boron tribromide was added to the above solution which has been cooled down to −70° C. The thus prepared mixture was warmed up to room temperature, and stirred for 1 hour.

Chipped ice was added to the resulting reaction solution to collect a dichloromethane layer which was subsequently dried to distill off the solvent. The resulting residue was dissolved in 50 ml of tetrahydrofuran. With stirring under ice cooling in a stream of argon, 1.9 g of (3R)-1-tert-butoxycarbonyl-3-hydroxypyrrolidine, 3.2 g of triphenylphosphine and 2.3 g of diethyl azodicarboxylate were added to the resulting mixture. The thus prepared mixture was stirred at room temperature for 18 hours. After distilling off the solvent, the resulting residue was purified by subjecting it to silica gel column chromatography using a n-hexane/ethyl acetate mixture as an elution solvent. In this way, 4 g of the title compound was obtained.

$^1$H-NMR (CDCl$_3$) δ:1.48 (9H, s), 1.95–2.20 (2H, m), 2.65 (2H, dd), 3.15–3.70 (7H, m), 4.78–5.00 (1H, m), 6.80 (2H, d), 6.98 (1H, s), 7.17 (2H, d), 7.5 (1H, dd), 7.82 (1H, d), 7.98 (1H, d)

REFERENCE EXAMPLE 67

Preparation of ethyl 2-[4-[((3S)-1-tert-butoxycarbonyl-3-pyrrolidinyl)thio]phenyl]-3-(5-cyanobenzo[b]thien-2-yl)-2-yl)-2-ethoxycarbonylpropionate a) 20.2 g of ethyl 4-mercaptophenylacetate was dissolved in 450 ml of tetrahydrofuran. With ice cooling and with stirring, 21.0 g of (3R)-1-tert-butoxycarbonyl-3-hydroxypyrrolidine, 29.4 g of triphenylphosphine and 19.5 g of diethyl azodicarboxylate were added to the above solution. The thus prepared mixture was stirred at room temperature for 18 hours. After distilling off the solvent, the resulting residue was purified by subjecting it to silica gel column chromatography using a n-hexane/ethyl acetate mixture as an elution solvent, thereby obtaining 7.0 g of ethyl 2-[4-[((3S)-1-tert-butoxycarbonyl-3-pyrrolidinyl)thio]phenyl]acetate.

$^1$H-NMR (CDCl$_3$) δ:1.25 (3H, t, J=7.2Hz), 1.45 (9H, s), 1.7–2.4 (2H, m), 3.2–4.4 (5H, m), 3.58 (2H, s), 4.15 (2H, q, J=7.2Hz), 7.0–7.6 (4H, m)

b) 4.0 g of ethyl 2-[4-[((3S)-1-tert-butoxycarbonyl-3-pyrrolidinyl)thio]phenyl]acetate obtained in the above step a) was dissolved in 21 ml of N,N-dimethylformamide, followed by the addition of 4.02 ml of diethyl carbonate. With stirring at a temperature of 130° C., 530 mg (60%) of sodium hydride was added to the thus prepared solution, and the resulting mixture was stirred for 10 minutes, followed by further adding 106 mg of sodium hydride and by additional stirring for 10 minutes. The resulting reaction solution was poured into ice water, neutralized with dilute hydrochloric acid, extracted with ethyl acetate, and then dried. After distilling off the solvent, the resulting residue was purified by subjecting it to silica gel column chromatography using a n-hexane/ethyl acetate mixture as an elution solvent, thereby obtaining 1.74 g of ethyl 2-[4-[((3S)-1-tert-butoxycarbonyl-3-pyrrolidinyl)thio]phenyl]-2-ethoxycarbonylacetate in an oily form.

$^1$H-NMR (CDCl$_3$) δ:1.27 (6H, t, J=7.2Hz), 1.46 (9H, s), 1.4–2.4 (2H, m), 3.0 –4.0 (5H, m), 4.22 (4H, q, J=7.2Hz), 4.58 (1H, s), 7.2–7.5 (4H, m)

c) 1.7 g of ethyl 2-[4-[((3S)-1-tert-butoxy-carbonyl-3-pyrrolidinyl)thio]phenyl]-2-ethoxycarbonyl acetate obtained in the above step b) was dissolved in a solvent mixture of 20 ml of tetrahydrofuran and 1 ml of N,N-dimethylformamide, followed by the addition of 155 mg of sodium hydride (60%) and by subsequent stirring for 20 minutes. 980 mg of 2-bromomethylbenzo[b]thiophene-5-carbonitrile was added to the above reaction solution, and the mixture was stirred for 24 hours. The resulting reaction solution was poured into ice water, extracted with ethyl acetate, and then dried. After distilling off the solvent, the resulting residue was purified by subjecting it to silica gel column chromatography using a n-hexane/ethyl acetate mixture as an elution solvent, thereby obtaining 2.05 g of the title compound in an oily form.

$^1$H-NMR (CDCl$_3$) δ:1.23 (6H, t, J=7.2Hz), 1.46 (9H, s), 1.50–2.50 (2H, m), 3.2–4.4 (5H, m), 3.89 (2H, s), 4.25 (4H, q, J=7.2Hz), 7.28 (4H, s), 7.44 (1H, dd, J=8.4 and 1.5Hz), 7.78 (1H, d, J=8.4Hz), 7.91 (1H, dd)

REFERENCE EXAMPLE 68

Preparation of ethyl 2-[4-[((3S)-1-tert-butoxycarbonyl-3-pyrrolidinyl)oxy]phenyl]-3-(5-cyanobenzo[b]thien-2-yl)-2-propionate In a solvent mixture of 50 ml of tetrahydrofuran and 50 ml of ethanol were dissolved 3.0 g of (5-cyanobenzo[b]thien-2-yl)methyltriphenylphosphoniumchloride and 2.55 g of ethyl 2-[4-[((3S)-1-tert-butoxycarbonyl-3-pyrrolidinyl)oxy]phenyl]-2-oxoacetate. With stirring at room temperature, 1.07 g of 1,8-diazabicyclo[5.4.0]-7-undecene was added to the thus prepared solution, and the resulting mixture was stirred for 1 hour at room temperature. After distilling off the solvent, the resulting residue was purified by subjecting it to silica gel column chromatography using a toluene/ethyl acetate mixture as an eluant, thereby obtaining ethyl 2-[4-[((3S)-1-tert-butoxycarbonyl-3-pyrrolidinyl)oxy]phenyl]-3-(5-cyanobenzo[b]thien-2-yl)acrylate as a mixture of E and Z forms. The thus obtained compound was dissolved in a solvent mixture of 50 ml of tetrahydrofuran and 50 ml of ethanol, and the resulting solution was mixed with 5.0 g of 10% palladium carbon catalyst (50% wet type), and subjected to catalytic hydrogenation under normal pressure. After removing the catalyst by filtration and distilling off the solvent, the resulting residue was purified by subjecting it to silica gel column chromatography using a toluene/ethyl acetate mixture as an eluant, thereby obtaining 2.2 g of the title compound in a viscous and oily form.

$^1$H-NMR (CDCl$_3$) δ: 1.17 (3H, t, J=7.0Hz), 1.47 (9H, s), 1.90–2.20 (2H, m), 3.10–3.95 (7H, m), 4.10 (2H, q, J=7.0Hz), 4.84 (1H, br), 6.81 (2H, d, J=9.0Hz), 7.20 (1H, s), 7.25 (2H, d, J=9.0Hz), 7.44 (1H, dd, J=9.0 and 1.6Hz), 7.81 (1H, dd, J=9.0 and 1.6Hz), 7.94 (1H, s)

The following compounds of Reference Examples 69 to 75 were prepared in accordance with the procedure described in Reference Example 68.

REFERENCE EXAMPLE 69 ethyl 2-[4-[2-(tert-butoxycarbonylamino)-1-tert-butoxycarbonylaminomethyl)ethoxy]phenyl]-3-(5-cyanobenzo[b]thien-2-yl)propionate viscous oil $^1$H-NMR (CDCl$_3$) δ: 1.25 (3H, t, J=7.0Hz), 1.45 (18H, s), 2.90–4.50 (8H, m), 6.80–7.35 (5H, m), 7.45 (1H, dd, J=8.3 and 1.3Hz), 7.80 (1H, d, J=8.3Hz), 7.93 (1H)

REFERENCE EXAMPLE 70 ethyl 2-[4-[((2S)-1-tert-butoxycarbonyl-2-pyrrolidinyl)methoxy]phenyl]-3-(5-cyanobenzo[b]thien-2-yl)propionate $^1$H-NMR (CDCl$_3$) δ:1.17 (3H,t), 1.47 (9H, s), 2.00 (4H, br), 3.40 (2H, br), 3.60–4.30 (6H), 6.90 (2H, d, J=10Hz), 7.25 (2H, d, J=10Hz), 7.00–8.00 (4H, m)

REFERENCE EXAMPLE 71 ethyl 2-[4-[(1-tert-butoxycarbonyl-4-piperidinyl)oxy]phenyl]-3-(5-cyanobenzo[b]thien-2-yl)propionate solid $^1$H-NMR (CDCl$_3$) δ: 1.10 (3H, t, J=6.0Hz), 1.50 (9H, s), 1.70–2.00 (4H, m), 3.20–4.00 (4H, m), 4.15 (2H, q), 4.30–4.60 (1H, br), 6.80–8.10 (8H)

REFERENCE EXAMPLE 72 ethyl 2-[4-(2-tert-butoxycarbonylaminoethoxy)phenyl]-3-(5-cyanobenzo[b]thien-2-yl)propionate viscous oil $^1$H-NMR (CDCl$_3$) δ:1.16 (3H, t, J=7.0Hz), 1.45 (9H, s), 3.05–4.40 (9H), 5.12 (1H, br), 6.84 (2H, d, J=8.3Hz), 7.01 (1H, s), 7.25 (2H, d, J=8.3Hz), 7.41 (1H, dd, J=8.3 and 1.2Hz), 7.77 (1H, d, J=8.3Hz), 7.89 (1H, s)

REFERENCE EXAMPLE 73 ethyl 2-[4-[((2S)-1-tert-butoxycarbonyl-5-oxo-2-pyrrolidinyl)methoxy]phenyl]-3-(5-cyanobenzo[b]thien-2-yl)propionate viscous oil $^1$H-NMR (CDCl$_3$) δ:1.17 (3H, t), 1.42 (9H,s), 1,80–2.25 (2H, m), 2.30–2.60 (2H, m), 3.20 (1H, dd), 3.37 (1H, dd), 3.50–3.82 (1H, dd), 3.82–4.50 (4H, m), 4.80–5.10 (1H, m), 6.75–8.10 (8H, m)

REFERENCE EXAMPLE 74 ethyl 2-[4-[((2R, 4S)-1-tert-butoxycarbonyl-2-methyl-4-pyrrolidinyl)oxy]phenyl]-3-(6-cyanobenzo[b]thien -2-yl)propionate $^1$H-NMR (CDCl$_3$) δ:1.15–1.50 (6H, m), 1.50 (9H, s), 1.80–2.60 (2H, m), 3.00–4.50 (8H, m), 4.80–5.10 (1H, m), 6.80–8.20 (8H, m)

REFERENCE EXAMPLE 75 ethyl 2-[4-[((3S)-1-tert-butoxycarbonyl-3-pyrrolidinyl)oxy]phenyl]-3-(6-cyanobenzo[b]thien-2-yl)propionate $^1$H-NMR (CDCl$_3$) β:1.17 (3H, t), 1.46 (9H, s), 2.10 (2H, m), 3.60 (6H, m), 3.83 (1H, m), 4.10 (2H, q), 4.85 (1H, br), 6.86 (2H, d), 7.04 (1H, s), 7.25 (2H), 7.55 (1H, dd), 7.65 (1H, d), 8.04 (1H)

REFERENCE EXAMPLE 76

Preparation of ethyl (+)-2-[4-[((2S)-1-tert-butoxycarbonyl-2-pyrrolidinyl)methoxy]phenyl]-3-(5-cyanobenzo[b]thien-2-yl)propionate and ethyl (−)-2-[4-[((2S)-3-pyrrolidinyl)methoxy]phenyl]-3-(5-cyanobenzo[b]thien-2-yl)propionate 5.0 g of ethyl 2-[4-[((2S)-1-tert-butoxycarbonyl-2-pyrrolidinyl)methoxy]phenyl]-3-(5-cyanobenzo[b]thien-2-yl)propionate was separated into (+) and (−) forms using a column for optical isomer separation, thereby obtaining 2.5 g (+) and 1.7 g (−) of the title compounds.

(−) form:

mp: 102°–104° C.

$[α]_D^{24}$=−142.00 (c=1,000, EtOH)

¹H-NMR (CDCl₃) δ:1.13–1.22 (3H, m), 1.47 (9H, s), 1.80–2.10 (4H, m), 3,25–3.50 (4H, m), 3.64–3.75 (1H, m), 3.70–3.90 (1H, br), 3.90 (1H, br), 4.05–4.20 (4H, m), 6.88 (2H, d, J =8.3Hz), 7.02 (1H, s), 7.23 (2H, d, J=8.3Hz), 7.45 (1H, d, J=8.3Hz), 7.80 (1H, d, J=8.3Hz), 7.94 (1H, s)

HPLC: Column; an amylose-based column for use in the separation of optical isomers (CHIRALPAK AD, 20 φ×250 mm, Daicel Chemical Industries, Ltd.)
Solvent; n-hexane:iso-propanol=70:30
Flow rate; 4 ml/min
Retention time; 20 to 23 minutes (+) form:
mp: 111°–112° C.
$[\alpha]_D^{24}$=+55.19 (c=1.000, EtOH)
¹H-NMR (CDCl₃) δ:1.13–1.22 (3H, m), 1.47 (9H, s), 1.80–2.10 (4H, m), 3.25–3.50 (4H, m), 3.64–3.75 (1H, m), 3.70–3.90 (1H, br), 3.90 (1H, br), 4.05–4.20 (4H, m), 6.88 (2H, d, J =8.3Hz), 7.02 (1H, s), 7.23 (2H, d, J=8.3Hz), 7.45 (1H, d, J=8.3Hz), 7.80 (1H, d, J=8.3Hz), 7.94 (1H, s)

HPLC: Column; an amylose-based column for use in the separation of optical isomers (CHIRALPAK AD, 20 φ×250 mm, Daicel Chemical Industries, Ltd.)
Solvent; n-hexane:iso-propanol=70:30
Flow rate; 4 ml/min
Retention time; 23 to 27 minutes

REFERENCE EXAMPLE 77

Preparation of ethyl (−) -2-[4-[(1-tert-butoxycarbonyl-4-piperidinyl)oxy]phenyl]-3-(7-cyano-2-naphthyl)propionate and ethyl (+)-2-[4-[(1-tert-butoxycarbonyl-4-piperidinyl)oxy]phenyl]-3-(7-cyano-2-naphthyl)propionate These compounds were prepared in the same manner as described in Reference Example 76.
(−) form:
$[\alpha]_D^{24}$=−100.78° (c=1.024, CHCl₃)
¹H-NMR (CDCl₃) δ:1.11 (3H, t, J=6.9Hz), 1.47 (9H, s), 1.70–1.80 (2H, m), 1.85–1.95 (2H, m), 3.15–3.20 (1S, m), 3.30–3.40 (2H, m), 3.50–3.60 (1H, m), 3.65–3.75 (2H, m), 3.85–3.90 (1H, br), 4.0–4.1 (2H, m), 4.40–4.45 (1H, m), 6.85 (2H, d, J=8.3Hz), 7.23 (2H, d), 7.40–7.45 m), 7.53–7.58 (1H, m), 7.62 (1H, s), 7.77 (2H, d), 7.85 (1H, d, J=8.3Hz), 8.12 (1H, s)

HPLC: Column; an amylose-based column for use in the separation of optical isomers (CHIRALPAK AD, 4.6 φ×250 mm, Daicel Chemical Industries, Ltd.)
Solvent; n-hexane:iso-propanol=90:10
Flow rate; 1 ml/min
Retention time; 26.9 minutes (+) form:
$[\alpha]_D^{24}$=+95.84° (c=1.010, CHCl₃)
¹H-NMR (CDCl₃) δ:1.11 (3H, t, J=7.3Hz), 1.65–1.70 (2H, m), 1.85–2.00 (2H, m), 3.15–3.20 (1H, m), 3.30–3.35 (2H, m), 3.50–3.60 (1H, m), 3.65–3.75 (2H, m), 3.85–3.90 (1H, br),4.0–4.1 (2H, m), 4.40–4.45 (1H, m), 6.85 (2H, d, J=8.8Hz), 7.23 (2H, d, J=8.3Hz), 7.40–7.45 (m, 1H, Ar-H), 7.52–7.57 (1H, m), 7.62 (1H, s), 7.77 (1H, d, J=8.3Hz), 7.85 (1H, d, J=8.3Hz), 8.11(1H, s)

HPLC: Column; an amylose-based column for use in the separation of optical isomers (CHIRALPAK AD, 4.6 φ×250 mm, Daicel Chemical Industries, Ltd.)
Solvent; n-hexane:iso-propanol=90:10
Flow rate; 1 ml/min
Retention time; 31 minutes

REFERENCE EXAMPLE 78

Preparation of ethyl (+)-2-[4-[((2S)-1-tert-butoxycarbonyl-2-pyrrolidinyl)methoxy]phenyl]-3-(5-cyanobenzo[b]thien-2-yl)propionate 54.0 g of 2-[4-[((2S)-1-tert-butoxycarbonyl-2-pyrrolidinyl)methoxy]phenyl]-3-(5-cyanobenzo[b]thien-2-yl)propionate was dissolved in 400 ml of dry ethanol during heating, and 800 ml of dry n-hexane was added to the resulting solution. To the thus prepared mixture were added 100 mg of sodium hydride and seed crystals of ethyl (+)-2-[4-[((2S)-1-tert-butoxycarbonyl-2-pyrrolidinyl)methoxy]phenyl]-3-(5-cyanobenzo[b]thien-2-yl)propionate. After stirring at room temperature for 4 hours, the thus stirred mixture was further mixed with 100 mg of sodium hydride, and the stirring was continued for additional 18 hours at room temperature, followed by collecting precipitated crystals by filtration. The thus collected crystals were recrystallized from 22 volumes (w/v) of an ethanol/n-hexane mixture (30:70, w/v). By repeating the recrystallization step three times, 37.0 g of the title compound was obtained with a diastereoisomer purity of 99.5% or more.

REFERENCE EXAMPLE 79

Preparation of ethyl (+)-2-[4-[((3S)-tert-butoxycarbonyl-3-pyrrolidinyl)oxy]phenyl]-3-(7-cyano-2-naphthyl)propionate This compound was obtained in similar manner to the procedure of Reference Example 78.

REFERENCE EXAMPLE 80

Preparation of ethyl 2-[4-[((2R)-1-tert-butoxycarbonyl-2-pyrrolidinyl)methoxy]phenyl]-3-(5-cyanobenzo[b]thien-2-yl)-2-ethoxycarbonylpropionate 4.1 g of ethyl 2-[4-[((2R)-1-tert-butoxycarbonyl-2-pyrrolidinyl)methoxy]phenyl]-2-ethoxycarbonylacetate was dissolved in 100 ml of tetrahydrofuran. At room temperature, the thus prepared solution was mixed with 0.38 g of 60% sodium hydride and stirred for 30 minutes. With stirring at room temperature, to the resulting reaction solution was added dropwise 10 ml of a tetrahydrofuran solution containing 2.1 g of 2-bromomethylbenzo[b]-thiophene-5-carbonitrile. After concentrating the reaction solution to dryness, the resulting residue was purified by subjecting it to silica gel column chromatography using a toluene/chloroform mixture as an elution solvent, thereby obtaining 4.34 g of the title compound in an oily form.
¹H-NMR (CDCl₃) δ:1.21 (6H), 1.46 (9H, s), 2.0 (4H, br), 3.40 (2H, br), 3.88 (3H), 4.22 (6H), 6.90 (3H), 7.20 (2H, d), 7.50 (1H), 7.78 (1H, d), 7.93 (1H, d)

The following compounds of Reference Examples 81 and 82 were prepared in accordance with the procedure described in Reference Example 80.

REFERENCE EXAMPLE 81 ethyl 3-(5-cyanobenzo[b]thien-2-yl)-2-ethoxycarbonyl-2-[4-[(2-imidazolin-2-yl)methoxy]phenyl]propionate viscous oil $^1$H-NMR (CDCl$_3$) δ:1.22 (6H, t), 3.63 (4H, s), 3.89 (2H, s), 4.24 (4H), 4.69 (2H, s), 6.86 (3H), 7.27 (2H), 7.42 (1H), 7.76 (1H), 7.88 (1H)

REFERENCE EXAMPLE 82 ethyl 2-[4-[((3S)-1-tert-butoxycarbonyl-3-pyrrolidinyl)oxy]phenyl]-3-(5-cyano-2-benzothiazolyl)-2-ethoxycarbonylpropionate viscous oil $^1$H-NMR (CDCl$_3$) 1.22 (6H, t), 1.46 (9H, s), 2.09 (2H, br), 3.56 (4H, br), 4.13 (2H), 4.28 (4H, q), 4.85 (1H, br), 6.82 (2H, d), 7.26 (2H, d), 7.63 (1H, dd), 7.95 (1H, d), 8.25 (1H, d)

REFERENCE EXAMPLE 83

Preparation of ethyl 3-(5-cyanobenzo[b]thien-2-yl)-2-[4-[2-(ethoxycarbonylimino)hexahydropyrimidine-5-yl]oxy]phenyl]propionate 1.0 g of ethyl 2-[4 -[2-(tert-butoxycarbonylamino)-1-(tert-butoxycarbonylaminomethyl)ethoxy]phenyl]-3-(5-cyanobenzo[b]thien-2-yl)propionate was dissolved in 2 ml of anisole. 10 ml of trifluoroacetic acid was added to the above solution while stirring under ice cooling, and the thus prepared mixture was stirred-at room temperature for 1 hour. The resulting reaction solution was concentrated under a reduced pressure, and the thus obtained residue was dissolved in water and washed with n-hexane. The resulting water layer was adjusted to pH 9–10 with concentrated aqueous ammonia and then extracted with chloroform. The resulting organic layer was concentrated to dryness, and the thus obtained residue was dissolved in 20 ml of dry ethanol. To the thus prepared solution was added 300 mg of ethyl N-(ethoxy(methylthio)methylene) carbamate which has been synthesized in accordance with the procedure disclosed in *Journal of the Chemical Society*, Parkin I, 1973, pp. 2644–2646. Thereafter, the thus prepared mixture was stirred for 20 hours, and the resulting precipitate was collected to obtain 560 mg of the title compound.

mp: 179°–182° C.

IR (KBr): 2230, 1725, 1638, 1512, 1337 cm$^{-1}$ $^1$H-NMR (CDCl$_3$) δ:1.13 (3H, t, J=7.0Hz), 1.17 (3H, t, J=7.0Hz), 3.10–4.30 (11H, m), 4.50–4.80 (1H, m), 6.89 (2H, d, J=8.75Hz), 7.03 (1H, s), 7.26 (2H, d, J=8.75Hz), 7.46 (1H, dd, J=8.31 and 1.75Hz), 7.82 (1H, d, J=8.31Hz), 7.95 (1H, d), 8.70–9.50 (2H, br)

REFERENCE EXAMPLE 84

Preparation of ethyl 3-(5-cyanobenzo[b]thien-2-yl)-2-[4-[[2-(imino)hexahydropropyrimidin-5-yl]oxy]phenyl]propionate hydrochloride a) 2.9 g of potassium thiocyanate was dissolved in 150 ml of dry acetone. With stirring under ice cooling, to the above solution was added dropwise 6.8 g of p-nitrobenzyl chloroformate which had been dissolved in 20 ml of acetone. The thus prepared mixture was stirred for 2 hours with ice cooling, and the resulting mixture was mixed with 1.15 g of methanol, and stirred at room temperature for 20 hours. Thereafter, crystals thus precipitated were collected by filtration and washed with chloroform to obtain 2.88 g of p-nitrobenzyl methoxy(thiocarbamoyl) carbamate in the form of powder.

$^1$H-NMR (CDCl$_3$) δ:4.03 (3H, s), 5.33 (2H, s), 7.70 (2H, d, J=9.0Hz), 8.80 (2H, d, J=9.0Hz)

b) 3.5 g of p-nitrobenzyl methoxy(thiocarbamoyl) carbamate obtained in the above step a) and 1.79 g of anhydrous potassium carbonate were dissolved in a mixture solution of 40 ml of water and 40 ml of dioxane. 1.72 g of dimethyl sulfate was gradually added dropwise to the thus prepared solution, and the resulting mixture was stirred at room temperature for 30 minutes. To the resulting reaction solution was added again 300 mg of anhydrous potassium carbonate, followed by the dropwise addition of 300 mg of dimethyl sulfate. The reaction solution thus obtained was diluted with ethyl acetate, washed with water and saturated sodium chloride aqueous solution in that order, and then concentrated. Thereafter, crystals thus precipitated were collected by filtration, and washed thoroughly with n-pentane to obtain 3.23 g of p-nitrobenzyl N-(methoxy(methylthio)methylene) carbamate.

$^1$H-NMR (CDCl$_3$) δ: 2.40 (3H, s), 4.00 (3H, s), 5.28 (2H, s), 7.56 (2H, d, J=9.0Hz), 8.22 (2H, d, J=9.0Hz)

c) In 10 ml portion of anisole was dissolved 2.0 g of ethyl 2-[4-[2-(tert-butoxycarbonylamino)-1-(tertbutoxycarbonylaminomethyl)ethoxy]phenyl]-3-(5-cyanobenzo[b]thien-2-yl)propionate. 30 ml of trifluoroacetic acid was added to the above solution during stirring under ice cooling, and the mixture was stirred at room temperature for 2 hours. The resulting reaction solution was concentrated under a reduced pressure, and the thus obtained residue was dissolved in water, and washed with n-hexane. The resulting water layer was adjusted to pH 10 with concentrated aqueous ammonia and then extracted with chloroform. The resulting organic layer was concentrated to dryness, and the thus obtained residue was dissolved in 50 ml of tetrahydrofuran. To the thus prepared solution was added 921 mg of p-nitrobenzyl N-(methoxy(methyl-thio)methylene) carbamate obtained in the above step b), followed by stirring for 18 hours. After distilling off the solvent, the resulting residue was purified by subjecting it to silica gel column chromatography using a chloroform/ethanol mixture as an elution solvent, thereby obtaining 1.5 g of ethyl 3-(5-cyanobenzo[b]thien-2-yl)-2-[4-[[2-(p-nitrobenzyloxycarbonylimino)hexahydropyrimidin-5-yl]oxy]phenyl]propionate in an viscous and oily form.

$^1$H-NMR (CDCl$_3$) δ:1.17 (3H, t, J=7.0Hz), 3.00–4.30 (1H, m), 4.40–4.70 (1H, m), 5.08 (2H, s), 6.81 (2H, d, J=8.3Hz), 7.03 (1H, s), 7.10–7.56 (5H, m), 7.81 (1H, d, J=9.3Hz), 7.94 (1H, s), 8.10 (2H, d, J=8.75Hz), 8.70–9.40 (2H, br)

d) In 100 ml portion of ethanol was dissolved 1.5 g of ethyl 3-(5-cyanobenzo[b]thien-2-yl)-2-[4-[[2-(p-nitrobenzyloxycarbonylimino)hexahydropyrimidin-5-yl]oxy]phenyl]propionate obtained in the above step c). To the thus prepared solution were added 0.5 g of ammonium chloride and 0.5 g of 10% palladium carbon catalyst (50% wet type). The resulting mixture was subjected to 2 hours of catalytic hydrogenation under normal pressure. After removing the catalyst by filtration and distilling off the solvent, the resulting residue was purified by subjecting it to silica gel column chromatography using a chloroform/ethanol mixture as an elution solvent, thereby obtaining 1.0 g of the title compound.

$^1$H-NMR (CDCl$_3$) δ: 1.21 (3H, t, J=7.0Hz), 3.00–3.90 (7H, m), 4.17 (2H, q, J=7.0Hz), 4.50–4.80 (1H, br), 6 87 (2H, d, J=8.75Hz), 7.01 (1H, s), 7.06–7.36 (5H), 7,44 (1H, dd, J=7.0 and 1.3Hz), 7.81 (1H, s), 8.07 (2H, s)

REFERENCE EXAMPLE 85

Preparation of ethyl 3-(5-cyanobenzo[b]thien-2-yl)-2-[4-[2-yl)-pyrrolin-2-yl)aminoethoxy]phenyl]propionate hydrochloride With stirring, 1.3 g of ethyl 2-[4-(2-tertbutoxycarbonylaminoethoxy)phenyl]-3-(5-cyanobenzo[b]thien-2-yl)propionate was dissolved in 50 ml of ethanol, and then stirred. To this solution was added 25 ml of ethanol containing 13% (w/v) of hydrochloric acid. The thus prepared mixture was stirred at 50° C. for 30 minutes. After distilling off the solvent, the resulting residue was dissolved in 50 ml of ethanol, and then stirred. The thus prepared solution was mixed with 782 mg of 2-ethoxy-1-pyrroline, and the mixture was refluxed under heating for 1.5 hours. After cooling, crystals thus precipitated were collected by filtration to obtain 1.1 g of the title compound.
mp: 212°–215° C.
$^1$H-NMR (CDCl$_3$) δ: 1.14 (1.5H, t, J=7.0Hz), 1.16 (1.5H, t, J=7.0Hz), 2.16 (2H, t, J=7.5Hz), 2.87 (2H, t, J=8.0Hz), 3.20–4.40 (9H), 6.87 (2H, d, J=8.3Hz), 7.13 (1H, s), 7.27 (2H, d, J=8.3Hz), 7.48 (1H, dd, J=8.3 and 1.3Hz), 7.92 (1H, d, J=8.3Hz), 8.04 (1H, s), 10.04 (1H, br), 10.40 (1H, br)

REFERENCE EXAMPLE 86

Preparation of methyl 2-[4-[((3S)-1-tert-butoxycarbonyl-3-pyrrolidinyl)oxy]phenyl]-3-(5-cyano-2-indolyl)propionate In a solvent mixture of 50 ml of tetrahydrofuran and 50 ml of methanol were dissolved 5.0 g of (5-cyano-2-indolyl)methyltriphenylphosphonium bromide and 3.6 g of methyl 2-[4-[((3S)-1-tert-butoxycarbonyl-3-pyrrolidinyl)oxy]phenyl]-2-oxoacetate. With stirring at room temperature, 1.07 g of 1,8-diazabicyclo[5.4.0]-7-undecene was added to the thus prepared solution, and the mixture was stirred at the same temperature for 2 hours. After distilling off the solvent, the resulting residue was purified by subjecting it to silica gel column chromatography using a dichloromethane/acetone mixture as an eluant, thereby obtaining methyl 2-[4-[((3S)-1-tert-butoxycarbonyl-3-pyrrolidinyl)oxy]phenyl]-3-(5-cyano-2-indolyl)acrylate as a mixture of E and Z forms. The thus obtained compound was dissolved in a solvent mixture of 50 ml of tetrahydrofuran and 50 ml of methanol, and the resulting solution was mixed with 5.0 g of palladium oxide.1H$_2$O.barium sulfate, and then subjected to catalytic hydrogenation under normal pressure. After removing the catalyst by filtration and distilling off the solvent, the resulting residue was purified by subjecting it to silica gel column chromatography using a dichloromethane/acetone mixture as an eluant. In this way, 3.5 g of the title compound was obtained in a viscous and oily form.
$^1$H-NMR (CDCl$_3$) δ: 1.46 (9H, s), 2.00–2.20 (2H, m), 2.95–4.22 (7H, m), 4.75–4.90 (1H, br), 6.23 (1H, d), 6.80 (2H, d), 7.18 (2H, d), 7.20–7.40 (2H, m), 7.80 (1H, s), 8.80 (1H, br)

The following compounds of Reference Examples 87 to 92 were prepared in accordance with the procedure described in Reference Example 86.

REFERENCE EXAMPLE 87 methyl 2-[4-[((3S)-1-tert-butoxycarbonyl-3-pyrrolidinyl)oxy]phenyl]-3-(6-cyano-2-indolyl)propionate
viscous oil
$^1$H-NMR (CDCl$_3$) δ:1.50 (9H, s), 2.00–2.25 (2H, br), 3.13 (1H, dd), 3.37–3.75 (3H, m), 3.97 (1H, dd), 4.70–4.90 (1H, br), 6.37 (1H, s), 6.80 (2H, d), 7.10–7.70 (5H, m), 9.25 (1H)

REFERENCE EXAMPLE 88 methyl 2-[4-[((3S)-1-tert-butoxycarbonyl-3-pyrrolidinyl)oxy]phenyl]-3-(6-cyano-1-methyl-2-indolyl)propionate
viscous oil
$^1$H-NMR (CDCl$_3$) δ:1.45 (9H, s), 2.00–2.25 (2H, br), 3.13 (1H, dd), 3.60 (3H, s), 3.62 (3H, s), 3.90–4.10 (1H, dd), 4.75–4.90 (1H, br), 6.30 (1H, s), 6.80 (2H, d), 7.10–7.70 (5H, m), 9.25 (1H)

REFERENCE EXAMPLE 89 methyl 2-[4-[((3R)-1-tert-butoxycarbonyl-3-pyrrolidinyl)oxy]phenyl]-3-(6-cyano-1-ethyl-2-indolyl)propionate
viscous oil
$^1$H-NMR (CDCl$_3$) δ:1.34 (3H, t, J=7.2Hz), 1.47 (9H, s), 2.00–2.30 (2H, m), 2.90–3.30 (3H, m), 3.40–3.80 (4H, m), 3.66 (3H, s), 4.15 (2H, q, J=7.2Hz), 4.70–5.00 (1H, br), 6.30 (1H, s), 6.84 (2H, d, J=8.8Hz), 7.27 (2H, d, J=8.8Hz), 7.26 (1H, d, J=7.0Hz), 7.54 (1H, d, J=7.0Hz)

REFERENCE EXAMPLE 90 methyl 2-[4-[((3S)-1-tert-butoxycarbonyl-3-pyrrolidinyl)oxy]phenyl]-3-(6-cyano-1-ethyl-2-indolyl)propionate
viscous oil
$^1$H-NMR (CDCl$_3$) δ:1.32 (3H, t, J=7.2Hz), 1.48 (9H, s), 2.00–2.30 (2H, m), 2.90–3.30 (3H, m), 3.40–3.80 (4H, m), 3.64 (3H, s), 4.15 (2H, q, J=7.2Hz), 4.70–5.00 (1H, br), 6.30 (1H, s), 6.84 (2H, d, J=8.8Hz), 7.26 (2H, d, J=8.8Hz), 7.26 (1H, d, J=7.0Hz), 7.54 (1H, d, J=7.0Hz)

REFERENCE EXAMPLE 91 methyl 2-[4-[((3S)-1-tert-butoxycarbonyl-3-pyrrolidinyl)oxy]phenyl]-3-[1-(2-chloroethyl)-6-cyano-2-indolyl]-propiate
viscous oil
$^1$H-NMR (CDCl$_3$) δ:1.47 (9H, s), 2.00–2.30 (2H, m), 3.00–4.20 (9H, m), 3.66 (3H, s), 4.20–4.60 (2H, m), 4.80–5.00 (1H, m), 6.37 (1H, s), 6.84 (2H, d), 7.20–7.80 (5H, m)

REFERENCE EXAMPLE 92 methyl 2-[4-[(1-tert-butoxycarbonyl-4-piperidinyl)oxy]phenyl]-3-(6-cyano-1-ethyl-2-indolyl)propionate
$^1$H-NMR (CDCl$_3$) δ:1.34 (3H, t), 1.60–2.00 (4H, m), 3.10 (1H, dd), 3.30–3.40 (2H, m), 3.57 (1H, dd), 3.62–3.75 (2H, m), 3.90–4.30 (3H, m), 4.35 (1H, m), 6.30 (1H, s), 6.90 (2H, d), 7.30 (3H, m), 7.54 (1H, d), 7.58 (1H, s)

REFERENCE EXAMPLE 93

Preparation of methyl 2-[4-[((3S)-1-tert-butoxycarbonyl-3-pyrrolidinyl)oxy]phenyl]-3-(5-cyano-1-methyl-2-indolyl)propionate 3.0 g of methyl 2-[4-[((3S)-1-tert-butoxy-carbonyl-3-pyrrolidinyl)oxy]phenyl]-3-(5-cyano-2-indolyl)propionate was dissolved in 30 ml of N,N-dimethylformamide, and then stirred under ice cooling. 270 mg of 60% sodium hydride was added to the above solution, and the stirring was continued for 10 minutes. The resulting reaction solution was mixed with 0.4 ml of methyl iodide, and the mixture was stirred at room temperature for 1 hour. The thus treated reaction solution was diluted with a toluene/ethyl acetate mixture, and then washed with an aqueous solution of ammonium chloride. After drying the resulting organic layer to distill off the solvent, the residue thus obtained was purified by subjecting it to silica gel column chromatography using a dichloromethane/acetone mixture as an elution solvent. In this way, 2.0 g of the title compound was obtained in a viscous and oily form.

$^1$H-NMR (CDCl$_3$) δ:1.45 (9H, s), 2.00–2.22 (2H, m), 3.05 (1H, dd), 3.35–3.80 (5H, m), 3.63 (3H, s), 4.00 (1H, dd), 4.75–5.00 (1H, br), 6.25 (1H, d), 6.85 (2H, d), 7.20–7.50 (2H, m), 7.90 (1H, s)

REFERENCE EXAMPLE 94

Preparation of ethyl 2-[4-[((3S)-1-tert-butoxycarbonyl-3-pyrrolidiny)oxy]phenyl]-3-(6-cyano-1,2,3,4-tetrahydro-2-naphthyl)propionate 9.0 g of (6-cyano-1,2,3,4-tetrahydro-2-naphthyl)methyltriphenylphosphonium p-toluenesulfonate was suspended in 150 ml of tetrahydrofuran, followed by gradual addition of 600 mg of 60% sodium hydride. The thus prepared mixture was refluxed under heating for 20 minutes. After cooling down to room temperature, to the resulting reaction solution was added 10 ml of a tetrahydrofuran solution containing 4.16 g of ethyl 2-[4-[((3S)-1-tert-butoxycarbonyl-3-pyrrolidinyl)oxy]phenyl]-2-oxoacetate. The resulting reaction mixture was stirred for 10 minutes, and then refluxed under heating for 2 hours. After cooling down to room temperature, the reaction product thus obtained was dissolved in ethyl acetate, and washed with water and saturated sodium chloride aqueous solution in that order. After drying the resulting organic layer to distill off the solvent, the thus obtained residue was purified by subjecting it to silica gel column chromatography using a n-hexane/ethyl acetate mixture as an elution solvent, thereby obtaining 3.90 g of ethyl 2-[4-[((3S)-1-tert-butoxycarbonyl-3-pyrrolidinyl)oxy]phenyl]3-(6-cyano-1,2,3,4-tetrahydro-2-naphthyl)acrylate in a yellow oily form as a mixture of E and Z forms. 2.58 g of the thus obtained E/Z mixture was dissolved in 40 ml of ethanol, and the resulting solution was mixed with 650 mg of palladium oxide.1H$_2$O.barium sulfate, and then subjected to catalytic hydrogenation under normal pressure for 5 hours. After removing the catalyst by filtration and distilling off the solvent, the resulting residue was purified by subjecting it to silica gel column chromatography using a n-hexane/ethyl acetate mixture as an elution solvent. In this way, 1.69 g of the title compound was obtained in a yellow oily form.

$^1$H-NMR (CDCl$_3$) δ:1.20 (3H, t, J=7.0Hz), 1.45 (9H, s), 1.50–3.90 (16H, m), 4.10 (2H, q),. 4.82 (1H, m), 6.81 (2H, q, J=9.0Hz), 7.00–7.40 (5H, m)

REFERENCE EXAMPLE 95

Preparation of ethyl 2-[4-[((3S)-1-tert-butoxycarbonyl-3-pyrrolidinyl)oxy]phenyl]-3-(5-cyano-2-benzimidazolyl)propionate a) 3.42 g of 3,4-diaminobenzonitrile and 4.06 g of ethyl chloroacetoimidate hydrochloride were dissolved in 100 ml of ethanol, and the solution was refluxed under heating for 3 hours. After cooling and distilling off the solvent, the resulting residue was dissolved in ethyl acetate, washed with water, and then dried. After distilling off the solvent, the crystals thus precipitated were collected by filtration to obtain 2.7 g of 2-chloromethyl-5-benzimidazolecarbonitrile. mp: 144°–146° C.

$^1$H-NMR (CDCl$_3$) δ:4.83 (2H, s), 7.48 (1H, d, J=7.1Hz), 7.57 (1H, d, J=7.1Hz), 7.95 (1H, s)

b) 1.0 g of 2-chloromethyl-5-benzimidazolecarbonitrile obtained in the above step a) and 2.19 g of triphenylphosphine were dissolved in 30 ml of 1,2-dichloroethane, and the solution was heated at a temperature of 140° C. for 1 hour. After cooling and distilling off the solvent, the thus obtained residue and 2.03 g of ethyl 2-[4-[((3S)-1-tert-butoxycarbonyl-3-pyrrolidinyl)oxy]phenyl]-2-oxoacetate were dissolved in a solvent mixture of 20 ml of tetrahydrofuran and 20 ml of ethanol. With stirring at room temperature, 1.1 g of 1,8-diazabicyclo[5.4.0]-7-undecene was added to the thus prepared solution, and the mixture was stirred at the same temperature for 72 hours. After distilling off the solvent, the resulting residue was purified by subjecting it to silica gel column chromatography using a chloroform/ethanol mixture as an elution solvent, thereby obtaining 1.5 g of oily ethyl 2-[4-[((3S)-1-tert-butoxycarbonyl-3-pyrrolidinyl)oxy]phenyl]-3-(5-cyano-2-benzimidazolyl)acrylate as a mixture of E and Z forms. The thus obtained E/Z mixture was dissolved in a solvent mixture consisting of 50 ml of tetrahydrofuran and 50 ml of ethanol, and the resulting solution was mixed with 1.5 g of palladium oxide.1H$_2$O.barium sulfate, and then subjected to catalytic hydrogenation under normal pressure. After removing the catalyst by filtration and distilling off the solvent, the resulting residue was purified by subjecting it to silica gel column chromatography using a chloroform/ethanol mixture as an elution solvent. In this way, 320 mg of the title compound was obtained in a viscous and oily form.

$^1$H-NMR (CDCl$_3$) δ:1.14 (3H, t, J=7.0Hz), 1.48 (9H, s), 1.90–2.30 (2H, br), 3.05–3.90 (6H, m), 4.12 (2H, q, J=7.0Hz), 4.00–4.30 (1H), 4.70–4.95 (1H, br), 6.79 (2H, d, J =8.8Hz), 7.19 (2H, d, J=8.8Hz), 7.35–8.10 (3H, m)

FD MS (m/z): 504 (M$^+$), 505 (M$^+$+1)

REFERENCE EXAMPLE 96

Preparation (+)-((2S)-1-p-toluenesulfonyl-2-pyrrolidinyl)methyl 2-[4-[((3S)-1-tert-butoxycarbonyl-3-pyrrolidinyl)oxy]phenyl]-3-(6-cyano-2-indoyl)propionate and (−)-[((2S)-1-p-toluenesulfonyl-2-2-pyrrolidinyl)methyl 2-[4[((3S)-1-tert-butoxycarbonyl-3-pyrrolidinyl]oxy]phenyl]-3-(6-cyano-2-indolyl)propionate a) An aqueous solution containing 3 g of sodium hydroxide dissolved in 10 ml of water was added to 100 ml of a methanol solution containing 22 g of methyl 2-[4-[((3S)-1-tert-butoxycarbonyl-3-pyrrolidinyl)oxy]phenyl]-3-(6-cyano-2-indolyl)propionate, and the resulting mixture was stirred at room temperature for 24 hours. After distilling off the solvent, the remaining portion was adjusted to pH 4–5 with citric acid and then extracted with ethyl acetate. By drying the extract to distill off the solvent, 20 g of 2-[4-[((3S)-1-tert-butoxycarbonyl-3-pyrrolidinyl)oxy]phenyl]-3-(6-cyano-2-indolyl)propionic acid was obtained.
IR (KBr): 3352, 2218, 1710, 1677 cm$^{-1}$ b) In 300 ml of dioxane were dissolved 20 g of 2-[4-[((3S)-1-tert-butoxycarbonyl-3-pyrrolidinyl)oxy]phenyl]-3-(6-cyano-2-indolyl)propionic acid obtained in the above step a) and 11.9 g of ((2S)-1-p-toluenesulfonyl-2pyrrolidinyl)methanol. The thus prepared solution was mixed with a catalytically effective amount of 4-dimethylaminopyridine and 9 g of 1,3-dicyclohexylcarbodiimide while stirring under ice cooling, and the mixture was stirred at room temperature for 24 hours. After removing precipitated materials by filtration and distilling off the solvent, the resulting residue was purified by subjecting it to silica gel column chromatography using a chloroform/acetone mixture as an elution solvent, thereby obtaining 10.5 g of (+)-((2S)-1-p-toluenesulfonyl-2-pyrrolidinyl)methyl 2-[4-[((3S)-1-tert-butoxycarbonyl-3-pyrrolidinyl)oxy]phenyl]-3-(6-cyano-2-indolyl)propionate.
$^1$H-NMR (CDCl$_3$) δ:1.00–1.80 (4H, m), 1.46 (9H, s), 2.00–2.30 (2H, m), 2.43 (3H, s), 3.00–4.40 (12H, m), 4.75–5.00 (1H, m), 6.30 (1H, s), 6.82 (2H, d), 7.10–7.90 (9H, m), 9.00 (1H, s)

By eluting the column again with the same solvent system, 9.5 g of (−)-((2S)-1-p-toluenesulfonyl-2-pyrrolidinyl)methyl 2-[4-[((3S)-1-tert-butoxycarbonyl-3-pyrrolidinyl)oxy]phenyl]-3-(6-cyano-2-indolyl)propionate was obtained.
$^1$H-NMR (CDCl$_3$) δ: 1.10–2.00 (4H, m), 1.44 (9H, s), 2.00–2.25 (2H, m), 2.41 (3H, s), 2.95–4.10 (10H, m), 4.20 (2H, d), 4.70–4.90 (1H, m), 6.25 (1H, s), 6.80 (2H, d), 7.10–7.80 (9H, m), 9.20 (1H, s)

REFERENCE EXAMPLE 97

Preparation of methyl 2-[4-[((3S)-1-tert-butoxycarbonyl-3-pyrrolidinyl)oxy]phenyl]3-(6-cyano-1-ethoxycarbonylmethyl-2-indolyl)propionate 3.0 g of methyl 2-[4-[((3S)-1-tert-butoxy-carbonyl-3-pyrrolidinyl)oxy]phenyl]-3-(6-cyano-2-indolyl)propionate was dissolved in 30 ml of N,N-dimethylformamide. The thus prepared solution was mixed with 280 mg of 60% sodium hydride while stirring under ice cooling, and the stirring was continued for 20 minutes at the same temperature. The resulting reaction solution was mixed with 0.7 ml of bromoacetate, and the mixture was stirred for 1 hour. The thus treated reaction solution was mixed with dilute hydrochloric acid, extracted with a toluene/ethyl acetate mixture, washed with water, and then dried. After distilling off the solvent, the resulting residue was purified by subjecting it to silica gel column chromatography using a dichloromethane/acetone mixture as an elution solvent. In this way, 3.2 g of the title compound was obtained in a viscous and oily form.
$^1$H-NMR (CDCl$_3$) δ:1.26 (3H, t), 1.46 (9H, s), 3.02 (1H, dd), 3.30–3.70 (5H, m), 3.66 (3H, s), 4.00 (1H, dd), 4.20 (2H, q), 4.80 (2H, s), 4.78–4.90(1H, m), 6.40 (1H, s), 6.90 (2H, d), 7.20–7.70 (5H, m)

REFERENCE EXAMPLE 98

Preparation of 2-[4-[(3S)-1-tert-butoxycarbonyl-3-pyrrolidinyl)oxy]phenyl]-3-(6-cyano-2-indolyl)propanol 2.7 g of methyl 2-[4-[((3S)-1-tert-butoxycarbonyl-3-pyrrolidinyl)oxy]phenyl]-3-(6-cyano-2-indolyl)propionate was dissolved in 30 ml of tetrahydrofuran, followed by the addition of 660 mg of sodium borohydride. 12 ml of methanol was added dropwise to the thus prepared solution while stirring under ice cooling, and the resulting mixture was stirred at room temperature for 3 hours. The resulting reaction solution was mixed with 10% citric acid aqueous solution, extracted with dichloromethane, and then dried. After distilling off the solvent, the resulting residue was purified by subjecting it to silica gel Column chromatography using a dichloromethane/methanol mixture as an elution solvent. In this way, 2.2 g of the title compound was obtained in an oily form.
$^1$H-NMR (CDCl$_3$) δ:1.48 (9H, s), 1.95–2.25 (2H, m), 2.48 (1H, t), 3.00–3.22 (2H, m), 3.40–3.69 (6H, m), 3.70–3.90 (1H, m), 4.70–4.90 (1H, m), 6.21 (1H, s), 6.80 (2H, d), 7.00–7.65 (5H, m), 9.20 (1H, s)

REFERENCE EXAMPLE 99

Preparation of ethyl 2-[2-[4[((3S)-1-tert-butoxycarbonyl-3-pyrrolidinyl)oxy]phenyl]-3-hydroxypropyl]-6-cyano-1-indoleacetate 2.0 g of 2-[4-[((3S)-1-tert-butoxycarbonyl-3-pyrrolidinyl)oxy]phenyl]-3-(6-cyano-2-indolyl)propanol was dissolved in 30 ml of N,N-dimethylformamide. 280 mg of 60% sodium hydride was added to the above solution while stirring under ice cooling, and the stirring was continued for 20 minutes at the same temperature. The resulting reaction solution was mixed with 0.5 ml of ethyl bromoacetate, and the mixture was stirred for 1 hour. The thus treated reaction solution was mixed with an aqueous solution of ammonium chloride, extracted with a toluene/ethyl acetate mixture, washed with water, and then dried. After distilling off the solvent, the resulting residue was purified by subjecting it to silica gel column chromatography using a dichloromethane/acetone mixture as an elution solvent. In this way, 1.5 g of the title compound was obtained in a viscous and oily form.
$^1$H-NMR (CDCl$_3$) δ:1.23 (3H, t), 1.45 (9H, s), 1.90–2.20 (2H, s), 4.20 (2H, q), 4.50–4.90 (3H), 6.20 (1H, s), 6.78 (2H, d)

REFERENCE EXAMPLE 100

Preparation of 2-[2-[4-[((3S)-1-tert-butoxycarbonyl-3-pyrrolidinyl)oxy]phenyl]ethyl]-6-indolecarbonitrile a) In 40 ml of tetrahydrofuran were dissolved 1.31 g of p-hydroxybenzaldehyde, 1.87 g of (3R)-1-tert-butoxycarbonyl-3-hydroxypyrrolidine and 2.88 g of triphenylphosphine. With stirring at room temperature, 1.91 g of diethyl azodicarboxylate was added to the thus prepared solution, and the mixture was stirred for 45 minutes. After distilling off the solvent, the resulting residue was purified by subjecting it to silica gel column chromatography using a benzene/ethyl acetate mixture as an elution solvent. In this way, 2.9 g of 4-[((3S)-1-tert-butoxycarbonyl-3-pyrrolidinyl)oxy]benzaldehyde was obtained in an oily form.
$^1$H-NMR (CDCl$_3$) δ:1.48 (9H, s), 2.00–2.40 (2H, m), 3.30–3.80 (4H, m), 4.90–5.10 (1H, m), 6.98 (2H, d, J=9.0Hz), 7.84 (2H, d, J=9.0Hz), 9.89 (1H, s)

b) 0.93 g of 4-[((3S)-1-tert-butoxycarbonyl-3-pyrrolidinyl)oxy]benzaldehyde obtained in the above step a) and 1.6 g of (6-cyano-2-indolyl)methyltriphenylphosphonium bromide were dissolved in a solvent mixture of 20 ml of methanol and 20 ml of tetrahydrofuran. 490 mg of 1,8-diazabicyclo[5.4.0]-7-undecene was dissolved in the thus prepared solution while stirring under ice cooling, and the resulting mixture was stirred at room temperature for 3 hours. After distilling off the solvent, the resulting residue was purified by subjecting it to silica gel column chromatography using a chloroform/methanol mixture as an elution solvent, thereby obtaining 700 mg of 2-[2-[4-[((3S)-1-tert-butoxycarbonyl-3-pyrrolidinyl)oxy]phenyl]vinyl]-6-indolecarbonitrile as a mixture of E and Z forms.

$^1$H-NMR (CDCl$_3$) δ:1.43 (9H, s), 1.90–2.23 (2H, m), 3.30–3.70 (4H, m), 4.75–4.95 (1H, m), 8.65 (1H, br)

c) 700 mg of 2-[2-[4-[((3S)-1-tert-butoxy-carbonyl-3-pyrrolidinyl)oxy]phenyl]vinyl]-6-indolecarbonitrile obtained in the above step b) was dissolved in a solvent mixture of 20 ml of methanol and 40 ml of tetrahydrofuran. 70 mg of palladium oxide.1H$_2$O.barium sulfate was added to the solution prepared above, and the mixture was subjected to catalytic hydrogenation under normal pressure for 3 hours. After removing the catalyst by filtration and distilling off the solvent, the resulting residue was purified by subjecting it to silica gel column chromatography using a chloroform/methanol mixture as an elution solvent. In this way, 650 mg of the title compound was obtained in a viscous and oily form.

$^1$H-NMR (CDCl$_3$) δ:1.50 (9H, s), 1.95–2.20 (2H, m), 4.70–4.90 (1H, m), 6.30 (1H, s), 6.75 (2H, d), 7.10 (2H, d), 7.10–7.65 (3H, m), 9.46 (1H, br)

REFERENCE EXAMPLE 101

Preparation of ethyl 2-[2-[4-[((3S)-1-tert-butoxycarbonyl-3-pyrrolidinyl)oxy]phenyl]ethyl]-6-cyano-1-indoleacetate 2.4 g of 2-[2-[4-[((3S)-1-tert-butoxycarbonyl-3-pyrrolidinyl)oxy]phenyl]ethyl]-6-indolecarbonitrile was dissolved in 50 ml of N,N-dimethylformamide. 300 mg of 60% sodium hydride was added to the thus prepared solution during stirring under ice cooling, and the resulting mixture was warmed up to room temperature and stirred at the same temperature for 20 minutes. 0.76 ml of ethyl bromoacetate was added to the above mixture during stirring under ice cooling, followed by stirring for 1 hour. The resulting reaction solution was mixed with an ammonium chloride aqueous solution and extracted with a toluene/ethyl acetate mixture, and the resulting organic layer was washed with water and dried. After distilling off the solvent, the resulting residue was purified by subjecting it to silica gel column chromatography using a dichloromethane/acetone mixture as an elution solvent. In this way, 2.3 g of the title compound was obtained in a viscous and oily form.

$^1$H-NMR (CDCl$_3$) δ:1.2 (3H, t), 2.00–2.20 (2H, m), 2.95 (4H, s), 3.30–3.60 (4H, m), 4.18 (2H, q), 4.70 (2H, s), 6.36 (1H, s), 6.75 (2H, d), 7.00–7.60 (5H, m)

REFERENCE EXAMPLE 102

Preparation of 2-[[4-[(1-tert-butoxycarbonyl-4-piperidinyl)oxy]phenyl]methyl]-5-benzofurancarbonitrile a) 5.07 g of potassium hydroxide was added to 30 ml of diethylene glycol, and the mixture was stirred at room temperature during which 5.5 g of 80% hydrazine dihydrate.2H$_2$O and 5.0 g of 5-bromo-2-(4-methoxybenzoyl)benzofuran were further added. The thus prepared mixture was refluxed under heating. After cooling, the resulting reaction solution was adjusted to pH 4–5, extracted with benzene, and then dried. After distilling off the solvent, the resulting residue was purified by subjecting it to silica gel column chromatography using a n-hexane/isopropanol mixture as an elution solvent, thereby obtaining 3.95 g of 5-bromo-2-(4-methoxybenzyl)benzofuran as a brown oily material.

$^1$H-NMR (CDCl$_3$) δ:3.80 (3H, s), 4.02 (2H, s), 6.23 (1H, s), 6.90 (2H, d, J=9.0Hz), 7.20–7.40 (4H, m), 7.57 (1H, m)

b) 3.95 g of 5-bromo-2-(4-methoxybenzyl)benzofuran obtained in the above step a) and 1.67 g of cuprous cyanide were suspended in 20 ml of N-methyl-2-pyrrolidone, and the suspension was heated at a temperature of 200° to 220° C. in a stream of nitrogen. After cooling, the resulting reaction product was dissolved in chloroform, and insoluble materials were removed by filtration. The resulting organic layer was washed with water and concentrated to dryness. Thereafter, the thus obtained residue was purified by subjecting it to silica gel column chromatography using a n-hexane/isopropyl ether mixture as an elution solvent, thereby obtaining 3.10 g of 2-(4-methoxybenzyl)-5-benzofurancarbonitrile. mp: 78°–80° C.

$^1$H-NMR (CDCl$_3$) δ: 3.80 (3H, s), 4.10 (2H, s), 6.39 (1H, s), 6.90 (2H, d, J=9.0Hz), 7.22 (2H, d), 7.46 (2H, d), 7.78 (1H, s)

c) 3.0 g of 2-(4-methoxybenzyl)-5-benzofurancarbonitrile obtained in the above step b) was dissolved in 30 ml of dichloromethane, and the solution was cooled down to −50° C. With stirring, to the above solution was added dropwise 20 ml of a dichloromethane solution containing 2.23 ml of boron tribromide. After gradually warming up the mixture to room temperature, stirring was continued for 1 hour. The resulting reaction solution was diluted with chloroform, washed with dilute hydrochloric acid, and then dried. After distilling off the solvent, the crystals thus precipitated were collected by filtration to obtain 2.48 g of 2-(4-hydroxybenzyl)-5-benzofurancarbonitrile in the form of yellow prism crystals.

$^1$H-NMR (CDCl$_3$) δ:4.02 (2H, s), 6.45 (1H, s), 6.77 (2H, d, J=9.0Hz), 7.10 (2H, d), 7.48 (2H, d), 7.81 (1H, s)

d) In 50 ml of tetrahydrofuran were dissolved 1.50 g of 2-(4-hydroxybenzyl)-5-benzofurancarbonitrile obtained in the above step c), 2.37 g of triphenylphosphine and 1.21 g of 1-tert-butoxycarbonyl-4-hydroxypiperidine. With stirring at room temperature, the thus prepared solution was mixed with 1.57 g of diethyl azodicarboxylate, and the stirring was continued for 40 hours. After distilling off the solvent, the resulting residue was purified by subjecting it to silica gel column chromatography using a n-hexane/ethyl acetate mixture as an elution solvent. In this way, 1.30 g of the title compound was obtained in the form of colorless needle crystals.

mp: 144°–146° C.

$^1$H-NMR (CDCl$_3$) δ:1.47 (9H, s), 1.60–2.00 (4H, m), 3.20–3.90 (4H, m), 4.05 (2H, s), 4.44 (1H, m), 6.41 (1H, s), 6.87 (2H, d, J=9.0Hz), 7.20 (2H, d, J=9.0Hz), 7.47 (2H), 7.79 (1H, s)

REFERENCE EXAMPLE 103

Preparation of 3-[3-[4-[((3S)-1-tert-butoxycarbonyl-3-pyrrolidinyl)oxy]phenyl]propyl]-5-benzofurancarbonitrile a) 2.14 g of (5-cyano-3-benzofuranyl)methyltriphenylphosphonium chloride and 0.7 g of 4-methoxyphenylacetaldehyde were dissolved in a solvent mixture of 100 ml of tetrahydrofuran and 100 ml of ethanol. The thus prepared solution was mixed with 0.71 g of 1,8-diaza-bicyclo[5.4.0]-7-undecene and stirred for 24 hours. After distilling off the solvent, the resulting residue was purified by subjecting it to silica gel column chromatography using toluene as an elution solvent, thereby obtaining 0.86 g of yellow and oily 3-[3-(4-methoxyphenyl)allyl]-5-benzofurancarbonitrile as a mixture of E and Z forms. The thus obtained E/Z mixture was dissolved in 100 ml of ethanol, and the solution was subjected to catalytic hydrogenation under normal pressure in the presence of 370 mg of 5% palladium carbon catalyst. Thereafter, the catalyst was removed by filtration, and the solvent was distilled off to obtain 0.6 g of 3-[3-(4-methoxyphenyl)propyl]-5-benzofurancarbonitrile. The thus obtained methoxy compound was dissolved in 20 ml of dichloromethane. With stirring at −40° C., to the resulting solution was added dropwise 10 ml of a dichloromethane solution containing 0.4 ml of boron tribromide. The resulting mixture was warmed up to room temperature and stirred for 2 hours. The resulting reaction solution was poured into cold dilute hydrochloric acid and extracted with chloroform. After drying the resulting organic layer and distilling off the solvent, the thus obtained residue was purified by subjecting it to silica gel column chromatography using toluene as an elution solvent. In this way, 280 mg of 3-[3-(4-hydroxyphenyl)propyl]-5-benzofurancarbonitrile.

$^1$H-NMR (CDCl$_3$) δ:2.0 (2H, m), 2.64 (4H, m), 6.80 (2H, d), 7.16 (2H, d), 7.52 (3H, m), 7.79 (1H)

b) In 20 ml of tetrahydrofuran were dissolved 280 mg of 3-[3-(4-hydroxyphenyl)propyl]-5-benzofurancarbonitrile obtained in the above step a), 280 mg of (3R)-1-tert-butoxycarbonyl-3-hydroxypyrrolidine and 400 mg of triphenylphosphine. With stirring at room temperature, the thus prepared solution was mixed with 265 mg of diethyl azodicarboxylate, and the stirring was continued for 24 hours. After distilling off the solvent, the resulting residue was purified by subjecting it to silica gel column chromatography using a n-hexane/ethyl acetate mixture as an elution solvent. In this way, 400 mg of the title compound was obtained in a yellow and oily form.

$^1$H-NMR (CDCl$_3$) δ:1.46 (9H, s), 2.05 (4H, m), 2.66 (4H, m), 3.60 (4H, br), 4.85 (1H, br), 6.85 (2H, d), 7.05 (2H, d), 7.53 (3H, m), 7.83 (1H)

REFERENCE EXAMPLE 104

Preparation of 4-[((3S)-1-tert-butoxycarbonyl-3-pyrrolidinyl)oxy]-3-methoxybenzaldehyde In 50 ml of tetrahydrofuran were dissolved 3.04 g of vanillin, 3.74 g of (3R)-1-tert-butoxycarbonyl-3-hydroxypyrrolidine and 5.24 g of triphenylphosphine. The thus prepared solution was mixed with 4.00 g of diethyl azodicarboxylate, and the mixture was stirred at room temperature for 18 hours. After concentrating the resulting reaction solution, the thus obtained residue was purified by subjecting it to silica gel column chromatography using an ethanol/chloroform mixture as an elution solvent. In this way, 5.0 g of the title compound was obtained in an oily form.

$^1$H-NMR (CDCl$_3$) δ: 1.47 (9H, s), 2.00–2.40 (2H, m), 3.50–3.80 (4H, m), 3.90 (3H, s), 5.02 (1H, br), 6.80–7.60 (3H, m), 9.86 (1H, s)

REFERENCE EXAMPLE 105

Preparation of 4-[[4-(N-acetyl)aminomethylcyclohexyl]methoxy]benzaldehyde

The title compound was prepared in accordance with the procedure as described in Reference Example 104.

$^1$H-NMR (CDCl$_3$) δ: 0.80–2.10 (10H, m), 3.13 (2H, dd, J=6.1 and 6.1Hz), 3.84 (2H, d, J=6.1Hz), 5.56 (1H, br), 6.97 (2H, d, J=8.7Hz), 7.82 (2H, d, J=8.7Hz), 9.88 (1H, s)

REFERENCE EXAMPLE 106

Preparation of 3-acetoxy-4-[((3S)-1-acetyl-3-pyrrolidinyl)oxy]benzaldehyde a) 5.5 g of 4-[((3S)-1-tert-butoxycarbonyl-3-pyrrolidinyl)oxy]-3-methoxybenzaldehyde was dissolved in 20 ml of dichloromethane, followed by the addition of 30 ml of formic acid. The thus prepared mixture was stirred at room temperature for 1 hour and then at 50° C. for 1 hour. The solvent and formic acid were distilled off under a reduced pressure, and the resulting residue was dissolved in 100 ml of tetrahydrofuran. The thus prepared solution was mixed with 2.68 g of acetyl chloride, and 8.63 g of triethylamine was added dropwise thereto while stirring under ice cooling. Thereafter, the solvent was distilled off, and the residue thus obtained was dissolved in chloroform, and washed with water, followed by drying of the resulting organic layer. After distilling off the solvent, the resulting residue was purified by subjecting it to silica gel column chromatography using toluene as an elution solvent, thereby obtaining 4.3 g of 4-[((3S)-1-acetyl-3-pyrrolidinyl)oxy]-3-methoxybenzaldehyde as a viscous oil.

$^1$H-NMR (CDCl$_3$) δ:2.04 (5H, m), 3.50–4.00 (4H, m), 3.90 (3H, s), 5.10 (1H, br), 6.80–7.60 (3H, m), 9.86 (1H, s)

b) 4.3 g of 4-[((3S)-1-acetyl-3-pyrrolidinyl)oxy]-3-methoxybenzaldehyde obtained in the above step a) was dissolved in 40 ml of dichloromethane, and the solution was cooled down to −70° C. With stirring, to the above solution was added dropwise 12.6 g of boron tribromide. The thus prepared reaction solution was warmed up to 0° C. and then poured into ice water, followed by extraction with chloroform. The resulting organic layer was concentrated to dryness, and the thus obtained residue was crystallized from a chloroform/n-hexane solvent system, thereby obtaining 2.0 g of 4-[((3S)-1-acetyl-3-pyrrolidinyl)oxy]-3-hydroxybenzaldehyde. The thus obtained compound was used in the following reaction without further purification.

$^1$H-NMR (CDCl$_3$:DMSO-d$_6$=9:1) δ:2.00–2.50 (5H, m), 3.50–4.00 (4H, m), 5.32 (1H, br), 6.96 (1H, d, J=8.0Hz), 7.22–7.58 (2H, m), 9.81 (1H, s)

c) 1.1 g of 4-[((3S)-1-acetyl-3-pyrrolidinyl)oxy]-3-hydroxybenzaldehyde obtained in the above step b) was suspended in 5 ml of pyridine, followed by the addition of 0.86 g of acetic anhydride. The thus prepared mixture was stirred at room temperature for 1 hour. After drying the resulting reaction solution under a reduced pressure, the thus obtained residue was purified by subjecting it to silica gel column chromatography using an ethanol/chloroform mixture as an elution solvent. In this way, 1.30 g of the title compound was obtained in an oily form.

$^1$H-NMR (CDCl$_3$) δ:2.06 (3H, s), 2.28 (3H, s), 2.00–2.40 (2H, m), 3.40–3.90 (4H, m), 5.60 (1H, br), 6.90–7.90 (3H, m), 9.90 (1H, s)

REFERENCE EXAMPLE 107

Preparation of 4-[(1-trityl-4-imidazolyl)methoxy]benzaldehyde 1.22 g of p-hydroxybenzaldehyde and 4.08 g of 4-chloromethyl-1-tritylimidazole were dissolved in 40 ml of N,N-dimethylformamide, followed by adding 1.66 g of anhydrous potassium carbonate and subsequently stirring at room temperature for 40 hours. The thus prepared reaction solution were partitioned between water and benzene, and the resulting organic layer was concentrated to dryness. The resulting residue was purified by subjecting it to silica gel column chromatography using chloroform as an elution solvent, and the thus purified product was crystallized from a n-hexane/benzene solvent system. In this way, 2.3 g of the title compound was obtained.
mp: 181°–182° C.
$^1$H-NMR (CDCl$_3$) δ:5.09 (2H, s), 6.90 (1H, d, J=1.1Hz), 7.00–7.40 (17H, m), 7.47 (1H, d, J=1.1Hz), 7.81 (2H, d, J=8.8Hz), 9.88 (1H, s)

REFERENCE EXAMPLE 108

Preparation of 2-[2-[4-[((3S)-1-acetyl-3-pyrrolidinyl)oxy]-3-hydroxyphenyl]ethyl]-5-furancarbonitrile a) 1.3 g of 3-acetyloxy-4-[((3S)-1-acetyl-3-pyrrolidinyl)oxy]benzaldehyde and 2.22 g of (5-cyano-2-benzofuranyl)methyltriphenylphosphonium chloride were dissolved in a solvent mixture of 10 ml of tetrahydrofuran and 10 ml of ethanol, followed by the addition of 0.943 g of 1,8-diazabicyclo[5.4.0]-7-undecene and by subsequent stirring at room temperature for 2 hours. To the mixture obtained were further added 1.88 g of 1,8-diazabicyclo[5.4.0]-7-undecene and 3 ml of water, followed by stirring at room temperature for 2 hours. The thus prepared reaction solution was adjusted to pH 4–5 with 10% citric acid aqueous solution and concentrated under a reduced pressure, and the resulting residue was extracted with chloroform, and then dried. After distilling off the solvent, the resulting residue was purified by subjecting it to silica gel column chromatography using a chloroform/ethanol mixture as an elution solvent, thereby obtaining 1.8 g of 2-[2-[4-[((3S)-1-acetyl-3-pyrrolidinyl)oxy]-3-hydroxyphenyl]vinyl]-5-benzofurancarbonitrile as a powdery mixture of E and Z forms.
$^1$H-NMR (CDCl$_3$) δ:2.00–2.50 (5H, m), 3.40–4.00 (4H, m), 5.00 (1H, br), 6.30–7.90 (9H, m)

b) 1.8 g of 2-[2-[4-[((3S)-1-acetyl-3-pyrrolidinyl)oxy]-3-hydroxyphenyl]vinyl]-5-benzofurancarbonitrile obtained in the above step a) was dissolved in a solvent mixture of 300 ml of tetrahydrofuran and 300 ml of ethanol, and the solution was subjected to catalytic reduction under normal pressure for 5 hours in the presence of 340 mg of palladium oxide.1H$_2$O.barium sulfate. After removing the catalyst by filtration and concentrating the resulting filtrate, the crystals thus precipitated were collected by filtration to obtain 1.6 g of the title compound in the form of colorless crystals.
mp: 191°–193° C.
IR (KBr): 2224, 1644, 1512 cm$^{-1}$
$^1$H-NMR (CDCl$_3$) δ:2.09 (3H, s), 2.00–2.50 (2H, m), 3.04 (4H, s), 3.50–3.90 (4H, m), 4.96 (1H, br), 6.40 (1H, s), 6.50–6.90 (3H, m), 7.50 (2H, s), 7.80 (1H, s)

The following compounds of Reference Examples 109 and 110 were prepared in accordance with the procedure as described in Reference Example 108.

REFERENCE EXAMPLE 109

2-[2-[4-[[4-(N-acetyl)aminomethylcyclohexyl]methoxy]phenyl]ethyl]-5-benzofurancarbonitrile
mp: 159°–161° C.

$^1$H-NMR (CDCl$_3$) δ:0.80–2.10 (10H, m), 1.99 (3H, s), 3.04 (4H, s), 3.19 (2H, dd, J=6.1 and 6.1Hz), 3.63 (2H, d, J=6.1Hz), 5.50 (1H, br), 6.40 (1H, s), 6.79 (2H, d, J=8.3Hz), 7.08 (2H, d, J=8.3Hz), 7.49 (2H), 7.79 (1H)

REFERENCE EXAMPLE 110

2-[2-[4-[(1-trityl-4-imidazolyl)methoxy]phenyl]ethyl]-5-benzofurancarbonitrile
mp: 165°–167° C.
$^1$H-NMR (CDCl$_3$) δ:3.03 (4H, s), 4.97 (2H, s), 6.38 (1H, s), 6.90–7.70 (22H, m), 7.78 (1H, s)

REFERENCE EXAMPLE 111

Preparation of 2-[2-[4-[(1-imidazolyl)methyl]phenyl]ethyl]-5-benzofurancarbonitrile a) 911 mg of 4-hydroxymethylbenzaldehyde and 2.0 g of (5-cyano-2-benzofuranyl)methyltriphenylphosphonium chloride were dissolved in a solvent mixture of 10 ml of tetrahydrofuran and 10 ml of ethanol, followed by the addition of 845 mg of 1,8-diazabicyclo[5.4.0]-7-undecene and by subsequent stirring at room temperature for 1 hour. After distilling off the solvent, the resulting residue was purified by subjecting it to silica gel column chromatography, thereby obtaining 2.3 g of 2-[2-(4-hydroxymethylphenyl)vinyl]-5-benzofurancarbonitrile as a mixture of E and Z forms. 2.3 g of the thus obtained E/Z mixture was dissolved in a solvent mixture of 10 ml of tetrahydrofuran and 10 ml of ethanol, and the solution was subjected to catalytic hydrogenation under normal pressure for 7 hours in the presence of 800 mg of palladium oxide.1H$_2$O.barium sulfate. After removing the catalyst by filtration and distilling off the solvent, the resulting residue was purified by subjecting it to silica gel column chromatography using chloroform as an elution solvent to obtain 835 mg of 2-[2-(4-hydroxymethylphenyl)ethyl]-5-benzofurancarbonitrile as crystals.
mp: 123°–124° C.
$^1$H-NMR (CDCl$_3$) δ:1.60 (1H, s), 3.10 (4H, s), 4.67 (2H, s), 6.41 (1H, s), 7.20 (2H, d, J=8.2Hz), 7.34 (2H, d, J=8.2Hz), 7.52 (2H, s), 7.82 (1H, s)

b) 835 mg of 2-[2-(4-hydroxymethylphenyl)ethyl]-5-benzofurancarbonitrile obtained in the above step a) was dissolved in 15 ml of thionyl chloride, and the solution was stirred at room temperature for 1 hour. Thereafter, thionyl chloride was distilled off, and the resulting residue was dissolved in 30 ml of acetonitrile, together with 550 mg of N-acetylimidazole and 600 mg of sodium iodide. The thus prepared solution was refluxed for 3 hours. After distilling off the solvent, the resulting residue was purified by subjecting it to silica gel column chromatography using chloroform as an elution solvent. In this way, 800 mg of the title compound was obtained in the form of brown crystals.
mp: 72°–73° C.
$^1$H-NMR (CDCl$_3$) δ:3.08 (4H, s), 5.09 (2H, s), 6.40 (1H, s), 6.89 (1H, s), 7.00–7.18 (5H, m), 7.49 (2H, s), 7.56 (1H, s), 7.79 (1H, s)

REFERENCE EXAMPLE 112

Preparation of 4-[2-(5-cyano-2-benzofuranyl)ethyl]benzoic acid a) 5.17 g of methyl 4-formylbenzoate and 13.97 g of (5-cyano-2-benzofuranyl)methyltriphenylphosphonium chloride were dissolved in a solvent mixture of 50 ml of tetrahydrofuran and 50 ml of methanol. A 5.02 g of 1,8-diazabicyclo[5.4.0]-7-undecene was added to the thus prepared solution while stirring under ice cooling, followed by stirring at room temperature for 2 hours. By collecting the precipitated crystals through a filter, methyl 4-[2-(5-cyano-2-benzofuranyl)vinyl]benzoate was obtained as a mixture of E and Z forms. The thus obtained crystals were dissolved in a solvent mixture of 300 ml of tetrahydrofuran and 100 ml of ethanol, and the solution was subjected to catalytic hydrogenation under normal pressure for 2 hours in the presence of 2.0 g of palladium oxide.1H$_2$O.barium sulfate. After removing the catalyst by filtration and concentrating the resulting filtrate, the thus obtained residue was purified by subjecting it to silica gel column chromatography using benzene as an elution solvent to obtain 8.1 g of methyl 4-[2-(5-cyano-2-benzofuranyl)ethyl]benzoate in the form of prism crystals.

mp: 114°–115° C.

$^1$H-NMR (CDCl$_3$) δ:3.13 (4H, s), 3.90 (3H, s), 6.31 (1H, s), 7.26 (2H, d, J=8.5Hz), 7.50 (2H, s), 7.80 (1H, s), 7.98 (2H, d, J=8.5Hz)

b) 1.5 g of methyl 4-[2-(5-cyano-2-benzofuranyl)ethyl]benzoate obtained in the above step a) was dissolved in a solvent mixture of 20 ml of tetrahydrofuran and 20 ml of ethanol, followed by the addition of 11 ml of 1N sodium hydroxide aqueous solution and by subsequent stirring at room temperature for 14 hours. Thereafter, the resulting reaction solution was adjusted to pH 2 with concentrated hydrochloric acid, and the thus precipitated crystals were collected by filtration, washed with water, and then dried. In this way, 1.41 g of the title compound was obtained.

mp: 234°–235° C.

$^1$H-NMR (DMSO-d$_6$) δ:3.13 (4H, s), 6.70 (1H, s), 7.44 (2H, d, J=8.0Hz), 7.69 (2H, s), 7.88 (2H, d, J=8.0Hz), 8.06 (1H, s)

REFERENCE EXAMPLE 113

Preparation of 2-[2-[4-[(4-methyl-1-piperazinyl)carbonyl]phenyl]ethyl]-5-benzofurancarbonitrile 1.35 g of 4-[2-(5-cyano-2-benzofuranyl)ethyl]benzoic acid was refluxed for 2 hours in 15 ml of thionyl chloride. Thereafter, thionyl chloride was distilled off, and the thus obtained residue was dissolved in 10 ml of tetrahydrofuran. The thus prepared solution was added dropwise to 20 ml of a tetrahydrofuran solution containing 1.0 g of 1-methylpiperazine which was stirred under ice cooling. After stirring at room temperature for 1 hour and subsequent removal of the solvent by distillation, the resulting residue was dissolved in chloroform and washed with saturated sodium bicarbonate aqueous solution. After drying the resulting organic layer and distilling off the solvent, the thus obtained residue was purified by subjecting it to silica gel column chromatography using a chloroform/ethanol mixture as an elution solvent. In this way, 1.35 g of the title compound was obtained in the form of crystals.

mp: 115°–116° C.

$^1$H-NMR (DMSO-d$_6$) δ:2.34 (3H, s), 2.43 (4H, br), 3.11 (4H, s), 3.64 (4H, br), 6.42 (1H, s), 7.26 (2H, d, J=9.0Hz), 7.40 (2H, d, J=9.0Hz), 7.50 (2H, s), 7.80 (1H, s)

REFERENCE EXAMPLE 114

Preparation of 2-[2-[4-[[(2-pyrazinyl)amino]carbonyl]phenyl]ethyl]-5-benzofurancarbonitrile a) At room temperature, 1 g of 4-[2-(5-cyano-2-benzofuranyl)ethyl]benzoic acid and 578 mg of 1-hydroxybenzotriazole were dissolved in 100 ml of dichloromethane, followed by the addition of 780 mg of 1,3-dicyclohexylcarbodiimide and by subsequent stirring at the same temperature for 3 hours. After distilling off the solvent, the resulting residue was purified by subjecting it to silica gel column chromatography using a chloroform/ethanol mixture as an elution solvent, and the thus purified product was crystallized from a benzene/n-hexane mixture. In this way, 1.1 g of 2-[2-[4-[[(1-benzotriazolyl)oxy]carbonyl]phenyl]ethyl]-5-benzofurancarbonitrile was obtained in a powdery form.

mp: 171°–172° C.

$^1$H-NMR (CDCl$_3$) δ: 3.14 (4H, s), 6.48 (1H, s), 7.30–8.30 (11H, m)

MS (m/z): 409 (M$^+$+1)

b) 100 mg of 2-[2-[4-[[(1-benzotriazolyl)oxy]carbonyl]phenyl]ethyl]-5-benzofurancarbonitrile obtained in the above step a) and 23.3 mg of aminopyrazine were dissolved in 2 ml of N,N-dimethylformamide. The thus prepared solution was mixed with 13.0 mg of 60% sodium hydride and stirred at room temperature for 2 hours. The resulting reaction solution was diluted with ethyl acetate, washed with water, and then dried. After distilling off the solvent, the resulting residue was purified by subjecting it to silica gel column chromatography to obtain 55 mg of the title compound in a powdery form.

mp: 183°–185° C.

$^1$H-NMR (CDCl$_3$) δ: 3.17 (4H, s), 6.42 (1H, s), 7.34 (2H, d, J=9.0Hz), 7.59 (2H, s), 7.81 (1H, s), 7.90 (2H, d, J=9.0Hz), 8.26 (1H, dd, J=3.0 and 1.6Hz), 8.40 (1H, d, J=3.0Hz), 8.65 (1H, br), 9.74 (1H, d, J=1.6Hz)

REFERENCE EXAMPLE 115

Preparation of methyl [5-[((3S)-1-tert-butoxycarbonyl-3-pyrrolidinyl)oxy]-2-[2-(5-cyano-2-benzofuranyl)ethyl]phenyl]oxyacetate a) in 40 ml of tetrahydrofuran were dissolved 1.38 g of 2,4-dihydroxybenzaldehyde, 1.87 g of (3R)-1-tert-butoxycarbonyl-3-hydroxypyrrolidine and 2.88 g of triphenylphosphone. The thus prepared solution was mixed with 1.91 g of diethyl azodicarboxylate and stirred at room temperature for 1 hour. After distilling off the solvent, the resulting residue was purified by subjecting it to silica gel column chromatography, thereby obtaining 1.2 g of 4-[((3S)-1-tert-butoxycarbonyl-3-pyrrolidinyl)oxy]-2-hydroxybenzaldehyde in a viscous and oily form.

$^1$H-NMR (CDCl$_3$) δ:1.47 (9H, s), 2.00–2.36 (2H, m), 3.30–3.75 (4H, m), 4.94 (1H, quint), 6.38 (1H, d, J=2.1Hz), 6.52 (1H, dd, J=8.0 and 2.1Hz), 7.44 (1H, d, J=8.0Hz), 9.72 (1H, s), 11.45 (1H, s)

b) 1.27 g of 4-[((3S)-1-tert-butoxycarbonyl-3-pyrrolidinyl)oxy]-2-hydroxybenzaldehyde obtained in the above step a) and 0.884 g of ethyl bromoacetate were dissolved in 100 ml of acetone. The thus prepared solution was mixed with 1.12 g of anhydrous potassium carbonate, and the mixture was refluxed for 1.5 hours. After cooling, insoluble materials were removed by filtration, and the solvent was distilled off. Thereafter, the resulting residue was purified by subjecting it to silica gel column chromatography to obtain 1.44 g of ethyl [2-formyl-5-[((3S)-1-tert-butoxycarbonyl-3-pyrrolidinyl)oxy]phenyl]oxyacetate in a viscous and oily form.

$^1$H-NMR (CDCl$_3$) δ:1.30 (3H, t, J=7.0Hz), 1.47 (9H, s), 2.00–2.28 (2H, m), 3.36–3.70 (4H, m), 4.28 (2H, q), 4.71 (2H, s), 4.94 (1H, quint), 6.31 (1H, d, J=2.2Hz), 6.53 (1H, dd, J=8.8 and 2.2Hz), 7.84 (1H, s), 10.39 (1H, s)

c) 1.44 g of ethyl [2-formyl-5-[((3S)-1-tert-butoxycarbonyl-3-pyrrolidinyl)oxy]phenyl]oxyacetate obtained in the above step b) and 1.71 g of (5-cyano-2-benzofuranyl)methyltriphenylphosphonium chloride were dissolved in a solvent mixture of 10 ml of tetrahydrofuran and 10 ml of methanol. The thus prepared solution was mixed with 0.664 g of 1,8-diazabicyclo[5.4.0]-7-undecene, and the mixture was stirred for 1 hour. After distilling off the solvent, the resulting residue was purified by subjecting it to silica gel column chromatography using a benzene/ethyl acetate mixture as an eluant, thereby obtaining 1.8 g of an olefinic compound as a mixture of E and Z forms. 1.8 g of the thus obtained olefinic compound was dissolved in a solvent mixture of 40 ml of tetrahydrofuran and 40 ml of ethanol, and the resulting solution was subjected to catalytic hydrogenation under normal pressure in the presence of 0.22 g of palladium oxide.barium sulfate.1H$_2$O. After removing the catalyst by filtration, the resulting residue was purified by subjecting it to silica gel column chromatography using a benzene/ethyl acetate mixture as an eluant. In this way, 1.6 g of the title compound was obtained in a viscous oily form. (Ester interchange was effected during the reaction.)

$^1$H-NMR (CDCl$_3$) δ:1.46 (9H, s), 1.96–2.08 (2H, m), 3.08 (4H, s), 3.36–3.68 (4H, m), 3.80 (3H, m), 4.62 (2H, s), 4.80 (1H, br), 6.30 (1H, s), 6.36 (1H, d, J=8.0Hz), 6.43 (1H,s), 7.02 (1H, d, J=8.0Hz), 7.46 (2H, s), 7.77 (1H,s)

INVENTIVE EXAMPLE 1 ethyl 3-(5-amidino-2-benzofuranyl)-2-[4-[((3S)-3-pyrrolidinyl)oxy]phenyl]propionate dihydrochloride 1.96 g of ethyl 2-[4-[((3S)-1-tert-butoxy-carbonyl-3-pyrrolidinyl)oxy]phenyl]-3-(5-cyano-2-benzofuranyl)propionate was dissolved in 150 ml of ethanol. With ice cooling and stirring, hydrogen chloride was bubbled into the thus prepared solution to a saturation level, followed by allowing it to stand for 18 hours. The resulting reaction solution was concentrated to dryness under a reduced pressure, the thus obtained residue was dissolved in 300 ml of an ethanol solution containing 15% (w/v) of ammonia and the solution was allowed to stand still for 18 hours. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. Fractions of interest thus pooled were subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid, and then concentrated to dryness. In this way, 610 mg of the title compound was obtained in a solid form.

$^1$H-NMR (DMSO-d$_6$) δ:1.08 (3H, t, J=7.0), 1.90–2.30 (2H, m), 3.00–3.80 (6H, m), 3.80–4.30 (3H, m), 5.08 (1H, br), 6.73 (1H, s), 6.93 (2H, d, J=8.3Hz), 7.33 (2H, d, J=8.3Hz), 7.73 (2H, s), 8.08 (1H, s), 9.25 (2H, br), 9.40 (2H, br), 9.50–10.00 (2H, br)

The following compounds of Inventive Examples 2 to 17 were prepared in accordance with the procedure of Inventive Example 1.

INVENTIVE EXAMPLE 2 ethyl 3-(5-amidino-2-benzofuranyl)-2-[4-[((2S,4S)-2-carbamoyl-4-pyrrolidinyl)oxy]phenyl]propionate dihydrochloride
(solid)

$^1$H-NMR (DMSO-d$_6$) δ:1.10 (3H, t, J=7.0 Hz), 1.70–3.20 (2H, m), 3.00–4.50 (8H, m), 5.00–5.30 (1H, br), 6.71 (1H, s), 6.87 (2H, d, J=8.3Hz), 7.30 (2H, d, J=8.3Hz), 7.72 (2H, s), 8.10 (1H, s), 9.00–10.00 (6H)

INVENTIVE EXAMPLE 3 ethyl 3-(5-amidino-2-benzofuranyl)-2-[4-[((2S,4S)-2-dimethylcarbamoyl-4-pyrrolidinyl)oxy]phenyl] propionate dihydrochloride
(solid)

$^1$H-NMR (DMSO-d$_6$) δ:1.11 (3H, t, J=7.0Hz), 1.70–3.30 (2H, m), 2.91 (3H, s), 2.96 (3H, s), 3.00–4.20 (7H, m), 4.70 (1H, br), 5.10 (1H, br), 6.69 (1H, s), 6.86 (2H, d, J=8.7Hz), 7.29 (2H, d, J=8.7Hz), 7.69 (2H, s), 8.07 (1H, s), 8.80 (1H, br), 9.10 (2H, br), 9.34 (2H, br), 10.08 (1H, br)

INVENTIVE EXAMPLE 4 ethyl 2-(5-amidino-2-benzofuranyl)-3-[4-[((3S)-3-pyrrolidinyl)oxy]phenyl]propionate dihydrochloride
(solid)

$^1$H-NMR (DMSO-d$_6$) δ:1.08 (3H, t, J=7.0Hz), 1.80–2.30 (2H, br), 2.70–3.70 (6H, m), 4.08 (2H, q, J=7.0Hz), 4.35 (1H, t, J=7.9Hz), 5.08 (1H, br), 6.84 (2H, d, J=8.3Hz), 6.96 (1H, s), 7.17 (2H, d, J=8.3Hz), 7.79 (2H, s), 8.12 (1H, s), 9.33 (2H, br), 9.51 (2H, br), 9.80 (2H, br)

INVENTIVE EXAMPLE 5 ethyl 3-(5-amidino-2-benzofuranyl)-3-[4-[((3S)-3-pyrrolidinyl)oxy]phenyl]propionate dihydrochloride
(solid)

$^1$H-NMR (DMSO-d$_6$) δ:1.17 (3H, t, J=7Hz), 2.0–2.2 (2H, m), 3.0–3.8 (6H, m), 4.07 (2H, q), 4.5–4.7 (1H, m), 5.13 (1H, m), 6.94 (1H, s), 6.94 (2H, d, J=9Hz), 7.32 (2H, d, J=9Hz), 7.73 (2H, s), 8.13 (1H, s), 9.21 (2H, br), 9.40 (2H, br), 9.4–10.0 (2H, br)

INVENTIVE EXAMPLE 6 ethyl 3-(5-amidino-3-benzofuranyl)-2-[4-[((3S)-3-pyrrodinyl)oxy]phenyl]propionate dihydrochloride
(solid)

$^1$H-NMR (DMSO-d$_6$) δ:1.06 (3H, t), 2.10 (2H, br), 3.0–3.7 (7H), 4.05 (2H, q), 5.09 (1H, br), 6.95 (2H, d), 7.28 (2H, d), 7.77 (3H), 8.21 (1H, s), 9.2–9.8 (6H)

INVENTIVE EXAMPLE 7 ethyl 2-[2-(5-amidino-2-benzofuranyl)ethyl]-5-[((3S)-3-pyrrolidinyl)oxy]benzoate dihydrochloride
(solid)

$^1$H-NMR (DMSO-d$_6$) δ:1.29 (3H, t, J=7.0Hz), 2.00–2.35 (2H, m), 2.90–3.60 (8H, m), 4.18 (2H, q, J=7.0Hz), 5.20 (1H, br), 6.75 (1H, s), 7.20 (1H, dd, J=7.9 and 2.8Hz), 7.39 (1H, d, J=7.9Hz), 7.41 (1H, d, J=2.8Hz), 7.74 (2H, s), 8.09 (1H, s), 9.23 (2H, br), 9.40 (2H, br), 9.50–10.20 (2H, br)

INVENTIVE EXAMPLE 8 ethyl [2-[2-(5-amidino-2-benzofuranyl)ethyl]-5-[((3S)-3-pyrrolidinyl)oxy]phenyl]acetate dihydrochloride
(solid)
$^1$H-NMR (DMSO-d$_6$) δ:1.18 (3H, t, J=7.0Hz), 2.0–2.30 (2H, m), 3.02 (4H, s), 3.00–4.00 (6H, m), 4.90 (2H, q, J=7.0Hz), 5.12 (1H, br), 6.80–7.00 (3H, m), 7.24 (1H, d, J=8.64Hz), 7.76 (2H, s), 8.12 (1H, s), 9.29 (2H, br), 9.45 (2H, br), 9.40–10.10 (2H, br)

INVENTIVE EXAMPLE 9 ethyl 5-amidino-2-[2-[4-[((3S)-3-pyrrolidinyl)oxy]phenyl]ethyl]-3-benzofurancarboxylate dihydrochloride
(solid)
$^1$H-NMR (DMSO-d$_6$) δ:1.36 (3H, t), 2.08 (2H, m), 4.30 (2H), 5.00 (1H, br), 6.90 (2H, d), 7.10 (2H, d), 7.83 (2H), 8.34 (1H, s), 9.27 (2H, br), 9.51 (4H, br)

INVENTIVE EXAMPLE 10 ethyl 3-(5-amidinobenzo[b]thien-2-yl)-2-[4-[((3S)-3-pyrrolidinyl)oxy]phenyl]propionate dihydrochloride
(solid)
$^1$H-NMR (DMSO-d$_6$) δ:1.19 (3H, t, J=7.0Hz), 2.00–2.40 (2H, m), 3.00–4.20 (9H, m), 5.08 (1H, br), 6.92 (2H, d, J=8.75Hz), 7.27 (1H, s), 7.31 (2H, d, J=8.75Hz), 7.68 (1H, dd, J=8.3 and 1.5Hz), 8.10 (1H, d, J=8.3Hz), 8.27 (1H, d, J=1.5Hz), 9.19 (2H, br), 9.42 (2H, br), 9.10–10.00 (2H, br)

INVENTIVE EXAMPLE 11 ethyl 3-(6-amidinobenzo[b]thien-2-yl)-2-[4-[((3S)-3-pyrrolidinyl)oxy]phenyl]propionate dihydrochloride
(solid)
$^1$H-NMR (DMSO-d$_6$) δ:1.05 (3H, t), 2.10 (2H, m), 3.30 (7H, m), 4.0 (2H, q), 5.05 (1H, br), 6.90 (2H, d), 7.22 (3H, m), 7.60–7.90 (2H, m), 8.38 (1H, s), 9.10 (2H, br), 9.35 (2H, br), 9.40 (2H, br)

INVENTIVE EXAMPLE 12 ethyl 3-(6-amidino-1-ethyl-2-indolyl)-2-[4-[(4-piperidinyl)oxy]phenyl]propionate dihydrochloride
(solid)
$^1$H-NMR (DMSO-d$_6$) δ:1.05 (3H, t), 1.28 (3H), 1.83 (2H, br), 2.08 (2H, br), 2.90–3.20 (5H, br), 3.90–4.40 (3H, m), 4.62 (1H, br), 6.34 (1H, s), 6.97(2H, d), 7.34 (2H, d), 7.47 (1H, d), 7.58 (1H, d), 8.13 (1H, s), 8.90–9.40 (6H, br)

INVENTIVE EXAMPLE 13 ethyl 3-(6-amidino-1-ethyl-2-indolyl)-2-[4-[((3R)-3-pyrrolidinyl)oxy]phenyl]propionate dihydrochloride
(solid)
$^1$H-NMR (DMSO-d$_6$) δ:1.08 (3H, t, J=7.0Hz), 1.31 (3H, t, J =7.0Hz), 2.10–2.30 (2H, br), 3.17.(1H, dd), 3.20–3.40 (2H, m), 3.90–4.40 (5H, m), 5.14 (1H, br), 6.37 (1H, s), 6.97 (2H, d, J=8.8Hz), 7.38 (2H, d, J=8.8Hz), 7.49 (1H, d, J=8.3Hz), 7.62 (1H, d, J=8.3Hz), 8.14 (1H, s), 8.99 (2H, br), 9.32 (2H, br), 9.50–9.70 (2H, br)

INVENTIVE EXAMPLE 14 ethyl 3-(6-amidino-1-methyl-2-indolyl)-2-[4-[((3S)-3-pyrrolidinyl)oxy]phenyl]propionate dihydrochloride (ester interchange due to the use of ethanol solvent)
(solid)
$^1$H-NMR (DMSO-d$_6$) δ:1.05 (3H, t), 1.95–2.30 (2H, m), 3.76 (3H, s), 4.02 (2H, q), 4.00–4.30 (1H, m), 5.00–5.20 (1H, m), 6.38 (1H, s), 7.00 (2H, d), 7.40 (2H, d), 7.50–7.70 (2H, m), 8.25 (1H, s), 9.30–10.10(6H)

INVENTIVE EXAMPLE 15 ethyl 3-(6-amidino-2-naphthyl)-2-[4-[((3S)-3-pyrrolidinyl)oxy]phenyl]propionate dihydrochloride
(solid)
$^1$H-NMR (DMSO-d$_6$) δ:1.06 (3H, t, J=7.0Hz), 2.00–2.20 (2H, m), 3.00–4.00 (7H, m), 3.99 (2H, q, J=7.0Hz), 5.11 (1H, m), 6.92 (2H, d, J=9.0Hz), 7.31 (2H, d, J=9.0Hz), 7.55 (1H, d, J=8.0Hz), 7.80–8.10 (4H, m), 8.51 (1H, s), 9.40 (2H, br), 9.58 (2H, br), 9.50–10.00 (2H, br)

INVENTIVE EXAMPLE 16 ethyl 3-(7-amidino-2-naphthyl)-2-[4-[((3S)-3-pyrrolidinyl)oxy]phenyl]propionate dihydrochloride
(solid)
$^1$H-NMR (DMSO-d$_6$) δ:1.01 (3H, t, J=7.0Hz), 2.00–2.20 (2H, m), 3.10–3.80 (7H, m), 3.98 (2H, q, J=7.0Hz), 5.10 (1H, m), 6.93 (2H, d, J=9.0Hz), 7.32 (2H, d, J=9.0Hz), 7.50–8.10 (5H, m), 8.44 (1H, m), 9.41 (2H, br), 9.59 (2H, br), 9.30–10.00 (2H, br)

INVENTIVE EXAMPLE 17 ethyl 3-(7-amidino-2-naphthyl)-2-[4-[(4-piperidinyl)methoxy]phenyl]propionate dihydrochloride
(solid)
$^1$H-NMR (DMSO-d$_6$) δ: 1.01 (3H, t, J=7.1Hz), 1.45–1.55 (2H, m), 1.85–1.95 (2H, m), 2.80–2.95 (2H, m), 3.15–3.50 (5H, m), 3.81 (2H, d), 3.95–4.05 (2H, m), 4.05–4.15 (1H, m), 6.87 (2H, d, J=8.3Hz), 7.27 (2H, d, J=8.3Hz), 7.58–7.63 (1H, m), 7.75–7.80 (1H, m), 7.84 (1H, s), 7.95 (1H, d, J=8.8Hz), 8.07 (1H, d, J=8.8Hz), 8.40 (1H, s), 9.29 (2H), 9.53 (2H)

INVENTIVE EXAMPLE 18

3-(7-amidino-2-naphthyl)-2-[4-[(4-piperidinyl)methoxy]phenyl]propionic acid hydrochloride monohydrate 1.51 g of ethyl 3-(7-amidino-2-naphthyl)-2-[4-[(4-piperidinyl)methoxy]phenyl]propionate dihydrochloride was dissolved in 50 ml of concentrated hydrochloric acid, and the solution was allowed to stand still in a sealed container at room temperature for 62 hours. After drying the resulting reaction solution under a reduced pressure, the thus obtained residue was purified by applying it to a column packed with a highly porous polymer type synthetic adsorbent (styrene-divinylbenzene polymer: HP-20). Thereafter, the thus eluted fractions of interest were pooled, and mixed with a small amount of ethanol, and then the crystals thus precipitated were collected by filtration. In this way, 0.79 g of the title compound was obtained in the form of crystals.
mp: 285°–287° C. (decomp.)

(Since solubility of the thus formed product to any solvent was very low, the compound was made into dihydrochloride with hydrochloric acid and then dried prior to the NMR measurement.)

$^1$H-NMR (DMSO-$d_6$) δ: 1.45–1.60 (2H, m), 1.85–1.95 (2H, m), 1.95–2.05 (1H, br), 2.8–2.9 (2H, m), 3.1–3.2 (1H, m), 3.2–3.3 (2H, m), 3.4–3.5 (1H, m), 3.80 (2H, d, J=6.4Hz), 3.9–4.0 (1H, m), 6.87 (2H, d, J=8.8Hz), 7.27 (2H, d, J=8.8Hz), 7.60 (1H, d, J=8.l8Hz), 7.75–7.80 (1H, m), 7.83 (1H, s), 7.94 (1H, d, J=8.8Hz), 8.07 (1H, d, J=8.3Hz) 8.40 (1H, s), 8.8–8.9 (1H, br), 9.33 (2H), 9.54 (2H)

INVENTIVE EXAMPLE 19

3-(5-amidino-2-benzofuranyl)-2-[4-[((3S)-3-pyrrolidinyl)oxy]phenyl]propionic acid dihydrochloride 3.2 g of ethyl 3-(5-amidino-2-benzofuranyl)-2-[4-[((3S)-3-pyrrolidinyl)oxy]phenyl]propionate dihydrochloride was dissolved in 80 ml of 2N hydrochloric acid, and the solution was refluxed under heating for 30 minutes. After cooling and distilling off the solvent, the resulting residue was purified by subjecting it to column chromatography using a column packed with a highly porous polymer type synthetic adsorbent (styrene-divinylbenzene polymer: Diaion HP-20) and using 5–10% acetonitrile as an elution solvent. Thereafter, the thus eluted fractions of interest were pooled, adjusted to pH 2–3 with dilute hydrochloric acid, and then concentrated to dryness. In this way, 1.25 g of the title compound was obtained in a solid form.

$^1$H-NMR (DMSO-$d_6$) δ: 2.00–2.30 (2H, m), 3.00–3.80 (6H, m), 4.10 (1H, t, J=7.2Hz), 5.10 (1H, br), 6.74 (1H, s), 6.94 (2H, d, J=8.3Hz), 7.40 (2H, d, J=8.3Hz), 7.74 (2H, s), 8.09 (1H, s), 9.22 (2H, br), 9.40 (2H, br), 9.10–10.00 (2H, br)

The following compounds of Inventive Examples 20 to 26 were prepared in accordance with the procedure of Inventive Example 19.

INVENTIVE EXAMPLE 20

3-(5-amidino-2-benzofuranyl)-2-[4-[((2S,4S)-2-dimethylcarbamoyl-4-pyrrolidinyl)oxy]phenyl]propionic acid dihydrochloride
(solid)

$^1$H-NMR (DMSO-$d_6$) δ: 1.80–3.00 (2H, m), 2.89 (3H, s), 2.95 (3H, s), 3.00–3.70 (4H, m), 4.09 (1H, t, J=7.9Hz), 4.70 (1H, br), 5.12 (1H, br), 6.71 (1H, s), 6.86 (2H, d, J=8.3Hz), 7.30 (2H, d, J=8.3Hz), 7.73 (2H, s), 8.10 (1H, s), 8.76 (1H, br), 9.30 (2H, br), 9.46 (2H, br), 10.80 (1H, br)

INVENTIVE EXAMPLE 21

2-(5-amidino-2-benzofuranyl)-3-[4-[((3S)-3-pyrrolidinyl)oxy]phenyl]propionic acid dihydrochloride
(solid)

$^1$H-NMR (DMSO-$d_6$) δ:1.90–2.30 (2H, m), 2.90–3.70 (6H, m), 4.26 (1H, t, J=7.9Hz), 5.06 (1H, br), 6.83 (2H, d, J=8.3Hz), 6.93 (1H, s), 7.17 (2H, d, J=8.3Hz), 7.78 (2H, s), 8.14 (1H, s), 9.30 (2H, br), 9.47 (2H, br), 9.80 (2H, br)

INVENTIVE EXAMPLE 22

3-(5-amidino-2-benzofuranyl)-3-[4-[((3S)-3-pyrrolidinyl)oxy]phenyl]propionic acid dihydrochloride
(solid)

$^1$H-NMR (DMSO-$d_6$) δ: 2.0–2.2 (2H, m), 3.0–4.0 (6H, m), 4.6 (1H, m), 5.10 (1H, m), 6.92 (1H, s), 6.92 (2H, d, J=9.0Hz), 7.32 (2H, d, J=9.0Hz), 7.73 (2H, s), 8.16 (1H, s), 9.30 (2H, br), 9.46 (2H, br), 9.6–10.0 (2H, br)

INVENTIVE EXAMPLE 23

2-[2-(5-amidino-2-benzofuranyl)ethyl]-5-[((3S)-3-pyrrolidinyl)oxy]benzoic acid dihydrochloride
(solid)

$^1$H-NMR (DMSO-$d_6$) δ:1.90–2.30 (2H, m), 2.90–3.70 (8H, m), 4.96 (1H, br), 6.75 (1H, s), 7.08 (1H, dd, =7.9 and 2.8Hz), 7.28 (1H, d, J=7.9Hz), 7.41 (1H, d, =2.8Hz), 7.75 (2H, s), 8.09 (1H, s), 9.25 (2H, br), 9.42 (2H, br), 9.50–10.00 (2H, br)

INVENTIVE EXAMPLE 24

[2-[2-(5-amidino-2-benzofuranyl)ethyl]-5-[((3S)-3-pyrrolidinyl)oxy]phenyl]acetic acid dihydrochloride
(solid)

$^1$H-NMR (DMSO-$d_6$) δ:1.95–2.30 (2H, m), 3.03 (4H, s), 5.04 (1H, br), 6.68–6.90 (3H, m), 7.14 (1H, d, J=8.3Hz), 7.74 (2H, s), 8.10 (1H, s), 9.38 (2H, br), 9.66 (2H, br), 9.00–10.00 (2H, br)

INVENTIVE EXAMPLE 25

3-(5-amidinobenzo[b]thien-2-yl)-2-[4-[((3S)-3-pyrrolidinyl)oxy]phenyl]propionic acid dihydrochloride
(solid)

$^1$H-NMR (DMSO-$d_6$) δ:1.90–2.40 (2H, m), 3.00–4.10 (7H, m), 5.14 (1H, br), 6.93 (2H, d, J.=8.2Hz), 7.28 (1H, s), 7.33 (2H, d, J=8.2Hz), 7.70 (1H, d, J=8.8Hz), 8.09 (1H, d, J=8.8Hz), 8.26 (1H, s), 9.24 (2H, br), 9.47 (2H, br), 9.00–10.20 (2H, br)

INVENTIVE EXAMPLE 26

3-(7-amidino-2-naphthyl)-2-[4-[((3S)-3-pyrrolidinyl)oxy]phenyl]propionic acid dihydrochloride
(solid)

$^1$H-NMR (DMSO-$d_6$) δ: 2.00–2.20 (2H, m), 3.00–3.70 (6H, m), 4.01 (1H, m), 5.11 (1H, m), 6.92 (2H, d, J=9.0Hz), 7.33 (2H, d, J=9.0Hz), 7.50–8.20 (5H, m), 8.43 (1H, s), 9.00–10.00 (2H, br)

INVENTIVE EXAMPLE 27 ethyl (+)-3-(7-amidino-2-naphthyl)-2-[4-[((3S)-3-pyrrolidinyl)oxy]phenyl]propionate dihydrochloride 123.1 g of ethyl (+)-2-[4-[((3S)-1-tert-butoxycarbonyl-3-pyrrolidinyl)oxy]phenyl]-3-(7-cyano-2-naphthyl)propionate was dissolved in a solvent mixture of 480 ml of dichloromethane and 1286 ml of ethanol. With stirring at −10° C., hydrogen chloride was bubbled into the thus prepared solution to a saturation level, and the resulting solution was allowed to stand still for 26 hours at a temperature of −8° to −5° C. Thereafter, the resulting reaction solution was concentrated under a reduced pressure at a temperature of 10° C. or below to obtain 154 g of an oily material. The thus obtained oily material was dissolved in 1480 ml of ethanol and, while keeping the inner temperature at −10° C. or below, ammonia gas was introduced until its concentration became 21% (w/w) or more. After maintaining at a temperature of −8° to −5° C. for 107 hours, the resulting reaction solution was concentrated under a reduced pressure at a temperature of 10° C. or below to distill off the solvent, and the thus obtained residue was dissolved in 200 ml of water. After adjusting to pH 3–5 with dilute hydrochloric acid, the resulting solution was purified by subjecting it to column chromatography using a column packed with a highly porous polymer type synthetic adsorbent (styrene-divinylbenzene polymer: Diaion HP-20) and using a water/acetonitrile mixture as an elution solvent. Thereafter, thus eluted fractions of interest were pooled, mixed with a small amount of dilute hydrochloric acid, and then concentrated to dryness. In this way, 107 g of the title compound was obtained in the form of a colorless solid.

$^1$H-NMR (DMSO-$d_6$) δ:1.01 (3H, t, J=7.2Hz), 2.00–2.30 (2H, m), 3.1–3.6 (6H, m), 3.90–4.05 (2H, m), 4.05–4.15 (1H, m), 5.10 (1H, br), 6.93 (2H, d, J=8.8Hz), 7.32 (2H), 7.60 (1H, d, J=8.3Hz), 7.78 (1H, d, J=8.3Hz), 7.85 (1H, s), 7.96 (1H, d, J=8.3Hz), 8.08 (1H, d, J=8.3Hz), 8.41 (1H, s), 9.20–9.30 (2H, br), 9.40–9.70 (4H, br)

The following compounds of Inventive Examples 28 to 32 were prepared in accordance with the procedure of Inventive Example 27.

INVENTIVE EXAMPLE 28 ethyl (−)-3-(7-amidino-2-naphthyl)-2-[4-[((3S)-3-pyrrolidinyl)oxy]phenyl]propionate dihydrochloride (solid)

$^1$H-NMR (DMSO-$d_6$) δ:1.02 (3H, t, J=7.2Hz), 2.00–2.30 (2H, m), 3.1–3.6 (6H, m), 3.90–4.05 (2H, m), 4.05–4.15 (1H, m) 5.10 (1H, br), 6.94 (2H, d, J=8.8Hz), 7.32 (2H), 7.60 (1H, d, J=8.3Hz), 7.78 (1H, d, J=8.3Hz), 7.86 (1H, s), 7.96 (1H, d, J=8.3Hz), 8.08 (1H, d, J=8.3Hz), 8.42 (1H, s), 9.20–9.30 (2H, br), 9.40–9.70 (4H, br)

INVENTIVE EXAMPLE 29 ethyl (+)-3-(5-amidinobenzo[b]thien-2-yl)-2-[4-[((2S)-2-pyrrolidinyl)methoxy]phenyl]propionate dihydrochloride (solid)

$^1$H-NMR (DMSO-$d_6$) δ:1.10 (3H, t, J=7.3Hz), 1.73 (1H, dq, J=12.3 and 8.3Hz), 1.84–2.05 (2H, m), 2.06–2.16 (1H, m), 3.12–3.27 (2H, br), 3.39 (1H, dd, J=15.0 and 7.8Hz), 3.64 (1H, dd, J=15.0 and 7.8Hz), 3.80–3.93 (1H, br), 4.00–4.24 (5H, m), 6.93 (2H, d, J=8.3Hz), 7.30 (1H, s), 7.31 (2H, d), 7.67 (1H, d, J=8.3Hz), 8.11 (1H, d, J=8.3Hz), 8.23 (1H, s), 9.12–9.30 (3H), 9.45 (2H, s), 9.43 (2H, s), 9.74–9.94 (1H, br)

INVENTIVE EXAMPLE 30 ethyl (−)-3-(5-amidinobenzo[b]thien-2-yl)-2-[4-[((2S)-2-pyrrolidinyl)methoxy]phenyl]propionate dihydrochloride (solid)

$^1$H-NMR (DMSO-$d_6$) δ:1.09 (3H, t, J=7.3Hz), 1.72 (1H, dq, J=12.1 and 8.3Hz), 1.84–2.03 (2H, m), 2.06–2.16 (1H, m), 3.12–3.27 (2H, br), 3.39 (1H, dd, J=15.0 and 7.8Hz), 3.64 (1H, dd, J=15.0 and 7.8Hz), 3.80–3.93 (1H, br), 4.00–4.24 (5H, m), 6.93 (2H, d, J=8.8Hz, 2 x ArH), 7.30 (1H, s), 7.31 (2H, d, J=8.8Hz), 7.67 (1H, dd, J=8.3 and 1.5Hz), 8.11 (1H, d, J=8.3Hz), 8.23 (1H, d, J=1.5Hz), 9.10–9.25 (1H, br), 9.21 (2H, s), 9.43 (2H, s), 9.74–9.84 (1H, br)

INVENTIVE EXAMPLE 31 ethyl (+)-3-(7-amidino-2-naphthyl)-2-[4-[(4-piperidinyl)oxy]phenyl]propionate dihydrochloride solid $^1$H-NMR (DMSO-$d_6$) 1.01 (3H, t, J=7.1Hz), 1.75–1.85 (2H, m), 2.05–2.15 (2H, m), 3.0–3.1 (2H, m), 3.1–3.2 (3H, m), 3.9–4.0 (2H, m), 4.0–4.1 (1H, br), 4.1–4.2 (1H, m), 4.61 (1H, br), 6.95 (2H, d, J=8.8Hz), 7.29 (2H, d, J=8.8Hz), 7.61 (1H, d, J=8.3Hz), 7.78 (1H, d, J=8.3Hz), 7.84 (1H, s), 7.95 (1H, d, J=8.3Hz), 8.07 (1H, d, J=8.8Hz), 8.38 (1H, s), 8.9–9.1 (2H, br), 9.20 (2H, br), 9.49 (2H, br)

INVENTIVE EXAMPLE 32 ethyl (−)-3-(7-amidino-2-naphthyl)-2-[4-[(4-piperidinyl)oxy]phenyl]propionate dihydrochloride (solid)

$^1$H-NMR (DMSO-$d_6$) δ:1.01 (3H, t, J=7.1Hz), 1.75–1.80 (2H, m), 2.05–2.15 (2H, m), 3.0–3.1 (2H, m), 3.1–3.3 (3H, m), 3.50–3.60 (1H, m), 3.65–3.75 (2H, M), 3.9–4.0 (2H, m), 4.0–4.1 (1H, br), 4.1–4.2 (1H, m), 4.61 (1H, br), 6.95 (2H, d, J=8.3Hz), 7.29 (2H, d, J=8.3Hz), 7.61 (1H, d, J=8.8Hz), 7.78 (1H, d, J=8.3Hz), 7.84 (1H, s), 7.95 (1H, d, J=8.3Hz), 8.07(1H, d, J=8.8Hz), 8.39 (1H, s), 8.9–9.1 (2H, br), 9.23 (2H, br), 9.50 (2H, br)

INVENTIVE EXAMPLE 33 ethyl (+)-2-[4-[((3S)-1-acetimidoyl-3-pyrrolidinyl)oxy]phenyl]-3-(7-amidino-2-naphthyl)propionate dihydrochloride In 1,000 ml of ethanol was dissolved 105.3 g of ethyl (+)-3-(7-amidino-2-naphthyl)-2-[4-[((3S)-3-pyrrolidinyl)oxy]phenyl]propionate dihydrochloride. With stirring at room temperature, the thus prepared solution was mixed with 51.5 g of ethyl acetimidate hydrochloride. With ice cooling and stirring, 89 ml of triethylamine was added dropwise to the above solution while keeping the inner temperature at 3° to 5° C., and the stirring was continued for 2.5 hours while keeping the temperature at 5° C. or below. After distilling off the solvent under a reduced pressure at a low temperature, the resulting reaction solution was adjusted to pH 4–5 with dilute hydrochloric acid, followed by further distillation under a reduced pressure to remove the solvent. The resulting residue was purified by subjecting it to column chromatography using a column packed with a highly porous polymer type synthetic adsorbent (styrene-divinylbenzene polymer: Diaion HP-20) and using a water/acetonitrile mixture as an elution solvent. Thereafter, thus eluted fractions of interest were pooled, mixed with a small amount of dilute hydrochloric acid, and then concentrated to dryness. In this way, 110.1 g of the title compound was obtained in the form of a colorless solid.

$^1$H-NMR (DMSO-$d_6$) δ: 1.02 (3H, m), 2.10–2.35 (2H, m), 2.26 (1.5H, s), 2.31 (1.5H, s), 3.19 (1H, m), 3.40–3.85 (5H, m), 3.90–4.05 (2H, m), 4.05–4.15 (1H, m), 5.13 (0.5H, br), 5.20 (0.5H, br), 6.90–6.97 (2H, m), 7.32 (2H, m), 7.61 (1H, d, J=8.3Hz), 7.80 (1H, dd, J=8.3 and 1.5Hz), 7.85 (1H, s), 7.96 (1H, d, J=8.3Hz), 8.08 (1H, d, J=8.3Hz), 8.43 (1H, s), 8.52 (0.5H, br), 8.61 (0.5H, br), 9.28–9.40 (3H, br), 9.50–9.60 (2H, br)

The following compounds of Inventive Examples 34 to 38 were prepared in accordance with the procedure of Inventive Example 33.

INVENTIVE EXAMPLE 34 ethyl (−)-2-[4-[((3S)-1-acetimidoyl-3-pyrrolidinyl)oxy]phenyl]-3-[7-amidino-2-naphthyl]propionate dihydrochloride
(solid)
$^1$H-NMR (DMSO-$d_6$) δ:1.02 (3H, m), 2.10–2.35 (2H, m), 2.26 (1.5H, s), 2.30 (1.5H, s), 3.19 (1H, m), 3.40–3.85 (5H, m), 3.90–4.05 (2H, m), 4.05–4.15 (1H, m), 5.13 (0.5H, br), 5.20 (0.5H, br), 6.90–6.97 (2H, m), 7.32 (2H, m), 7.61 (1H, d, J=8.3Hz), 7.80 (1H, dd, J=8.3 and 1.5Hz), 7.84 (1H, s), 7.96 (1H, d, J=8.3Hz), 8.08 (1H, d, J=8.3Hz), 8.42 (1H, s), 8.52 (0.5H, br), 8.61 (0.5H, br), 9.28–9.40 (3H, br), 9.50–9.60 (2H, br)

INVENTIVE EXAMPLE 35 ethyl (+)-2-[4-[((2S)-1-acetimidoyl-3-pyrrolidinyl)methoxy]phenyl]-3-(5-amidinobenzo[b]thien-2-yl)propionate dihydrochloride
(solid)
$^1$H-NMR (DMSO-$d_6$) δ:1.09 (3H, t, J=7.3Hz), 1.95–2.60 (4H, m), 2.26 (1H, s), 2.47 (2H, s), 3.30–3.70 (4H, m), 3.90–4.10 (5H, m), 4.40–4.60 (1H, m), 6.85–6.95 (2H, m), 7.28–7.33 (3H, m), 7.67 (1H, d, J=8.3Hz), 8.11 (1H, d, J=8.3Hz), 8.23 (1H, s), 8.54 (⅔H, s), 8.69 (⅓H, s), 9.23 (2H, s), 9.35–9.50 (3H, m)

INVENTIVE EXAMPLE 36 ethyl (−)-2-[4-[((2S)-1-acetimidoyl-3-pyrrolidinyl)methoxy]phenyl]-3-(5-amidinobenzo[b]thien-2-yl)propionate dihydrochloride
(solid)
$^1$H-NMR (DMSO-$d_6$) δ: 1.09 (3H, t, J=7.3Hz), 1.95–2.60 (4H, m), 2.26 (1H, s), 2.47 (2H, s), 3.30–3.70 (4H, m), 3.90–4.10 (5H, m), 4.40–4.60 (1H, m), 6.85–6.95 (2H, m),° 7.28–7.33 (3H, m), 7.67 (1H, d, J=8.3Hz), 8.10 (1H, d, J=8.3Hz), 8.23 (1H, s), 8.51 (⅔H, s), 8.66 (⅓H, s), 9.16 (2H, s), 9.30–9.48 (3H, m)

INVENTIVE EXAMPLE 37

(+)-2-[4-[(1-acetimidoyl-4-piperidinyl)oxy]phenyl]-3-(7-amidino-2-naphthyl)propionate dihydrochloride
(solid)
$^1$H-NMR (DMSO-$d_6$) δ: 1.01 (3H, t, J=6.9Hz), 1.65–1.80 (2H, m), 2.0–2.1 (2H, m), 2.30 (3H, s), 3.1–3.2 (1H, m), 3.2–3.8 (5H, m), 3.9–4.0 (2H, m), 4.0–4.1 (1H, br), 4.67 (1H, br), 6.95 (2H, d, J=8.8Hz), 7.30 (2H, d, J=8.8Hz), 7.61 (1H, d, J=8.3Hz), 7.78–7.84 (1H, m), 7.84 (1H, s), 7.95 (1H, d, J=8.3Hz), 8.08 (1H, d, J=8.3Hz), 8.40 (1H, s), 8.80–9.55 (6H)

INVENTIVE EXAMPLE 38 ethyl (−)-2-[4-[(1-acetimidoyl-4-piperidinyl)oxy]phenyl]-3-(7-amidino-2-naphthyl)propionate dihydrochloride
(solid)
$[α]_D$=−67.69° (c=0.585, $H_2O$)

INVENTIVE EXAMPLE 39

(+)-2-[4-[((3S)-1-acetimidoyl-3-pyrrolidinyl)oxy]phenyl]-3-(7-amidino-2-naphthyl)propionic acid dihydrochloride While keeping the inner temperature at −5° C. or below, 110.1 g of ethyl (+)-2-[4-[((3S)-1-acetimidoyl-3-pyrrolidinyl)oxy]phenyl]-3-(7-amidino-2-naphthyl)propionate dihydrochloride was dissolved in 3,300 ml of concentrated hydrochloric acid, and the resulting solution was allowed to stand still for 232 hours at 5° C. The resulting reaction solution was concentrated by distilling off hydrochloric acid and water under a reduced pressure. The resulting residue was purified by subjecting it to column chromatography using a column packed with a highly porous polymer type synthetic adsorbent (styrene-divinylbenzene polymer: Diaion HP-20) and using a water/ acetonitrile mixture as an elution solvent. Thereafter, the thus eluted fractions of interest were pooled, mixed with a small amount of dilute hydrochloric acid, and then concentrated to dryness. In this way, 103.6 g of the title compound was obtained in the form of a light yellow solid.
$^1$H-NMR (DMSO-$d_6$) δ:2.10–2.4 (2H, m), 2.28 (1.5H, s), 2.31 (1.5H, s), 3.10–3.30 (1H, m), 3.40–4.10 (6H, m), 5.14 (0.5H, br), 5.20 (0.5H, br), 6.90–7.00 (2H, m), 7.35–7.40 (2H, m), 7.60 (1H, d, J=8.3Hz), 7.80 (1H, d, J=8.3Hz), 7.84 (1H, s), 7.94 (1H, d, J=8.3Hz), 8.06 (1H, d, J=8.3Hz), 8.42 (1H, s), 8.55 (0.5H, br), 8.65 (0.5H, br), 9.30–9.70 (5H)
HPLC: Column; a ligand exchange type column with D-penicillamine as the optically active site (SUMICHIRAL OA-5000, 4.6 φ×150 mm, Sumika Analysis Center)
Solvent;2 mM copper sulfate aqueous solution: acetonitrile=85:15 (v/v)
Flow rate; 1 ml/min
Column temperature; 60° C.
Retention time; 43.60 minutes The following compounds of Inventive Examples 40 to 44 were prepared in accordance with the procedure of Inventive Example 39.

INVENTIVE EXAMPLE 40

(−)-2-[4-[((3S)-1-acetimidoyl-3-pyrrolidinyl)oxy]phenyl]-3-(7-amidino-2-naphthyl)propionic acid dihydrochloride
(solid)
$^1$H-NMR (DMSO-$d_6$) δ:2.05–2.4 (2H, m), 2.28 (1.5H, s), 2.31 (1.5H, s), 3.10–3.30 (1H, m), 3.40–4.10 (6H, m), 5.13 (0.5H, br), 5.20 (0.5H, br), 6.90–7.00 (2H, m), 7.35–7.40 (2H, m), 7.60 (1H, d, J=8.3Hz), 7.81 (1H, d, J=8.3Hz), 7.84 (1H, s), 7.94 (1H, d, J=8.3Hz), 8.06 (1H, d, J=8.3Hz), 8.42 (1H, s), 8.55 (0.5H, br), 8.64 (0.5H, br), 9.30–9.70 (5H)
HPLC: Column; a ligand exchange type column with D-penicillamine as the optically active site (SUMICHIRAL OA-5000, 4.6 φ×150 mm, Sumika Analysis Center)
Solvent; 2 mM copper sulfate aqueous solution: acetonitrile=85:15 (v/v)
Flow rate: 1 ml/min
Column temperature; 60° C.
Retention time; 38.14 minutes

INVENTIVE EXAMPLE 41

(+)-2-[4-[((2S)-1-acetimidoyl-2-pyrrolidinyl)methoxy]phenyl]-3-(5-amidinobenzo[b]thien-2-yl)propionic acid dihydrochloride (solid)
$^1$H-NMR (DMSO-$d_6$) δ:1.95–2.60 (4H, m), 2.25 (1H, s), 2.44 (2H, s), 3.15–3.80 (5H, m), 4.40–4.60 (1H, m), 6.83–6.95 (2H, m), 7.26 (1H, s), 7.32 (2H, d, J=8.8Hz), 7.61 (1H, d, J=8.5Hz), 8.04 (1H, d, J=8.5Hz), 8.21 (1H, s), 8.40–10.90 (6H)

INVENTIVE EXAMPLE 42

(−)-2-[4-[((2S)-1-acetimidoyl-2-pyrrolidinyl)methoxy]phenyl]-3-(5-amidinobenzo[b]thien-2-yl)propionic acid dihydrochloride (solid)
$^1$H-NMR (DMSO-$d_6$) δ:1.95–2.60 (4H, m), 2.25 (1H, S), 2.44 (2H, s), 3.15–3.75 (4H, m), 3.82 (1H, t, J=7.5Hz), 4.40–4.60 (1H, m), 6.83–6.95 (2H, m), 7.27 (1H, s), 7.31 (2H, d, J=8.8Hz), 7.64 (1H, d, J=8.8Hz), 8.06 (1H, d, J=8.8Hz), 8.2 1 (1H, s), 8.40–10.40 (6H)

INVENTIVE EXAMPLE 43

(+)-2-[4-[(1-acetimidoyl-4-piperidinyl)oxy]phenyl]-3-(7-amidino-2-naphthyl)propionic acid dihydrochloride (solid)
$^1$H-NMR (DMSO-$d_6$) δ:1.65–1.80 (2H, m), 1.95–2.05 (2H, m), 2.31 (3H, s), 3.1–3.2 (1H, m), 3.3–3.9 (5H, m), 3.95–4.05 (1H, m), 4.66 (1H, br), 6.95 (2H, d, J=8.8HZ), 7.29 (2H, d, J=8.3Hz), 7.60 (1H, d, J=8.8Hz), 7.81 (1H, d, J=8.8Hz), 7.84 (1H, s), 7.95 (1H, d, J=8.8Hz), 8.07 (1H, d, J=8.8Hz), 8.43 (1H, s), 8.80–9.65 (6H)

INVENTIVE EXAMPLE 44

(−)-2-[4-[(1-acetimidoyl-4-piperidinyl)oxy]phenyl]-3-(7-amidino-2-naphthyl)propionic acid dihydrochloride (solid)
$^1$H-NMR (DMSO-$d_6$) δ:1.65–1.80 (2H, m), 2.00–2.10 (2H, m), 2.30 (3H, s), 3.1–3.2 (1H, m), 3.3–3.85 (5H, m), 3.95–4.05 (1H, m), 4.66 (1H, m), 6.95 (2H, d, J=8.8Hz), 7.30 (2H, d, J=8.8Hz), 7.61 (1H, d, J=8.8Hz), 7.78 (1H, d, J=8.8Hz), 7.85 (1H, s), 7.95 (1H, d, J=8.8Hz), 8.08 (1H, d, J=8.8Hz), 8.40 (1H, s), 8.60–9.65 (6H)

INVENTIVE EXAMPLE 45

(+)-2-[4-[((3S)-1-acetimidoyl-3-pyrrolidinyl)oxy]phenyl]-3-(7-amidino-2-naphthyl)propionic acid hydrochloride pentahydrate 102.6 g of (+)-2-[4-[((3S)-1-acetimidoyl-3-pyrrolidinyl)oxy]phenyl]-3-(7-amidino-2-naphthyl)propionic acid dihydrochloride was dissolved in 1,000 ml of water. With stirring, the thus prepared solution was adjusted to pH 4.8 by gradually adding a strongly basic OH type ion exchange resin (Amberlite IRA-410). Thereafter, the resin was removed by filtration, and the resulting filtrate was concentrated to dryness. The thus obtained residue (94.6 g) was dissolved in 142 ml of water, and the solution was mixed with 1,570 ml of ethanol, and stirred at room temperature for 1 hour. After removing thus formed crystals by filtration, the resulting mother liquor was seeded with the crystals of interest, and stirred at 8° C. for 40 hours. Thereafter, the thus precipitated crystals were collected by suction filtration, washed with ethanol, and then air-dried for 6.5 hours under normal pressure at a relative humidity of 60 to 70%. In this way, 70.3 g of the title compound was obtained in the form of colorless prism crystals.

$[\alpha]_D^{24}$=+57.4° (C=1.000, $H_2O$) (solubilization at 40° C., measured after 30 minutes of heating at this temperature)
$^1$H-NMR (DMSO-$d_6$) δ:2.20–2.35 (2H, m), 2.29 (1.5H, s), 2.32 (1.5H, s), 2.80–2.95 (1H, m), 3.30–4.00 (6H, m), 5.16 (0.5H, br), 5.22 (0.5H, br), 6.90–7.00 (2H, m), 7.45–7.51 (2H, m), 7.57 (1H, d, J=8.3Hz), 7.66 (1H, d, J=8.0Hz), 7.93 (1H, d, J=8.3Hz), 7.97 (1H, d, J=8.3Hz), 8.11 (1H, s), 8.68 (1H, br), 8.70–9.30 (br), 11.50–12.20 (br)

Elementary analysis
theoretical value ($C_{26}H_{28}N_4O_3 \cdot HCl \cdot 5H_2O$): C, 54.68; H, 6.88; N, 9.80; Cl, 6.21
analytical value: C, 54.77; H, 6.76; N, 9.68; Cl, 6.42

Based on the results of crystal X-ray analysis, the thus obtained title compound was judged to be (2S)-2-[4-[((3S)-1-acetimidoyl-3-pyrrolidinyl)oxy]phenyl]-3-(7-amidino-2-naphthyl)propionic acid

INVENTIVE EXAMPLE 46 methyl (+)-3-(6-amidino-2-indolyl)-2-[4-[((3S)-3-pyrrolidinyl)oxy]phenyl]propionate dihydrochloride During ice cooling, hydrogen chloride was bubbled into a solvent mixture of 10 ml of dichloromethane and 20 ml of methanol. To the thus saturated solution was added 10 ml of a dichloromethane solution containing 450 mg of (+)-((2S)-1-p-toluenesulfonyl-2-pyrrolidinyl)methyl 2-[4-[((3S)-1-tert-butoxycarbonyl-3-pyrrolidinyl)oxy]phenyl]-3-(6-cyano-2-indolyl)propionate. The thus prepared mixture was allowed to stand still for 72 hours at 5° C. After concentration to dryness under a reduced pressure at a temperature of 40° C. or below, the resulting residue was dissolved in 20 ml of ethanol solution containing 14% (w/v) of ammonia and stirred at room temperature for 24 hours. After distilling off the solvent, the thus obtained residue was subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid, and then concentrated to dryness. In this way, 95 mg of the title compound was obtained in a solid form.

$^1$H-NMR (DMSO-$d_6$) δ:2.30 (2H, m), 3.30 (1H, dd), 3.50–3.60 (5H, m), 3.70 (3H, s), 4.20 (1H, t), 5.20 (1H, m), 6.33 (1H, s), 6.96 (2H, d), 7.33 (2H, d), 7.40 (1H, d), 7.64 (1H, d), 7.80 (1H, s), 9.30–9.80 (6H, m)

INVENTIVE EXAMPLE 47 methyl (−)-3-(6-amidino-2-indolyl)-2-[4-[((3S)-3-pyrrolidinyl)oxy]phenyl]propionate dihydrochloride This compound was prepared in accordance with the procedure of Inventive Example 46.
(solid)
$^1$H-NMR (DMSO-$d_6$) δ:2.30 (2H, m), 3.30 (1H, dd), 3.50–3.60 (5H, m), 3.70 (3H, s), 4.20 (1H, t), 5.20 (1H, m), 6.33 (1H, s), 6.96 (2H, d), 7.33 (2H, d), 7.40 (1H, d), 7.64 (1H, d), 7.80 (1H, s), 9.30–9.80 (6H, m)

INVENTIVE EXAMPLE 48

(+)-3-(6-amidino-2-indolyl)-2-[4-[((3S)-3-pyrrolidinyl)oxy]phenyl]propionic acid dihydrochloride 1.8 g of methyl (+)-3-(6-amidino-2-indolyl)-2-[4-[((3S)-3-pyrrolidinyl)oxy]phenyl]propionate dihydrochloride was dissolved in. 60 ml of concentrated hydrochloric acid, and the solution was stirred at 5° C. for 7 days. After concentrating the resulting reaction solution to dryness under a reduced pressure at a temperature of 50° C. or below, the thus obtained residue was subjected to reversed phase high performance liquid chromatography using a column packed with octadecyl-bonded silica gel and using a water/acetonitrile mixture as an elution solvent. Thereafter, thus eluted fractions of interest were pooled, mixed with dilute hydrochloric acid, and then concentrated to dryness. In this way, 1.3 g of the title compound was obtained in a solid form.
IR (KBr): 3600–3300, 1730, 1680 cm$^{-1}$

INVENTIVE EXAMPLE 49

(−)-3-(6-amidino-2-indolyl)-2-[4-[((3S)-3-pyrrolidinyl)oxy]phenyl]propionic acid dihydrochloride This compound was prepared in accordance with the procedure of Inventive Example 48.
(solid)
IR (KBr): 3600–3300, 1730, 1680 cm$^{-1}$

INVENTIVE EXAMPLE 50

3-(5-amidino-2-benzofuranyl)-2-[4-[((3S)-1-methyl-3-pyrrolidinyl)oxy]phenyl]propionic acid dihydrochloride 1.0 g of ethyl 3-(5-cyano-2-benzofuranyl)-2-[4-[((3S)-1-methyl-3-pyrrolidinyl)oxy]phenyl]propionate was dissolved in 70 ml of ethanol. During ice cooling and stirring, hydrogen chloride was bubbled into the thus prepared solution to a saturation level. The thus saturated solution was allowed to stand still at 25° C. for 20 hours. After distilling off the solvent under a reduced pressure, the thus obtained residue was dissolved in 50 ml of ethanol containing 14% (w/v) of ammonia, and the resulting solution was allowed to stand still at 25° C. for 20 hours. Thereafter, the solvent was removed by distillation to obtain ethyl 3-(5-amidino-2-benzofuranyl)2-[4-[((3S)-1-methyl-3-pyrrolidinyl)oxy]phenyl]propionate dihydrochloride. The thus obtained ester compound was dissolved in 50 ml of 2N hydrochloric acid and refluxed under heating for 30 minutes. After distilling off the solvent under a reduced pressure, the resulting residue was subjected to column chromatography using a column packed with a highly porous polymer type synthetic adsorbent (styrene-divinylbenzene polymer: Diaion HP-20) and using a water/acetonitrile mixture as an elution solvent. Fractions of interest thus pooled were subjected to reversed phase high performance liquid chromatography using a column packed with octadecyl-bonded silica gel and using a water/acetonitrile mixture as an elution solvent. Thereafter, thus eluted fractions of interest were pooled, mixed with dilute hydrochloric acid, and then concentrated to dryness. In this way, 200 mg of the title compound was obtained in a solid form.
$^1$H-NMR (DMSO-d$_6$) δ:2.40–3.40 i(6H, m), 2.92 (3H, m), 5.10–5.40 (1H, br), 6.82 (1H, s), 7.01 (2H, d, J=8.4Hz), 7.43 (2H, d, J=8.4Hz), 7.82 (2H, s), 8.17 (1H, s), 9.34 (2H, br), 9.53 (2H, br)

The following compounds of Inventive Examples 51 to 82 were prepared in accordance with the procedure of Inventive Example 50.

INVENTIVE EXAMPLE 51

2-[4-[((3S)-1-acetyl-3-pyrrolidinyl)oxy]phenyl]-3-(5-amidino-2-benzofuranyl) propionic acid hydrochloride
(solid)
$^1$H-NMR (DMSO-d$_6$) δ:1.90–2.38 (5H, m), 3.00–3.90 (6H, m), 4.06 (1H, t, J=7.2Hz), 4.88 (1H, br), 6.67 (1H, s), 6.87 (2H, d, J=8.3Hz), 7.29 (2H, d, J=8.3Hz), 7.70 (2H, s), 8.08 (1H, s), 9.20 (2H, br), 9.41 (2H, br)

INVENTIVE EXAMPLE 52

3-(5-amidino-2-benzofuranyl)-2-[4-[((3S)-1-dimethylcarbamoyl-3-pyrrolidinyl)oxy]phenyl]propionic acid hydrochloride
(solid)
$^1$H-NMR (DMSO-d$_6$) δ:1.84–2.20 (2H, m), 2.75 (6H, s), 3.00–3.90 (6H, m), 4.09 (1H, t, J=7.2Hz), 4.87–5.10 (1H, br), 6.68 (1H, s), 6.87 (2H, d, J=8.75Hz), 7.29 (2H, d, J=8.75Hz), 7.70 (2H, s), 8.07 (1H, s), 9.23 (2H, br), 9.39 (2H, br)

INVENTIVE EXAMPLE 53

3-(5-amidino-2-benzofuranyl)-2-[4-[((2S)-2-pyrrolidinyl)methoxy]phenyl]propionic acid dihydrochloride
(solid)
$^1$H-NMR (DMSO-d$_6$) δ:1.95 (4H, br), 6.71 (1H, s), 6.97 (2H, d), 7.27 (2H, d), 7.71 (2H, s), 8.06 (1H, s), 9.15–9.35 (5H), 9.7 (1H)

INVENTIVE EXAMPLE 54

3-(5-amidino-2-benzofuranyl)-2-[4-[(tetrahydro-3-furanyl)oxy]phenyl]propionic acid hydrochloride
(solid)
$^1$H-NMR (DMSO-d$_6$) δ:1.6–2.4 (2H, m), 3.0–3.9 (6H, m), 4.0 (1H, dd), 4.8–5.1 (1H, m), 6.75 (1H, s), 6.9 (2H, d), 7.32 (2H), 7.77 (2H, s), 8.1 (1H, s), 9.37 (4H, d)

INVENTIVE EXAMPLE 55

3-(5-amidino-3-methyl-2-benzofuranyl)-2-[4-[((3S)-3-pyrrolidinyl)oxy]phenyl]propionic acid dihydrochloride
(solid)
$^1$H-NMR (DMSO-d$_6$) δ:2.06 (5H, m), 5.05 (1H, br), 6.94 (2H, d), 7.22 (2H, d), 7.70 (2H, s), 8.08 (1H, s), 9.10–9.50 (6H, m)

INVENTIVE EXAMPLE 56

3-(5-amidino-7-methoxy-2-benzofuranyl)-2-[4-[((3S)-3-pyrrolidinyl)oxy]phenyl]propionic acid dihydrochloride
(solid)
$^1$H-NMR (DMSO-d$_6$) δ:1.90–2.40 (2H, m), 2.90–3.80 (6H, m), 4.03 (3H, s), 5.00–5.20 (1H, br), 6.65 (1H, s), 6.91 (2H, d, J=8.3Hz), 7.31 (2H, d, J=8.3Hz), 7.32 (1H, s), 7.68 (1H, s), 9.16 (2H, br), 9.40 (2H, br), 9.20–10.0 (2H, br)

INVENTIVE EXAMPLE 57

3-(5-amidino-3-benzofuranyl)-2-[4-[((3S)-3-pyrrolidinyl)oxy]phenyl]propionic acid dihydrochloride
(solid)
¹H-NMR (DMSO-d₆) δ:2.1 (2H, br), 3.00–4.00 (7H, m), 5.08 (1H, br), 6.90 (2H, d, J=8Hz), 7.30 (2H, d, J=8Hz), 7.77 (3H), 8.22 (1H, s), 9.0–10.00 (6H)

INVENTIVE EXAMPLE 58

5-amidino-2-[2-[4-[((3S)-3-pyrrolidinyl)oxy]phenyl]ethyl]-3-benzofurancarboxylic acid dihydrochloride
(solid)
¹H-NMR (DMSO-d₆) δ: 2.07 (2H, m), 3.00–3.50 (8H), 5.05 (1H, br), 6.85 (2H, d, J=8.0Hz), 7.15 (2H, d, J=8.0Hz), 7.82 (2H, s), 8.35 (1H, s), 9.30 (2H, br), 9.50 (4H, br)

INVENTIVE EXAMPLE 59

3-[2-[2-(5-amidinobenzo[b]thien-2-yl)ethyl]-4-ethoxy-5-[((3S)-3-pyrrolidinyl)oxy]phenyl]propionic acid dihydrochloride
(solid)
¹H-NMR (DMSO-d₆) δ:1.30 (3H, t, J=7.0Hz), 2.00–3.90 (14H, m), 4.01 (2H, q, J=7.0Hz), 6.94 (1H, s), 6.96 (1H, s), 7.39 (1H, s), 7.79 (1H, d, J=9.0Hz), 8.20 (1H, d, J=9.0Hz), 8.37 (1H, s), 9.41 (2H, br), 9.59 (2H, br), 9.0–10.0 (2H, br)

INVENTIVE EXAMPLE 60

3-[2-[2-[5-amidinobenzo[b]thien-2-yl]ethyl]-5-[((3S)-3-pyrrolidinyl)oxy]phenyl]propionic acid dihydrochloride
(solid)
¹H-NMR (DMSO-d₆) δ:2.00–4.80 (14H, m), 5.08 (1H, m), 6.77 (1H, d, J=8.5Hz), 6.82 (1H, s), 7.18 (1H, d, J=8.5Hz), 7.35 (1H, s), 7.72 (1H, d, J=8.7Hz), 8.16 (1H, d, J=8.7Hz), 8.29 (1H, s), 9.31 (2H, br), 9.51 (2H, br), 9.3–9.8 (2H, br)

INVENTIVE EXAMPLE 61

4-(5-amidinobenzo[b]thien-2-yl)-3-[4-[((3S)-3-pryrrolidinyl)oxy]phenyl]butyric acid dihydrochloride
(solid)
¹H-NMR (DMSO-d₆) δ: 2.00–2.30 (2H, m), 5.00–5.20 (1H, m), 6.85 (2H, d), 7.20 (1H, S), 7.25 (2H, d), 7.65 (1H, dd), 8.05–8.25 (2H, m)

INVENTIVE EXAMPLE 62

3-(5-amidinobenzo[b]thien-2-yl)-2-[4-[[2-(ethoxycarbonylimino)hexahydropyrimidine-5-yl]oxy]phenyl]propionic acid dihydrochloride
(solid)
¹H-NMR (DMSO-d₆) δ: 1.27 (3H, t, J=7.0Hz), 3.00–4.04 (br), 4.24 (2H, q, J=7.0Hz), 4.90–5.10 (1H, br), 6.99 (2H, d, J=8.3Hz), 7.34 (2H, d, J=8.3Hz), 7.39 (1H, s), 7.68 (1H, dd, J=9.0 and 1.8Hz), 8.10 (1H, d, J=9.0Hz), 8.24 (1H, d, J=1.8Hz), 8.98 (2H, br), 9.23 (2H, br), 9.44 (2H, br), 11.65 (1H, s)

INVENTIVE EXAMPLE 63

3-(5-amidinobenzo[b]thien-2-yl)-2-[4-[[2-(imino)hexahydropyyrimidine-5-yl]oxy]phenyl]propionic acid dihydrochloride
(solid)
¹H-NMR (DMSO-d₆) δ:3.20–4.20 (3H, m), 3.44 (4H), 4.80–5.00 (1H, br), 6.98 (2H, d, J=8.31Hz), 7.17 (2H, s), 7.29 (1H, s), 7.34 (2H, d, J=8.31Hz), 7.70 (1H, dd, J=8.2 and 2.0Hz),8.06 (2H, s), 8.12 (1H, d, J=8.2Hz), 8.25 (1H, s), 9.46 (2H, br), 9.57 (2H, br)

INVENTIVE EXAMPLE 64

3-(5-amidinobenzo[b]thien-2-yl)-2-[4-[((2S)-2-pyrrolidinyl)methoxy]phenyl]propionic acid dihydrochloride
(solid)
¹H-NMR (DMSO-d₆) δ:1.95 (4H, m), 3.00–4.20 (8H, m), 6.95 (2H, d, J=8.0Hz), 7.28 (3H), 7.70 (1H, d, J=8.0Hz), 8.06 (1H, d, J=8.0Hz), 8.23 (1H, s), 9.20–9.50 (6H)

INVENTIVE EXAMPLE 65

3-(5-amidinobenzo[b]thien-2-yl)-2-[4-[(4-piperidinyl)oxy]phenyl]propionic acid dihydrochloride
(solid)
¹H-NMR (DMSO-d₆) 1.80–2.15 (4H, m), 3.00–3.25 (4H, m), 3.30–4.00 (3H, m), 4.60–4.70 (1H, m), 6.97 (2H, d, J=8.3Hz), 7.31 (3H, m), 7.69 (1H, dd), 8.13 (1H, d, J=8.8Hz), 8.26 (1H, s), 9.31 (2H, br), 9.50 (2H, br), 9.00–10.00 (2H, br)

INVENTIVE EXAMPLE 66

3-(5-amidinobenzo[b]thien-2-yl)-2-[4-[(2-aminoethyl)oxy]phenyl]propionic acid dihydrochloride
(solid)
¹H-NMR (DMSO-d₆) δ:3.00–4.40 (7H, m), 6.93 (2H, d, J=8.3Hz), 7.29 (1H, s), 7.32 (2H, d, J=8.3Hz), 7.67 (1H, dd, J=9.0 and 1.0Hz), 8.20 (1H, d, J=9.0Hz), 8.32 (1H, s), 8.10–8.60 (3H, br), 9.24 (2H, br), 9.46 (2H, br)

INVENTIVE EXAMPLE 67

3-(5-amidinobenzo[b]thien-2-yl)-2-[4-[2-(1-pyrrolin-2-yl)aminoethoxy]phenyl]propionic acid dihydrochloride
(solid)
¹H-NMR (DMSO-d₆) δ:1.88–2.30 (2H, m), 2.60–3.00 (2H, m), 3.00–4.30 (9H, m), 6.90 (2H, d, J=8.3Hz), 7.30 (1H, s), 7.31 (2H, d, J=8.3Hz), 7.70 (1H, dd, J=8.50 and 1.00Hz), 8.11 (1H, d, J=8.50Hz), 8.25 (1H, s), 9.28 (2H, br), 9.48 (2H, br), 10.00 (1H, br),. 10.19 (1H, br)

INVENTIVE EXAMPLE 68

3-(5-amidino-2-indolyl)-2-[4-[((3S)-3-pyrrolidinyl)oxy]phenyl]propionic acid dihydrochloride
(solid)
¹H-NMR (DMSO-d₆) δ:2.00–2.35 (2H, m), 4.00–4.30 (1H, m), 5.00–5.30 (1H, br), 6.37 (1H, s), 7.00 (2H, d), 7.40 (2H, d), 7.60 (2H, d), 8.10 (1H, s), 11.60 (1H, s)

INVENTIVE EXAMPLE 69

3-(6-amidino-2-indolyl)-2-[4-[((3S)-3-pyrrolidinyl)oxy]phenyl]propionic acid dihydrochloride
(solid)

$^1$H-NMR (DMSO-d$_6$) δ:2.20 (2H, m), 3.40 (4H, m), 5.16 (1H, br), 6.36 (1H, s), 7.00 (2H, d), 7.27 (2H, d), 7.36–7.96 (3H, m), 9.20–9.50 (6H, m), 11.80 (1H, s)

INVENTIVE EXAMPLE 70

3-(5-amidino-2-indolyl)-2-[4-[((3R)-tetrahydro-3-furanyl)oxy]phenyl]propionic acid hydrochloride
(solid)
$^1$H-NMR (DMSO-d$_6$) δ:5.00 (1H, br), 6.28 (1H, s), 6.82 (2H, d), 7.30 (2H, d), 7.58 (2H, s), 8.00 (1H, s), 9.10 (4H), 11.8 (1H, s)

INVENTIVE EXAMPLE 71

3-(5-amidino-2-indolyl)-2-[4-[((3S)-tetrahydro-3-furanyl)oxy]phenyl]propionic acid hydrochloride
(solid)
$^1$H-NMR (DMSO-d$_6$) δ:5.10 (1H, br), 6.27 (1H, s), 6.82 (2H, d), 7.29 (2H, d), 7.58 (2H, s), 8.00 (1H, s), 9.12 (4H), 11.8 (1H, s)

INVENTIVE EXAMPLE 72

3-(5-amidino-1-methyl-2-indolyl)-2-[4-[((3S)-3-pyrrolidinyl)oxy]phenyl]propionic acid dihydrochloride
(solid)
$^1$H-NMR (DMSO-d$_6$) δ:1.90–2.25 (2H, m), 3.73 (3H, s), 5.00–5.20 (1H, br), 6.40 (1H, s), 6.95 (2H, d), 7.40 (2H, d), 7.62 (2H, s), 8.10 (1H, s), 9.00–9.80 (6H, br)

INVENTIVE EXAMPLE 73

3-(6-amidino-1-ethyl-2-indolyl)-2-[4-[((3S)-3-pyrrolidinyl)oxy]phenyl]propionic acid dihydrochloride
(solid)
$^1$H-NMR (DMSO-d$_6$) δ:1.30 (3H, t), 1.95–2.30 (2H, m), 5.10 (1H, m), 6.37 (1H, s), 6.92 (2H, d), 7.30–7.70 (4H, m), 8.10 (1H, s), 9.30–9.90 (6H, br)

INVENTIVE EXAMPLE 74

3-(6-amidinol-1-ethyl-2-indolyl)-2-[4-[((3R)-3-pyrrolidinyl)oxy]phenyl]propionic acid dihydrochloride
(solid)
$^1$H-NMR (DMSO-d$_6$) δ:1.31 (3H, t), 2.00–4.50 (11H), 5.11 (1H, br), 6.38 (1H, s), 6.96 (2H, d, =8.4Hz), 7.30–7.70 (4H, m), 8.17 (1H, s), 9.07 (2H, br), 9.34 (2H, br), 9.30–10.00 (2H, br)

INVENTIVE EXAMPLE 75

3-[6-amidino-1-(2-chloroethyl)-2-indolyl]-2-[4-[((3S)-3-pyrrolidinyl)oxy]phenyl]propionic acid dihydrochloride
(solid)
$^1$H-NMR (DMSO-d$_6$) δ:2.00–5.00 (13H), 5.13 (1H, br), 6.42 (1H, s), 6.97 (2H, d, J=8.4Hz), 7.40 (2H, d, J=8.4Hz), 7.50–7.70 (2H, m), 8.22 (1H, s), 9.13 (2H, br), 9.39 (2H, br), 9.50–10.00 (2H, br)

INVENTIVE EXAMPLE 76

3-(6-amidino-1,2,3,4-tetrahydro-2-naphthyl)-2-[4-[((3S)-3-pyrrolidinyl)oxy]phenyl]propionic acid dihydrochloride
(solid)
$^1$H-NMR (DMSO-d$_6$) δ: 1.30–4.00 (16H, m), 5.10 (1H, m), 6.94 (2H, d, J=9.0Hz), 7.20–7.70 (5H, m), 9.18 (2H, br), 9.34 (2H, br), 9.50–10.00 (2H, br)

INVENTIVE EXAMPLE 77

3-(5-amidino-2-benzimidazolyl)-2-[4-[((3S)-3-pyrrolidinyl)oxy]phenyl]propionic acid dihydrochloride
(solid)
$^1$H-NMR (DMSO-d$_6$) δ:1.98–2.28 (2H, br), 3.00–4.80 (7H, m), 5.00–5.20 (1H, br), 6.93 (2H, d, J=9.0Hz), 7.34 (2H, d, J=9.0Hz), 7.91 (2H, s), 8.28 (1H, s), 9.36 (2H, br), 9.61 (2H, br), 9.40–10.10 (2H, br)

INVENTIVE EXAMPLE 78

3-(7-amidino-2-naphthyl)-2-[4-[((3R)-3-pyrrolidinyl)oxy]phenyl]propionic acid dihydrochloride
(solid)
$^1$H-NMR (DMSO-d$_6$) δ: 2.00–2.20 (2H, m), 3.00–4.20 (7H, m), 5.10 (1H, br), 6.92 (2H, d, J=9.0Hz), 7.33 (2H, d, J=9.0Hz), 7.50–8.20 (5H, m), 8.43 (1H, s), 9.39 (2H, br), 9.60 (2H, br), 9.50–10.00 (2H, br)

INVENTIVE EXAMPLE 79

3-(7-amidino-2-naphthyl)-2-[4-[(4-piperidinyl)oxy]phenyl]propionic acid hydrochloride
(solid)
$^1$H-NMR (DMSO-d$_6$) δ: 1.70–2.20 (4H, m), 2.80–4.10 (7H, m), 4.50–4.80 (1H, m), 6.95 (2H, d, J=8.0Hz), 7.30 (2H, d, J=8.0Hz), 7.60–8.50 (6H, m), 9.35 (2H, br), 9.57 (2H, br), 9.10–9.80 (2H, br)

INVENTIVE EXAMPLE 80

3-(6-amidino-1-carboxyethyl-2-indolyl)-2-[4-[((3S)-3-pyrrolidinyl)oxy]phenyl]propionic acid dihydrochloride
(solid)
$^1$H-NMR (DMSO-d$_6$) δ: 1.98–2.30 (2H, m), 2.80–3.80 (6H, m), 3.90–4.25 (1H, t), 5.00–5.50 (3H, br), 6.41 (1H, s), 7.00 (2H, d), 7.42 (2H, d), 7.60–7.90 (2H, m), 8.30 (1H, s), 9.10–10.00 (6H, br)

INVENTIVE EXAMPLE 81

6-amidino-2-[3-hydroxy-2-[4-[((3S)-3-pyrrolidinyl)oxy]phenyl]propyl]-1-indoleacetic acid dihydrochloride
(solid)
$^1$H-NMR (DMSO-d$_6$) δ:1.95–2.20 (2H, m), 4.90–5.15 (3H, m), 6.20 (1H, s), 6.90 (2H, d), 7.25 (2H, d), 7.57 (2H, m), 8.20 (1H, s), 9.20–9.90 (6H, br)

INVENTIVE EXAMPLE 82

6-amidino-2-[2-[4-[((3S)-3-pyrrolidinyl)oxy]phenyl]ethyl]-1-indoleacetic acid dihydrochloride
(solid)
$^1$H-NMR (DMSO-d$_6$) δ:1.90–2.30 (2H, m), 3.10–3.50 (4H, 4.80–5.30 (3H, br), 6.42 (1H, s), 6.90 (2H, d), 7.25 (2H, d), 7.60 (3H, m), 8.25 (1H, s), 9.20–10.00 (6H, br)

INVENTIVE EXAMPLE 83 ethyl 3-(5-amidinobenzo[b]thien-2-yl)-2-ethoxycarbonyl-2-[4-[((2R)-2-pyrrolidinyl)methoxy]phenyl]propionate dihydrochloride 4.34 g of ethyl 2-[4-[((2R )-1-tert-butoxy-carbonyl-2-pyrrolidinyl)methoxy]phenyl]-3-(5-cyanobenzo[b]thien-2-yl)-2-ethoxycarbonylpropionate was dissolved in 150 ml of ethanol. During ice cooling and stirring, hydrogen chloride was bubbled into the thus prepared solution to a saturation level. The thus saturated solution was allowed to stand still at room temperature for 18 hours. After distilling off the solvent under a reduced pressure, the thus obtained residue was dissolved in 100 ml of ethanol solution containing 13% (w/v) of ammonia, and the resulting solution was allowed to stand still for 24 hours. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. Fractions of interest thus pooled were subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid and then concentrated to dryness. In this way, 1.0 g of the title compound was obtained in the form of light yellow solid.

$^1$H-NMR (DMSO-d$_6$) δ:1.15 (6H, t, J=7.0Hz), 2.0 (4H, br), 3.00–4.00 (3H), 3.95 (2H), 4.2 (4H), 7.00 (2H, d), 7.16 (1H), 7.31 (2H, d), 7.70 (1H, dd), 8.10 (1H, d), 8.26 (1H, d), 9.20–9.60 (5H), 9.9 (1H)

INVENTIVE EXAMPLE 84

3-(5-amidinobenzo[b]thien-2-yl)-2-[4-[(2-imidazolin-2-yl)methoxy]phenyl]propionic acid dihydrochloride 1.6 g of ethyl 3-(5-cyanobenzo[b]thien-2-yl)-2-ethoxycarbonyl-2-[4-[(2-imidazolin-2-yl)methoxy]phenyl]propionate was dissolved in 100 ml of ethanol. During ice cooling and stirring, hydrogen chloride was bubbled into the thus prepared solution to a saturation level. The thus saturated solution was allowed to stand still at 5° C. for 18 hours. After distilling off the solvent under a reduced pressure, the thus obtained residue was dissolved in 100 ml of ethanol solution containing 13% (w/v) of ammonia, and the resulting solution was allowed to stand still at room temperature for 24 hours. Thereafter, the solvent was distilled off to obtain ethyl 3-(5-amidinobenzo[b]thien-2-yl)-2-ethoxycarbonyl-2-[4-[(2-imidazolin-2-yl)methoxy]phenyl]propionate dihydrochloride. The thus obtained ester compound was dissolved in 50 ml of 5N hydrochloric acid, and the solution was refluxed under heating for 1 hour. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. Fractions of interest thus pooled were subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid, and then concentrated to dryness. In this way, 200 mg of the title compound was obtained in the form of a light yellow solid.

$^1$H-NMR (DMSO-d$_6$) δ:3.35 (1H, dd), 3.65 (1H, dd), 3.89 (4H, s), 3.99 (1H, t), 5.07 (2H, s), 6.98 (2H, d), 7.32 (1H, s), 7.37 (2H, d), 7.66 (1H, d), 8.12 (1H, d), 8.21 (1H, s), 9.10 (2H), 9.39 (2H), 10.38 (2H).

The following compounds of Inventive Examples 85 and 86 were prepared in accordance with the procedure of Inventive Example 82.

INVENTIVE EXAMPLE 85

3-(5-amidinobenzo[b]thien-2-yl)-2-[4-[((3S)-3-pyrrolidinyl)thio]phenyl]propionic acid dihydrochloride (solid)

$^1$H-NMR (DMSO-d$_6$) δ:1.5–4.5 (10H, m), 6.95 (2H, d), 7.32 (1H, s), 7.40 (2H, d), 7.71 d), 8.13 (1H, d), 8.28 (1H, s), 9.3 (2H, br), 9.5 (2H, br), 9.8 (2H, br)

INVENTIVE EXAMPLE 86

3-(5-amidino-2-benzothiazolyl)-2-[4-[((3S)-3-pyrrolidinyl)oxy]phenyl]propionic acid dihydrochloride (solid)

$^1$H-NMR (DMSO-d$_6$) δ:2.08 (2H, br), 3.00–4.25 (7H), 5.10 (1H, br), 6.95 (2H, d),-7.34 (2H, d), 7.82 (1H, dd), 8.29 (1H, d), 8.41 (1H, d), 9.20–9.60 (6H)

FAB MS (m/z): 411 (M$^+$+1)

INVENTIVE EXAMPLE 87

2-[4-[((3S)-1-acetimidoyl-3-pyrrolidinyl)oxy]phenyl]-3-(5-amidino-2-benzofuranyl)propionic acid dihydrochloride 1.1 g of 3-(5-amidino-2-benzofuranyl)-2-[4-[((3S)-3-pyrrolidinyl)oxy]phenyl]propionic acid dihydrochloride was dissolved in 20 ml of water. During ice cooling and stirring, 1.4 g of ethyl acetimidate hydrochloride was added gradually to the thus prepared solution while adjusting the pH of the solution to 8.5 with 1N sodium hydroxide aqueous solution. The resulting mixture was stirred for 15 minutes with ice cooling, and then adjusted to pH 2.0 with dilute hydrochloric acid. After concentrating the resulting reaction solution to dryness, the thus obtained residue was subjected to reversed phase high performance liquid chromatography using a column packed with octadecyl-bonded silica gel and using a water/acetonitrile mixture as -an elution solvent. Thereafter, the thus eluted fractions of interest were pooled, mixed With dilute hydrochloric acid, and then concentrated to dryness. In this way, 780 mg of the title compound was obtained in a solid form.

$^1$H-NMR (DMSO-d$_6$) δ: 1.90–2.40 (5H, m), 2.90–4.30 (7H, br), 4.96 (1H, br), 6.73 (1H, s), 6.93 (2H, d, J=8.8Hz), 7.33 (2H, d, J=8.8Hz), 7.73 (2H, s), 8.10 (1H, s), 8.50–8.80 (1H, br), 9.33 (2H, br), 9.46 (3H, br)

The following compounds of Inventive Examples 88 to 91 were prepared in accordance with the procedure of Inventive Example 87.

INVENTIVE EXAMPLE 88

2-[4-[((3S)-1-acetimidoyl-3-pyrrolidinyl)oxy]phenyl]-3-(5-amidinobenzo[b]thien-2-yl)propionic acid dihydrochloride (solid)

¹H-NMR (DMSO-d₆) δ:2.00–2.50 (5H, m), 3.10–4.20 (7H, m), 4.96 (1H, br), 6.93 (2H, d, J=7.9Hz), 7.2 (1H, s), 7.34 (2H, d, J=7.9Hz), 7.73 (1H, d, J=8.3Hz), 8.10 (1H, d, J=8.3Hz), 8.30 (1H, s), 8.50–9.30 (1H, br), 9.37 (2H, br), 9.54 (2H, br)

INVENTIVE EXAMPLE 89

2-[4-[((3S)-1-acetimidoyl-3-pyrrolidinyl)oxy]phenyl]-3-(5-amidino-2-benzothiazolyl)propionic acid dihydrochloride (solid)

¹-NMR (DMSO-d₆) δ:2.00 (2H, br), 2.26 (1.5H), 2.30 (1.5H), 3.00–4.25 (7H), 5.17 (1H, br), 6.99 (2H, d), 7.31 (2H, d), 7.88 (1H, d), 8.25 (1H, d), 8.44 (1H, d), 8.50 (1H), 9.33 (2H, br), 9.55 (2H, br)

INVENTIVE EXAMPLE 90

2-[4-[((3R)-1-acetimidolyl-3-pyrrolidinyl)oxy]phenyl]-3-(6-amidino-1-ethyl-2-indolyl)propionic acid dihydrochloride (solid)

¹H-NMR (DMSO-d₆) δ:1.31 (3H, t, J=7.0Hz), 2.15–2.40 (2H, m), 2.28 (1.5H), 2.31 (1.5H), 3.15 (1H, dd), 3.40–4.05 (5H), 4.10 (1H, t), 4.28 (2H, m), 5.16 (0.5H, br), 5.22 (0.5H, br), 6.40 (1H, s), 6.97 (2H, dd), 7.40 (2H), 7.48 (1H, d, J=8.3Hz), 7.62 (1H, d, J=8.3Hz), 8.13 (1H, s), 8.50 (0.5H, s), 8.59 (0.5H, s), 8.98 (2H, s), 9.32 (2H, s), 9.25–9.35 (1H)

INVENTIVE EXAMPLE 91

2-[4-[((3S)-1-acetimidoyl-3-pyrrolidinyl)oxy]phenyl]-3-(7-amidino-2-naphthyl)propionic acid dihydrochloride (solid)

¹H-NMR (DMSO-d₆) δ:2.00–2.40 (5H, m), 2.90–4.10 (7H, m), 5.15 (1H, br), 6.93 (2H, d, J=8.0Hz), 7.33 (2H, d, J=8.0Hz), 7.50–8.40 (6H, m), 8.50–8.70 (1H), 9.30 (3H, br), 9.55 (2H, br)

INVENTIVE EXAMPLE 92

2-[4-[((2R)-1-acetimidoyl-2-pyrrolidinyl)methoxy]phenyl]-3-(5-amidinobenzo[b]thien-2-yl)propionic acid dihydrochloride 1.0 g of ethyl 3-(5-amidinobenzo[b]thien-2-yl)-2-ethoxycarbonyl-2-[4-[((2R)-2-pyrrolidinyl)methoxy]phenyl]propionate dihydrochloride was dissolved in 20 ml of ethanol, followed by the addition of 0.42 g of ethyl acetimidate hydrochloride. 0.51 g of triethylamine was added to the thus prepared solution during stirring under ice cooling, and the resulting mixture was warmed up to room temperature and stirred for 18 hours. Thereafter, the solvent was distilled off to obtain ethyl 2-[4-[((2R)-1-acetimidoyl-2-pyrrolidinyl)methoxy]phenyl]-2-ethoxycarbonyl-3-(5-amidinobenzo[b]thien-2-yl)propionate dihydrochloride. The thus obtained ester compound was dissolved in 50 ml of 5N hydrochloric acid and refluxed under heating for 60 minutes. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. Fractions of interest were pooled and concentrated, and the resulting residue was subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid, and then concentrated to dryness. In this way, 360 mg of the title compound was obtained in the form of a light yellow solid.

¹H-NMR (DMSO-d₆) δ:2.00 (4H, br), 2.24–2.43 (3H), 3.00–4.00 (5H), 4.00 (2H), 4.50 (1H, br), 6.90 (2H, d), 7.30 (3H), 7.70 (1H, d), 8.10 (1H, d), 8.23 (1H, s), 9.20–9.60 (5H, m)

INVENTIVE EXAMPLE 93

3-(5-amidinobenzoyl[b]thien-2-yl)-2-[4-[((3S)-1-benzimidoyl-3-pyrrolidinyl)oxy]phenyl]propionic acid dihydrochloride 1.0 g of ethyl 3-(5-amidinobenzo[b]thien-2-yl)-2-[4-[((3S)-3-pyrrolidinyl)oxy]phenyl]propionate dihydrochloride was dissolved in 15 ml of ethanol. To this solution was added 773 mg of ethyl benzimidate hydrochloride which has been prepared by allowing benzonitrile to react with ethanol in the presence of hydrogen chloride. 631 mg of triethylamine was added to the thus prepared solution during stirring under ice cooling, and the mixture was warmed up to room temperature, and stirred for 18 hours. Thereafter, the solvent was distilled off to obtain ethyl 3-(5-amidinobenzo[b]thien-2-yl)-2-[4-[((3S)-1-benzimidoyl-3-pyrrolidinyl)oxy]phenyl]propionate dihydrochloride. The thus obtained ester compound was dissolved in 60 ml of 3N hydrochloric acid and refluxed under heating for 30 minutes. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. Fractions of interest were pooled and concentrated, and the resulting residue was subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid, and then concentrated to dryness. In this way, 350 mg of the title compound was obtained in the form of a light yellow solid.

¹H-NMR (DMSO-d₆) δ:2.00–2.80 (2H, m), 3.00–3.30 (7H, m), 4.04 (0.5H, br), 4.30 (0.5H, br), 6.80–7.90 (11H, m), 8.12 (1H, d, J=8.3Hz), 8.30 (1H, s), 9.20–9.70 (6H, m)

The following compounds of Inventive Examples 94 to 100 were prepared in accordance with the procedure of Inventive Example 93.

INVENTIVE EXAMPLE 94

3-(5-amidinobenzo[b]thien-2-yl)-2-[4-[((3S)-1-n-hexan-imidoyl-3-pyrrolidinyl)oxy]phenyl]propionic acid dihydrochloride (solid)

¹H-NMR (DMSO-d₆) δ:0.80–0.95 (3H, m), 1.20–1.40 (4H, m), 1.45–1.70 (2H, m), 2.15–2.40 (2H, m), 2.45–2.60 (2H, m), 3.25–3.90 (6H, m), 3.96 (1H, t, J=7.5Hz), 6.85–7.00 (2H, m), 7.25–7.40 (3H, m), 7.69 (1H, dd, J=8.3 and 1.5Hz), 8.11 (1H, d, J=8.3Hz), 8.25 (1H, s), 8.58 (0.5H, s), 8.66 (0.5H, s), 9.20–9.30 (3H, br), 9.47 (2H, br)

INVENTIVE EXAMPLE. 95

3-(5-amidinobenzo[b]thien-2-yl)-2-[4-[((3S)-1-cy-clopropanecarboximidoyl-3-pyrrolidinyl)oxy]phenyl]propionic acid dihydrochloride (solid)
¹H-NMR (DMSO-d₆) δ:0.90–1.30 (3H, m), 1.80–4.10 (10H, m), 5.10–5.30 (1H, m), 6.96 (2H, d, J=8.4Hz), 7.32 (1H, s), 7.36 (2H, d, J=8.4Hz), 7.71 (1H, d, J=7.4Hz), 8.14 (1H, d, J=7.4Hz), 8.29 (1H, 8.40–8.70 (2H, m), 9.36 (2H, br), 9.52 (2H, br)

INVENTIVE EXAMPLE 96

2-[-4-[((2S)-1-acetimidoyl-2-pyrrolidinyl]methoxy]phenyl]-3-(5-amidinobenzo[b]thien-2-yl)propionic acid dihydrochloride (solid)
¹H-NMR (DMSO-d₆) δ:2.05 (4H, br), 2.25–2.43 (3H), 3.00–4.50 (8H), 6.95 (2H), 7.30 (3H), 7.70 (1H, d), 8.10 (1H, d), 8.25 (1H, s), 8.60 (1H, s), 9.20–9.60 (5H, m)

INVENTIVE EXAMPLE 97

2-[4-[((1-acetimidoyl-4-piperidinyl)oxy]phenyl]-3-(5-amidinobenzo[b]thien-2-yl) propionic acid dihydrochloride (solid)
¹H-NMR (DMSO-d₆) δ:1.65–2.10 (4H, m), 2.32 (3H, s), 3.20–4.00 (7H, m), 4.60–4.70 (1H, m), 6.96 (2H, d, J=8.3Hz), 7.30 (3H, m), 7.69 (1H, d, J=8.3Hz), 8.10 (1H, d, J=8.3Hz), 8.26 (1H, s), 8.95 (1H, s), 9.32 (2H, br), 9.52 (2H, br)

INVENTIVE EXAMPLE 98

2-[4-[(1-acetimidoyl-4-piperidinyl)oxy]phenyl]-3-(6-amidino-1-ethyl-2-indolyl)propionic acid dihydrochloride ¹H-NMR (DMSO-d₆) δ:1.30 (3H, t, J=7.0Hz), 1.73–2.10 (4H, m), 2.31 (3H, s), 3.10 (1H, m), 3.30–3.80 (5H), 4.05 (1H, t), 4.30 (2H, m), 4.70 (1H, br), 6.38 (1H, s), 6.97 (2H, d, J=8.5Hz), 7.37 (2H, d, J=8.5Hz), 7.48 (1H, d, J=8.3Hz), 7.61 (1H, d, J=8.3Hz), 8.14 (1H, s), 8.86 (1H, br), 9.15–9.50 (5H, m)

INVENTIVE EXAMPLE 99

3-(7-amidino-2-naphthyl)-2-[4-[((3S)-1-butanimidoyl-3-pyrrolidinyl)oxy]phenyl]propionic acid dihydrochloride (solid)
¹H-NMR (DMSO-d₆) δ: 0.60–4.00 (16H), 5.00 (1H, br), 6.79 (2H, d, J=8.0Hz), 7.21 (2H, d, J=8.0Hz), 7.30–8.10 (5H, m), 8.34 (1H, s), 8.30 (1H, s), 8.40–8.70 (1H), 9.00–10.00 (5H)

INVENTIVE EXAMPLE 100

3-(7-amidino-2-naphthyl)-2-[4-[((3S)-1-benzimidoyl-3-pyrrolidinyl)oxy]phenyl]propionate acid dihydrochloride (solid)
¹H-NMR (DMSO-d₆) δ:2.00–4.10 (9H), 4.90 (0.5H, br), 5.20 (0.5H, br), 6.70–8.10 (14H, m), 8.32 (1H, s), 9.10–9.50 (4H)

INVENTIVE EXAMPLE 101

3-(5-amidinobenzo[b]thien-2-yl)-2-[4-[[(3S)-1-(N-methyl-acetimidoyl)-3-pyrrolidinyl]oxy]phenyl]propionic acid dihydrochloride 2.0 g of 3-(5-amidinobenzo[b]thien-2-yl)-2-[4-[((3S)-3-pyrrolidinyl)oxy]phenyl]propionic acid dihydrochloride was dissolved in a solvent mixture of 10 ml of water and 10 ml of acetonitrile. With stirring, to the thus prepared solution was gradually added 20 g of ethyl (N-methyl)acetimidate hydrochloride which has been prepared in accordance with the procedure disclosed in *The Journal of Organic Chemistry* (vol.33, pp.1679–1681, 1968), while maintaining the pH level of the solution at 8.5 with 2N sodium hydroxide aqueous solution. After distilling off the solvent, the resulting residue was washed with dichloromethane and then subjected to column chromatography using a column packed with a highly porous polymer type synthetic adsorbent (styrene-divinylbenzene polymer: Diaion HP-20) and using a water/acetonitrile mixture as an elution solvent, thereby effecting desalting. Fractions of interest thus pooled were subjected to reversed phase high performance liquid chromatography using a column packed with octadecyl-bonded silica gel. Thereafter, the thus eluted fractions of interest were pooled and then concentrated to dryness by passing through a Cl type of strongly basic ion exchange resin (Diaion SA-10, Nippon Rensui Co., Ltd.). In this way, 370 mg of the title compound was obtained in a solid form.

¹H-NMR (DMSO-d₆) δ:2.00–2.44 (2H, m), 2.30 (1.5H), 2.33 (1.5H), 2.98 (3H), 3.06–4.20 (7H, m), 5.00–5.40 (1H, br), 6.92 (2H, d, J=8.3Hz), 7.128 (1H, s), 7.33 (2H, d, J=8.3Hz), 7.72 (1H, d, J=9.01Hz), 8.06 (1H, d, J=9.0Hz), 8.28 (1H, s), 8.8–9.20 (1H, br), 9.23 (2H, br), 9.50 (2H, br)

INVENTIVE EXAMPLE 102

3-(5-amidino-2-benzofuranyl)-2-[4-[((2R)-2-amino-1-butyl)oxy]phenyl]propionic acid dihydrochloride In 300 ml of tetrahydrofuran were dissolved 1.1 g of ethyl 3-(5-cyano-2-benzofuranyl)-2-(4-hydroxyphenyl)propionate, 1.24 g of (2R)-2-tert-butoxycarbonyl-amino-1-butanol and 1.72 g of triphenylphosphine. The thus prepared solution was mixed with 1.14 g of diethyl azodicarboxylate and stirred at room temperature for 18 hours. The resulting solution was further mixed with 0.83 g of (2R)-2-tert-butoxycarbonylamino-1-butanol, 1.2 g of triphenylphosphine and 0.76 g of diethyl azodicarboxylate, and the mixture was stirred at room temperature for 18 hours. After concentrating the thus prepared reaction solution to dryness, the resulting residue was purified by subjecting it to silica gel column chromatography using a toluene/ethyl acetate mixture as a developing solvent, thereby obtaining 660 mg of ethyl 2-[4-[((2R)-2-tert-butoxycarbonylamino-1-butyl)oxy]phenyl]-3-(5-cyano-2-benzofuranyl)propionate in a colorless and oily form.

Thereafter, 660 mg of ethyl 2-[4-[((2R)-2-tert-butoxycarbonylamino-1-butyl)oxy]phenyl]-3-(5-cyano-2-benzofuranyl)propionate obtained above was treated and purified in the same manner as described in Inventive Example 50 to obtain 78 mg of the title compound in a solid form.

¹H-NMR (DMSO-d₆) δ:1.04 (3H, t), 1.70 (2H), 3.0–4.2 (6H), 6.71 (1H, s), 6.99 (2H, d),1 7.27 (2H, d), 7.72 (2H, s), 8.07 (1H, s), 8.3 (3H, br), 9.34–9.40 (4H)

INVENTIVE EXAMPLE 103

3-(5-amidino-2-benzofuranyl)-2-[4-[((2S)2-amino-1-butyl)oxy]phenyl]propionate acid dihydrochloride This compound was obtained in a solid form with a yield of 620 mg by repeating the process of Inventive Example 102, except that (2S)-2-tert-butoxycarbonylamino-1-butanol was used instead of (2R)-2-tert-butoxycarbonylamino-1-butanol.

$^1$H-NMR (DMSO-d$_6$) δ:1.04 (3H, t), 1.70 (2H), 3.0–4.2 (6H), 6.68 (1H, s), 6.96 (2H, d), 7.24 (2H, d), 7.70 (2H, s), 8.05 (1H, s), 8.4 (3H, br), 9.40 (4H, br)

INVENTIVE EXAMPLE 104

3-[4-[((3S)-1-acetimidoyl-3-pyrrolidinyl)oxy]phenyl]-4-(5-amidinobenzo[b]thien-2-yl)butyric acid dihydrochloride 1 ml of thionyl chloride was added dropwise to 50 ml of ethanol. With stirring at room temperature, to this solution was added 1.0 g of 4-(5-amidinobenzo[b]thien-2-yl)-3-[4-[((3S)-3-pyrrolidinyl)oxy]phenyl]butyric dihydrochloride, followed by refluxing under heating for 1 hour. After cooling and subsequent removal of the solvent by distillation, the thus prepared reaction solution was thoroughly dried under a reduced pressure to obtain ethyl 4-(5-amidinobenzo[b]thien-2-yl)-3-[4-[((3S)-3-pyrrolidinyl)oxy]phenyl]butyrate dihydrochloride. The thus obtained ester compound was dissolved in 20 ml of tetrahydrofuran. During ice cooling and stirring, the thus prepared solution was mixed with triethylamine and then with 360 mg of ethyl acetimidate hydrochloride, and the resulting mixture was stirred for 1 hour. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. Fractions of interest were pooled and concentrated to dryness, and the resulting residue was dissolved in 50 ml of 2N hydrochloric acid and refluxed under heating for 1 hour. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. The fractions of interest were pooled and subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid, and then concentrated to dryness. In this way, 850 mg of the title compound was obtained in a solid form.

$^1$H-NMR (DMSO-d$_6$) δ:2.0–2.45l(2H, m), 2.32 (3H, d), 2.5–2.9 (2H, m), 3.1–4.0 (7H, m), 5.1–5.35 (1H, m), 6.92 (2H, d), 7.30 (2H, d), 7.8 (1H, d), 8.20 (1H, d), 8.37 (1H, s), 8.6–8.9 (1H, m), 9.30–9.80 (5H)

FAB MS (m/z): 465

INVENTIVE EXAMPLE 105

2-[4-[((3S)-1-(acetimidoyl-3-pyrrolidinyl)oxy]phenyl]-3-(6-amidino-1-ethyl-2-indolyl)propionic acid dihydrochloride This compound was prepared in accordance with the procedure of Inventive Example 104.

(solid)

$^1$H-NMR (DMSO-d$_6$) δ:1.35 (3H, t), 2.37 (3H), 4.10–4.40 (1H, m), 6.42 (1H, s), 7.00 (2H, a), 7.45 (2H, d), 7.60 (2H, m), 8.30 (1H, s), 8.70 (1H, br), 9.25–9.80 (5H)

INVENTIVE EXAMPLE 106

3-[4-[((3S)-1-acetimidoyl-3-pyrrolidinyl)oxy]phenyl]-2-(5-amidinobenzo[b]thien-2-yl)propionic acid dihydrochloride 2.0 g of ethyl 3-[4-[((3S)-1-tert-butoxycarbonyl-3-pyrrolidinyl)oxy]phenyl]-2-(5-cyanobenzo[b]thien-2-yl)propionate was dissolved in 100 ml of ethanol. With ice cooling and stirring, hydrogen chloride was bubbled into the thus prepared solution to a saturation level. The resulting solution was allowed to stand still at room temperature for 18 hours. After distilling off the solvent, the thus obtained residue was dissolved in 100 ml of ethanol solution containing 13% ammonia, and the solution was allowed to stand still for 18 hours. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent, thereby obtaining 1.1 g of ethyl 2-(5-amidinobenzo[b]thien-2-yl)-3-[4-[((3S)-3-pyrrolidinyl)oxy]phenyl]propionate dihydrochloride. 1.1 g of the i thus obtained compound was dissolved in 15 ml of ethanol, and the solution was mixed with 566 mg of ethyl acetimidate hydrochloride and 694 mg of triethylamine in that order, followed by 18 hours of stirring at room temperature. After distilling off the solvent, the thus obtained residue was dissolved in 50 ml of 2N hydrochloric acid, and then refluxed under heating for 30 minutes. After cooling and subsequently distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. Fractions of interest thus pooled were subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid, and then concentrated to dryness. In this way, 490 mg of the title compound was obtained in a solid form.

$^1$H-NMR (DMSO-d$_6$) δ:2.1–2.4 (2H, m), 2.22 (1.5H), 2.29 (1.5H), 3.08 (1H, dd, J=13.7 and 7.8Hz), 3.30–4.00 (5H, m), 4.36 (1H), 5.00–5.20 (1H), 6.80–6.90 (2H, m), 7.15–7.25 (2H, m), 7.44 (1H, s), 7.72 (1H, d, J=8.3Hz), 8.15 (1H, d, J=8.3Hz), 8.32 (1H, s), 8.58 (0.5H), 8.66 (0.5H), 9.32 (2H, br), 9.38 (0.5H), 9.45 (0.5H), 9.50 (2H, br)

The following compounds of Inventive Examples 107 to 110 were prepared in accordance with the procedure of Inventive Example 106.

INVENTIVE EXAMPLE 107

2-[4-[((3R)-1-acetimidoyl-3-pyrrolidinyl)oxy]phenyl]-3-(7-amidino-2-naphthyl)propionic acid dihydrochloride (solid)

¹H-NMR (DMSO-d₆) δ:2.00–2.40 (5H, m), 2.90–4.10 (7H, m), 5.20 (1H, br), 6.93 (2H, d, J=8.0Hz), 7.33 (2H, d, J=8.0Hz), 7.56 (1H, d), 7.70l-8.20 (4H, m), 8.45 (1H, s), 8.50–8.80 (1H), 9.45 (3H, br), 9.63 (2H, br)

INVENTIVE EXAMPLE 108

2-[4-[(1-acetimidoyl-4-piperidinyl)oxy]phenyl]-3-(7-amidino-2-naphthyl)propionic acid dihydrochloride
(solid)
¹H-NMR (DMSO-d₆) δ:1.50–2.10 (4H, m), 2.31 (3H, s), 3.00–4.20 (7H, m), 4.60–4.80 (1H, m), 6.95 (2H, d, J=9.0Hz), 7.31 (2H, d, J=9.0Hz), 7.50–8.50 (6H, m), 8.93 (1H), 9.45 (3H, br), 9.62 (2H, br)

INVENTIVE EXAMPLE 109

3-(7-amidino-2-naphthyl)-2-[4-[(1-butanimidoyl-4-piperidinyl)oxy]phenyl]propionic acid dihydrochloride
(solid)
¹H-NMR (DMSO-d₆) δ:0.96 (3H, t, J=7.0Hz), 1.57 (2H, m), 1.71 (2H, br), 2.03 (2H, br), 2.52 (2H, t), 3.18 (1H, m), 3.40–3.90 (5H), 4.00 (1H, t), 4.68 (1H, br), 6.96 (2H, d, J=8.0Hz), 7.30 (2H, d, J=8.0Hz), 7.60–8.40 (6H, m), 8.86 (1H), 9.32 (3H, br), 9.58 (2H, br)

INVENTIVE EXAMPLE 110

2-[4-[((2R,4S)-1-acetimidoyl-2-methyl-4-pyrrolidinyl)oxy]phenyl]-3-(5-amidinobenzo[b]thien-2-yl)propionic acid dihydrochloride
(solid)
¹H-NMR (DMSO-d₆) δ:1.35 (3H, m), 2.27 (1.5H, s), 2.37 (1.5H, s), 5.10–5.50 (1H, br), 7.00 (2H, d), 7.10–8.70 (6H, m), 9.10–9.60 (6H, br)
FAB MS (m/z): 465 (M⁺+1)

INVENTIVE EXAMPLE 111

3-(5-amidinobenzo[b]thien-2-yl)-2-[4-[((2S)-5-oxo-2-pyrrolidinyl)methoxy]phenyl]propionic acid hydrochloride a) 3.2 g of ethyl 2-[4-[((2S)-1-tert-butoxy-carbonyl-5-oxo-2-pyrrolidinyl)methoxy]phenyl]-3-(5-cyanobenzo[b]thien-2-yl)propionate was dissolved in a solvent mixture of 50 ml of ethanol and 50 ml of dichloromethane. During ice-cooling and stirring, hydrogen chloride was bubbled into this solution to a saturation level. The thus prepared reaction mixture was allowed to stand still at 5° C. for 48 hours. After distilling off the solvent, the thus obtained residue was dissolved in 100 ml of ethanol solution containing 13% (w/v) of ammonia, and the solution was maintained at room temperature for 24 hours. Thereafter, the solvent was removed by distillation to obtain ethyl 3-(5-amidinobenzo[b]thien-2-yl)-2-[4-[((2S)-5-oxo-2-pyrrolidinyl)methoxy]phenyl]propionate hydrochloride. The thus obtained ester compound was dissolved in a solvent mixture of 30 ml of tetrahydrofuran and 30 ml of water. To the resulting mixture was added 1.6 g of 2-(tert-butoxycarbonylimino)-2-phenylacetonitrile and 2 ml of 1,8-diazabicyclo[5.4.0]-7-undecene. After stirring at room temperature for 24 hours, the resulting reaction solution was extracted with ethyl acetate and dried. After distilling off the solvent, the thus obtained residue was purified by subjecting it to silica gel column chromatography using a chloroform/methanol mixture as an eluant, thereby obtaining 2.4 g of ethyl 3-[5-(N-tert-butoxycarbonyl)aminoiminomethylbenzo[b]thien-2-yl]-2-[4-[((2S)-5-oxo-2-pyrrolidinyl)methoxy]phenyl]propionate in a solid form.
¹H-NMR (CDCl₃) δ:1.18 (3H, t), 1.58 (9H, s), 1.80–2.50 (4H, m), 3.28 (1H, dd), 3.70 (1H, dd), 3.80–4.50 (6H, m)

b) 2.4 g of ethyl 3-[5-(N-tert-butoxycarbonyl)aminoiminomethylbenzo[b]thien-2-yl]-2-[4-[((2S)-5-oxo-2-pyrrolidinyl)methoxy]phenyl]propionate obtained in the above step a) was dissolved in 30 ml of tetrahydrofuran. The thus prepared solution was mixed with an aqueous solution of 200 mg of sodium hydroxide dissolved in 5 ml of water, and the mixture was stirred for 72 hours. After distilling off the solvent, the thus obtained residue was dissolved in 10 ml of concentrated hydrochloric acid, and the solution was stirred at room temperature for 1 hour. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. Thereafter, thus eluted fractions of interest were pooled, mixed with hydrochloric acid, and then concentrated to dryness. In this way, 1.1 g of the title compound was obtained.
¹H-NMR (DMSO-d₆) δ:1.70–2.30 (4H, m), 6.90 (2H, d), 7.29 (2H, d), 7.30 (1H, s)
FAB MS (m/z): 438 (M⁺+1)

INVENTIVE EXAMPLE 112

2-[2-[4-[(4-imidazolyl)methoxy]phenyl]ethyl]-5-benzofurancarboxamidine dihydrochloride 3.53 g portion of 2-[2-[4-[(1-trityl-4-imidazolyl)methoxy]phenyl]ethyl]-5-benzofurancarbonitrile was dissolved in a solvent mixture of 150 ml of ethanol and 100 ml of dichloromethane. Hydrogen chloride acid gas was bubbled into the thus prepared solution while stirring under ice cooling, and the thus saturated solution was maintained at room temperature for 24 hours. After distilling off the solvent, the thus obtained residue was dissolved in an ethanol solution containing 15% (w/v) of ammonia, and the solution was stirred at room temperature for 80 hours. After distilling off the solvent, the resulting residue was dissolved in a mixture of 100 ml of formic acid and 2 ml of concentrated hydrochloric acid, and the thus prepared solution was stirred for 6 hours. After removing formic acid by distillation, the thus obtained residue was dissolved in hot water, and insoluble materials were removed by filtration. After concentrating the thus obtained filtrate to dryness, the resulting residue was subjected to column chromatography using a column packed with a highly porous polymer type synthetic adsorbent (styrene-divinylbenzene polymer: Diaion HP-20) and using a water/acetonitrile mixture as an elution solvent. Fractions of interest were pooled and concentrated, and the resulting residue was subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid, and then concentrated to dryness. In this way, 730 mg of the title compound was obtained in the form of a light yellow solid.
¹H-NMR (DMSO-d₆) δ: 2.95 (4H, m), 5.12 (2H, s), 6.72 (1H, s), 6.94 (2H, d, J=8.7Hz), 7.20 (2H, d, J=8.7Hz), 7.72 (2H, s), 7.75 (1H, s), 8.08 (1H, s), 9.13 (3H, br), 9.38 (2H, br)

INVENTIVE EXAMPLE 113

2-[2-[4-[((3S)-3-pyrrolidinyl)oxy]phenyl]ethyl]-6-indolecarboxamidine dihydrochloride 650 mg of 2-[2-[4-[((3S)-1-tert-butoxycarbonyl-3pyrrolidinyl)oxy]phenyl]ethyl]-6-indolecarbonitrile was dissolved in a solvent mixture of 100 ml of ethanol and 30 ml of dichloromethane. During ice cooling and stirring, hydrogen chloride was bubbled into the thus prepared solution to a saturation level. The resulting solution was allowed to stand still at room temperature for 24 hours. After distilling off the solvent, the resulting residue was dissolved in an ethanol solution containing 11% (w/v) of ammonia, and the solution was stirred at room temperature for 24 hours. After distilling off the solvent, the resulting residue was subjected to reversed phase high performance liquid chromatography using a column packed with octadecyl-bonded silica gel and using a water/acetonitrile mixture as an elution solvent. Thereafter, the thus eluted fractions of interest were pooled, mixed with dilute hydrochloric acid, and then concentrated to dryness. In this way, 90 mg of the title compound was obtained in the form of crystals.
mp: 229° to 233° C.
$^1$H-NMR (DMSO-$d_6$) δ:1.95–2.35 (2H, m), 5.00–5.30 (1H, br), 6.36 (1H, s), 6.80–7.80 (7H, m), 8.00 (1H, s), 9.30–9.60 (6H, br)

The following compounds of Inventive Examples 114 to 121 were prepared in accordance with the procedure of Inventive Example 113.

INVENTIVE EXAMPLE 114

2-[3-hydroxy-2-[4-[((3S)-3-pyrrolidinyl)oxy]phenyl]propyl]-6-indolecarboxamidine dihydrochloride
(solid)
$^1$H-NMR (DMSO-$d_6$) δ:1.97–2.30 (2H, m), 2.90–4.60 (9H, m), 5.00–5.20 (1H, br), 6.22 (1H, s), 6.90 (2H, d), 7.18–7.70 (2H, m), 7.96 (1H, s), 9.10–9.90 (6H, br), 11.05 (1H, s)

INVENTIVE EXAMPLE 115

2-[2 -[4-[[((2-pyrazinyl)amino]carbonyl]phenyl]ethyl]-5-benzofurancarboxamidine dihydrochloride
(solid)
$^1$H-NMR (DMSO-$d_6$) δ:3.20 (4H, 6.78 (1H, s), 7.08 (1H, br), 7.48 (2H, d, J=7.9Hz), 7.80 (2H, s), 8.03 (2H, d, J =7.9Hz), 8.12 (1H, s), 8.40–8.60 (2H, m), 9.25 (2H, br), 9.39 (3H, br), 11.05 (1H, s)

INVENTIVE EXAMPLE 116

2-[2-[4-[(1-imidazolyl)methyl]phenyl]ethyl]-5-benzofurancarboxamidine dihydrochloride
(solid)
$^1$H-NMR (DMSO-$d_6$) δ: 3.10 (4H, s), 5.45 (2H, s), 6.72 (1H, s), 7.24 (2H, d, J=8.3Hz), 7.40 (2H, d, J=8.3Hz), 7.66 (1H, s), 7.72 (2H, s), 7.80 (1H, s), 8.12 (1H, s), 9.30 (2H, br), 9.45 (3H, br)

INVENTIVE EXAMPLE 117

2-[2-[4-[(4-methyl-1-piperazinyl)carbonyl]phenyl]ethyl]-5-benzofurancarboxamidine dihydrochloride
$^1$H-NMR (DMSO-$d_6$) δ: 2.80 (3H, s), 4.09 (4H, s), 3.10 (4H, br), 4.00 (4H, br), 6.74 (1H, s), 7.36 (4H, s), 7.74 (2H, s), 8.12 (1H, s), 9.28 (2H, br), 9.48 (2H, br)

INVENTIVE EXAMPLE 118

3-[3-[4-[((3S)-3-pyrrolidinyl)oxy]phenyl]propyl]-5-benzofurancarboxamidine dihydrochloride
(solid)
$^1$H-NMR (DMSO-$d_6$) δ: 2.10 (4H, m), 2.70 (4H, m), 3.30 (4H), 5.07 (1H, br), 6.90 (2H, d), 7.15 (2H, d), 7.79 (2H, s), 8.00 (1H, s), 8.23 (1H, s), 9.20–9.80 (6H, br)

INVENTIVE EXAMPLE 119

2-[[4-[(4-piperidinyl)oxy]phenyl]methyl]-5-benzofurancarboxamidine dihydrochloride
(solid)
$^1$H-NMR (DMSO-$d_6$) δ: 1.70–2.20 (2H, m), 2.70–3.30 (4H, m), 4.14 (2H, s), 4.60–4.80 (1H, m), 6.79 (1H, s), 6.97 (2H, d, J=9.0Hz), 7.26 (2H, d, J=9.0Hz), 7.74 (2H, s), 8.13 (1H, s), 9.30 (2H, br), 9.44 (2H, br), 9.00–9.60 (2H, br)

INVENTIVE EXAMPLE 120

2-[2-[4-[((3S)-1-acetyl-3-pyrrolidinyl)oxy]-3-hydroxyphenyl]ethyl]-5-benzofurancarboxamidine hydrochloride
mp: 175°–176° C.
$^1$H-NMR (DMSO-$d_6$) δ:1.80–2.20 (5H, m), 2.70–3.80 (8H, m), 4.88 (1H, br), 6.60 (1H, d, J=8.3Hz), 6.77 (1H, s), 6.82 (1H, d, J=8.3Hz), 7.72 (1H, d, J=8.1Hz), 7.80 (1H, d, J=8.1Hz), 8.08 (1H, s), 8,90–8.98 (1H, br), 9.23 (2H, br), 9.40 (2H, br)

INVENTIVE EXAMPLE 121

2-[2-[4-[(4-(N-acetyl)aminomethylcyclohexyl)methoxy]phenyl]ethyl]-5-benzofurancarboxamidine hydrochloride
(solid)
$^1$H-NMR (DMSO-$d_6$) δ:0.70–2.00 (10H, m), 1.83 (3H, s), 2.75–3.20 (6H, m), 3.70 (2H, d, J=5.7Hz), 6.64 (1H, s), 6.77 (2H, d, J=8.8Hz), 7.15 (2H, d, J=8.8Hz), 7.65–7.68 (3H), 8.04 (1H, s), 9.00 (2H, br), 9.31 (2H, br)

INVENTIVE EXAMPLE 122

2-[2-[4-[((3S)-1-formimidoyl-3-pyrrolidinyl)oxy]phenyl]ethyl]-5-benzofurancarboxamidine dihydrochloride a) The procedure of Inventive Example 100 was followed to synthesize 2-[2-[4-[((3S)-1-tert-butoxy-carbonyl-3-pyrrolidinyl)oxy]phenyl]ethyl]-5-benzofurancarbonitrile.
$^1$H-NMR (CDCl$_3$) δ: 1.66 (9H, s), 3.04 (4H, s), 3.30–3.70 (4H, br), 4.85 (1H), 6.40 (1H, s), 6.80 (2H, d), 7.12 (2H, d), 7.52 (2H, s), 7.82 (1H, s)

b) 1.66 g of 2-[2-[4-[((3S)-1-tert-butoxy-carbonyl-3-pyrrolidinyl)oxy]phenyl]ethyl]-5-benzofurancarbonitrile obtained in the above step a) was treated and purified in accordance with the procedure of Inventive Example 113, thereby obtaining 800 mg of 2-[2-[4-[((3S)-3-pyrrolidinyl)oxy]phenyl]ethyl]-5-benzofurancarboxamidine dihydrochloride.
$^1$H-NMR (DMSO-$d_6$) δ:1.90–2.30 (2H, m), 3.06 (4H, br), 3.00–3.80 (4H, br), 5.08 (1H, br), 6.73 (1H, s), 6.88 (2H, d), 7.19 (2H, d), 7.74 (2H, s), 8.11 (1H, s), 9.26 (2H, br), 9.47 (2H, br)

c) 1.0 g of 2-[2-[4-[((3S)-3-pyrrolidinyl)oxy]phenyl]ethyl]-5-benzofurancarboxamidinedihydrochloride obtained in the above step b) was dissolved in 15 ml of water. During ice cooling and stirring, 1.83 g of benzyl methaneimidate hydrochloride was added to the above solution while maintaining the reaction solution at pH 8 with 1N sodium hydroxide aqueous solution. The thus prepared mixture was stirred for 20 minutes with ice cooling on an ice bath. The resulting reaction solution was adjusted to pH 2.0 with dilute hydrochloric acid, washed with diethyl ether, and then concentrated to dryness. Thereafter, the resulting residue was subjected to column chromatography using a column packed with a highly porous polymer type synthetic adsorbent (styrene-divinylbenzene polymer: Diaion HP-20) and using a water/acetonitrile mixture as an elution solvent. In this way, 0.76 g of the title compound was obtained in a solid form.

$^1$H-NMR (DMSO-d$_6$) δ: 1.80–2.60 (2H, m), 3.08 (4H, br), 3.20–4.00 (4H, br), 5.14 (1H, br), 6.80 (1H, s), 6.92 (2H, d), 7.25 (2H, d), 7.76 (1H, d), 7.86 (1H, d), 8.21 (1H, s), 8.40 (1H, br), 9.08 (1H, br), 9.18 (2H, br), 9.57 (3H, br)

INVENTIVE EXAMPLE 123

2-[2-[3-hydroxy-4-[((3S)-3-pyrrolidinyl)oxy]phenyl]ethyl]-5-benzofurancarboxamidine dihydrochloride 1.0 g of 2-[2-[4-[((3S)-1-acetyl-3-pyrrolidinyl)oxy]-3-hydroxyphenyl]ethyl]-5-benzofurancarboxamidine hydrochloride was dissolved in 30 ml of 6N hydrochloric acid, and the solution was refluxed under heating for 4 hours. After distilling off the solvent, the resulting residue was subjected to column chromatography using a column packed with a highly porous polymer type synthetic adsorbent (styrene-divinylbenzene polymer: Diaion HP-20) and using a water/acetonitrile mixture as an elution solvent. In this way, 320 mg of the title compound was obtained in a solid form. (solid)

$^1$H-NMR (DMSO-d$_6$) δ:1.90–2.20 (2H, m), 2.70–3.50 (8H, m), 5.08 (1H, br), 6.66 (1H, dd, J=9.0 and 1.8Hz), 6.80 (2H, s), 6.94 (1H, s), 7.76 (2H, s), 8.12 (1H, s), 9.26 (2H, br), 9.44 (2H, br), 9.74 (2H, br)

INVENTIVE EXAMPLE 124

2-[2-[4-[(4-aminomethylcyclohexyl)methoxy]phenyl]ethyl]-5-benzofurancarboxamidine dihydrochloride This compound was obtained in similar manner to the procedure of Inventive Example 123.
(solid)

$^1$H-NMR (DMSO-d$_6$) δ:0.80–2.00 (10H, m), 2.90–3.20 (4H, m), 3.73 (4H, m), 6.72 (1H, s), 6.79 (2H, d, J=8.5Hz), 7.14 (2H, d, J=8.5Hz), 7.73 (2H, s), 8.07 (3H, br), 9.18 (2H, br), 9.38 (2H, br)

INVENTIVE EXAMPLE 125

[2-[2-(5-amidino-2-benzofuranyl)ethyl]-5-[((3S)-3-pyrrolidinyl)oxy]phenyl]oxyacetic acid dihydrochloride 1.6 g of methyl [5-[((3S)-1-tert-butoxycarbonyl-3-pyrrolidinyl)oxy]-2-[2-(5-cyano-2-benzofuranyl)ethyl]phenyl] oxyacetate was dissolved in 100 ml of ethanol. With ice cooling and stirring, hydrogen chloride was bubbled into the thus prepared solution to a saturation level. The thus treated solution was warmed up to room temperature and then maintained at this temperature for 18 hours. After distilling off the solvent, the thus obtained residue was dissolved in 20 ml of ethanol, and the solution was added dropwise to an aqueous solution of 5N sodium hydroxide under stirring. After 10 minutes of stirring, the resulting reaction solution was saturated with sodium chloride, extracted with chloroform three times (200 ml, 100 ml and 100 ml in that order), and then dried on a potassium carbonate/magnesium sulfate mixture. After distilling off the solvent, the thus obtained residue was dissolved in 50 ml of ethanol. The resulting solution was mixed with 1.0 g of ammonium chloride and then with 200 ml of ethanol solution containing 12% ammonia, and the mixture was stirred for 96 hours. After distilling off the solvent, the thus obtained residue was subjected to reversed phase high performance liquid chromatography using a column packed with octadecyl-bonded silica gel and using a water/acetonitrile mixture as an elution solvent. Thereafter, thus eluted fractions of interest were pooled, mixed with dilute hydrochloric acid, and then concentrated to dryness. In this way, 0.7 g of the title compound was obtained in a powdery form.

$^1$H-NMR (DMSO-d$_6$) δ: 1.96–2.32 (2H, br), 2.80–3.60 (8H, br), 4.75 (2H, s), 5.10 (1H, br), 6.48 (1H, d, J=8.8Hz), 6.51 (1H, s), 6.76 (1H, s), 7.54 (1H, d, J=8.8Hz), 7.74 (2H, s), 8.10 (1H, s), 9.27 (2H, br), 9.42 (2H, br), 9.00–10.20 (2H, br)

INVENTIVE EXAMPLE 126 ethyl [2-[2-(5-amidino-2-benzofuranyl)ethyl]-5-[((3S)-3-pyrrolidinyl)oxy]phenyl]oxyacetate dihydrochloride 0.65 g of [2-[2-(5-amidino-2-benzofuranyl)ethyl]-5-[((3S)-3-pyrrolidinyl)oxy]phenyl]oxyacetic acid dihydrochloride was dissolved in 50 ml of ethanol. 0.2 ml of thionyl chloride was added to the above solution with ice cooling, and the resulting mixture was stirred at room temperature for 18 hours. Thereafter, the resulting reaction solution was concentrated to dryness, dissolved once in water, and then concentrated again to dryness. In this way, 0.65 g of the title compound was obtained in a solid form.

$^1$H-NMR (DMSO-d$_6$) δ:1.20 (3H, t), 2.11 (2H, br), 3.30 (4H, br), 4.20 (2H, q), 4.84 (2H, s), 5.08 (1H, br), 6.53 (2H, s), 6.75 (1H, s), 7.10 (1H, d), 7.72 (2H, s), 8.07 (1H, s), 9.18 (2H), 9.38 (2H), 9.66 (2H, br)

TEST EXAMPLE 1

Measurement of Solubility in Water

A fixed amount of water was added to a varying amounts of each sample, and the mixture was agitated on a shaker at 25° C. for 10 minutes. The results are shown in Table 1.

TABLE 1

| Compound | Solubility in Water |
| --- | --- |
| DABE[*1] | 5 mg/1 ml or less |
| Compound of Inventive Example 19 | 450 mg/1 ml or more |
| Compound of Inventive Example 21 | 600 mg/1 ml or more |
| Compound of Inventive Example 25 | 500 mg/1 ml or more |
| Compound of Inventive Example 45 | 200 mg/1 ml or more |
| Compound of Inventive Example 73 | 450 mg/1 ml or more |
| Compound of Inventive Example 96 | 400 mg/1 ml or more |
| Compound of Inventive Example 104 | 450 mg/1 ml or more |
| Compound of Inventive Example 108 | 350 mg/1 ml or more |

[*1]: DABE, 1,2-bis(5-amidino-2-benzofuranyl)ethane

Thus, the compounds of the present invention are clearly more soluble in water than the prior art.

TEST EXAMPLE 2

Measurement of Anticoagulant Activity

A blood plasma sample was prepared from human blood using a centrifuge. A 100 μl portion of the blood plasma preparation was added to 100 μl of physiological saline solution containing with or without a compound to be tested, and the mixture was allowed to stand still at 37° C. for 2 minutes. 100 μl of 0.02M calcium chloride solution which has been incubated at 37° C. in advance was added to the mixture. Thereafter, clotting time was measured using CLOTEC (Sanko Junyaku Co., Ltd.). A clotting time measured without adding a compound to be tested was used as a control, and a concentration of the test compound which doubles the control clotting time was calculated (hereinafter referred to as "CT2") as an index of the anticoagulant activity. Typical examples of the results are shown in Table 2.

TEST EXAMPLE 3

Measurement of Activated Blood Coagulation Factor X (FXa) Inhibition Activity A 180 μl portion of physiological saline solution containing a compound to be tested was mixed with 200 μl of Tris-HCl buffer (pH 8.4) and 100 μl of 1 mM S-2222 (KabiVitrum AB) aqueous solution, and the mixture was incubated at 37° C. 20 μl of Tris-HCl buffered saline (pH 7.45) containing 0.6 unit/ml of human FXa was added to the mixture. After 15 minutes of incubation at the same temperature, the reaction was stopped by adding 100 μl of 60% acetic acid, and absorbance of the reaction mixture was measured. A reaction mixture with no addition of a test compound was used as a blank, and another reaction mixture in which 60% acetic acid was added prior to the addition of FXa was used as a control. A concentration of each compound to be tested which inhibits 50% of the FXa activity was calculated (hereinafter, referred to as "$IC_{50}$") as an index of the FXa inhibition activity. Typical examples of the results are shown in Table 2.

TEST EXAMPLE 4

Measurement of Thrombin Inhibition Activity

A 100 μl portion of Tris-HCl buffered saline (pH 7.45) (TBS) containing 6 mg/ml of fibrinogen (Type 1, Daiichi Pure Chemicals Co., Ltd.) was mixed with 100 μl of physiological saline solution. At 37° C., 100 μl of Tris-HCl buffered saline (pH 7.45) (TBS) containing varying amounts of thrombin (for topical application use, Sankyo Co., Ltd.) was added to the mixture prepared above to measure clotting time using CLOTEC (Sanko Junyaku Co., Ltd.) and to prepare a calibration curve. Inhibition ratio (%) of each compound to be tested was obtained by measuring clotting time using 100 μl of physiological saline solution to which each compound has been added. A concentration of each compound which inhibits 50% of the thrombin activity was calculated based on the inhibition percentage (hereinafter, referred to as "$IC_{50}$") and concentration of the compound was determined as an index of the Anti-thrombin activity. Typical examples of the results are also shown in Table 2.

TABLE 2

| Compound | Anti-Coagulation CT2 (μM) | FXa Inhibition $IC_{50}$ (μM) | Thrombin Inhibition $IC_{50}$ (μM) |
| --- | --- | --- | --- |
| DABE | 1.6 | 0.095 | 5 |
| Compound of Inventive Example 41 | 0.32 | 0.032 | 9.0 |
| Compound of Inventive Example 43 | 0.18 | 0.013 | >400 |
| Compound of Inventive Example 45 | 0.49 | 0.041 | >2000 |
| Compound of Inventive Example 48 | 3 | 0.36 | 50 |
| Compound of Inventive Example 68 | 1.45 | 0.17 | 190 |
| Compound of Inventive Example 89 | 5 | 0.6 | >600 |
| Compound of Inventive Example 94 | 1.1 | 0.1 | 370 |
| Compound of Inventive Example 95 | 0.8 | 0.16 | 26 |
| Compound of Inventive Example 96 | 0.54 | 0.044 | 29 |
| Compound of Inventive Example 97 | 0.23 | 0.045 | 170 |
| Compound of Inventive Example 98 | 0.3 | 0.011 | 2.5 |
| Compound of Inventive Example 104 | 0.64 | 0.086 | 230 |
| Compound of Inventive Example 105 | 0.35 | 0.054 | 6.8 |
| Compound of Inventive Example 106 | 2.3 | 0.56 | 100 |
| Compound of Inventive Example 108 | 0.3 | 0.018 | 250 |

As is evident from the results shown in Table 2, each compound of the present invention shows a strong anticoagulant activity through its specific Anti-FXa activity, in comparison with DABE which is generally known as an anticoagulant agent.

TEST EXAMPLE 5

Measurement of Anticoagulant Activity in Oral Administration

An aqueous solution of each compound to be tested was administered orally to each male STD:Wistar rat individual under an anesthetic, at a dose of 10 ml/kg body weight. Blood samples were collected periodically and blood plasma preparations were obtained from the samples to measure activated partial thromboplastin time (APTT). In the same manner, APTT was measured by administering pure water and used as a control. A test/control APTT ratio was calculated and used as an index of the anticoagulant activity. Typical examples of the results are shown in Table 3.

TABLE 3

| | Test/Control APTT Ratio | | | |
| --- | --- | --- | --- | --- |
| Compound (dose) | 0.5 hr | 1 hr | 2 hr | 4 hr |
| Compound of Inventive Example 45 (100 mg/kg) | 1.63 | 1.52 | 1.48 | 1.28 |
| Compound of Inventive Example 48 (100 mg/kg) | 1.46 | 1.42 | 1.41 | 1.18 |
| Compound of Inventive Example 61 (100 mg/kg) | 1.40 | 1.28 | 1.21 | 1.09 |
| Compound of Inventive Example 89 (100 mg/kg) | 1.24 | 1.22 | 1.17 | 1.14 |
| Compound of Inventive | 1.68 | 1.64 | 1.57 | 1.42 |

TABLE 3-continued

| Compound (dose) | Test/Control APTT Ratio | | | |
|---|---|---|---|---|
| | 0.5 hr | 1 hr | 2 hr | 4 hr |
| Example 96 (100 mg/kg) | | | | |
| Compound of Inventive Example 98 (100 mg/kg) | 4.07 | 3.96 | 3.37 | 2.19 |
| Compound of Inventive Example 105 (100 mg/kg) | 2.69 | 3.60 | 2.41 | 1.66 |
| Compound of Inventive Example 108 (100 mg/kg) | 2.12 | 2.18 | 1.69 | 1.39 |

As shown in Table 3, a prolongation effect on plasma clotting time was observed clearly by the oral administration of each compound of the present invention.

TEST EXAMPLE 6

Toxicity Test by Single Oral Administration to Rat

The compound of Inventive Example 45 was dissolved in distilled water, and administered orally to each of two six-week old male Slc:SD rats, at a dose of 2,000 mg/kg body weight. No mortal case was found during 14 days of observation.

TEST EXAMPLE 7

Toxicity Test by Repeated Oral Administration to Rat

Each of the compounds of the present invention was dissolved in distilled water and administered orally to each of five five-week old male Slc:SD rats, at a dose of 800 mg/kg body weight. The oral administration was carried out once a day and repeated for 10 days to observe mortality. The results are =shown in Table 4.

TABLE 4

| Compound | Individual Numbers Administered | Mortal Case |
|---|---|---|
| Compound of Inventive Example 19 | 5 | 0 |
| Compound of Inventive Example 25 | 5 | 0 |
| Compound of Inventive Example 45 | 5 | 0 |
| Compound of Inventive Example 69 | 5 | 0 |
| Compound of Inventive Example 88 | 5 | 0 |

TEST EXAMPLE 8

Antithrombotic Effect by Oral Administration to Rat in an Arteriovenous Shunt Model Amtithrombotic effect by oral administration of the compound of the present invention was measured by slightly modifying the procedure disclosed in *Thrombosis Research*, vol. 54, pp. 399–410, 1989.

A predetermined amount of a compound to be tested was dissolved in purified water and administered orally to a male STD:Wistar rat, and the rat was anesthetized 15 minutes after the administration. An artery clip was attached to proximally the carotid artery of the thus anesthetized rat to stop blood circulation and to insert and fix an end of a shunt filled with physiological saline, while the other end of the shunt was inserted into the jugular vein and fixed. In this instance, the shunt was prepared by indwelling a copper wire (0.17 mm in diameter and 20 cm in length) in a polyethylene tube (Hibiki No. 5; ⅔ mm in outer diameter and 21 cm in length) and connecting each end of the tube with a polyethylene tube (Hibiki No. 3; 1 mm in outer diameter and 3 cm in length) using a 3 mm silicone tube. After 30 minutes of the administration, the artery clip was removed to flow blood into the shunt. After 7 minutes of the blood recirculation, the copper wire was pulled out together with formed thrombus and washed with 10 ml of physiological saline. Thereafter, the amount of thrombus formed on the copper wire was determined as protein in accordance with the procedure disclosed in *Journal of Biological Chemistry*, vol. 193, pp. 265–275, 1951. As a control, water was administered instead of the compound to be tested to calculate thrombosis inhibition rate after administration of the compound. The results are shown in Table 5.

TABLE 5

| Compound | Dose (mg/kg) | Thrombus formed (μg) | Thrombosis inhibition (%) |
|---|---|---|---|
| Water | — | 890 ± 102 | — |
| Compound of Example 45 | 10 | 585 ± 85[*1] | 34 |
| " | 30 | 356 ± 51[*1] | 60 | mean ± S.E. (n = 6)
[*1]: $p < 0.05$ (per control)

As shown in Table 5, a significant thrombosis inhibition effect was observed with oral administration.

While the invention has been described in detail and with reference to specific embodiments thereof, it will be apparent to one skilled in the art that various changes and modifications can be made therein without departing from the spirit and scope thereof.

What is claimed is:

1. An aromatic amidine derivative represented by the following general formula (1) or a pharmaceutically acceptable salt thereof:

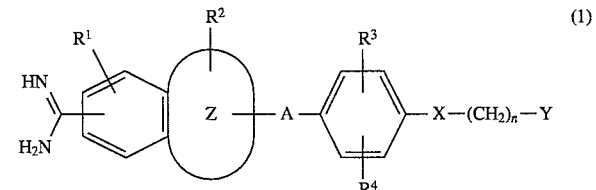

wherein $R^1$ is a hydrogen atom or a alkoxy group;

$R^2$ is a hydrogen atom, a alkyl group, a alkoxy group, a carboxyl group, an alkoxycarbonyl group, a carboxyalkyl group or an alkoxycarbonylalkyl group;

$R^3$ is a hydrogen atom, a carboxyl group, an alkoxycarbonyl group, a carboxyalkyl group, an alkoxycarbonylalkyl group, a carboxyalkoxy group or an alkoxycarbonylalkoxy group;

$R^4$ is a hydrogen atom, a hydroxyl group, a alkyl group or a alkoxy group;

n is an integer of 0 to 4;

A is an alkylene group having a carbon number of 1 to 4, which may have 1 or 2 substituents selected from the group consisting of hydroxyalkyl, carboxyl, alkoxycarbonyl, carboxyalkyl and alkoxycarbonylalkyl;

X is a single bond, an oxygen atom, a sulfur atom or a carbonyl group;

Y is a piperidinyl group optionally substituted with a member selected from the group consisting of an alkyl group, an alkanoyl group, a carbamoyl group, a mono- or dialkylcarbamoyl group, a formimidoyl group, an alkanoimidoyl group, a benzimidoyl group, a carboxyl group, an alkoxycarbonyl group, a carboxyalkyl group, an alkylcarbonylalkyl group, an aminoalkyl group, an alkanoylamino group, an alkanoylaminoalkyl group, an imino group, and alkoxycarbonylimino group, the group represented by

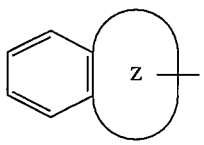

is a member selected from the group consisting of indolyl, benzofuranyl, benzothienyl, benzimidazolyl, benzoxazolyl, benzothiazolyl, naphthyl, tetrahydronaphthyl and indanyl; and said alkyl, alkoxy or akanoyl group has a carbon number of 1 to 6.

2. The aromatic amidine derivative or salt thereof according to claim 1, wherein said group represented by

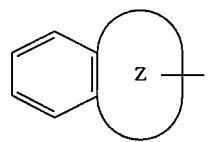

is a member selected from the group consisting of indolyl, benzofuranyl, benzothienyl, benzimidazolyl, benzothiazolyl, naphthyl and tetrahydronaphthyl.

3. An aromatic amidine derivative, 2-[4-[(1-acetimidoyl-4-piperidinyl)oxy]phenyl]-3-(7-amidino-2-naphthyl)propionic acid, or a salt thereof.

4. An aromatic amidine derivative, (+)-2-[4-[(1-acetimidoyl-4-piperidinyl)oxy]phenyl]-3-(7-amidino-2-naphthyl)propionic acid, or a salt thereof.

5. An anticoagulation composition comprising an anticoagulative effective amount of the compound of claim 1 or a salt thereof as an active ingredient and a pharmaceutically acceptable carrier.

6. An anticoagulation composition comprising an anticoagulative effective amount of the compound of claim 2 or a salt thereof as an active ingredient and a pharmaceutically acceptable carrier.

7. An anticoagulation composition comprising an anticoagulative effective amount of the compound of claim 4 or a salt thereof as an active ingredient and a pharmaceutically acceptable carrier.

* * * * *